US008420666B2

(12) United States Patent
Rudra et al.

(10) Patent No.: US 8,420,666 B2
(45) Date of Patent: Apr. 16, 2013

(54) PYRAZOLO (3, 4-B) PYRIDINE DERIVATIVES AS PHOSPHODIESTERASE INHIBITORS

(75) Inventors: Sonali Rudra, Gurgaon (IN); Nidhi Gupta, New Delhi (IN); Lalit Kumar Baregama, Chittorgarh (IN); Ritu Agarwal, Hooghly (IN); Vinayak Vasantrao Khairnar, Nashik (IN); Mandadapu Raghu Ramaiah, Guntur (IN); Venkata P. Palle, Pune (IN); Sarala Balachandran, Mumbai (IN); Atul Kondaskar, Nagpur (IN); Manohar Salla, Gurgaon (IN); Abhijit Ray, New Delhi (IN); Sunanda G. Dastidar, New Delhi (IN); Lalitha Vijaykrishnan, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 499 days.

(21) Appl. No.: 12/531,043

(22) PCT Filed: Mar. 14, 2008

(86) PCT No.: PCT/IB2008/050943
§ 371 (c)(1),
(2), (4) Date: May 7, 2010

(87) PCT Pub. No.: WO2008/111010
PCT Pub. Date: Sep. 18, 2008

(65) Prior Publication Data
US 2010/0292196 A1    Nov. 18, 2010

(30) Foreign Application Priority Data

Mar. 14, 2007 (IN) .............................. 550/DEL/2007

(51) Int. Cl.
*C07D 513/02* (2006.01)
*C07D 515/02* (2006.01)
*A01N 43/42* (2006.01)
*A61K 31/44* (2006.01)

(52) U.S. Cl.
USPC .......................................... 514/300; 546/119

(58) Field of Classification Search .................. 514/300; 546/119
See application file for complete search history.

(56) References Cited

U.S. PATENT DOCUMENTS

| 3,312,590 A | 4/1967 | Elks et al. ................... 167/58 |
| 3,436,389 A | 4/1969 | Nathansohn et al. ..... 260/239.55 |
| 3,506,694 A | 4/1970 | Oxley ...................... 260/397.45 |
| 3,639,434 A | 2/1972 | Oxley et al. ............. 260/397.45 |
| 3,642,896 A | 2/1972 | Collin .......................... 260/570.6 |
| 3,644,353 A | 2/1972 | Lunts et al. .................. 260/247.5 |
| 3,652,554 A | 3/1972 | Anner et al. ............. 260/239.55 |
| 3,700,681 A | 10/1972 | Barth ............................. 260/296 |
| 3,705,233 A | 12/1972 | Lunts et al. ...................... 424/45 |
| 3,721,687 A | 3/1973 | Elks et al. ................ 260/397.45 |
| 3,780,177 A | 12/1973 | Ercoli et al. ..................... 424/243 |
| 3,928,326 A | 12/1975 | Brattsand et al. ........ 260/239.55 |
| 3,929,768 A | 12/1975 | Brattsand et al. ........ 260/239.55 |
| 3,937,838 A | 2/1976 | Wetterlin et al. ............. 424/311 |
| 3,947,478 A | 3/1976 | Woods et al. .............. 260/397.3 |
| 3,980,778 A | 9/1976 | Ayer et al. ..................... 424/243 |
| 3,983,233 A | 9/1976 | Brattsand et al. ............. 424/241 |
| 3,992,534 A | 11/1976 | Brattsand et al. ............. 424/241 |
| 3,994,974 A | 11/1976 | Murakami et al. ............ 260/562 |
| 4,011,258 A | 3/1977 | Wetterlin et al. ............. 260/479 |
| 4,014,909 A | 3/1977 | Torossian et al. ........ 260/397.45 |

(Continued)

FOREIGN PATENT DOCUMENTS

| EP | 0 542 355 | 5/1993 |
| EP | 0 542 356 | 5/1993 |

(Continued)

OTHER PUBLICATIONS

Vippagunta et al, "Crystalline Solids" Advanced Drug Delivery Reviews, vol. 48, pp. 3-26 (2001).*

(Continued)

*Primary Examiner* — Niloofar Rahmani

(57) ABSTRACT

The present invention relates to phosphodiesterase (PDE) type 4, phosphodiesterase (PDE) type 7 and dual PDE type 4/PDE type 7 inhibitors. Compounds disclosed herein having the structure of Formula 1: can be useful in the treatment, prevention, inhibition or suppression of CNS diseases, for example, multiple sclerosis; various pathological conditions such as diseases affecting the immune system, including AIDS, rejection of transplant, auto-immune disorders such as T-cell related diseases, for example, rheumatoid arthritis; inflammatory diseases such as respiratory inflammation diseases including chronic obstructive pulmonary disease (COPD), asthma, bronchitis, allergic rhinitis, adult respiratory distress syndrome (ARDS) and other inflammatory diseases including but not limited to psoriasis, shock, atopic dermatitis, eosinophilic granuloma, allergic conjunctivitis, osteoarthritis; gastrointestinal inflammation diseases such as Crohn's disease, colitis, pancreatitis as well as different types of cancers including leukaemia; especially in humans. Processes for the preparation of disclosed compounds, pharmaceutical compositions containing the disclosed compounds and their use as PDE type 4, PDE type 7 and dual PDE type 4/PDE type 7 inhibitors are provided.

(I)

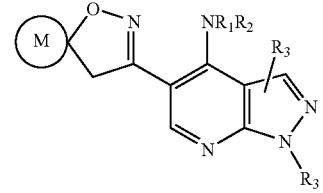

14 Claims, No Drawings

U.S. PATENT DOCUMENTS

| | | | |
|---|---|---|---|
| 4,076,708 A | 2/1978 | Green et al. | 260/239.57 |
| 4,081,541 A | 3/1978 | Bertelli | 424/243 |
| 4,098,803 A | 7/1978 | Torossian et al. | 260/397.45 |
| 4,124,707 A | 11/1978 | Green et al. | 424/241 |
| 4,158,055 A | 6/1979 | Shultz et al. | 424/241 |
| 4,226,862 A | 10/1980 | Riva et al. | 424/243 |
| 4,242,334 A | 12/1980 | Stache et al. | 424/243 |
| 4,290,962 A | 9/1981 | Tachi et al. | 260/397.45 |
| 4,298,604 A | 11/1981 | Hammell | 424/240 |
| 4,335,121 A | 6/1982 | Phillipps et al. | 424/241 |
| 4,419,364 A | 12/1983 | Olsson et al. | 424/300 |
| 4,472,392 A | 9/1984 | Anderson et al. | 424/243 |
| 4,472,393 A | 9/1984 | Shapiro | 424/243 |
| 4,579,985 A | 4/1986 | Minderhoud et al. | 585/310 |
| 4,587,236 A | 5/1986 | Annen et al. | 514/179 |
| 4,619,921 A | 10/1986 | Kalvoda et al. | 514/180 |
| 4,745,121 A * | 5/1988 | Bare | 514/303 |
| 4,780,469 A | 10/1988 | Toda et al. | 514/382 |
| 4,826,868 A | 5/1989 | Wachter et al. | 514/407 |
| 4,859,692 A | 8/1989 | Bernstein et al. | 514/381 |
| 4,873,259 A | 10/1989 | Summers, Jr. et al. | 514/443 |
| 4,992,474 A | 2/1991 | Skidmore et al. | 514/653 |
| 5,015,746 A | 5/1991 | Mizushima et al. | 552/569 |
| 5,126,375 A | 6/1992 | Skidmore et al. | 514/651 |
| 5,243,076 A | 9/1993 | Skidmore et al. | 564/346 |
| 5,278,156 A | 1/1994 | Mizushima et al. | 514/179 |
| 5,482,934 A | 1/1996 | Calatayud et al. | 514/174 |
| 5,565,473 A | 10/1996 | Belley et al. | 514/313 |
| 5,583,152 A | 12/1996 | Bernstein et al. | 514/415 |
| 5,837,699 A | 11/1998 | Sequeira et al. | 514/169 |
| 5,889,015 A | 3/1999 | Sequeira et al. | 514/172 |
| 5,976,573 A | 11/1999 | Kim | 424/489 |
| 6,127,353 A | 10/2000 | Yuen et al. | 514/172 |
| 6,180,781 B1 | 1/2001 | Yuen et al. | 540/114 |
| 6,337,324 B1 | 1/2002 | Harmenberg et al. | 514/171 |
| 6,339,099 B1 | 1/2002 | Lam et al. | 514/378 |
| 6,723,713 B2 | 4/2004 | Sequeira et al. | 514/169 |
| 2003/0176421 A1 | 9/2003 | Watson et al. | 514/224.2 |
| 2005/0208582 A1 | 9/2005 | Ohi et al. | 435/7.1 |
| 2012/0004201 A1* | 1/2012 | Rudra et al. | 514/171 |

FOREIGN PATENT DOCUMENTS

| | | |
|---|---|---|
| EP | 0 419 049 | 4/1995 |
| EP | 1 040 829 | 10/2000 |
| EP | 1 251 128 | 10/2002 |
| WO | WO 97/48697 | 12/1997 |
| WO | WO 97/49702 | 12/1997 |
| WO | WO 98/09961 | 3/1998 |
| WO | WO 98/57951 | 12/1998 |
| WO | WO 99/23076 | 5/1999 |
| WO | WO 99/23077 | 5/1999 |
| WO | WO 00/59902 | 10/2000 |
| WO | WO 02/32898 | 4/2002 |
| WO | WO 02/32899 | 4/2002 |
| WO | WO 02/50070 | 6/2002 |
| WO | WO 02/051832 | 7/2002 |
| WO | WO 02/051837 | 7/2002 |
| WO | WO 03/047520 | 6/2003 |
| WO | WO 2004/037814 | 5/2004 |
| WO | WO 2004/056823 | 7/2004 |
| WO | WO 2004/080463 | 9/2004 |
| WO | WO 2005/009958 | 2/2005 |
| WO | WO 2005/021515 | 3/2005 |
| WO | WO 2005/063767 | 7/2005 |
| WO | WO 2006/001894 | 1/2006 |
| WO | WO 2006/004188 | 1/2006 |
| WO | WO 2006/016237 | 2/2006 |
| WO | WO 2006/021848 | 3/2006 |
| WO | WO 2006/050076 | 5/2006 |
| WO | WO 2006/056863 | 6/2006 |
| WO | WO 2006/058120 | 6/2006 |
| WO | WO 2006/060456 | 6/2006 |
| WO | WO 2006/060535 | 6/2006 |
| WO | WO 2006/082492 | 8/2006 |
| WO | WO 2006/092691 | 9/2006 |
| WO | WO 2006/117657 | 11/2006 |
| WO | WO 2007/031977 | 3/2007 |
| WO | WO 2007/036733 | 4/2007 |

OTHER PUBLICATIONS

Netterwald, "Screened Gems" Drug Discovery & Development, vol. 9(9), pp. 22-26 (2007).*

Sutherland and Rall, "The Relation of Adenosine-3',5'-Phosphate and Phosphorylase to the Actions of Catecholamines and Other Hormones", *Pharmacological Reviews*, 12:265-299 (1960).

Zhang et al., "Phosphodiesterase-4 as a potential drug target", *Expert Opinion on Therapeutic Targets*, 9(6):1283-1305 (2005).

Houslay et al., "Keynote Review: Phosphodiesterase-4 as a therapeutic target", *Drug Discovery Today*, 10(22):1503-1519 (2005).

Beavo and Reifsnyder, "Primary sequence of cyclic nucleotide phosphodiesterase isozymes and the design of selective inhibitors", *Trends in Pharmacological Sciences*, 11:150-155 (1990).

Nicholson et al., "Differential modulation of tissue function and therapeutic potential of selective inhibitors of cyclic nucleotide phosphodiesterase isoenzymes", *Trends in Pharmacological Sciences*, 12:19-27 (1991).

Verghese et al., "Anti-Neutrophil Activity of Cyclic Nucleotide Phosphodiesterase Inhibitors with Varying Cardiotonic Potencies", *Journal of Molecular Cell Cardiology*, 12(suppl. II):S61 (1989).

Giembycz and Smith, "Phosphodiesterase 7A: A New Therapeutic Target for Alleviating Chronic Inflammation?", *Current Pharmaceutical Design*, 12(00):1-14 (2006).

Li, Yee, and Beavo, "CD3- and CD28-Dependent Induction of PDE7 Required for T Cell Activation", *Science*, 283(5403):848-851 (1999).

Yamamoto, et al., "Pharmacological profile of a novel phosphodiesterase 7A and -4 dual inhibitor, YM-393059, on acute and chronic inflammation models", *European Journal of Pharmacology*, 550(1-3):166-172 (2006).

Yamamoto et al., "Amelioration of collagen-induced arthritis in mice by a novel phosphodiesterase 7 and 4 dual inhibitor, YM-393059", *European Journal of Pharmacology*, 559:219-226 (2007).

Misra et al., "1*H*-Pyrazolo[3,4-*b*]pyridine Inhibitors of Cyclin-Dependent Kinases", *Bioorganic & Medicinal Chemistry Letters*, 13:1133-1136 (2003).

Ochiai et al., "Discovery of New Orally Active Phosphodiesterase (PDE4) Inhibitors", *Chemical and Pharmaceutical Bulletin*, 52(9):1098-1104 (2004).

Allegretti et al., "One-pot, new stereoselective synthesis of *endo*-tropanamine", *Tetrahedron Letters*, 42:4257-4259 (2001).

Yamamoto et al., "The effects of a novel phosphodiesterase 7A and -4 dual inhibitor, YM-393059, on T-cell-related cytokine production in vitro and in vivo", *European Journal of Pharmacology*, 541(1-2):106-114 (2006).

Martínez et al., "Benzyl Derivatives of 2,1,3-Benzo- and Benzothieno[3,2-*a*]thiadiazine 2,2-Dioxides: First Phosphodiesterase 7 Inhibitors", *Journal of Medicinal Chemistry*, 43(4):683-689 (2000).

Hebb and Robertson, "PDEs as drug targets for CNS immune disorders", *Current Opinion in Investigational Drugs*, 9(7):744-753 (2008).

Navarro et al., "Inhibition of Phosphodiesterase Type IV Suppresses Human Immunodeficiency Virus Type 1 Replication and Cytokine Production in Primary T Cells: Involvement of NF-κB and NFAT", *Journal of Virology*, 72(6):4712-4720 (1998).

Sandeep et al., "Phosphodiesterase as a novel target in Cancer Chemotherapy", *The Internet Journal of Pharmacology*, 7(1) (2009).

Lagente et al., "Selective PDE4 inhibitors as potent anti-inflammatory drugs for the treatment of airway diseases", *Mem Inst Oswaldo Cruz*, 100(Suppl. I):131-136 (2005).

Link et al., "Phosphodiesterase 4 inhibition but not beta-adrenergic stimulation suppresses tumor necrosis factor-alpha release in peripheral blood mononuclear cells in septic shock", *Critical Care*, 12(6):R159-167 (2008).

Miotla et al., "Suppression of Acute Lung Injury in Mice by an Inhibitor of Phosphodiesterase Type 4", *Am. J. Respir. Cell Mol. Biol.*, 18:411-420 (1998).

Tenor et al., "Phosphodiesterase isoenzyme families in human osteoarthritis chondrocytes—functional importance of phophodiesterase 4", *British Journal of Pharmacology*, 135(3):609-618 (2002).

Videla et al., "Selective Inhibition of Phosphodiesterase-4 Ameliorates Chronic Colitis and Prevents Intestinal Fibrosis", *Journal of Pharmacology and Experimental Therapeutics*, 316(2):940-945 (2006).

Malleo et al., "TNF-α as a Therapeutic Target in Acute Pancreatitis—Lessons from Experimental Models", *The Scientific World Journal*, 7:431-448 (2007).

Brown et al., "The mast cell and allergic diseases: role in pathogenesis and implications for therapy", *Clinical and Experimental Allergy*, 38:4-18 (2007).

Rothenberg, "Mechanisms of Disease—Eosinophilia", *The New England Journal of Medicine*, 338(22):1592-1600 (1998).

Cheng and Grande, "Cyclic Nucleotide Phosphodiesterase (PDE) Inhibitors: Novel Therapeutic Agents for Progressive Renal Disease", *Experimental Biology and Medicine*, 232:38-51 (2007).

Nikulina et al., "The phosphodiesterase inhibitor rolipram delivered after a spinal cord lesion promotes axonal regeneration and functional recovery", *Proceedings of the National Academy of Sciences*, 101(23):8786-8790 (2004).

\* cited by examiner

PYRAZOLO (3, 4-B) PYRIDINE DERIVATIVES AS PHOSPHODIESTERASE INHIBITORS

FIELD OF THE INVENTION

The present invention relates to phosphodiesterase (PDE) type 4, phosphodiesterase (PDE) type 7 and dual PDE type 4/PDE type 7 inhibitors.

Compounds disclosed herein can be useful in the treatment, prevention, inhibition or suppression of CNS diseases, for example, multiple sclerosis; various pathological conditions such as diseases affecting the immune system, including AIDS, rejection of transplant, auto-immune disorders such as T-cell related diseases, for example, rheumatoid arthritis; inflammatory diseases such as respiratory inflammation diseases including chronic obstructive pulmonary disease (COPD), asthma, bronchitis, allergic rhinitis, adult respiratory distress syndrome (ARDS) and other inflammatory diseases including but not limited to psoriasis, shock, atopic dermatitis, eosinophilic granuloma, allergic conjunctivitis, osteoarthritis; gastrointestinal inflammation diseases such as Crohn's disease, colitis, pancreatitis as well as different types of cancers including leukaemia; especially in humans.

Processes for the preparation of disclosed compounds, pharmaceutical compositions containing the disclosed compounds and their use as PDE type 4, PDE type 7 and dual PDE type 4/PDE type 7 inhibitors are provided.

BACKGROUND OF THE INVENTION

It is known that cyclic adenosine-3',5'-monophosphate (cAMP) exhibits an important role of acting as an intracellular secondary messenger (*Pharmacol. Rev.*, (1960), 12, 265). Its intracellular hydrolysis to adenosine 5'-monophosphate (AMP) causes number of inflammatory conditions which are not limited to COPD, asthma, arthritis, psoriasis, allergic rhinitis, shock, atopic dermatitis, Crohn's disease, adult respiratory distress syndrome (ARDS), eosinophilic granuloma, allergic conjunctivitis, osteoarthritis or colitis. PDE4 inhibitors are designed to inhibit the activity of PDE4, the enzyme which breaks down neuronal cAMP. Studies have shown that administering PDE4 inhibitors can have a restorative effect on memory loss in animal models, including those of Alzheimer's disease (*Expert Opin. Ther. Targets* (2005) 9(6):1283-1305; *Drug Discovery today*, 10, number 22, (2005) 1503-1519). The most important role in the control of cAMP (as well as of cGMP (cyclic guanosine monophosphate)) level is played by cyclic nucleotide phosphodiesterases (PDE) which represent a biochemically and functionally highly variable super family of enzymes. Eleven distinct families of cyclic nucleotide phosphodiesterases with more than 25 gene products are currently recognized. Although PDE1, PDE2, PDE3, PDE4, and PDE7 all use cAMP as a substrate, only PDE4 and PDE7 are highly selective for hydrolysis of cAMP. Inhibitors of PDE, particularly the PDE4 inhibitors, such as rolipram or Ro-1724 are therefore known as cAMP-enhancers. Immune cells contain type 4 and type 3 PDE, the PDE4 type being prevalent in human mononuclear cells. Thus the inhibition of phosphodiesterase type 4 has been a target for modulation and, accordingly, for therapeutic intervention in a range of disease processes.

The initial observation that xanthine derivatives, theophylline and caffeine inhibit the hydrolysis of cAMP led to the discovery of the required hydrolytic activity in the cyclic nucleotide phosphodiesterase (PDE) enzymes. Distinct classes of PDE's have been recognized (*TIPS*, (1990), 11, 150), and their selective inhibition has led to improved drug therapy (*TIPS*, (1991), 12, 19). Thus it was recognized that inhibition of PDE4 could lead to inhibition of inflammatory mediator release (*J. Mol. Cell. Cardiol.* (1989), 12 (Suppl. II), S 61) and airway smooth muscle relaxation.

The current approach of targeting PDE4 for alleviating the chronic inflammation associated with COPD is compromised by the dose limiting side effects that are proving difficult to overcome. Theoretically, an alternate strategy would be to use small molecule inhibitors to target other members of the cAMP dependent PDE family that share a common pulmonary cellular distribution to PDE4. It is hypothesized that such an approach would yield compounds with an improved therapeutic ratio. Of the novel cAMP family of proteins discovered so far, PDE7A offers itself as a promising candidate because of its cellular distribution in almost all pro inflammatory and immune cells (*Curr Pharm Des*. (2006); 12:1-14). Additionally, it has been shown to be a prime modulator of human T cell function as well (*Science*. (1999) February 5; 283 (5403):848-51).

Thus, dual specificity inhibitors that target both PDE4 and PDE7 would in principle, have an improved spectrum and a wider therapeutic window in the clinics. Compounds with dual PDE4 and PDE7 inhibitory effects have been shown to inhibit T cell function such as cytokine production, proliferation and activation of CD25 expression markers on T cells induced by antigen stimulation (*Eur. J. Pharmacol*. 541, 106-114, (2006)). Development of dual PDE4-PDE7 inhibitors would yield a novel class of drugs blocking T cell component of a disease partly through PDE7 inhibition as well as possess anti-inflammatory activity. (*Eur. J. Pharmacol*. 550, 166-172, (2006); *Eur. J. Pharmacol*. 559, 219-226, (2007)). More importantly, such a pharmacophore would be less limited by nausea and vomiting, a major side effect associated with PDE4 inhibition.

WO 2003/047520 discloses substituted aminomethyl compounds and derivatives thereof, which have been described to be useful as inhibitors of factor Xa. WO 2000/59902 discloses aryl sulfonyls, which have been described to be useful as inhibitors of factor Xa. WO 97/48697 discloses substituted azabicyclic compounds and their use as inhibitors of the production of TNF and cyclic AMP phosphodiesterase. WO 98/57951 and U.S. Pat. No. 6,339,099 describe nitrogen containing heteroaromatics and derivatives, which have been said to be the inhibitors of factor Xa. WO 2005/063767 and WO 2006/001894 disclose indoles, 1H-indazoles, 1,2-benzisoxazoles, and 1,2-benzisothiazoles, preparation and uses thereof. WO 2007/031977 discloses substituted pyrazolo[3,4-b]pyridines as phosphodiesterase inhibitors.

SUMMARY OF THE INVENTION

The present invention provides phosphodiesterase (PDE) type 4, PDE type 7 and dual PDE type 4/PDE type 7 inhibitors, which can be used for treatment, prevention, inhibition or suppression of CNS diseases, for example, multiple sclerosis; various pathological conditions such as diseases affecting the immune system, including AIDS, rejection of transplant, auto-immune disorders such as T-cell related diseases, for example, rheumatoid arthritis; inflammatory diseases such as respiratory inflammation diseases including chronic obstructive pulmonary disease (COPD), asthma, bronchitis, allergic rhinitis, adult respiratory distress syndrome (ARDS) and other inflammatory diseases including but not limited to psoriasis, shock, atopic dermatitis, eosinophilic granuloma, allergic conjunctivitis, osteoarthritis; gastrointestinal inflammation diseases such as Crohn's disease, colitis, pancreatitis as well as different types of cancers including leukaemia; especially in humans.

Pharmaceutically acceptable salts, pharmaceutically acceptable solvates, stereoisomers, tautomers, geometric isomers, racemates, regioisomers, prodrugs, metabolites, polymorphs or N-oxides of these compounds having the same type of activity are also provided.

Pharmaceutical compositions containing the compounds, which may also contain pharmaceutically acceptable carriers or diluents, can be used for treatment, prevention, inhibition or suppression of CNS diseases, for example, multiple sclerosis; various pathological conditions such as diseases affecting the immune system, including AIDS, rejection of transplant, auto-immune disorders such as T-cell related diseases, for example, rheumatoid arthritis; inflammatory diseases such as respiratory inflammation diseases including chronic obstructive pulmonary disease (COPD), asthma, bronchitis, allergic rhinitis, adult respiratory distress syndrome (ARDS) and other inflammatory diseases including but not limited to psoriasis, shock, atopic dermatitis, eosinophilic granuloma, allergic conjunctivitis, osteoarthritis; gastrointestinal inflammation diseases such as Crohn's disease, colitis, pancreatitis as well as different types of cancers including leukaemia; especially in humans.

Other aspects will be set forth in the accompanying description which follows and in part will be apparent from the description or may be learnt by the practice of the invention.

In accordance with one aspect, there are provided compounds having the structure of Formula I:

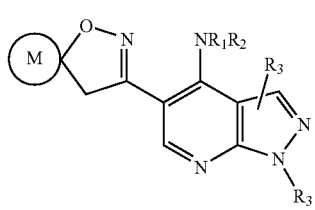

Formula I or their pharmaceutically acceptable salts, pharmaceutically acceptable solvates, stereoisomers, tautomers, geometric isomers, racemates, regioisomers, prodrugs, metabolites, polymorphs or N-oxides, wherein $R_1$ and $R_2$ independently can be hydrogen, aryl, heteroaryl, —$COR_4$, —$S(O)_mR_4$ (wherein $R_4$ can be hydrogen, alkyl, cycloalkyl, aryl, aralkyl, heteroaryl or heterocyclyl and m can be an integer from 0-2),

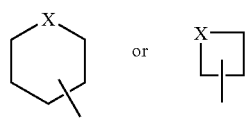

wherein X can be —O—, $S(O)_m$ (wherein m can be an integer from 0-2), C(=O), C=NOH, $CR_fR_q$ (wherein $R_f$ and $R_q$ independently can be hydrogen, hydroxy, carboxy or cyano) or $NR_5$ {wherein $R_5$ can be hydrogen, alkyl, alkenyl, alkynyl, cycloalkyl, cycloalkylalkyl, aryl, heteroaryl, heterocyclyl, —$COR_4$, —$S(O)_mR_4$, —$COOR_4$ or —$CONR_4R'_4$ (wherein $R_4$ and $R'_4$ independently can be hydrogen, alkyl, cycloalkyl, aryl, aralkyl, heteroaryl or heterocyclyl and m can be an integer from 0-2)};

$R_3$ can be hydrogen, alkyl, alkenyl, alkynyl, cycloalkyl, aryl, aralkyl, aralkenyl, cycloalkylalkyl, heterocyclyl, heteroaryl, heterocyclylalkyl or heteroarylalkyl;

M can be a 3-7 membered saturated, partially saturated or unsaturated ring containing carbon atoms wherein one or more carbon atoms optionally can be replaced by heteroatoms selected from O, $S(O)_m$ {wherein m can be an integer from 0-2} or $NR_6$ {wherein $R_6$ can be hydrogen, alkyl, alkenyl, alkynyl, cycloalkyl, cycloalkylalkyl, aryl, heteroaryl, heterocyclyl, —$COR_4$, —$S(O)_mR_4$, —$COOR_4$ or —$CONR_4R'_4$ (wherein $R_4$ and $R'_4$ independently can be hydrogen, alkyl, cycloalkyl, aryl, aralkyl, heteroaryl or heterocyclyl and m can be an integer from 0-2)}, or one or more carbon atoms optionally can be substituted with oxo, halogen, spino-attached heterocyclyl, hydroxy, cyano, alkyl, heteroaryl, heteroarylalkyl, —$(CH_2)_mNR_4R'_4$, —$(CH_2)_mOR_4$, —$(CH_2)_mCONR_4R'_4$, —$(CH_2)_mNR_4COR_4$ or —$(CH_2)_mCOOR_4$ (wherein m, $R_4$ and $R'_4$ can be the same as defined earlier).

In accordance with another aspect, there are provided methods for treating, preventing, inhibiting or suppressing inflammatory diseases, CNS diseases or autoimmune diseases, in a mammal, comprising administering a therapeutically effective amount of a PDE type 7 inhibitor or dual PDE type 4/PDE type 7 inhibitor having the structure of Formula Ia,

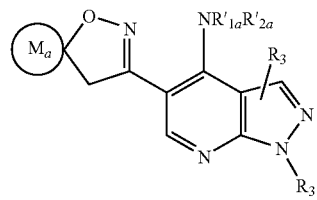

Formula Ia or their pharmaceutically acceptable salts, pharmaceutically acceptable solvates, stereoisomers, tautomers, geometric isomers, racemates, regioisomers, prodrugs, metabolites, polymorphs or N-oxides, wherein $R'_{1a}$ can be hydrogen, alkyl, alkenyl, alkynyl, acyl, aryl, aralkenyl, aralkyl, cycloalkyl alkyl, heteroaryl, heterocyclylalkyl, heteroarylalkyl, cycloalkyl or heterocyclyl;

$R'_{2a}$ can be cyclopropyl, cyclopentyl, alkyl, alkenyl, alkynyl, acyl, aralkenyl, aralkyl, cycloalkylalkyl, heterocyclylalkyl, heteroarylalkyl or heterocyclyl;

$R_3$ can be hydrogen, alkyl, alkenyl, alkynyl, cycloalkyl, aryl, aralkyl, aralkenyl, cycloalkylalkyl, heterocyclyl, heteroaryl, heterocyclylalkyl or heteroarylalkyl;

$M_a$ can be a 3-7 membered saturated, partially saturated or unsaturated ring containing carbon atoms wherein one or more carbon atoms optionally can be replaced by heteroatoms selected from O, $S(O)_m$ {wherein m can be an integer from 0-2} or $NR_7$ {wherein $R_7$ can be hydrogen, alkyl, alkenyl, alkynyl, cycloalkyl, aryl, heteroaryl or heterocyclyl}.

In accordance with another aspect, there are provided methods for the treatment, prevention, inhibition or suppression of multiple sclerosis, AIDS, rejection of transplant, rheumatoid arthritis, bronchitis, chronic obstructive pulmonary disease (COPD), asthma, psoriasis, allergic rhinitis, shock, atopic dermatitis, Crohn's disease, adult respiratory distress syndrome (ARDS), eosinophilic granuloma, allergic conjunctivitis, osteoarthritis, colitis, pancreatitis, and cancer in a mammal comprising administering a therapeutically effective amount of a PDE type 7 inhibitor or dual PDE type 4/PDE type 7 inhibitor having the structure of Formula Ia.

In accordance with another aspect, there are provided intermediates having the structure of Formula Ib:

Formula Ib

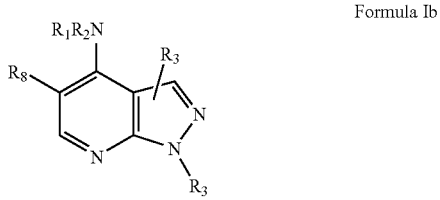

or their pharmaceutically acceptable salts, pharmaceutically acceptable solvates, stereoisomers, tautomers, geometric isomers, racemates, regioisomers, prodrugs, metabolites, polymorphs or N-oxides, wherein $R_1$ and $R_2$ independently can be hydrogen, aryl, aralkyl, heteroaryl, —$COR_4$, —$S(O)_mR_4$ (wherein $R_4$ can be hydrogen, alkyl, cycloalkyl, aryl, aralkyl, heteroaryl or
heterocyclyl and m can be an integer from 0-2),

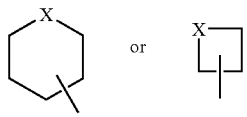

wherein X can be —O—, $S(O)_m$ (wherein m can be an integer from 0-2), C(=O), C=NOH, $CR_fR_q$ (wherein $R_f$ and $R_q$ independently can be hydrogen, hydroxy, carboxy or cyano) or $NR_5$ {wherein $R_5$ can be hydrogen, alkyl, alkenyl, alkynyl, cycloalkyl, cycloalkylalkyl, aryl, heteroaryl, heterocyclyl, —$COR_4$, —$S(O)_mR_4$, —$COOR_4$ or —$CONR_4R'_4$ (wherein $R_4$ and $R'_4$ independently can be hydrogen, alkyl, cycloalkyl, aryl, aralkyl, heteroaryl or heterocyclyl and m can be an integer from 0-2)};

$R_3$ can be hydrogen, alkyl, alkenyl, alkynyl, cycloalkyl, aryl, aralkyl, aralkenyl, cycloalkylalkyl, heterocyclyl, heteroaryl, heterocyclylalkyl or heteroarylalkyl;

$R_8$ can be

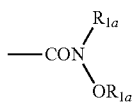

(wherein $R_{1a}$ can be alkyl), —CHO or —CH=$NOR_x$ (wherein $R_x$ can be hydrogen, alkyl or cycloalkyl).

The following definitions apply to terms as used herein.

The term "alkyl," unless otherwise specified, refers to a monoradical branched or unbranched saturated hydrocarbon chain having from 1 to 20 carbon atoms. Alkyl groups can be optionally interrupted by atom(s) or group(s) independently selected from oxygen, sulfur, a phenylene, sulphinyl, sulphonyl group or —N($R_\alpha$)—, wherein $R_\alpha$ can be hydrogen, alkyl, cycloalkyl, alkenyl, cycloalkenyl, alkynyl, aryl, acyl, aralkyl, —C(=O)$OR_\lambda$, $SO_mR_\psi$ (wherein m is an integer from 0-2 and $R_\psi$ is hydrogen, alkyl, alkenyl, alkynyl, cycloalkyl, aralkyl, aryl, heterocyclyl, heteroaryl, heteroarylalkyl or heterocyclylalkyl) or —C(=O)$NR_\lambda R_\pi$ {wherein $R_\lambda$ and $R_\pi$ are independently selected from hydrogen, halogen, hydroxy, alkyl, alkenyl, alkynyl, alkoxy, cycloalkyl, cycloalkenyl, aryl, aralkyl, heterocyclyl, heteroaryl, heterocyclylalkyl, heteroarylalkyl or carboxy}. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, tetradecyl, and the like. Alkyl groups may be substituted further with one or more substituents selected from alkenyl, alkynyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, aryl, heterocyclyl, heteroaryl, heterocyclylalkyl, cycloalkoxy, —CH=N—O($C_{1-6}$alkyl), —CH=N—NH($C_{1-6}$alkyl), —CH=N—N($C_{1-6}$alkyl)$C_{1-6}$alkyl, arylthio, thiol, alkylthio, aryloxy, nitro, aminosulfonyl, aminocarbonylamino, —NHC(=O)$R_\lambda$, —$NR_\lambda R_\pi$, —C(=O)$NR_\lambda R_\pi$, —NHC(=O)$NR_\lambda R_\pi$, —C(=O)heteroaryl, C(=O)heterocyclyl, —O—C(=O)$NR_\lambda R_\pi$, nitro or —$SO_mR_\psi$ (wherein $R_\lambda$, $R_\pi$, m and $R_\psi$ are the same as defined earlier). Unless otherwise constrained by the definition, alkyl substituents may be further substituted by 1-3 substituents selected from alkyl, alkenyl, alkynyl, carboxy, —$NR_\lambda R_\pi$, —C(=O)$NR_\lambda R_\pi$, —OC(=O)$NR_\lambda R_\pi$, —NHC(=O)$NR_\lambda R_\pi$, hydroxy, alkoxy, halogen, $CF_3$, cyano, and —$SO_mR_\psi$. Unless otherwise constrained by the definition, all substituents may be substituted further by 1-3 substituents selected from alkyl, alkenyl, alkynyl, carboxy, carboxyalkyl, —$NR_\lambda R_\pi$, —C(=O)$NR_\lambda R_\pi$, —O—C(=O)$NR_\lambda R_\pi$, hydroxy, alkoxy, halogen, $CF_3$, cyano, and —$SO_mR_\psi$ (wherein $R_\lambda$, $R_\pi$, m and $R_\psi$ are the same as defined earlier); or an alkyl group as defined above that has substituents as defined above and is also interrupted by 1-5 atoms or groups as defined above.

The term "alkenyl," unless otherwise specified, refers to a monoradical of a branched or unbranched unsaturated hydrocarbon group having from 2 to 20 carbon atoms with cis, trans or geminal geometry. Alkenyl groups can be optionally interrupted by atom(s) or group(s) independently chosen from oxygen, sulfur, phenylene, sulphinyl, sulphonyl and —N($R_\alpha$)— (wherein $R_\alpha$ is the same as defined earlier). In the event that alkenyl is attached to a heteroatom, the double bond cannot be alpha to the heteroatom. Alkenyl groups may be substituted further with one or more substituents selected from alkyl, alkenyl, alkynyl, alkoxy, cycloalkyl, cycloalkenyl, acyl, acylamino, acyloxy, —NHC(=O)$R_\lambda$, —$NR_\lambda R_\pi$, —C(=O)$NR_\lambda R_\pi$, —NHC(=O)$NR_\lambda R_\pi$, —O—C(=O)$NR_\lambda R_\pi$, alkoxycarbonylamino, azido, cyano, halogen, hydroxy, oxo, keto, carboxyalkyl, thiocarbonyl, carboxy, arylthio, thiol, alkylthio, aryl, aralkyl, aryloxy, heterocyclyl, heteroaryl, heterocyclylalkyl, heteroarylalkyl, aminosulfonyl, amino carbonyl amino, alkoxyamino, hydroxyamino, alkoxyamino, nitro or $SO_mR_\psi$ (wherein $R_\lambda$, $R_\pi$, m and $R_\psi$ are as defined earlier). Unless otherwise constrained by the definition, alkenyl substituents optionally may be substituted further by 1-3 substituents selected from alkyl, alkenyl, alkynyl, carboxy, hydroxy, alkoxy, halogen, —$CF_3$, cyano, —$NR_\lambda R_\pi$, —C(=O)$NR_\lambda R_\pi$, —O—C(=O)$NR_\lambda R_\pi$ and —$SO_mR_\psi$ (wherein $R_\lambda$, $R_\pi$, m and $R_\psi$ are as defined earlier). Groups, such as ethenyl or vinyl (CH=$CH_2$), 1-propylene or allyl (—$CH_2$CH=$CH_2$), iso-propylene (—C($CH_3$)=$CH_2$), and the like, exemplify this term.

The term "alkynyl," unless otherwise specified, refers to a monoradical of an unsaturated hydrocarbon, having from 2 to 20 carbon atoms. Alkynyl groups can be optionally interrupted by atom(s) or group(s) independently chosen from oxygen, sulfur, phenylene, sulphinyl, sulphonyl and —N($R_\alpha$)— (wherein $R_\alpha$ is the same as defined earlier). In the event that alkynyl groups are attached to a heteroatom, the triple bond cannot be alpha to the heteroatom. Alkynyl groups may be substituted further with one or more substituents selected from alkyl, alkenyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, arylthio, thiol, alkylthio, aryl, aralkyl, aryloxy, aminosulfonyl, aminocarbonylamino, hydroxyamino, alkoxyamino, nitro, heterocyclyl, heteroaryl, heterocyclylalkyl, heteroarylalkyl, —NHC(=O)$R_\lambda$, —$NR_\lambda R_\pi$, —NHC(=O)$NR_\lambda R_\pi$, —C(=O)$NR_\lambda R_\pi$, —O—C(=O)$NR_\lambda R_\pi$ or —$SO_m R_\psi$ (wherein $R_\lambda$, $R_\pi$, m and $R_\psi$ are the same as defined earlier). Unless otherwise constrained by the definition, alkynyl substituents optionally may be substituted further by 1-3 substituents selected from alkyl, alkenyl, alkynyl, carboxy, carboxyalkyl, hydroxy, alkoxy, halogen, $CF_3$, —$NR_\lambda R_\pi$, —C(=O)$NR_\lambda R_\pi$, —NHC(=O)$NR_\lambda R_\pi$, cyano or —$SO_m R_\psi$ (wherein $R_\lambda$, $R_\pi$, m and $R_\psi$ are the same as defined earlier).

The term "cycloalkyl," unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclooctyl, cyclopentyl, cyclohexyl and the like or multiple ring structures, including adamantanyl, and bicyclo [2.2.1] heptane or cyclic alkyl groups to which is fused an aryl group, for example, indane, and the like. Spiro and fused ring structures can also be included. Cycloalkyl groups may be substituted further with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, arylthio, thiol, alkylthio, aryl, aralkyl, aryloxy, aminosulfonyl, aminocarbonylamino, =$NOR_x$ (wherein $R_x$ is hydrogen, alkyl or cycloalkyl), —$NR_\lambda R_\pi$, —NHC(=O)$NR_\lambda R_\pi$, —NHC(=O)$R_\lambda$, —C(=O)$NR_\lambda R_\pi$, —O—C(=O)$NR_\lambda R_\pi$, nitro, heterocyclyl, heteroaryl, heterocyclylalkyl, heteroarylalkyl or $SO_m R_\psi$ (wherein $R_\lambda$, $R_\pi$, m and $R_\psi$ are the same as defined earlier). Carbonyl or sulfonyl group can replace carbon atom(s) of cycloalkyl. Unless otherwise constrained by the definition, cycloalkyl substituents optionally may be substituted further by 1-3 substituents selected from alkyl, alkenyl, alkynyl, carboxy, hydroxy, alkoxy, halogen, $CF_3$, —$NR_\lambda R_\pi$, —C(=O)$NR_\lambda R_\pi$, —NHC(=O)$NR_\lambda R_\pi$, —OC(=O)$NR_\lambda R_\pi$, cyano or —$SO_m R_\psi$ (wherein $R_\lambda$, $R_\pi$, m and $R_\psi$ are the same as defined earlier).

The term "cycloalkylalkyl" refers to alkyl-cycloalkyl group linked through alkyl portion, wherein the alkyl and cycloalkyl are as defined earlier.

The term "alkoxy" denotes the group O-alkyl wherein alkyl is the same as defined above.

The term "aryl," unless otherwise specified, refers to aromatic system having 6 to 14 carbon atoms, wherein the ring system can be mono-, bi- or tricyclic and carbocyclic aromatic groups. For example, aryl groups include, but are not limited to, phenyl, biphenyl, anthryl or naphthyl ring and the like, optionally substituted with 1 to 3 substituents selected from halogen (e.g., F, Cl, Br, I), hydroxy, alkyl, alkenyl, alkynyl, cycloalkyl, alkoxy, acyl, aryloxy, $CF_3$, cyano, nitro, $COOR_\psi$, NHC(=O)$R_\lambda$, —$NR_\lambda R_\pi$, —C(=O)$NR_\lambda R_\pi$, —NHC(=O)$NR_\lambda R_\pi$, —O—C(=O)$NR_\lambda R_\pi$, —$SO_m R_\psi$, carboxy, heterocyclyl, heteroaryl, heterocyclylalkyl, heteroarylalkyl, amino carbonyl amino, mercapto, haloalkyl, optionally substituted aryl, optionally substituted heterocyclylalkyl, thioalkyl, —$CONHR_\pi$, —$OCOR_\pi$, —$COR_\pi$, —$NHSO_2R_\pi$ or —$SO_2NHR_\pi$ (wherein $R_\lambda$, $R_\pi$, m and $R_\psi$ are the same as defined earlier). Aryl groups optionally may be fused with a cycloalkyl group, wherein the cycloalkyl group may optionally contain heteroatoms selected from O, N or S.

The term "aralkyl," unless otherwise specified, refers to alkyl-aryl linked through an alkyl portion (wherein alkyl and aryl are as defined above). Examples of aralkyl groups include benzyl, ethylphenyl, propylphenyl, naphthylmethyl and the like.

The term "aralkenyl," unless otherwise specified, refers to alkenyl-aryl linked through alkenyl portion (wherein alkenyl and aryl are as defined above).

The term "aryloxy" denotes the group O-aryl, wherein aryl is as defined above.

The term "cycloalkoxy" denotes the group O-cycloalkyl, wherein cycloalkyl is as defined above.

The term "carboxy," as defined herein, refers to —C(=O)$OR_\psi$, wherein $R_\psi$ is the same as defined above.

The term "heteroaryl," unless otherwise specified, refers to a monocyclic aromatic ring structure containing 5 or 6 ring atoms or a bicyclic or tricyclic aromatic group having from 8 to 10 ring atoms, with one or more heteroatom(s) independently selected from N, O or S and optionally substituted with 1 to 4 substituent(s) selected from halogen (e.g., F, Cl, Br, I), hydroxy, alkyl, alkenyl, alkynyl, cycloalkyl, acyl, carboxy, aryl, alkoxy, aralkyl, cyano, nitro, heterocyclyl, heteroaryl, —$NR_\lambda R_\pi$, CH=NOH, —$(CH_2)_w C(=O)R_\eta$ {wherein w is an integer from 0-4 and $R_\eta$ is hydrogen, hydroxy, $OR_\lambda$, $NR_\lambda R_\pi$, —$NHOR_\omega$, or —NHOH}, —C(=O)$NR_\lambda R_\pi$—NHC(=O)$NR_\lambda R_\pi$, —$SO_m R_\psi$, —O—C(=O)$NR_\lambda R_\pi$, —O—C(=O)$R_\lambda$, or —O—C(=O)$OR_\lambda$ (wherein m, $R_\psi$, $R_\lambda$, and $R_\pi$ are as defined earlier and $R_\omega$ is alkyl, cycloalkyl, aryl, heteroaryl, heterocyclyl, heteroarylalkyl or heterocyclylalkyl). Unless otherwise constrained by the definition, the substituents are attached to a ring atom, i.e., carbon or heteroatom in the ring. Examples of heteroaryl groups include oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, pyrazinyl, thienyl, isoxazolyl, triazinyl, furanyl, benzofuranyl, indolyl, benzthiazinyl, benzthiazinonyl, benzoxazinyl, benzoxazinonyl, quinazonyl, carbazolyl phenothiazinyl, phenoxazinyl, benzothiazolyl or benzoxazolyl, and the like.

The term "heterocyclyl," unless otherwise specified, refers to a non-aromatic cycloalkyl group having 5 to 10 atoms wherein 1 to 4 carbon atoms in a ring are replaced by heteroatoms selected from O, S(O)$_m$ (wherein m is an integer from 0-2) or N, and optionally are benzofused or fused heteroaryl having 5-6 ring members and/or optionally are substituted, wherein the substituents are selected from halogen (e.g., F, Cl, Br, I), hydroxy, alkyl, alkenyl, alkynyl, cycloalkyl, acyl, optionally substituted aryl, alkoxy, alkaryl, cyano, nitro, oxo, carboxy, optionally substituted heterocyclyl, optionally substituted heterocyclylalkyl, optionally substituted heteroaryl, —O—C(=O)$R_\lambda$, —O—C(=O)$OR_\lambda$, —C(=O)$NR_\lambda R_\pi$, $SO_m R_\psi$, —O—C(=O)$NR_\lambda R_\pi$, —NHC(=O)$NR_\lambda R_\pi$, —$NR_\lambda R_\pi$, mercapto, haloalkyl, thioalkyl, —$COOR_\psi$, —$COONHR_\lambda$, —$COR_\lambda$, —$NHSO_2R_\lambda$, or $SO_2NHR_\lambda$ (wherein m, $R_\psi$, $R_\lambda$ and $R_\pi$ are as defined earlier) or guanidine. Such ring systems can be mono-, bi- or tricyclic. Carbonyl or sulfonyl group can replace carbon atom(s) of heterocyclyl. Unless otherwise constrained by the definition, the substituents are attached to the ring atom, i.e., carbon or heteroatom in the ring. Also, unless otherwise constrained by the definition, the heterocyclyl ring optionally may contain one or more olefinic bond(s). Examples of heterocyclyl groups include tetrahydropyranyl, oxazolidinyl, tetrahydrofuranyl, dihydrofuranyl, benzoxazinyl, benzthiazinyl, imidazolyl, benzimidazolyl, tetrazolyl, carbaxolyl, indolyl, phenoxazinyl, phenothiazinyl, dihydropyridinyl, dihydroisoxazolyl, dihydrobenzofuryl, azabicyclohexyl, thiazolidinyl, dihydroindolyl, isoindole 1,3-dione, piperidinyl, piperazinyl, 3H-imidazo[4,5-b]pyridine, isoquinolinyl, dioxolanyl, 1H-pyrrolo[2,3-b]pyridine or piperazinyl and the like.

"Spiro-attached heterocyclyl" refers to heterocyclyl group attached to ring M of Formula I via one carbon atom common to both rings, i.e. ring M and heterocyclyl ring.

"Heteroarylalkyl" refers to alkyl-heteroaryl group linked through alkyl portion, wherein the alkyl and heteroaryl are as defined earlier.

"Heterocyclylalkyl" refers to alkyl-heterocyclyl group linked through alkyl portion, wherein the alkyl and heterocyclyl are as defined earlier.

"Acyl" refers to —C(=O)$R_z$ (wherein $R_z$ is alkyl, cycloalkyl, aryl, aralkyl, heteroaryl, heterocyclyl, heteroarylalkyl or heterocyclylalkyl).

"Amine," unless otherwise specified, refers to —$NH_2$. "Substituted amine" unless otherwise specified, refers to a group —$N(R_k)_2$ wherein each $R_k$ is independently selected from the group hydrogen provided that both $R_k$ groups are not hydrogen (defined as "amine"), alkyl, alkenyl, alkynyl, aralkyl, cycloalkyl, aryl, heteroaryl, heterocyclyl, heterocyclylalkyl, heteroarylalkyl, acyl, $S(O)_mR_\psi$ (wherein m and $R_\psi$ are the same as defined above), —C(=$R_v$)$NR_\lambda R_\pi$ (wherein $R_v$ is O or S and $R_\lambda$ and $R_\pi$ are the same as defined earlier) or NHC(=$R_v$)$NR_\pi R_\lambda$ (wherein $R_v$, $R_\pi$ and $R_\lambda$, are the same as defined earlier). Unless otherwise constrained by the definition, all amine substituents may optionally be further substituted by 1-3 substituents chosen from alkyl, aralkyl, cycloalkyl, aryl, heteroaryl, heterocyclyl, carboxy, —CO$OR_\psi$, hydroxy, alkoxy, halogen, $CF_3$, cyano, —C(=$R_v$)$NR_\lambda R_\pi$, —O(C=O)$NR_\lambda R_\pi$, —OC(=$R_v$)$NR_\lambda R_y$ (wherein $R_\lambda$, $R_\pi$ and $R_v$ are the same as defined earlier), —$S(O)_mR_\psi$ (wherein $R_\psi$ and m are the same as defined above).

"Thiocarbonyl" refers to —C(=S)H. Thiocarbonyl may be substituted and "Substituted thiocarbonyl" refers to —C(=S)R''', wherein R''' is selected from alkyl, cycloalkyl, aryl, aralkyl, heteroaryl, heterocyclyl, heteroarylalkyl, heterocyclylalkyl, amine or substituted amine. Unless otherwise constrained by the definition, all substituents optionally may be substituted further by 1-3 substituents selected from alkyl, aralkyl, cycloalkyl, aryl, heteroaryl, heterocyclyl, carboxy, hydroxy, alkoxy, halogen, $CF_3$, cyano, —C(=O)$NR_\lambda R_\pi$, —O—C(=O)$NR_\lambda R_\pi$ and —$SO_mR_\psi$ (wherein $R_\lambda$, $R_\pi$, m and $R_\psi$ are as defined earlier).

The term "oxo" means "=O". Oxo is attached at a carbon atom unless otherwise noted. Oxo, together with the carbon atom to which it is attached forms a carbonyl group (i.e., C=O).

The term "halogen" refers to fluorine, chlorine, bromine or iodine.

The compounds of the present invention can be used for treatment, prevention, inhibition or suppression of CNS diseases, for example, multiple sclerosis; various pathological conditions such as diseases affecting the immune system, including AIDS, rejection of transplant, auto-immune disorders such as T-cell related diseases, for example, rheumatoid arthritis; inflammatory diseases such as respiratory inflammation diseases including chronic obstructive pulmonary disease (COPD), asthma, bronchitis, allergic rhinitis, adult respiratory distress syndrome (ARDS) and other inflammatory diseases including but not limited to psoriasis, shock, atopic dermatitis, eosinophilic granuloma, allergic conjunctivitis, osteoarthritis; gastrointestinal inflammation diseases such as Crohn's disease, colitis, pancreatitis as well as different types of cancers including leukaemia; especially in humans.

In accordance with yet another aspect, there are provided processes for the preparation of the compounds as described herein.

DETAILED DESCRIPTION OF THE INVENTION

The compounds described herein may be prepared by techniques well known in the art and familiar to the average synthetic organic chemist. In addition, the compounds of present invention may be prepared by the following reaction sequences as depicted in Schemes I, II, III, IV, V, VI, VII, VIII, IX, X, XI, XI a, XII, XIII, XIV and XV.

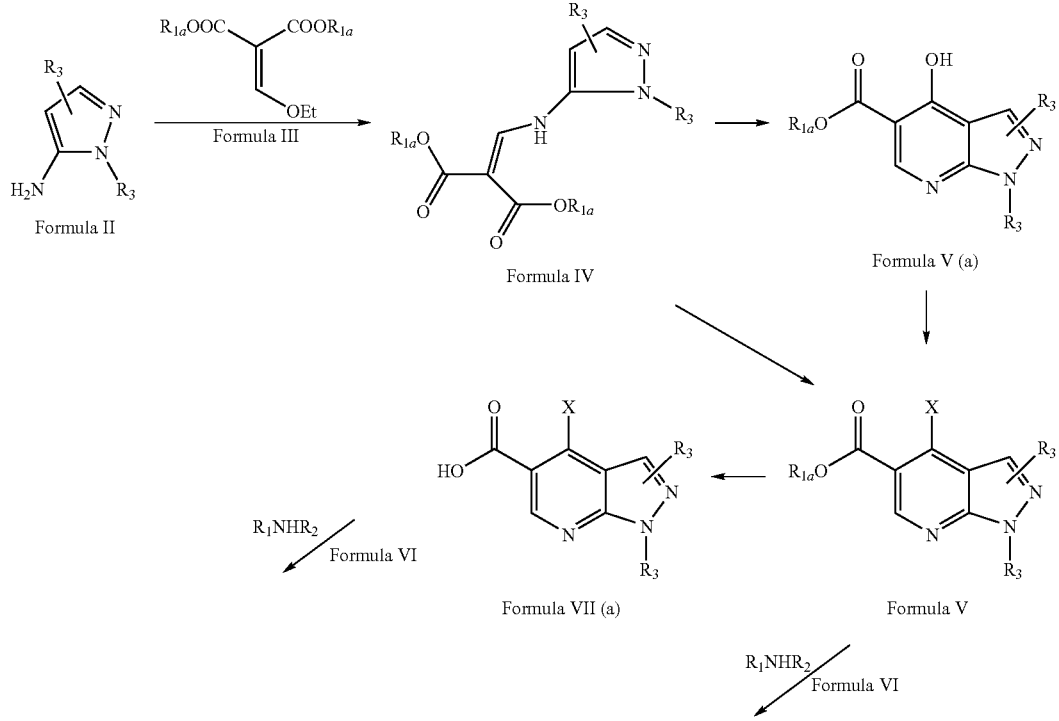

Scheme I

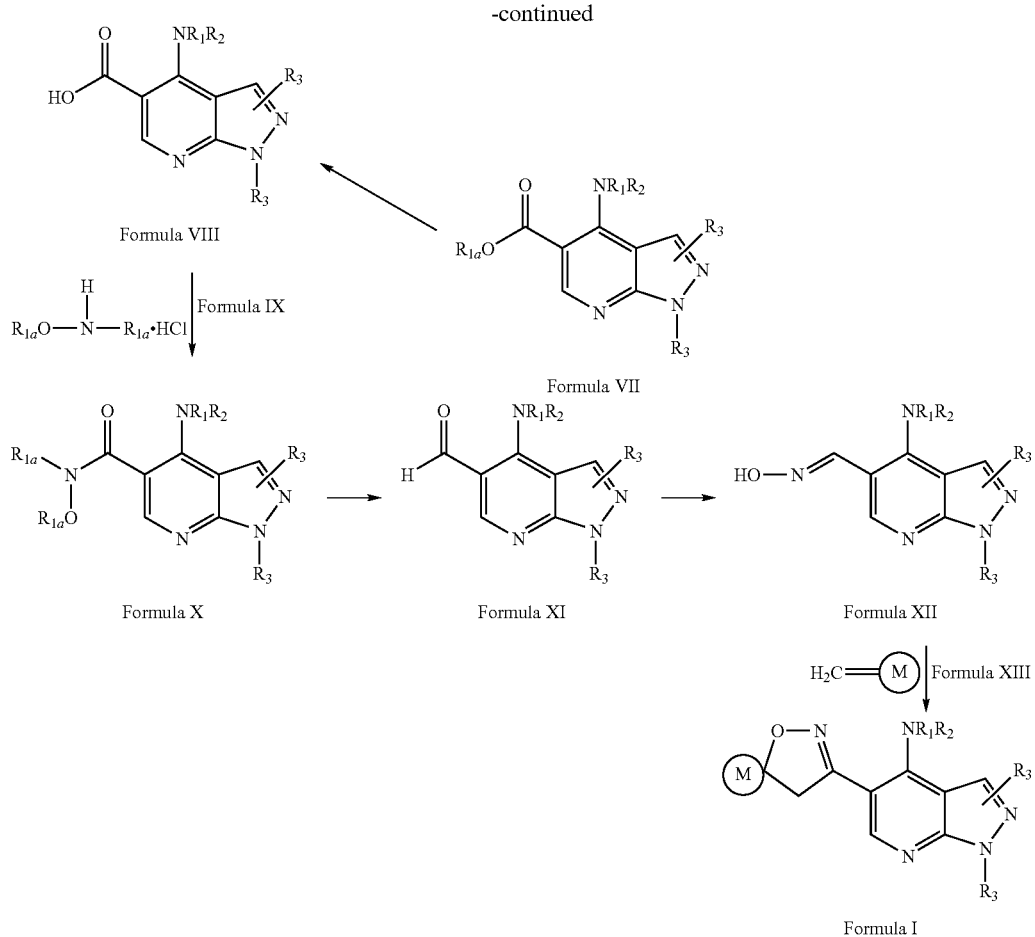

The compounds of Formula I can be prepared by following Scheme I. Accordingly, compounds of Formula II are reacted with compounds of Formula III to give compounds of Formula IV (wherein $R_{1a}$ is alkyl), which on heating give compounds of Formula V(a), which on reaction with phosphorous oxy halide give compounds of Formula V (wherein X is a halogen) or compounds of Formula IV are reacted with phosphorous oxy halide to give compounds of Formula V (wherein X is same as defined earlier), which on reaction with compounds of Formula VI give compounds of Formula VII (wherein $R_1$ and $R_2$ are the same as defined earlier), which on ester hydrolysis give compounds of Formula VIII, or compounds of Formula V on ester hydrolysis give compounds of Formula VII (a), which on reaction with compounds of Formula VI give compounds of Formula VIII (wherein $R_1$ and $R_2$ are the same as defined earlier), which on reaction with compounds of Formula IX give compounds of Formula X (wherein $R_{1a}$ is alkyl), which on reduction give compounds of Formula XI, which on reaction with hydroxylamine hydrochloride give compounds of Formula XII, which are finally reacted with compounds of Formula XIII to give compounds of Formula I (wherein $R_3$ and M are the same as defined earlier).

The compounds of Formula IV can be prepared by the reaction of compounds of Formula II with compounds of Formula III on heating.

The compounds of Formula V (a) can be prepared by the heating of compounds of Formula IV in one or more solvents, for example, alcohols, for example, methanol, ethanol, propanol or butanol in the presence of a high boiling medium, for example, diphenyl ether, dimethylsulfoxide or mixture(s) thereof.

The compounds of Formula V can be prepared by the reaction of compounds of Formula V a with phosphorous oxy halide on heating.

The compounds of Formula V can also be prepared by the reaction of compounds of Formula IV with phosphorous oxy halide on heating.

The ester hydrolysis of compounds of Formula V to give compounds of Formula VII (a) can be carried out in one or more solvents, for example, alcohols, for example, methanol, ethanol, propanol or butanol; ethers, for example, dioxane or tetrahydrofuran; or an alcohol and water mixture.

The ester hydrolysis of compounds of Formula V can be carried out in the presence of one or more inorganic bases, for example, alkali metal hydroxides, for example, potassium hydroxide, sodium hydroxide, lithium hydroxide or mixture(s) thereof.

The reaction of compounds of Formula VII (a) with compounds of Formula VI to give compounds of Formula VIII can be carried out in one or more solvents, for example, nitriles, for example, acetonitrile; ketones, for example, acetone; alcohols, for example, methanol, ethanol, propanol or butanol; ethers, for example, diethyl ether or tetrahydrofuran; amides, for example, dimethylformamide or dimethylacetamide; sulfoxides, for example, dimethylsulfoxide; hydrocarbons, for example, hexane or toluene; or mixture(s) thereof.

The reaction of compounds of Formula VII (a) with compounds of Formula VI can be carried out in the optional presence of one or more bases, for example, triethylamine, pyridine, potassium tert-butoxide, sodium hydride or mixture(s) thereof.

The reaction of compounds of Formula V with compounds of Formula VI to give compounds of Formula VII can be carried out in one or more solvents, for example, nitriles, for example, acetonitrile; ketones, for example, acetone; alcohols, for example, methanol, ethanol, propanol or butanol; ethers, for example, tetrahydrofuran or diethyl ether; amides, for example, dimethylformamide or dimethylacetamide; sulfoxides, for example, dimethylsulfoxide; hydrocarbons, for example, hexane or toluene; or mixture(s) thereof.

The reaction of compounds of Formula V with compounds of Formula VI can be carried out in the optional presence of one or more bases, for example, triethylamine, pyridine, potassium tert-butoxide, sodium hydride or mixture(s) thereof.

The ester hydrolysis of compounds of Formula VII to give compounds of Formula VIII can be carried out in one or more solvents, for example, alcohols, for example, methanol, ethanol, propanol or butanol; or an alcohol and water mixture.

The ester hydrolysis of compounds of Formula VII to give compounds of Formula VIII can be carried out in the presence of one or more inorganic bases, for example, alkali metal hydroxides, for example, potassium hydroxide, sodium hydroxide, lithium hydroxide or mixture(s) thereof.

The reaction of compounds of Formula VIII with compounds of Formula IX to give compounds of Formula X can be carried out in the presence of one or more activating reagents, for example, hydroxybenzotriazole, acetone oxime, 2-hydroxypyridine or mixture(s) thereof, and one or more coupling reagents, for example, 1-ethyl-3-(3-dimethylaminopropyl) carbodiimide hydrochloride, 1,3-dicyclohexyl carbodiimide or mixture(s) thereof in one or more solvents, for example, ethers, for example, tetrahydrofuran or diethyl ether; amides, for example, dimethylformamide or dimethylacetamide; sulfoxides, for example, dimethylsulfoxide; or mixture(s) thereof.

The reaction of compounds of Formula VIII with compounds of Formula IX can be carried out in the presence of one or more bases, for example, N-methylmorpholine; N-ethyldiisopropylamine; 4-dialkylaminopyridines, for example, 4-dimethylaminopyridine; or mixture(s) thereof.

The reduction of compounds of Formula X to give compounds of Formula XI can be carried out in one or more solvents, for example, ethers, for example, tetrahydrofuran or diethyl ether; amides, for example, dimethylformamide or dimethylacetamide; sulfoxides, for example, dimethylsulfoxide; hydrocarbons, for example, hexane or toluene; or mixture(s) thereof.

The reduction of compounds of Formula X to give compounds of Formula XI can be carried out in the presence of one or more reducing agents, for example, sodium bis(2-methoxyethoxy)aluminium hydride (vitride), lithium aluminium hydride or mixture(s) thereof.

The reaction of compounds of Formula XI with hydroxylamine hydrochloride to give compounds of Formula XII can be carried out in the presence of sodium acetate in one or more solvents, for example, alcohols, for example, methanol, ethanol, propanol or butanol; or mixture(s) thereof.

The reaction of compounds of Formula XII with compounds of Formula XIII to give compounds of Formula I can be carried out in the presence of one or more halogenating agents, for example, sodium hypochlorite, N-chlorosuccinimide, N-bromosuccinimide or mixture(s) thereof in one or more solvents, for example, nitriles, for example, acetonitrile; ketones, for example, acetone; alcohols, for example, methanol, ethanol, propanol or butanol; ethers, for example, tetrahydrofuran or diethyl ether; amides, for example, dimethylformamide or dimethylacetamide; sulfoxides, for example, dimethylsulfoxide; hydrocarbons, for example, hexane or toluene; halogenated hydrocarbons, for example, dichloromethane, dichloroethane or chloroform; or mixture(s) thereof.

The reaction of compounds of Formula XII with compounds of Formula XIII can be carried out in the optional presence of one or more bases, for example, triethyl amine, trimethyl amine or mixture(s) thereof.

Scheme II

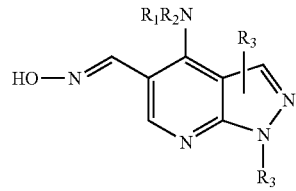

Formula XII

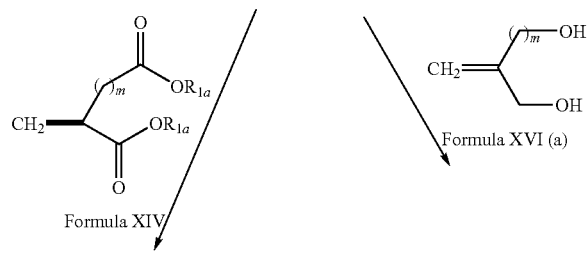

Formula XIV

Formula XVI (a)

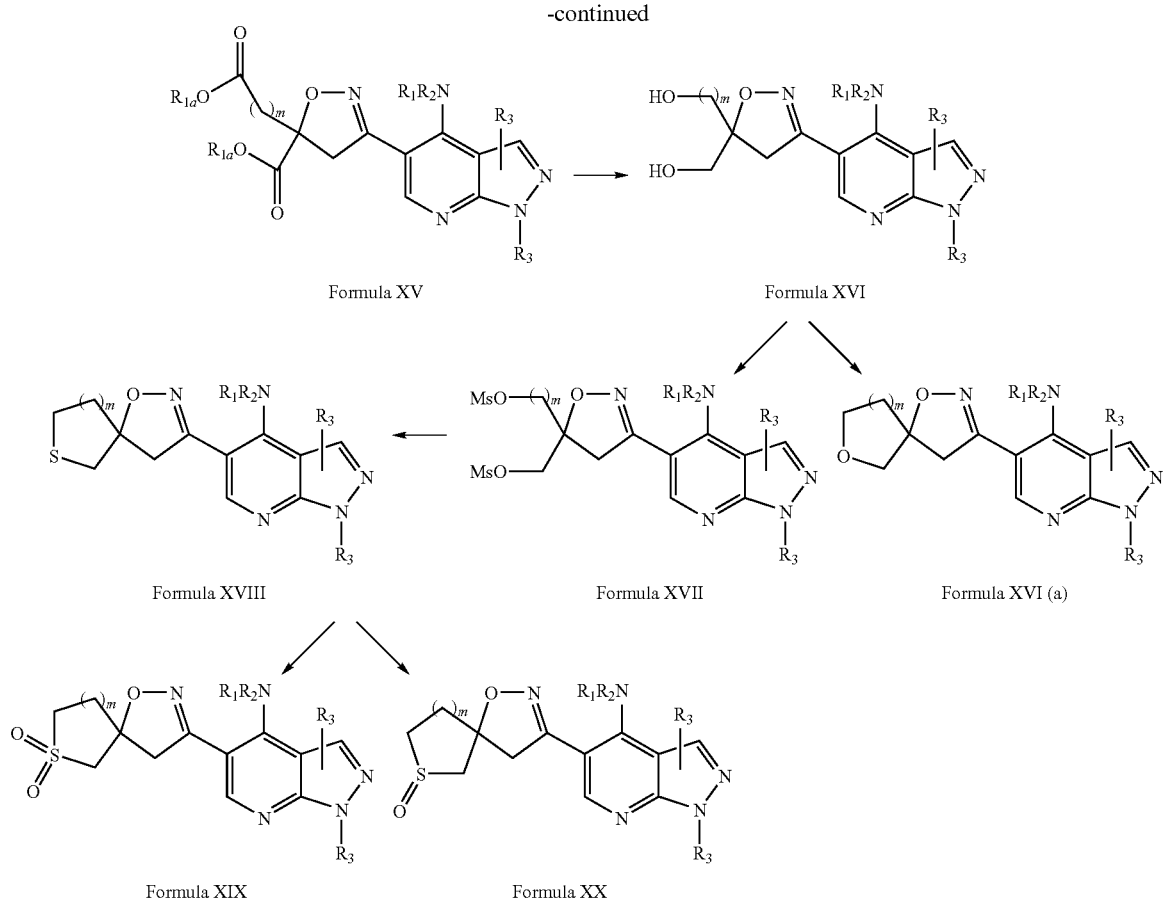

Formula XV
Formula XVI
Formula XVIII
Formula XVII
Formula XVI (a)
Formula XIX
Formula XX The compounds of Formulae XVI (a), XVIII, XIX and XX can be prepared by following Scheme II. Accordingly, compounds of Formula XII are reacted with compounds of Formula XIV to give compounds of Formula XV (wherein $R_{1a}$ is alkyl), which on reduction give compounds of Formula XVI or compounds of Formula XII are reacted with compounds of Formula XIV (a) to give compounds of Formula XVI, which on (i) cyclization give compounds of Formula XVI (a) (wherein $R_1$, $R_2$, $R_3$ are the same as defined earlier and m is an integer from 0-2).

(ii) mesylation give compounds of Formula XVII, which on cyclization give compounds of Formula XVIII, which are oxidized to give compounds of Formula XIX (wherein $R_1$, $R_2$, $R_3$ are the same as defined earlier and m is an integer from 0-2) or compounds of Formula XX (wherein $R_1$, $R_2$, $R_3$ are the same as defined earlier and m is an integer from 0-2).

The reaction of compounds of Formula XII with compounds of Formula XIV or compounds of Formula XIV (a) to give compounds of Formula XV or compounds of Formula XVI can be carried out, for example, by 1,3-dipolar cycloaddition reaction in the presence of one or more halogenating agents, for example, sodium hypochlorite, N-bromosuccinimide, N-chlorosuccinimide or mixture(s) thereof in one or more solvents, for example, nitriles, for example, acetonitrile; ketones, for example, acetone; alcohols, methanol, ethanol, propanol or butanol; ethers, for example, tetrahydrofuran or diethyl ether; amides, for example, dimethylformamide or dimethylacetamide; sulfoxides, for example, dimethylsulfoxide; hydrocarbons, for example, hexane or toluene; halogenated hydrocarbons, for example, dichloromethane, dichloroethane or chloroform; or mixture(s) thereof.

The reaction of compounds of Formula XII with compounds of Formula XIV or compounds of Formula XIV (a) to give compounds of Formula XV or compounds of Formula XVI can be carried out in the optional presence of one or more bases, for example, triethyl amine, trimethyl amine or mixture(s) thereof.

The reduction of compounds of Formula XV to give compounds of Formula XVI can be carried out in the presence of one or more reducing agents, for example, sodium borohydride, lithium aluminium hydride, borane dimethyl sulphide in one or more solvents, for example, alcohols, for example, methanol, ethanol, propanol or butanol; ethers, for example, tetrahydrofuran or diethyl ether; esters, for example, ethyl acetate; or mixture(s) thereof.

The cyclization of compounds of Formula XVI to give compounds of Formula XVI (a) can be carried out in Mitsunobu fashion with triaryl phosphines, for example, triphenylphosphine; dialkyl azodicarboxylates, for example, diisopropyl azodicarboxylate; and succinimide in one or more solvents, for example, ethers, for example, tetrahydrofuran or diethyl ether; halogenated hydrocarbons, for example, dichloromethane, dichloroethane or chloroform; amides, for example, dimethylformamide or dimethylacetamide; or mixture(s) thereof.

The mesylation of compounds of Formula XVI to give compounds of Formula XVII can be carried out in the presence of one or more mesylating agents, for example, methanesulfonyl chloride, methanesulfonic anhydride, trifluoromethanesulfonic anhydride or mixture(s) thereof in one or more solvents, for example, halogenated hydrocarbons, for example, dichloromethane, dichloroethane or chloroform; ethers, for example, tetrahydrofuran or diethyl ether; nitriles, for example, acetonitrile; or mixture(s) thereof.

The mesylation of compounds of Formula XVI to give compounds of Formula XVII can be carried out in the presence of one or more bases, for example, triethylamine, pyridine, 2,6-lutidene, diisopropyl ethylamine or mixture(s) thereof.

The cyclization of compounds of Formula XVII to give compounds of Formula XVIII can be carried out in the presence of one or more hydrated or anhydrous alkali metal sulphides, for example, sodium sulphide in one or more solvents, for example, ethers, for example, tetrahydrofuran or diethyl ether; amides, for example, dimethylformamide or dimethylacetamide; sulfoxides, for example, dimethylsulfoxide; halogenated hydrocarbons, for example, dichloromethane, dichloroethane or chloroform; or mixture(s) thereof.

The oxidation of compounds of Formula XVIII to give compounds of Formula XIX or compounds of Formula XX can be carried out in the presence of one or more oxidizing agents, for example, sodium periodate, m-chloroperbenzoic acid, tert-butyl hydroperoxide or mixture(s) thereof in one or more solvents, for example, alcohols, for example, methanol, ethanol, propanol or butanol; halogenated hydrocarbons, for example, dichloromethane, dichloroethane or chloroform; ethers, for example, tetrahydrofuran or diethyl ether; amides, for example, dimethylformamide or dimethylacetamide; sulfoxides, for example, dimethylsulfoxide; water or mixture(s) thereof Scheme III

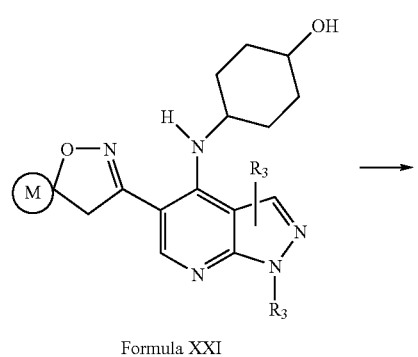

Formula XXI

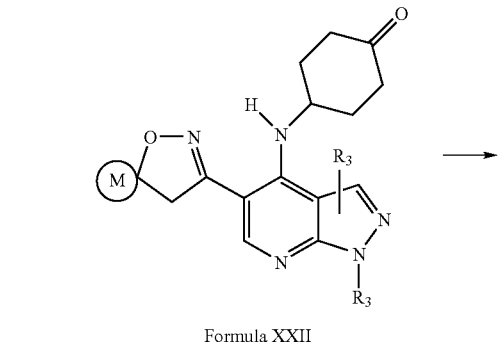

Formula XXII

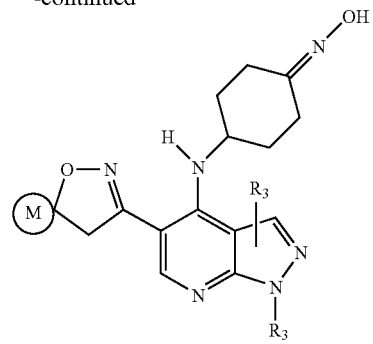

Formula XXIII

The compounds of Formulae XXII and XXIII can be prepared by following Scheme III. Accordingly, compounds of Formula XXI are oxidized to give compounds of Formula XXII, which are finally reacted with hydroxylamine hydrochloride to give compounds of Formula XXIII (wherein $R_3$ and M are the same as defined earlier).

The compounds of Formula XXI can be oxidized to give compounds of Formula XXII in the presence of one or more oxidizing agents, for example, pyridinium chlorochromate, pyridinium dichromate, dess martin periodinane or mixture(s) thereof in the presence of one or more solvents, for example, halogenated hydrocarbons, for example, dichloromethane, dichloroethane or chloroform; ethers, for example, tetrahydrofuran or diethyl ether; amides, for example, dimethylformamide or dimethylacetamide; sulfoxides, for example, dimethylsulfoxide or mixture(s) thereof.

The reaction of compounds of Formula XXII with hydroxylamine hydrochloride to give compounds of Formula XXIII can be carried out in the presence of one or more bases, for example, alkali metal carbonates, for example, sodium carbonate, potassium carbonate or cesium carbonate, alkali metal acetates, for example, sodium acetate or mixture(s) thereof in one or more solvents, for example, halogenated hydrocarbons, for example, dichloromethane, dichloroethane or chloroform; ethers, for example, tetrahydrofuran or diethyl ether; nitriles, for example, acetonitrile; amides, for example, dimethylformamide or dimethylacetamide; or mixture(s) thereof.

Scheme IV

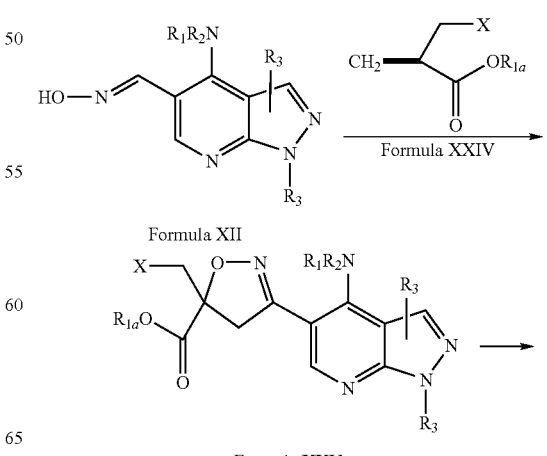

Formula XII

Formula XXIV

Formula XXV

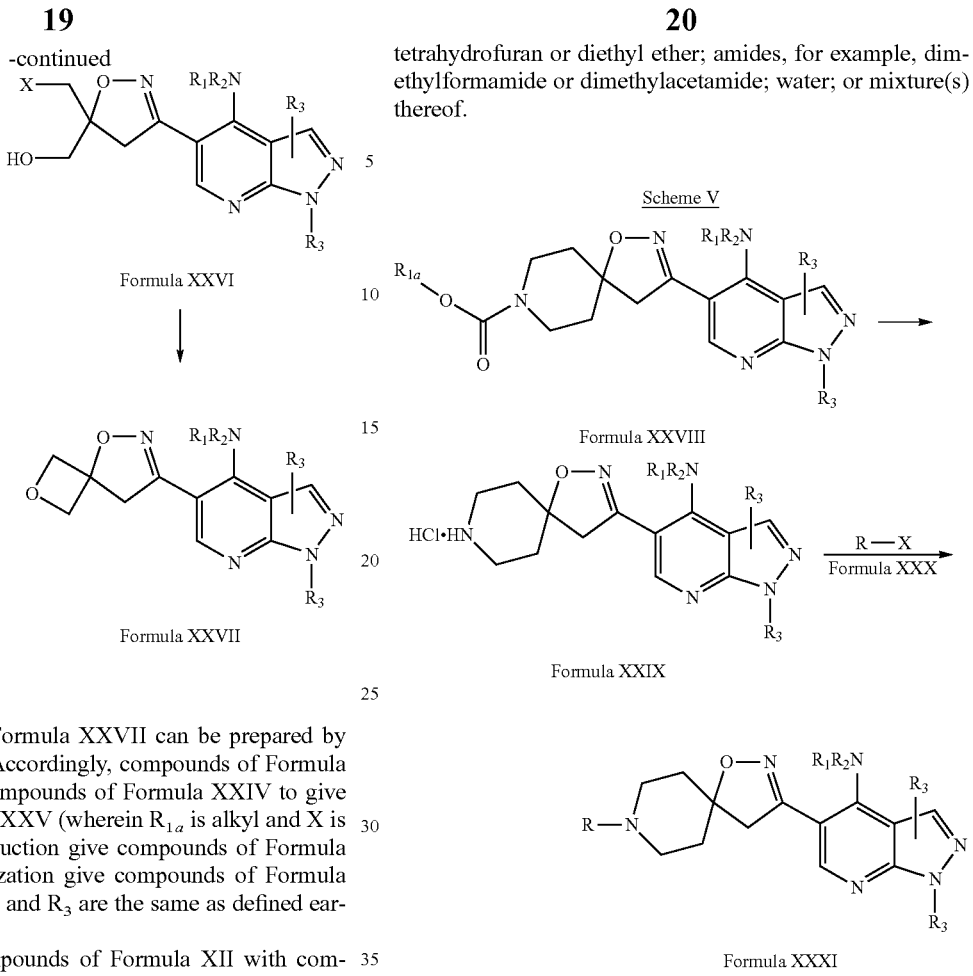

The compounds of Formula XXVII can be prepared by following Scheme IV. Accordingly, compounds of Formula XII are reacted with compounds of Formula XXIV to give compounds of Formula XXV (wherein $R_{1a}$ is alkyl and X is halogen), which on reduction give compounds of Formula XXVI, which on cyclization give compounds of Formula XXVII (wherein $R_1$, $R_2$ and $R_3$ are the same as defined earlier).

The reaction of compounds of Formula XII with compounds of Formula XXIV to give compounds of Formula XXV can be carried out, for example, by 1,3-dipolar cycloaddition reaction in the presence of one or more reagents, for example, sodium hypochlorite, N-bromosuccinimide, N-chlorosuccinimide or mixture(s) thereof in one or more solvents, for example, halogenated hydrocarbons, for example, dichloromethane, dichloroethane or chloroform; or mixture(s) thereof.

The reaction of compounds of Formula XII with compounds of Formula XXIV to give compounds of Formula XXV can be carried out in the optional presence of one or more bases, for example, triethyl amine, trimethyl amine or mixture(s) thereof.

The reduction of compounds of Formula XXV to give compounds of Formula XXVI can be carried out in the presence of one or more reducing agents, for example, sodium borohydride, lithium aluminium hydride, borane dimethyl sulphide or mixture(s) thereof in one or more solvents, for example, alcohols, for example, methanol, ethanol, propanol or butanol; ethers, for example, tetrahydrofuran or diethyl ether; esters, for example, ethyl acetate; or mixture(s) thereof.

The cyclization of compounds of Formula XXVI to give compounds of Formula XXVII can be carried out in the presence of one or more alkali metal hydroxides, for example, sodium hydroxide, potassium hydroxide or lithium hydroxide, alkali metal carbonates, for example, sodium carbonate, potassium carbonate or cesium carbonate, alkali metal alkoxides, for example, potassium t-butoxide, alkali metal hydrides, for example, sodium hydride or mixture(s) thereof in one or more solvents, for example, alcohols, for example, methanol, ethanol, propanol or butanol; ethers, for example, tetrahydrofuran or diethyl ether; amides, for example, dimethylformamide or dimethylacetamide; water; or mixture(s) thereof.

The compounds of Formulae XXIX and XXXI can be prepared by following Scheme V. Accordingly, deprotection of compounds of Formula XXVIII (wherein $R_{1a}$ is alkyl) give compounds of Formula XXIX, which on reaction with compounds of Formula XXX (wherein X is halogen) give compounds of Formula XXXI (wherein $R_1$, $R_2$, $R_3$ are the same as defined earlier and R is alkyl, cycloalkyl, cycloalkylalkyl, —$COR_4$ or —$SO_2R_4$ and $R_4$ is the same as defined earlier).

The deprotection of compounds of Formula XXVIII to give compounds of Formula XXIX can be carried out in the presence of one or more acids, for example, hydrochloric acid, trifluoroacetic acid, p-toluene sulphonic acid or mixture(s) thereof in one or more solvents, for example, alcohols, for example, methanol, ethanol, propanol or butanol; halogenated hydrocarbons, for example, dichloromethane, dichloroethane or chloroform; or mixture(s) thereof.

The reaction of compounds of Formula XXIX with compounds of Formula XXX to give compounds of Formula XXXI can be carried out in the presence of one or more inorganic bases, for example, alkali metal carbonates, for example, sodium carbonate, potassium carbonate or cesium carbonate, alkali metal hydrides, for example, sodium hydride or mixture(s) thereof or one or more organic bases, for example, triethyl amine, N-ethyldiisopropyl amine or mixture(s) thereof in one or more solvents, for example, halogenated hydrocarbons, for example, dichloromethane, dichloroethane or chloroform; amides, for example, dimethylformamide or dimethylacetamide; or mixture(s) thereof.

Scheme VI

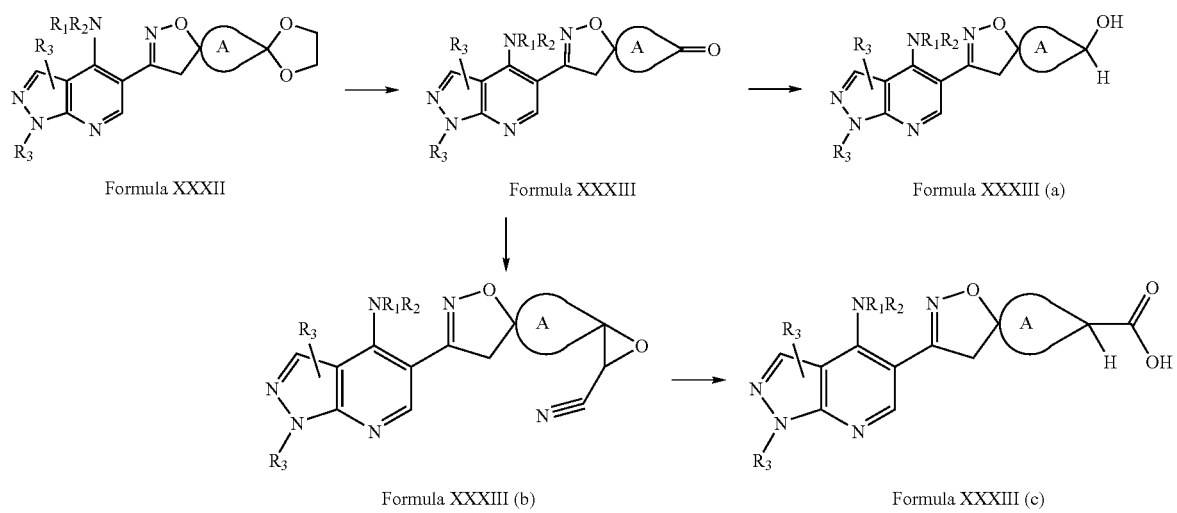

The compounds of Formulae XXXIII, XXXIII (a), and XXXIII (c) can be prepared by following Scheme VI. Accordingly, hydrolysis of compounds of Formula XXXII give compounds of Formula XXXIII, which on
  (a) reduction give compounds of Formula XXXIII (a) (wherein $R_1$, $R_2$ and $R_3$ are the same as defined earlier and A is a 3-7 membered saturated, partially saturated or unsaturated ring containing carbon atoms).
  (b) reaction with chloroacetonitrile give compounds of XXXIII (b), which are hydrolysed to give compounds of Formula XXXIII (c) (wherein $R_1$, $R_2$ and $R_3$ are the same as defined earlier and A is a 3-7 membered saturated, partially saturated or unsaturated ring containing carbon atoms).

The hydrolysis of compounds of Formula XXXII to give compounds of Formula XXXIII can be carried out in the presence of one or more acids, for example trifluoroacetic acid, p-toluene sulphonic acid or mixture(s) thereof in one or more solvents, for example, halogenated hydrocarbons, for example, dichloromethane, dichloroethane or chloroform; water or mixture(s) thereof.

The reduction of compounds of Formula XXXIII to give compounds of Formula XXXIII (a) can be carried out in the presence of reducing reagents, for example, sodium borohyride in combination with one or more lewis acid catalysts, for example cerium chloride, sodium triacetoxy borohydride or sodium cyanoborohydride or mixture(s) thereof in one or more solvents, for example, alcohols, for example, methanol, ethanol, propanol or butanol; halogenated hydrocarbons, for example, dichloromethane, dichloroethane or chloroform; or mixture(s) thereof.

The reaction of compounds of Formula XXXIII with chloroacetonitrile to give compounds of Formula XXXIII (b) can be carried out in the presence of one or more phase transfer catalysts, for example, benzyltriethyl ammonium chloride, benzyltriethyl ammonium iodide or 18-crown-6 in one or more solvents, for example, ethers, for example, tetrahydrofuran or diethyl ether; nitriles, for example, acetonitrile; or mixture(s) thereof.

The reaction of compounds of Formula XXXIII with chloroacetonitrile can be carried out in the presence of one or more bases, for example, alkali metal hydroxides, for example, potassium hydroxide, sodium hydroxide, lithium hydroxide, or mixture(s) thereof.

The hydrolysis of compounds of Formula XXXIII (b) to give compounds of Formula XXXIII (c) can be carried out in the presence of lewis acid reagents, for example, lithum bromide, magnesium bromide or mixture(s) thereof in one or more solvents, for example, water; nitriles, for example, acetonitrile; amides, for example, dimethylformamide or dimethylacetamide; or mixture(s) thereof.

Scheme VII

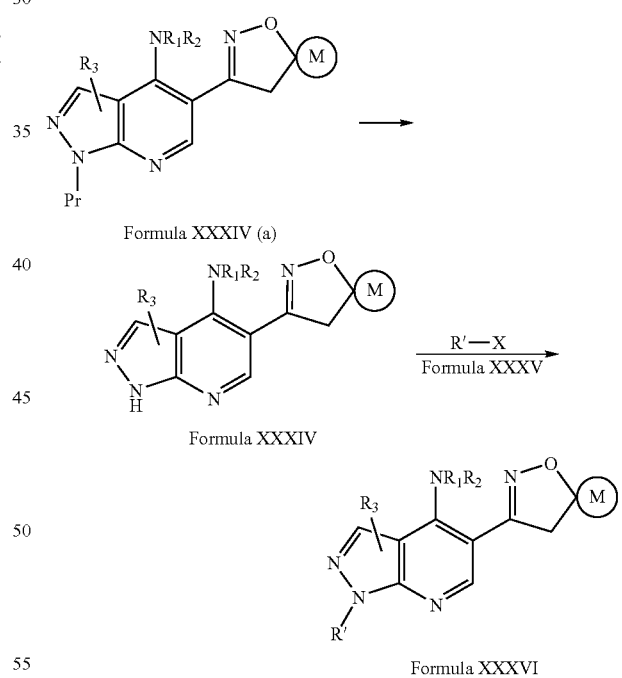

The compounds of Formulae XXXIV and XXXVI can be prepared by following Scheme VII. Accordingly, compounds of Formula XXXIV (a) (wherein Pr is a protecting group, for example, p-methoxy benzyl, benzyl or 2-furanylmethyl) are deprotected to give compounds of Formula XXXIV, which are reacted with compounds of Formula XXXV (wherein X is halogen) to give compounds of Formula XXXVI (wherein R' is alkyl, cycloalkyl or cycloalkylalkyl and $R_1$, $R_2$, $R_3$ and M are the same as defined earlier).

The deprotection of compounds of Formula XXXIV (a) to give compounds of Formula XXXIV can be carried out in the presence of ceric ammonium nitrate; or one or more oxidizing agents, for example, selenium dioxide; or one or more organic acids, for example, trifluoroacetic acid; or under hydrogenation conditions using hydrogen over palladium/carbon; in the optional presence of one or more solvents, for example, halogenated hydrocarbons, for example, dichloromethane, dichloroethane or chloroform; alcohols, for example, methanol, ethanol, propanol or butanol; esters, for example, ethyl acetate; or mixture(s) thereof.

The reaction of compounds of Formula XXXIV with compounds of Formula XXXV to give compounds of Formula XXXVI can be carried out in the presence of one or more inorganic bases, for example, alkali metal carbonates, for example, sodium carbonate, potassium carbonate or cesium carbonate, alkali metal hydrides, for example, sodium hydride or mixture(s) thereof or one or more organic bases, for example, triethyl amine, N-ethyldiisopropyl amine or mixture(s) thereof in one or more solvents, for example, halogenated hydrocarbons, for example, dichloromethane, dichloroethane or chloroform; amides, for example, dimethylformamide or dimethylacetamide; or mixture(s) thereof

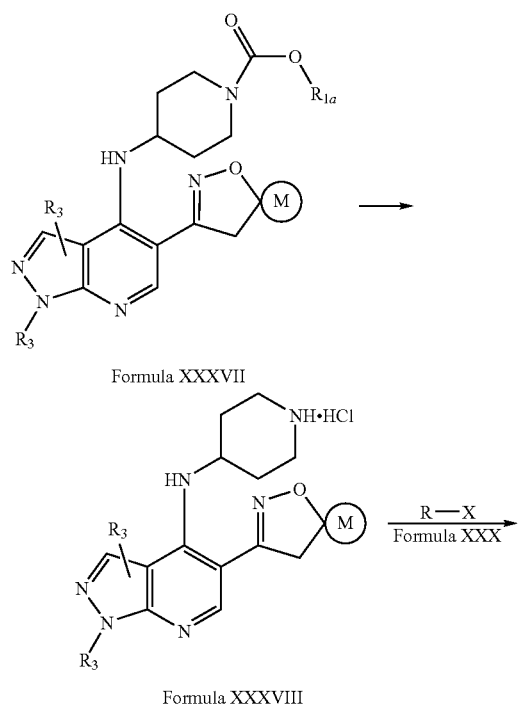

The compounds of Formulae XXXVIII and XXXIX can be prepared by following Scheme VIII. Accordingly, compounds of Formula XXXVII (wherein $R_{1a}$ is alkyl) are deprotected to give compounds of Formula XXXVIII, which are reacted with compounds of Formula XXX (wherein X is halogen) to give compounds of Formula XXXIX (wherein R is alkyl, cycloalkyl, cycloalkylalkyl, —$COR_4$ or —$SO_2R_4$ and $R_4$ is the same as defined earlier and $R_3$ and M are the same as defined earlier).

The deprotection of compounds of Formula XXXVII to give compounds of Formula XXXVIII can be carried out in the presence of one or more acids, for example, hydrochloric acid, trifluoroacetic acid, p-toluene sulphonic acid or mixture(s) thereof in one or more solvents, for example, alcohols, for example, methanol, ethanol, propanol or butanol; halogenated hydrocarbons, for example, dichloromethane, dichloroethane or chloroform; or mixture(s) thereof.

The reaction of compounds of Formula XXXVIII with compounds of Formula XXX to give compounds of Formula XXXIX can be carried out in the presence of one or more inorganic bases, for example, alkali metal carbonates, for example, sodium carbonate, potassium carbonate or cesium carbonate, alkali metal hydrides, for example, sodium hydride or mixture(s) thereof or one or more organic bases, for example, triethyl amine, N-ethyldiisopropyl amine or mixture(s) thereof in one or more solvents, for example, nitriles, for example, acetonitrile; halogenated hydrocarbons, for example, dichloromethane, dichloroethane or chloroform; amides, for example, dimethylformamide or dimethylacetamide; or mixture(s) thereof.

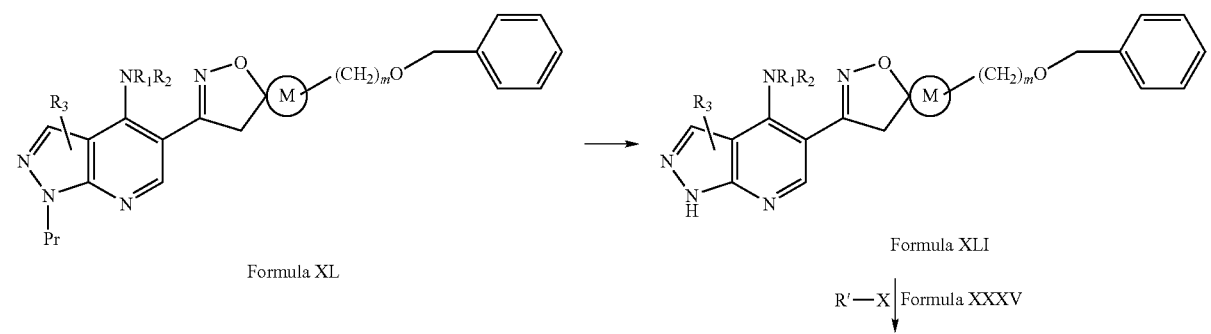

-continued

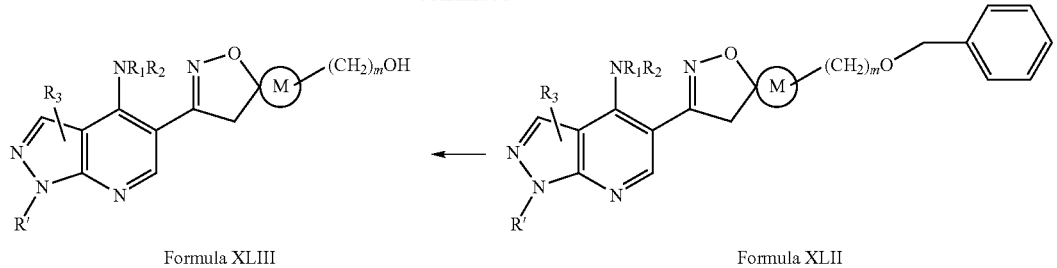

Formula XLIII          Formula XLII

The compounds of Formulae XLI, XLII and XLIIII can be prepared by following Scheme IX. Accordingly, compounds of Formula XL (wherein Pr is a protecting group, for example, p-methoxy benzyl, benzyl or 2-furanylmethyl) are deprotected to give compounds of Formula XLI, which are reacted with compounds of Formula XXXV (wherein X is as defined earlier) to give compounds of Formula XLII, which are finally debenzylated to give compounds of Formula XLIII (wherein R' is alkyl, cycloalkyl or cycloalkylalkyl and $R_1$, $R_2$, $R_3$, M and m are the same as defined earlier).

The deprotection of compounds of Formula XL to give compounds of Formula XLI can be carried out in the presence of eerie ammonium nitrate; or one or more oxidizing agents, for example, selenium dioxide; or one or more organic acids, for example, trifluoroacetic acid; or under hydrogenation conditions using hydrogen over palladium/carbon; in the optional presence of one or more solvents, for example, halogenated hydrocarbons, for example, dichloromethane, dichloroethane or chloroform; alcohols, for example, methanol, ethanol, propanol or butanol; esters, for example, esters, for example, ethyl acetate; or mixture(s) thereof.

The reaction of compounds of Formula XLI with compounds of Formula XXXV to give compounds of Formula XLII can be carried out in the presence of one or more inorganic bases, for example, alkali metal carbonates, for example, sodium carbonate, potassium carbonate or cesium carbonate, alkali metal hydrides, for example, sodium hydride or mixture(s) thereof or one or more organic bases, for example, triethyl amine, N-ethyldiisopropyl amine or mixture(s) thereof in one or more solvents, for example, halogenated hydrocarbons, for example, dichloromethane, dichloroethane or chloroform; amides, for example, dimethylformamide or dimethylacetamide; or mixture(s) thereof.

The debenzylation of a compounds of Formula XLII to give compounds of Formula XLIII can be carried out in the presence of one or more debenzylating agents, for example, palladium on carbon/hydrogen, palladium on carbon with ammonium formate, palladium hydroxide or mixture(s) thereof, in one or more solvents, for example, alcohols, for example, methanol, ethanol, propanol or butanol; or mixture(s) thereof.

Scheme X

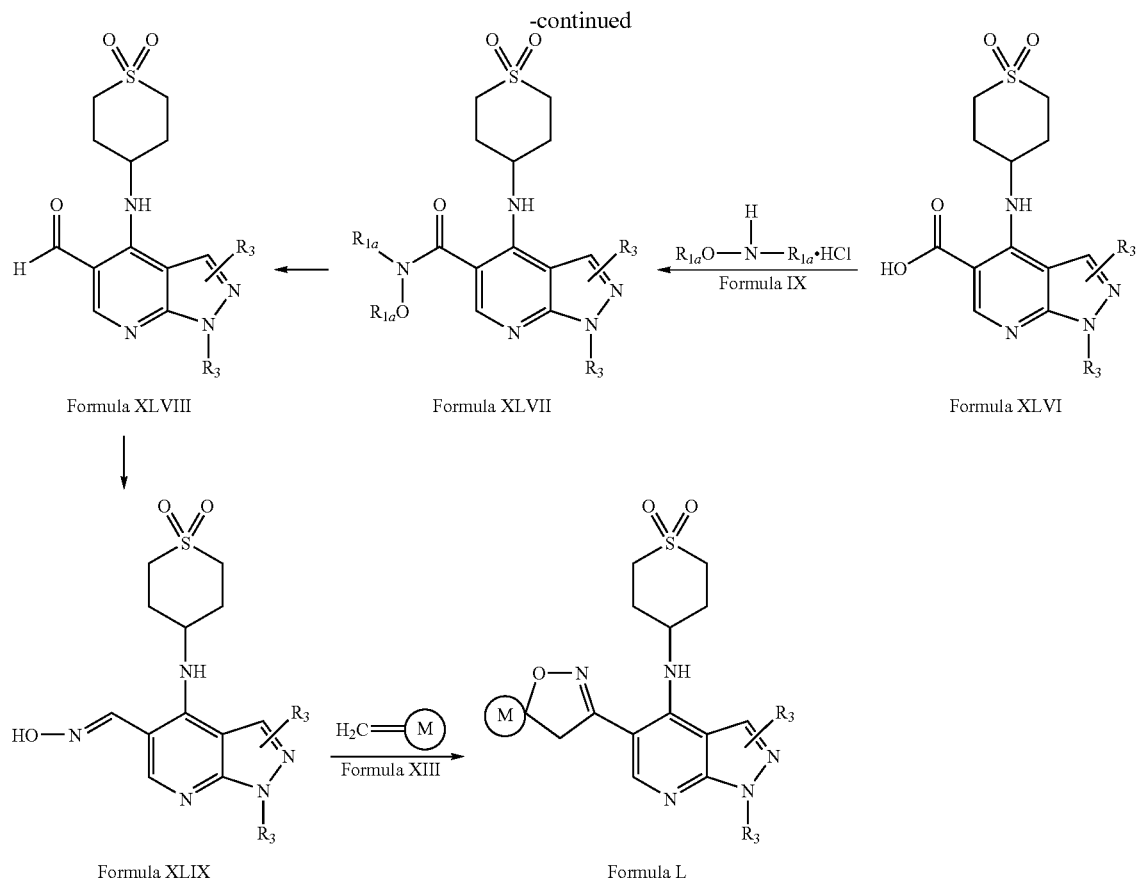

The compounds of Formula L can be prepared by following Scheme X. Accordingly, compounds of Formula V (wherein X is halogen and $R_{1a}$ is alkyl) are reacted with compounds of Formula VI (a) to give compounds of Formula XLIV, which on oxidation give compounds of Formula XLV, which on ester hydrolysis give compounds of Formula XLVI, which on reaction with compounds of Formula IX (wherein $R_{1a}$ is alkyl) give compounds of Formula XLVII, which on reduction give compounds of Formula XLVIII, which on reaction with hydroxylamine hydrochloride give compounds of Formula XLIX, which are reacted with compounds of Formula XIII to give compounds of Formula L (wherein $R_3$ and M are the same as defined earlier).

The reaction of compounds of Formula V with compounds of Formula VI (a) to give compounds of Formula XLIV can be carried out in one or more solvents, for example, nitriles, for example, acetonitrile; ketones, for example, acetone; alcohols, for example, methanol, ethanol, propanol or butanol; ethers, for example, diethyl ether or tetrahydrofuran; amides, for example, dimethylformamide or dimethylacetamide; sulfoxides, for example, dimethylsulfoxide; hydrocarbons, for example, hexane or toluene; or mixture(s) thereof.

The reaction of compounds of Formula V with compounds of Formula VI (a) can be carried out in the optional presence of one or more bases, for example, triethylamine, pyridine, potassium tert-butoxide, sodium hydride or mixture(s) thereof.

The oxidation of compounds of Formula XLIV to give compounds of Formula XLV can be carried out in the presence of one or more oxidizing agents, for example, m-chloroperbenzoic acid, oxone or hydrogen peroxide in one or more solvents, for example, halogenated hydrocarbons, for example, dichloromethane, dichloroethane or chloroform; or mixture(s) thereof.

The ester hydrolysis of compounds of Formula XLV to give compounds of Formula XLVI can be carried out in one or more solvents, for example, alcohols, for example, methanol, ethanol, propanol or butanol; or an alcohol and water mixture.

The ester hydrolysis of compounds of Formula XLV can be carried out in the presence of one or more inorganic bases, for example, alkali metal hydroxides, for example, potassium hydroxide, sodium hydroxide, lithium hydroxide or mixture(s) thereof.

The reaction of compounds of Formula XLVI with compounds of Formula IX to give compounds of Formula XLVII can be carried out in the presence of one or more activating reagents, for example, hydroxybenzotriazole, acetone oxime, 2-hydroxypyridine or mixture(s) thereof, and one or more coupling reagents, for example, 1-ethyl-3-(3-dimethylaminopropyl) carbodiimide hydrochloride, 1,3-dicyclohexyl carbodiimide or mixture(s) thereof in one or more solvents, for example, ethers, for example, diethyl ether or tetrahydrofuran; amides, for example, dimethylformamide or dimethylacetamide; sulfoxides, for example, dimethylsulfoxide; or mixture(s) thereof.

The reaction of compounds of Formula XLVI with compounds of Formula IX can be carried out in the presence of one or more bases, for example, N-methylmorpholine; N-ethyldiisopropylamine; 4-dialkylaminopyridines, for example, 4-dimethylaminopyridine; or mixture(s) thereof.

The reduction of compounds of Formula XLVII to give compounds of Formula XLVIII can be carried out in one or more solvents, for example, ethers, for example, diethyl ether or tetrahydrofuran; amides, for example, dimethylformamide or dimethylacetamide; sulfoxides, for example, dimethylsulfoxide; hydrocarbons, for example, hexane or toluene; or mixture(s) thereof.

The reduction of compounds of Formula XLVII can be carried out in the presence of one or more reducing agents, for example, sodium bis(2-methoxyethoxy)aluminum hydride (vitride), lithium aluminium hydride or mixture(s) thereof.

The reaction of compounds of Formula XLVIII with hydroxylamine hydrochloride to give compounds of Formula XLIX can be carried out in the presence of sodium acetate in one or more solvents, for example, alcohols, for example, methanol, ethanol, propanol, butanol or mixture(s) thereof.

The reaction of compounds of Formula XLIX with compounds of Formula XIII to give compounds of Formula L can be carried out in the presence of one or more halogenating agents, for example, sodium hypochlorite, N-chlorosuccinimide, N-bromosuccinimide or mixture(s) thereof, in one or more solvents, for example, nitriles, for example, acetonitrile; ketones, for example, acetone; alcohols, for example, methanol, ethanol, propanol or butanol; ethers, for example, diethyl ether or tetrahydrofuran; amides, for example, dimethylformamide or dimethylacetamide; sulfoxides, for example, dimethylsulfoxide; hydrocarbons, for example, hexane or toluene; halogenated hydrocarbons, for example, dichloromethane, dichloroethane or chloroform; or mixture(s) thereof.

The reaction of compounds of Formula XLIX with compounds of Formula XIII can be carried out in the optional presence of one or more bases, for example, triethyl amine, trimethyl amine or mixture(s) thereof.

Scheme XI

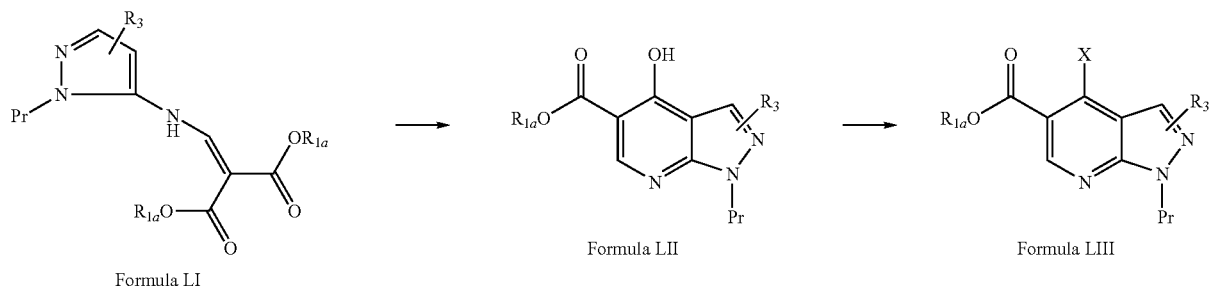

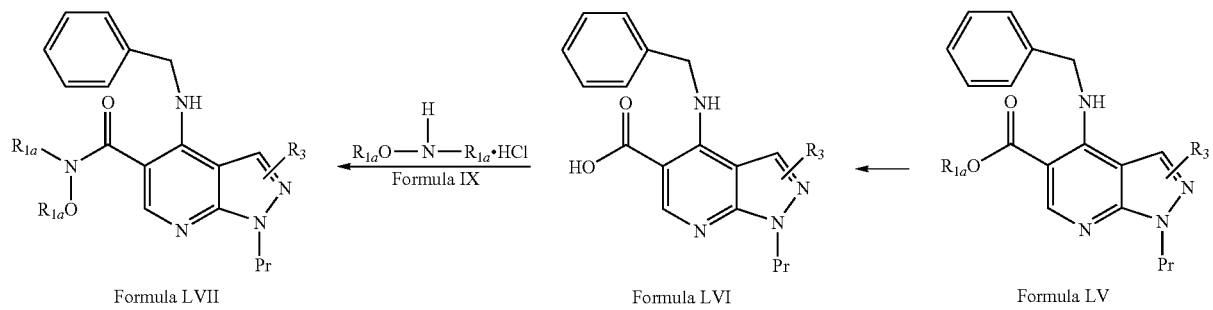

-continued
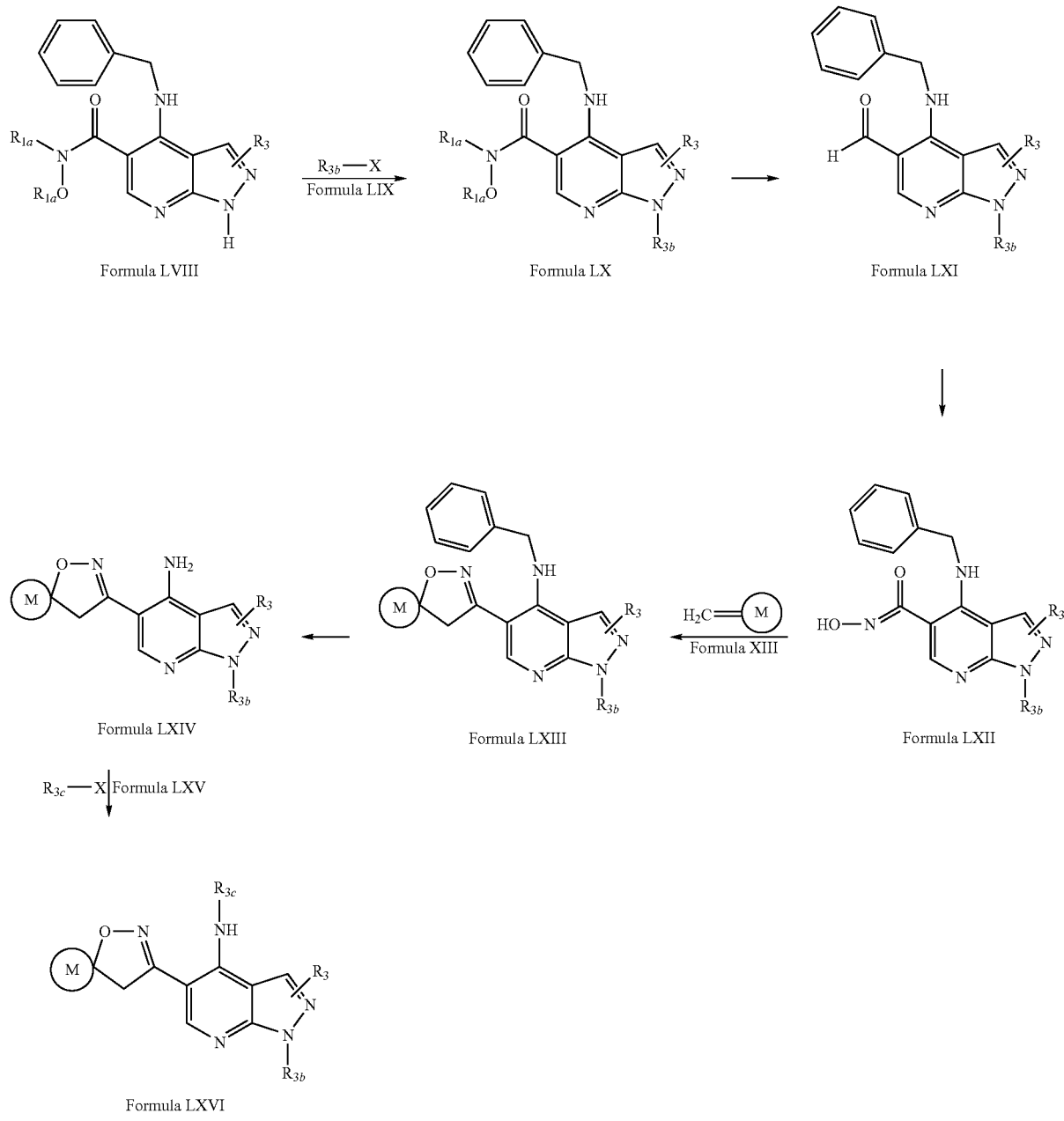
Scheme XI.a
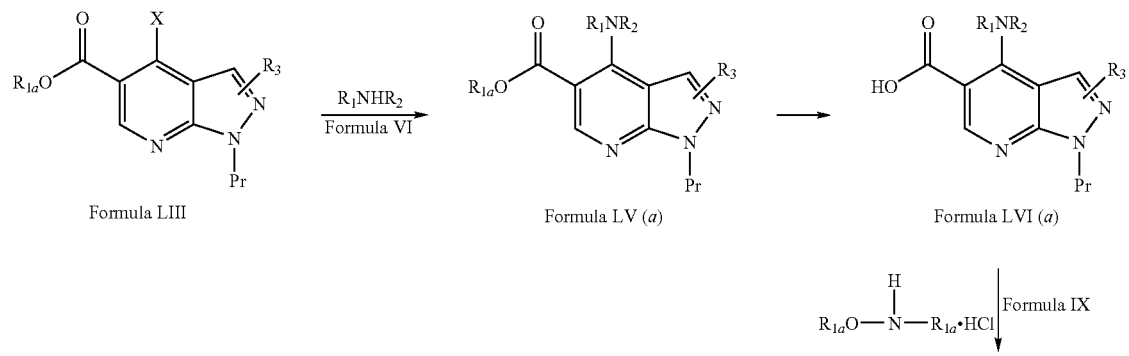

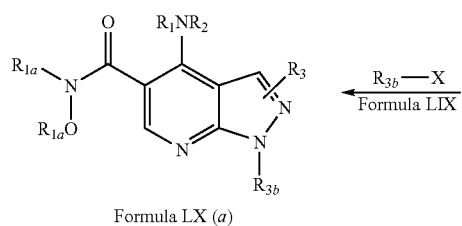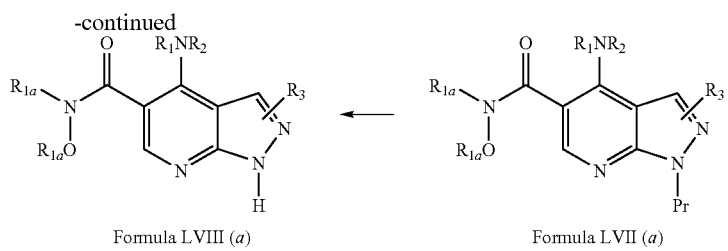

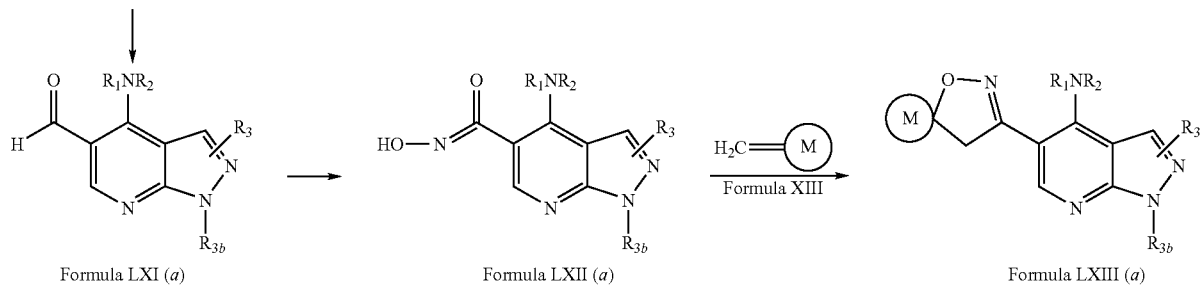

The compounds of Formula LXVI can be prepared by following Scheme XI. Accordingly, compounds of Formula LI (wherein $R_{1a}$ is alkyl and Pr is a protecting group, for example, p-methoxy benzyl, benzyl or 2-furanylmethyl) on heating give compounds of Formula LII, which on reaction with phosphorous oxy halide give compounds of Formula LIII (wherein X is a halogen), which on reaction with compounds of Formula LIV give compounds of Formula LV, which on ester hydrolysis give compounds of Formula LVI, which on reaction with compounds of Formula IX (wherein $R_{1a}$ is the same as defined earlier) give compounds of Formula LVII, which on deprotection give compounds of Formula LVIII, which on reaction with compounds of Formula LIX (wherein X is halogen) give compounds of Formula LX, which on reduction give compounds of Formula LXI, which on reaction with hydroxylamine hydrochloride give compounds of Formula LXII, which on reaction with compounds of Formula XIII give compounds of Formula LXIII, which on deprotection give compounds of Formula LXIV, which are finally reacted with compounds of Formula LXV (wherein X is halogen) to give compounds of Formula LXVI (wherein $R_{3b}$ is alkyl or cycloalkyl, $R_{3c}$ is aryl or heteroaryl and $R_3$ and M are the same as defined earlier).

The compounds of Formula LXIII (a) can be prepared by following Scheme XI a. Accordingly, compounds of Formula LIII (wherein X is halogen, $R_{1a}$ is alkyl and Pr is a protecting group, for example, p-methoxy benzyl, benzyl or 2-furanylmethyl) on reaction with compounds of Formula VI give compounds of Formula LV (a), which on ester hydrolysis give compounds of Formula LVI (a), which on reaction with compounds of Formula IX (wherein $R_{1a}$ is the same as defined earlier) give compounds of Formula LVII (a), which on deprotection give compounds of Formula LVIII (a), which on reaction with compounds of Formula LIX (wherein X is halogen) give compounds of Formula LX (a), which on reduction give compounds of Formula LXI (a), which on reaction with hydroxylamine hydrochloride give compounds of Formula LXII (a), which are finally reacted with compounds of Formula XIII to give compounds of Formula LXIII (a) (wherein $R_{3b}$ is alkyl or cycloalkyl and $R_1$, $R_2$, $R_3$ and M are the same as defined earlier).

The compounds of Formula LII can be prepared by heating of compounds of Formula LI in one or more solvents, for example, alcohols, for example, methanol, ethanol, propanol or butanol in the presence of a high boiling medium, for example, diphenyl ether, dimethylsulfoxide or mixture(s) thereof.

The compounds of Formula LIII can be prepared by the reaction of compounds of LII with phosphorous oxy halide on heating.

The reaction of compounds of Formula LIII with compounds of Formula LIV or compounds of Formula VI to give compounds of Formula LV or compounds of Formula LV (a), respectively can be carried out in one or more solvents, for example, nitriles, for example, acetonitrile; ketones, for example, acetone; alcohols, for example, methanol, ethanol, propanol or butanol; ethers, for example, diethyl ether or tetrahydrofuran; amides, for example, dimethylformamide or dimethylacetamide; sulfoxides, for example, dimethylsulfoxide; hydrocarbons, for example, hexane or toluene; or mixture(s) thereof.

The reaction of compounds of Formula LIII with compounds of Formula LIV or compounds of Formula VI can be carried out in the optional presence of one or more bases, for example, triethylamine, pyridine, potassium tert-butoxide, sodium hydride or mixture(s) thereof.

The ester hydrolysis of compounds of Formula LV or compounds of Formula LV (a) to give compounds of Formula LVI or compounds of Formula LVI (a), respectively can be carried out in one or more solvents, for example, alcohols, for example, methanol, ethanol, propanol or butanol; or an alcohol and water mixture.

The ester hydrolysis of compounds of Formula LV or compounds of Formula LV (a) can be carried out in the presence of one or more inorganic bases, for example, alkali metal hydroxides, for example, potassium hydroxide, sodium hydroxide, lithium hydroxide or mixture(s) thereof.

The reaction of compounds of Formula LVI or compounds of Formula LVI (a) with compounds of Formula IX to give compounds of Formula LVII or compounds of Formula LVII (a), respectively can be carried out in the presence of one or more activating reagents, for example, hydroxybenzotriazole, acetone oxime, 2-hydroxypyridine or mixture(s) thereof, and one or more coupling reagents, for example, 1-ethyl-3-(3-dimethylaminopropyl) carbodiimide hydrochloride, 1,3-dicyclohexyl carbodiimide or mixture(s) thereof in one or more solvents, for example, ethers, for example, diethyl ether or tetrahydrofuran; amides, for example, dimethylformamide or dimethylacetamide; sulfoxides, for example, dimethylsulfoxide; or mixture(s) thereof.

The reaction of compounds of Formula LVI or compounds of Formula LVI (a) with compounds of Formula IX can be carried out in the presence of one or more bases, for example, N-methylmorpholine; N-ethyldiisopropylamine; 4-dialkylaminopyridines, for example, 4-dimethylaminopyridine; or mixture(s) thereof.

The deprotection of compounds of Formula LVII or compounds of Formula LVII (a) to give compounds of Formula LVIII or compounds of Formula LVIII (a), respectively can be carried out in the presence of one or more acids, for example, hydrochloric acid, trifluoroacetic acid, p-toluene sulphonic acid or mixture(s) thereof in one or more solvents, for example, alcohols, for example, methanol, ethanol, propanol or butanol; halogenated hydrocarbons, for example, dichloromethane, dichloroethane or chloroform; or mixture(s) thereof.

The reaction of compounds of Formula LVIII or compounds of Formula LVIII (a) with compounds of Formula LIX to give compounds of Formula LX or compounds of Formula LX (a), respectively can be carried out in the presence of one or more inorganic bases, for example, alkali metal carbonates, for example, sodium carbonate or potassium carbonate, alkali metal hydrides, for example, sodium hydride or mixture(s) thereof or one or more organic bases, for example, triethyl amine, N-ethyldiisopropyl amine or mixture(s) thereof in one or more solvents, for example, nitriles, for example, acetonitrile; halogenated hydrocarbons, for example, dichloromethane, dichloroethane or chloroform; amides, for example, dimethylformamide or dimethylacetamide; or mixture(s) thereof.

The reduction of compounds of Formula LX or compounds of Formula LX (a) to give compounds of Formula LXI or compounds of Formula LXI (a), respectively can be carried out in one or more solvents, for example, ethers, for example, diethyl ether or tetrahydrofuran; amides, for example, dimethylformamide or dimethylacetamide; sulfoxides, for example, dimethylsulfoxide; hydrocarbons, for example, hexane or toluene; or mixture(s) thereof.

The reduction of compounds of Formula LX or compounds of Formula LX (a) can be carried out in the presence of one or more reducing agents, for example, sodium bis(2-methoxyethoxy)aluminum hydride (vitride), lithium aluminium hydride or mixture(s) thereof.

The reaction of compounds of Formula LXI or compounds of Formula LXI (a) with hydroxylamine hydrochloride to give compounds of Formula LXII or compounds of Formula LXII a, respectively can be carried out in the presence of sodium acetate in one or more solvents, for example, alcohols, for example, methanol, ethanol, propanol, butanol or mixture(s) thereof.

The reaction of compounds of Formula LXII or compounds of Formula LXII (a) with compounds of Formula XIII to give compounds of Formula LXIII or compounds of Formula LXIII (a), respectively can be carried out in the presence of one or more halogenating agents, for example, sodium hypochlorite, N-chlorosuccinimide, N-bromosuccinimide or mixture(s) thereof, in one or more solvents, for example, nitriles, for example, acetonitrile; ketones, for example, acetone; alcohols, for example, methanol, ethanol, propanol or butanol; ethers, for example, diethyl ether or tetrahydrofuran; amides, for example, dimethylformamide or dimethylacetamide; sulfoxides, for example, dimethylsulfoxide; hydrocarbons, for example, hexane or toluene; halogenated hydrocarbons, for example, dichloromethane, dichloroethane or chloroform; or mixture(s) thereof.

The reaction of compounds of Formula LXII or compounds of Formula LXII (a) with compounds of Formula XIII can be carried out in the optional presence of one or more bases, for example, triethyl amine, trimethyl amine or mixture(s) thereof.

The deprotection of compounds of Formula LXIII to give compounds of Formula LXIV can be carried out in the presence of palladium on carbon/hydrogen, palladium hydroxide/carbon with hydrogen, ammonium formate/palladium on carbon, in one or more solvents, for example, alcohols, for example, methanol, ethanol, propanol or butanol; halogenated hydrocarbons, for example, dichloromethane, dichloroethane or chloroform; or mixture(s) thereof.

The reaction of compounds of Formula LXIV with compounds of Formula LXV to give compounds of Formula LXVI can be carried out in the presence of one or more transition metal catalysts, for example, tris(dibenzylidineacetone)dipalladium(0), palladium(II) acetate, tetrakis(triphenylphosphine)palladium(0), tetrakis(methyldiphenylphosphine) palladium(0), trans-dichlorobis(methyldiphenylphosphine)palladium(II), dichlorobis(triphenylphosphine)palladium(II), bis[1,2-bis(diphenylphosphino)ethane]palladium(0), copper (I) iodide, cuprous oxide, cuprous bromide, cuprous chloride or mixture(s) thereof.

The reaction of compounds of Formula LXIV with compounds of Formula LXV can be carried out in the presence of one or more phosphine ligands, for example, xantphos, 1,1'-bis(di-tert-butylphosphino)ferrocene, 2,2'-bis(diphenylphosphino)diphenyl ether (DPEphos), bis(triethylphosphine) nickel (II) chloride, (R,S)-2,2'-bis(diphenylphosphino)-1,1'-binaphthyl, (S)-2,2'-bis(diphenylphosphino)-1,1'-binaphthyl, (R)-2,2'-bis(diphenylphosphino)-1,1'-binaphthyl or mixture(s) thereof.

The reaction of compounds of Formula LXIV with compounds of Formula LXV can be carried out in the presence of one or more bases, for example, amines, for example, N-ethyldiisopropylamine, triethyl amine or dimethylamino pyridine, alkali metal alkoxides, for example, sodium tert-butoxide, potassium tert-butoxide, sodium methoxide, lithium methoxide, potassium methoxide or cesium methoxide, alkali metal hydroxides, for example, sodium hydroxide, lithium hydroxide, potassium hydroxide or cesium hydroxide, alkali metal halides, for example, potassium fluoride, alkali metal carbonates, for example, sodium carbonate, potassium carbonate or cesium carbonate or mixture(s) thereof.

The reaction of compounds of Formula LXIV with compounds of Formula LXV can be carried out in one or more solvents, for example, ethers, for example, dioxane or tetrahydrofuran, amides, for example, dimethylformamide or dimethylacetamide; sulfoxides, for example, dimethylsulfoxide; hydrocarbons, for example, hexane or toluene; or mixture(s) thereof Scheme XII

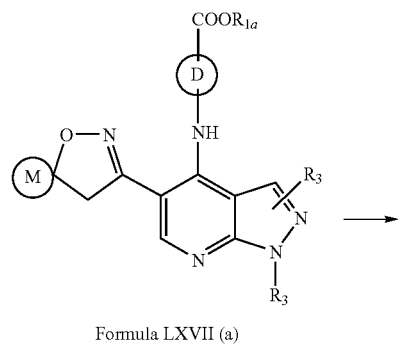

Formula LXVII (a)

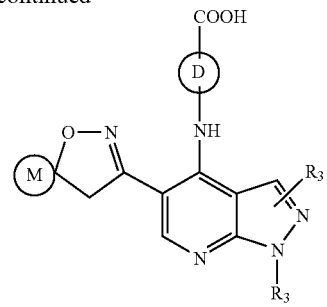

Formula LXVII

The compounds of Formula LXVII can be prepared by following Scheme XII. Accordingly, ester hydrolysis of compounds of Formula LXVII (a) (wherein $R_{1a}$ is alkyl) gives compounds of Formula LXVII (wherein $R_3$ and M are the same as defined earlier and ring D is cyclobutyl or cyclohexyl ring).

The ester hydrolysis of compounds of Formula LXVII (a) to give compounds of Formula LXVII can be carried out in the presence of one or more acids, for example, hydrochloric acid, trifluoroacetic acid, p-toluene sulphonic acid or mixture(s) thereof in one or more solvents, for example, halogenated hydrocarbons, for example, dichloromethane, dichloroethane or chloroform; or mixture(s) thereof Scheme XIII

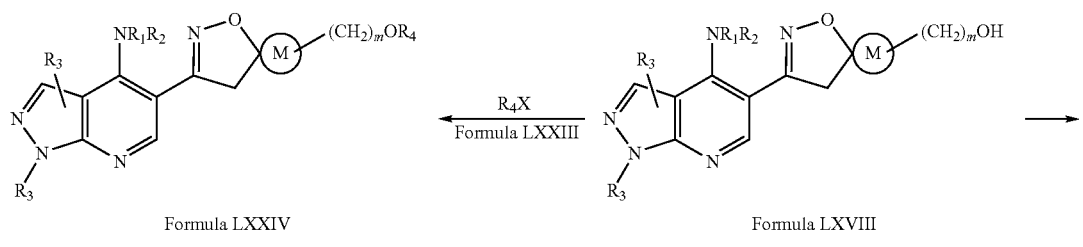

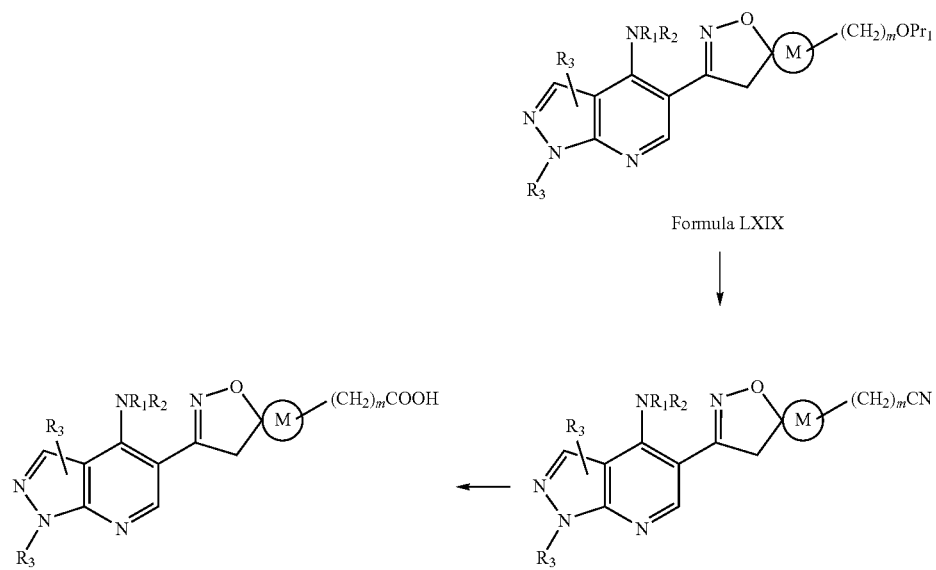

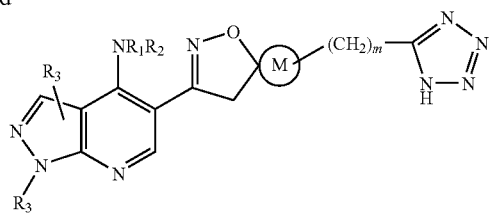

Formula LXXII

The compounds of Formulae LXX, LXXI, LXXII and LXXIV can be prepared by following Scheme XIII. Accordingly, compounds of Formula LXVIII are
- (a) protected to give compounds of Formula LXIX (wherein $Pr_1$ is a protecting group, for example, tosylate, mesylate or triflate) which on reaction with sodium cyanide give compounds of Formula LXX, which on
  - (i) hydrolysis give compounds of Formula LXXI (wherein $R_1$, $R_2$, $R_3$, m and M are the same as defined earlier).
  - (ii) cyclization give compounds of Formula LXXII (wherein $R_1$, $R_2$, $R_3$, m and M are the same as defined earlier).
- (b) reacted with compounds of Formula LXXIII (wherein X is halogen) to give compounds of Formula LXXIV (wherein $R_1$, $R_2$, $R_3$, $R_4$, m and M are the same as defined earlier).

The protection of compounds of Formula LXVIII to give compounds of Formula LXIX can be carried out with one or more protecting reagents, for example, p-toluene sulphonyl chloride, methyl sulphonyl chloride or trifluoromethanesulfonyl chloride in one or more solvents, for example, ethers, for example, dioxane, tetrahydrofuran or diethyl ether; halogenated hydrocarbons, for example, dichloromethane, dichloroethane or chloroform; amides, for example, dimethylformamide or dimethylacetamide; or mixture(s) thereof.

The protection of compounds of Formula LXVIII to give compounds of Formula LXIX can be carried out in the presence of one or more bases, for example, triethyl amine, trimethyl amine or mixture(s) thereof.

The reaction of compounds of Formula LXIX with sodium cyanide to give compounds of Formula LXX can be carried out in the presence of one or more solvents, for example, amides, for example, dimethylformamide, dimethylacetamide or mixture(s) thereof.

The hydrolysis of compounds of Formula LXX to give compounds of Formula LXXI can be carried out in one or more solvents, for example, alcohols, for example, methanol, ethanol, propanol or butanol; or an alcohol and water mixture.

The hydrolysis of compounds of Formula LXX can be carried out in the presence of one or more inorganic bases, for example, alkali metal hydroxides, for example, potassium hydroxide, sodium hydroxide, lithium hydroxide or mixture(s) thereof.

The cyclization of compounds of Formula LXX to give compounds of Formula LXXII can be carried out in the presence of sodium azide and triethyl amine hydrochloride in one or more solvents, for example, amides, for example, dimethylformamide or dimethylacetamide; sulfoxides, for example, dimethylsulfoxide; hydrocarbons, for example, hexane or toluene; or mixture(s) thereof.

The reaction of compounds of Formula LXVIII with compounds of Formula LXXIII to give compounds of Formula LXXIV can be carried out in the presence of one or more alkali metal hydroxides, for example, sodium hydroxide, potassium hydroxide or lithium hydroxide, alkali metal carbonates, for example, sodium carbonate, potassium carbonate or cesium carbonate, alkali metal alkoxides, for example, potassium t-butoxide, alkali metal hydrides, for example, sodium hydride or mixture(s) thereof in one or more solvents, for example, alcohols, for example, methanol, ethanol, propanol or butanol; ethers, for example, tetrahydrofuran or diethyl ether; amides, for example, dimethylformamide or dimethylacetamide; water; or mixture(s) thereof.

Scheme XIV

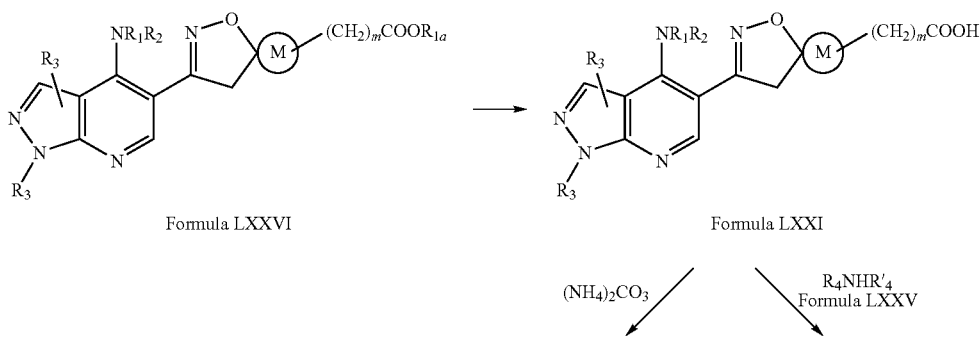

Formula LXXVI → Formula LXXI $(NH_4)_2CO_3$ / $R_4NHR'_4$ Formula LXXV

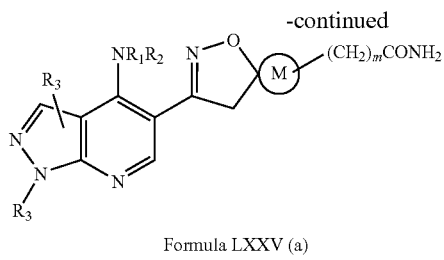

Formula LXXV (a)

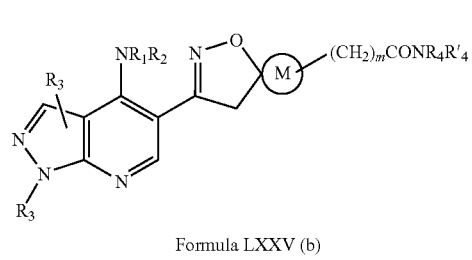

Formula LXXV (b)

The compounds of Formulae LXXI, LXXV (a) and LXXV (b) can be prepared by following Scheme XIV. Accordingly, compounds of Formula LXXVI (wherein $R_{1a}$ is alkyl) on ester hydrolysis give compounds of Formula LXXI, which are reacted with ammonium carbonate or compounds of Formula LXXV to give compounds of Formula LXXV (a) (wherein $R_1$, $R_2$, $R_3$, m and M are the same as defined earlier) or compounds of Formula LXXV (b) (wherein $R_1$, $R_2$, $R_3$, $R_4$, $R'_4$, m and M are the same as defined earlier) respectively.

The ester hydrolysis of compounds of Formula LXXVI to give compounds of Formula LXXI can be carried out in one or more solvents, for example, water; ethers, for example, diethyl ether or tetrahydrofuran; alcohols, for example, methanol, ethanol, propanol or butanol; or mixture(s) thereof.

The ester hydrolysis of compounds of Formula LXXVI can be carried out in the presence of one or more inorganic bases, for example, alkali metal hydroxides, for example, potassium hydroxide, sodium hydroxide, lithium hydroxide or mixture(s) thereof.

The reaction of compounds of Formula LXXI with ammonium carbonate or compounds of Formula LXXV to give compounds of Formula LXXV (a) or compounds of Formula LXXV (b), respectively can be carried out in the presence of one or more activating reagents, for example, hydroxybenzotriazole, acetone oxime, 2-hydroxypyridine or mixture(s) thereof, and one or more coupling reagents, for example, 1-ethyl-3-(3-dimethylaminopropyl) carbodiimide hydrochloride, 1,3-dicyclohexyl carbodiimide or mixture(s) thereof in one or more solvents, for example, ethers, for example, diethyl ether or tetrahydrofuran; amides, for example, dimethylformamide or dimethylacetamide; sulfoxides, for example, dimethylsulfoxide or mixture(s) thereof.

The reaction of compounds of Formula LXXI with ammonium carbonate or compounds of Formula LXXV can be carried out in the presence of one or more bases, for example, N-methylmorpholine; N-ethyldiisopropylamine; 4-dialkylaminopyridines, for example, 4-dimethylaminopyridine; or mixture(s) thereof Scheme XV

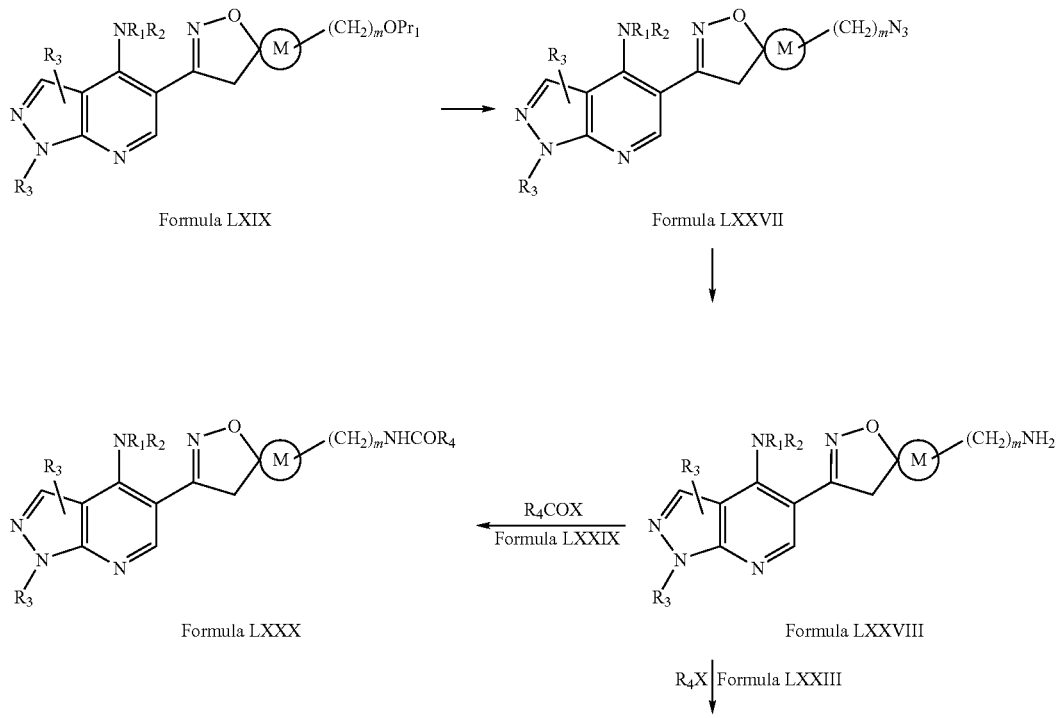

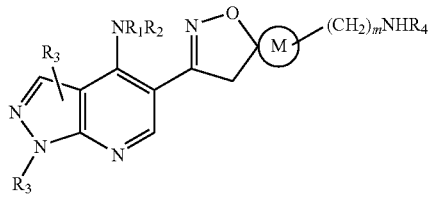

Formula LXXXI

The compounds of Formulae LXXVIII, LXXX and LXXXI can be prepared by following Scheme XV. Accordingly, compounds of Formula LXIX (wherein Pr$_1$ is a protecting group, for example, tosylate, mesylate or triflate) on reaction with sodium azide give compounds of Formula LXXVII, which on reduction give compounds of Formula LXXVIII, which on reaction with
- (a) compounds of Formula LXXIX (wherein X is halogen) give compounds of Formula LXXX (wherein R$_1$, R$_2$, R$_3$, R$_4$, m and M are the same as defined earlier).
- (b) compounds of Formula LXXIII (wherein X is halogen) give compounds of Formula LXXXI (wherein R$_1$, R$_2$, R$_3$, R$_4$, m and M are the same as defined earlier).

The reaction of compounds of Formula LXIX with sodium azide to give compounds of Formula LXXVII can be carried out in the one or more solvents, for example, amides, for example, dimethylformamide or dimethylacetamide; sulfoxides, for example, dimethylsulfoxide or mixture(s) thereof.

The reduction of compounds of Formula LXXVII to give compounds of Formula LXXVIII can be carried out in the presence of one or more reducing agents, for example, sodium borohydride, lithium boro hydride, lithium aluminium hydride or hydrogen in the presence of palladium/carbon in one or more solvents, for example, ethers, for example, diethyl ether, dioxane or tetrahydrofuran; alcohols, for example, methanol, ethanol, propanol or butanol; or mixture(s) thereof.

The reaction of compounds of Formula LXXVIII with compounds of Formula LXXIX or Formula LXXIII to give compounds of Formula LXXX or compounds of Formula LXXXI, respectively can be carried out in the presence of one or more inorganic bases, for example, alkali metal carbonates, for example, sodium carbonate, potassium carbonate or cesium carbonate, alkali metal hydrides, for example, sodium hydride or mixture(s) thereof or one or more organic bases, for example, triethyl amine, N-ethyldiisopropyl amine or mixture(s) thereof in one or more solvents, for example, halogenated hydrocarbons, for example, dichloromethane, dichloroethane or chloroform; amides, for example, dimethylformamide or dimethylacetamide; or mixture(s) thereof.

The compounds of Formula Ia can be prepared by following the methods disclosed in WO 2007/031977.

In the above schemes, where the specific solvents, bases, acids, reducing agents, oxidizing agents, activating reagents, coupling reagents, halogenating agents, transition metal catalysts, phosphine ligands, mesylating agents, lewis acid catalysts, debenzylating agents, protecting reagents etc., are mentioned, it is to be understood that other solvents, bases, acids, reducing agents, oxidizing agents, activating reagents, coupling reagents, halogenating agents, transition metal catalysts, phosphine ligands, mesylating agents, lewis acid catalysts, debenzylating agents, protecting reagents etc., known to those skilled in the art may be used. Similarly, the reaction temperature and duration may be adjusted according to the desired needs.

An illustrative list of intermediates includes these listed below:
4-(Cyclohexylamino)-1-ethyl-N-methoxy-N-methyl-1H-pyrazolo[3,4-b]pyridine-5-carboxamide (Intermediate No. 1),
1-Ethyl-N-methoxy-N-methyl-4-(tetrahydro-2H-pyran-4-ylamino)-1H-pyrazolo[3,4-b]pyridine-5-carboxamide (Intermediate No. 2),
1-Ethyl-4-[(4-hydroxycyclohexyl)amino]-N-methoxy-N-methyl-1H-pyrazolo[3,4-b]pyridine-5-carboxamide (Intermediate No. 3),
4-(Cyclopropylamino)-1-ethyl-N-methoxy-N-methyl-1H-pyrazolo[3,4-b]pyridine-5-carboxamide (Intermediate No. 4),
4-(Cyclopropylamino)-N-methoxy-N-1,3-trimethyl-1H-pyrazolo[3,4-b]pyridine-5-carboxamide (Intermediate No. 5),
4-(Cyclopentylamino)-1-ethyl-N-methoxy-N-methyl-1H-pyrazolo[3,4-b]pyridine-5-carboxamide (Intermediate No. 6),
4-(Cyclopentylamino)-N-methoxy-N-1,3-trimethyl-1H-pyrazolo[3,4-b]pyridine-5-carboxamide (Intermediate No. 7),
4-(Cyclohexylamino)-1-ethyl-1H-pyrazolo[3,4-b]pyridine-5-carbaldehyde (Intermediate No. 8),
1-Ethyl-4-(tetrahydro-2H-pyran-4-ylamino)-1H-pyrazolo[3,4-b]pyridine-5-carbaldehyde (Intermediate No. 9),
1-Ethyl-4-[(4-hydroxycyclohexyl)amino]-1H-pyrazolo[3,4-b]pyridine-5-carbaldehyde (Intermediate No. 10),
4-Cyclopropylamino-1-ethyl-1H-pyrazolo[3,4-b]pyridine-5-carbaldehyde (Intermediate No. 11),
4-Cyclopropylamino-1,3-dimethyl-1H-pyrazolo[3,4-b]pyridine-5-carbaldehyde (Intermediate No. 12),
4-(Cyclopentylamino)-1-ethyl-1H-pyrazolo[3,4-b]pyridine-5-carbaldehyde (Intermediate No. 13),
4-(Cyclopentylamino)-1,3-dimethyl-1H-pyrazolo[3,4-b]pyridine-5-carbaldehyde (Intermediate No. 14),
4-(Cyclohexylamino)-1-ethyl-1H-pyrazolo[3,4-b]pyridine-5-carbaldehyde oxime (Intermediate No. 15),
1-Ethyl-4-(tetrahydro-2H-pyran-4-ylamino)-1H-pyrazolo[3,4-b]pyridine-5-carbaldehyde oxime (Intermediate No. 16),
1-Ethyl-4-[(4-hydroxycyclohexyl)amino]-1H-pyrazolo[3,4-b]pyridine-5-carbaldehyde oxime (Intermediate No. 17),
4-Cyclopropylamino-1-ethyl-1H-pyrazolo[3,4-b]pyridine-5-carbaldehyde oxime (Intermediate No. 18),
4-(Cyclopropylamino)-1,3-dimethyl-1H-pyrazolo[3,4-b]pyridine-5-carbaldehyde oxime (Intermediate No. 19),
4-(Cyclopentylamino)-1-ethyl-1H-pyrazolo[3,4-b]pyridine-5-carbaldehyde oxime (Intermediate No. 20),
4-(Cyclopentylamino)-1,3-dimethyl-1H-pyrazolo[3,4-b]pyridine-5-carbaldehyde oxime (Intermediate No. 21),
tert-Butyl 4-({1-ethyl-5-[methoxy(methyl)carbamoyl]-1H-pyrazolo[3,4-b]pyridin-4-yl}amino)piperidine-1-carboxylate ((Intermediate No. 22), 1-Ethyl-N-methoxy-4-[(3-methoxyphenyl)amino]-N-methyl-1H-pyrazolo[3,4-b]pyridine-5-carboxamide (Intermediate No. 23),
4-[(1,1-Dioxidotetrahydro-2H-thiopyran-4-yl)amino]-1-ethyl-N-methoxy-N-methyl-1H-pyrazolo[3,4-b]pyridine-5-carboxamide (Intermediate No. 24),
4-(Benzylamino)-1-ethyl-N-Methoxy-N-methyl-1H-pyrazolo[3,4-b]pyridine-5-carboxamide (Intermediate No. 25),
1-Ethyl-4-[(3-methoxyphenyl)amino]-1H-pyrazolo[3,4-b]pyridine-5-carbaldehyde (Intermediate No. 26),
tert-Butyl 4-[(1-ethyl-5-formyl-1H-pyrazolo[3,4-b]pyridin-4-yl)amino]piperidine-1-carboxylate (Intermediate No. 27),
4-[(1,1-Dioxidotetrahydro-2H-thiopyran-4-yl)amino]-1-ethyl-1H-pyrazolo[3,4-b]pyridine-5-carbaldehyde (Intermediate No. 28),
4-(Benzylamino)-1-ethyl-1H-pyrazolo[3,4-b]pyridine-5-carbaldehyde (Intermediate No. 29),
1-Ethyl-4-[(3-methoxyphenyl)amino]-1H-pyrazolo[3,4-b]pyridine-5-carbaldehyde oxime (Intermediate No. 30),
4-(Benzylamino)-1-ethyl-1H-pyrazolo[3,4-b]pyridine-5-carbaldehyden oxime (Intermediate No. 31),
tert-Butyl 4-[(1-ethyl-5-[(E)-(hydroxyimino)methyl-1H-pyrazolo[3,4-b]pyridin-4-yl)amino]piperidine-1-carboxylate (Intermediate No. 32),
4-[(1,1-Dioxidotetrahydro-2H-thiopyran-4-yl)amino]-1-ethyl-1H-pyrazolo[3,4-b]pyridine-5-carbaldehyde oxime (Intermediate No. 33), An illustrative list of compounds includes these listed below:

N-cyclohexyl-1-ethyl-5-(1-oxa-2-azaspiro[4.4]non-2-en-3-yl)-1H-pyrazolo[3,4-b]pyridin-4-amine (Compound No. 1),
N-cyclohexyl-1-ethyl-5-(5-oxa-6-azaspiro[3.4]oct-6-en-7-yl)-1H-pyrazolo[3,4-b]pyridin-4-amine (Compound No. 2),
N-cyclohexyl-1-ethyl-5-(1-oxa-2-azaspiro[4.5]dec-2-en-3-yl)-1H-pyrazolo[3,4-b]pyridin-4-amine (Compound No. 3),
N-cyclohexyl-1-ethyl-5-(1-oxa-7-thia-2-azaspiro[4.4]non-2-en-3-yl)-1H-pyrazolo[3,4-b]pyridin-4-amine (Compound No. 4),
N-cyclohexyl-1-ethyl-5-(7-oxido-1-oxa-7-thia-2-azaspiro[4.4]non-2-en-3-yl)-1H-pyrazolo[3,4-b]pyridin-4-amine (Compound No. 5),
N-cyclohexyl-1-ethyl-5-(5-oxa-2-thia-6-azaspiro[3.4]oct-6-en-7-yl)-1H-pyrazolo[3,4-b]pyridin-4-amine (Compound No. 6),
1-Ethyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 7),
1-Ethyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 8),
1-Ethyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 9),
4-{[1-Ethyl-5-(1-oxa-2-azaspiro[4.4]non-2-en-3-yl)-1H-pyrazolo[3,4-b]pyridin-4-yl]amino}cyclohexanol (Compound No. 10),
4-{[1-Ethyl-5-(1-oxa-2-azaspiro[4.5]dec-2-en-3-yl)-1H-pyrazolo[3,4-b]pyridin-4-yl]amino}cyclohexanol (Compound No. 11),
N-cyclohexyl-5-(1,7-dioxa-2-azaspiro[4.4]non-2-en-3-yl)-1-ethyl-1H-pyrazolo[3,4-b]pyridin-4-amine (Compound No. 12),
4-{[1-Ethyl-5-(5-oxa-6-azaspiro[3.4]oct-6-en-7-yl)-1H-pyrazolo[3,4-b]pyridin-4-yl]amino}cyclohexanol (Compound No. 13),
N-cyclohexyl-5-(2,2-dioxido-5-oxa-2-thia-6-azaspiro[3.4]oct-6-en-7-yl)-1-ethyl-1H-pyrazolo[3,4-b]pyridin-4-amine (Compound No. 14),
tert-Butyl 3-[4-(cyclohexylamino)-1-ethyl-1H-pyrazolo[3,4-b]pyridin-5-yl]-1-oxa-2,8-diazaspiro[4.5]dec-2-ene-8-carboxylate (Compound No. 15),
4-{[1-Ethyl-5-(1-oxa-2-azaspiro[4.5]dec-2-en-3-yl)-1H-pyrazolo[3,4-b]pyridin-4-yl]amino}cyclohexanone (Compound No. 16),
4-{[1-Ethyl-5-(1-oxa-2-azaspiro[4.5]dec-2-en-3-yl)-1H-pyrazolo[3,4-b]pyridin-4-yl]amino}cyclohexanone oxime (Compound No. 17),
N-cyclohexyl-1-ethyl-5-(1-oxa-2,8-diazaspiro[4.5]dec-2-en-3-yl)-1H-pyrazolo[3,4-b]pyridin-4-amine hydrochloride salt (Compound No. 18),
4-{[1-Ethyl-5-(1,9,12-trioxa-2-azadispiro[4.2.4.2]tetradec-2-en-3-yl)-1H-pyrazolo[3,4-b]pyridin-4-yl]amino}cyclohexanol (Compound No. 19),
4-{[1-Ethyl-5-(5-oxa-6-azaspiro[3.4]oct-6-en-7-yl)-1H-pyrazolo[3,4-b]pyridin-4-yl]amino}cyclohexanone (Compound No. 20),
4-{[1-Ethyl-5-(1-oxa-2-azaspiro[4.4]non-2-en-3-yl)-1H-pyrazolo[3,4-b]pyridin-4-yl]amino}cyclohexanone (Compound No. 21),
3-{1-Ethyl-4-[(4-hydroxycyclohexyl)amino]-1H-pyrazolo[3,4-b]pyridin-5-yl}-1-oxa-2-azaspiro[4.5]dec-2-en-8-one (Compound No. 22),
N-cyclohexyl-5-[8-(2,2-dimethylpropanoyl)-1-oxa-2,8-diazaspiro[4.5]dec-2-en-3-yl]-1-ethyl-1H-pyrazolo[3,4-b]pyridin-4-amine (Compound No. 23),
N-cyclohexyl-1-ethyl-5-{8-[(trifluoromethyl)sulfonyl]-1-oxa-2,8-diazaspiro[4.5]dec-2-en-3-yl}-1H-pyrazolo[3,4-b]pyridin-4-amine (Compound No. 24),
N-cyclohexyl-1-ethyl-5-[8-(ethylsulfonyl)-1-oxa-2,8-diazaspiro[4.5]dec-2-en-3-yl]-1H-pyrazolo[3,4-b]pyridin-4-amine (Compound No. 25),
N-cyclohexyl-5-[8-(cyclopropylmethyl)-1-oxa-2,8-diazaspiro[4.5]dec-2-en-3-yl]-1-ethyl-1H-pyrazolo[3,4-b]pyridin-4-amine (Compound No. 26),
5-(8-Acetyl-1-oxa-2,8-diazaspiro[4.5]dec-2-en-3-yl)-N-cyclohexyl-1-ethyl-1H-pyrazolo[3,4-b]pyridin-4-amine (Compound No. 27),
N-cyclohexyl-5-(2,5-dioxa-6-azaspiro[3.4]oct-6-en-7-yl)-1-ethyl-1H-pyrazolo[3,4-b]pyridin-4-amine (Compound No. 28),
N-cyclopropyl-1-ethyl-5-(1-oxa-2-azaspiro[4.5]dec-2-en-3-yl)-1H-pyrazolo[3,4-b]pyridin-4-amine (Compound No. 29),
N-cyclopropyl-1-ethyl-5-(1-oxa-2-azaspiro[4.4]non-2-en-3-yl)-1H-pyrazolo[3,4-b]pyridin-4-amine (Compound No. 30),
N-cyclopropyl-1-ethyl-5-(5-oxa-6-azaspiro[3.4]oct-6-en-7-yl)-1H-pyrazolo[3,4-b]pyridin-4-amine (Compound No. 31),
N-cyclopentyl-1,3-dimethyl-5-(5-oxa-6-azaspiro[3.4]oct-6-en-7-yl)-1H-pyrazolo[3,4-b]pyridin-4-amine (Compound No. 32),
N-cyclopentyl-1,3-dimethyl-5-(1-oxa-2-azaspiro[4.4]non-2-en-3-yl)-1H-pyrazolo[3,4-b]pyridin-4-amine (Compound No. 33),
N-cyclopentyl-1,3-dimethyl-5-(1-oxa-2-azaspiro[4.5]dec-2-en-3-yl)-1H-pyrazolo[3,4-b]pyridin-4-amine (Compound No. 34), N-cyclopropyl-1,3-dimethyl-5-(1-oxa-2-azaspiro[4.4]non-2-en-3-yl)-1H-pyrazolo[3,4-b]pyridin-4-amine (Compound No. 35), N-cyclopropyl-1,3-dimethyl-5-(5-oxa-6-azaspiro[3.4]oct-6-en-7-yl)-1H-pyrazolo[3,4-b]pyridin-4-amine (Compound No. 36), N-cyclopropyl-1,3-dimethyl-5-(1-oxa-2-azaspiro[4.5]dec-2-en-3-yl)-1H-pyrazolo[3,4-b]pyridin-4-amine (Compound No. 37), N-cyclopentyl-1-ethyl-5-(5-oxa-6-azaspiro[3.4]oct-6-en-7-yl)-1H-pyrazolo[3,4-b]pyridin-4-amine (Compound No. 38), N-cyclopentyl-1-ethyl-5-(1-oxa-2-azaspiro[4.4]non-2-en-3-yl)-1H-pyrazolo[3,4-b]pyridin-4-amine (Compound No. 39), N-cyclopentyl-5-(1,7-dioxa-2-azaspiro[4.4]non-2-en-3-yl)-1,3-dimethyl-1H-pyrazolo[3,4-b]pyridin-4-amine (Compound No. 40), 1-(4-Methoxybenzyl)-N-(3-methoxyphenyl)-5-(1-oxa-2-azaspiro[4.4]non-2-en-3-yl)-1H-pyrazolo[3,4-b]pyridin-4-amine (Compound No. 41), (cis or trans) 3-[4-(Cyclohexylamino)-1-ethyl-1H-pyrazolo[3,4-b]pyridin-5-yl]-1-oxa-2-azaspiro[4.5]dec-2-en-8-ol (Compound No. 42), (trans or cis) 3-[4-(Cyclohexylamino)-1-ethyl-1H-pyrazolo[3,4-b]pyridin-5-yl]-1-oxa-2-azaspiro[4.5]dec-2-en-8-ol (Compound No. 43), 5-[2-(Benzyloxy)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 44), (cis or trans) 3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 45), 3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-one (Compound No. 46), 7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 47), 7-[4-(Cyclohexylamino)-1-ethyl-1H-pyrazolo[3,4-b]pyridin-5-yl]-5-oxa-6-azaspiro[3.4]oct-6-ene-2-carbonitrile (Compound No. 48), 5-(5-Oxa-6-azaspiro[3.4]oct-6-en-7-yl)-N-(tetrahydro-2H-pyran-4-yl)-1H-pyrazolo[3,4-b]pyridin-4-amine (Compound No. 49), 1-Methyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 50), 5-(1-Oxa-2-azaspiro[4.4]non-2-en-3-yl)-N-(tetrahydro-2H-pyran-4-yl)-1-(2,2,2-trifluoroethyl)-1H-pyrazolo[3,4-b]pyridin-4-amine (Compound No. 51), 1-Ethyl-N-[1-(methylsulfonyl)piperidin-4-yl]-5-(1-oxa-2-azaspiro[4.4]non-2-en-3-yl)-1H-pyrazolo[3,4-b]pyridin-4-amine (Compound No. 52), N-(1-acetylpiperidin-4-yl)-1-ethyl-5-(1-oxa-2-azaspiro[4.5]dec-2-en-3-yl)-1H-pyrazolo[3,4-b]pyridin-4-amine (Compound No. 53), N-(1-acetylpiperidin-4-yl)-1-ethyl-5-(1-oxa-2-azaspiro[4.4]non-2-en-3-yl)-1H-pyrazolo[3,4-b]pyridin-4-amine (Compound No. 54), 1-(4-Methoxybenzyl)-N-(tetrahydro-2H-pyran-4-yl)-5-(1,9,12-trioxa-2-azadispiro[4.2.4.2]tetradec-2-en-3-yl)-1H-pyrazolo[3,4-b]pyridin-4-amine (Compound No. 55), 5-(5-Oxa-6-azaspiro[3.4]oct-6-en-7-yl)-N-(tetrahydro-2H-pyran-4-yl)-1-(2,2,2-trifluoroethyl)-1H-pyrazolo[3,4-b]pyridin-4-amine (Compound No. 56), 7-[1-(4-Methoxybenzyl)-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 57), 1-(Cyclopropylmethyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 58), 1-Butyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 59), 1-(1-Methylethyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 60), 5-(5-Oxa-6-azaspiro[3.4]oct-6-en-7-yl)-1-propyl-N-(tetrahydro-2H-pyran-4-yl)-1H-pyrazolo[3,4-b]pyridin-4-amine (Compound No. 61), 5-(1-Oxa-2-azaspiro[4.5]dec-2-en-3-yl)-N-(tetrahydro-2H-pyran-4-yl)-1-(2,2,2-trifluoroethyl)-1H-pyrazolo[3,4-b]pyridin-4-amine (Compound No. 62), N-(1-Cyclopentylpiperidin-4-yl)-1-ethyl-5-(1-oxa-2-azaspiro[4.4]non-2-en-3-yl)-1H-pyrazolo[3,4-b]pyridin-4-amine (Compound No. 63), N-(1-butylpiperidin-4-yl)-1-ethyl-5-(1-oxa-2-azaspiro[4.4]non-2-en-3-yl)-1H-pyrazolo[3,4-b]pyridin-4-amine (Compound No. 64), 2-(4-{[1-Ethyl-5-(1-oxa-2-azaspiro[4.4]non-2-en-3-yl)-1H-pyrazolo[3,4-b]pyridin-4-yl]amino}piperidin-1-yl)ethanol (Compound No. 65), N-[1-(cyclopropylmethyl)piperidin-4-yl]-1-ethyl-5-(1-oxa-2-azaspiro[4.4]non-2-en-3-yl)-1H-pyrazolo[3,4-b]pyridin-4-amine (Compound No. 66), 1-Ethyl-N-[1-(1-methylethyl)piperidin-4-yl]-5-(1-oxa-2-azaspiro[4.4]non-2-en-3-yl)-1H-pyrazolo[3,4-b]pyridin-4-amine (Compound No. 67), 1-Ethyl-5-(1-oxa-2-azaspiro[4.4]non-2-en-3-yl)-N-(1-propylpiperidin-4-yl)-1H-pyrazolo[3,4-b]pyridin-4-amine (Compound No. 68), N-(1-cyclopentylpiperidin-4-yl)-1-ethyl-5-(1-oxa-2-azaspiro[4.5]dec-2-en-3-yl)-1H-pyrazolo[3,4-b]pyridin-4-amine (Compound No. 69), 1-Ethyl-N-[1-(1-methylethyl)piperidin-4-yl]-5-(1-oxa-2-azaspiro[4.5]dec-2-en-3-yl)-1H-pyrazolo[3,4-b]pyridin-4-amine (Compound No. 70), 1-Cyclopentyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 71), 1-(Cyclopropylmethyl)-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 72), 1-(1-Methylethyl)-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 73), 5-(1-Oxa-2-azaspiro[4.5]dec-2-en-3-yl)-1-propyl-N-(tetrahydro-2H-pyran-4-yl)-1H-pyrazolo[3,4-b]pyridin-4-amine (Compound No. 74), 1-Cyclopentyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 75), 1-(Cyclopropylmethyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 76), 1-(1-Methylethyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 77), 5-(1-Oxa-2-azaspiro[4.4]non-2-en-3-yl)-1-propyl-N-(tetrahydro-2H-pyran-4-yl)-1H-pyrazolo[3,4-b]pyridin-4-amine (Compound No. 78), 1-Methyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 79), N-Cyclohexyl-1-ethyl-5-(1,9,12-trioxa-2-azadispiro[4.2.4.2]tetradec-2-en-3-yl)-1H-pyrazolo[3,4-b]pyridin-4-amine (Compound No. 80), 3-[4-(Cyclohexylamino)-1-ethyl-1H-pyrazolo[3,4-b]pyridin-5-yl]-1-oxa-2-azaspiro[4.5]dec-2-en-8-one (Compound No. 81), 1-Ethyl-5-(1-oxa-2-azaspiro[4.4]non-2-en-3-yl)-N-piperidin-4-yl-1H-pyrazolo[3,4-b]pyridin-4-amine (Compound No. 82), Tert-butyl 4-{[1-ethyl-5-(1-oxa-2-azaspiro[4.4]non-2-en-3-yl)-1H-pyrazolo[3,4-b]pyridin-4-yl]amino}piperidine-1-carboxylate (Compound No. 83), 1-Ethyl-N-(1-ethylpiperidin-4-yl)-5-(1-oxa-2-azaspiro[4.5]dec-2-en-3-yl)-1H-pyrazolo[3,4-b]pyridin-4-amine (Compound No. 84), 1-Ethyl-N-(1-methylpiperidin-4-yl)-5-(1-oxa-2-azaspiro[4.5]dec-2-en-3-yl)-1H-pyrazolo[3,4-b]pyridin-4-amine (Compound No. 85), 1-Ethyl-5-(1-oxa-2-azaspiro[4.5]dec-2-en-3-yl)-N-piperidin-4-yl-1H-pyrazolo[3,4-b]pyridin-4-amine (Compound No. 86), Tert-butyl 4-{[1-ethyl-5-(1-oxa-2-azaspiro[4.5]dec-2-en-3-yl)-1H-pyrazolo[3,4-b]pyridin-4-yl]amino}piperidine-1-carboxylate (Compound No. 87), 1-Ethyl-5-(1-oxa-2-azaspiro[4.5]dec-2-en-3-yl)-N-(1-propylpiperidin-4-yl)-1H-pyrazolo[3,4-b]pyridin-4-amine (Compound No. 88), N-[1-(cyclopropylmethyl)piperidin-4-yl]-1-ethyl-5-(1-oxa-2-azaspiro[4.5]dec-2-en-3-yl)-1H-pyrazolo[3,4-b]pyridin-4-amine (Compound No. 89), 2-(4-{[1-Ethyl-5-(1-oxa-2-azaspiro[4.5]dec-2-en-3-yl)-1H-pyrazolo[3,4-b]pyridin-4-yl]amino}piperidin-1-yl)ethanol (Compound No. 90), N-cyclohexyl-1-(4-methoxybenzyl)-5-(1-oxa-2-azaspiro[4.4]non-2-en-3-yl)-1H-pyrazolo[3,4-b]pyridin-4-amine (Compound No. 91), 3-[1-(4-Methoxybenzyl)-4-(tetrahydro-2H-pyran-4-ylamino)-1H-pyrazolo[3,4-b]pyridin-5-yl]-1-oxa-2-azaspiro[4.5]dec-2-en-8-one (Compound No. 92), 7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 93), 1-Ethyl-N-(3-methoxyphenyl)-5-(1-oxa-2-azaspiro[4.4]non-2-en-3-yl)-1H-pyrazolo[3,4-b]pyridin-4-amine (Compound No. 94), (cis or trans) 3-[4-(Cyclohexylamino)-1-ethyl-1H-pyrazolo[3,4-b]pyridin-5-yl]-1-oxa-2-azaspiro[4.5]dec-2-ene-8-carboxylic acid (Compound No. 95), (trans or cis) 3-[4-(Cyclohexylamino)-1-ethyl-1H-pyrazolo[3,4-b]pyridin-5-yl]-1-oxa-2-azaspiro[4.5]dec-2-ene-8-carboxylic acid (Compound No. 96), 5-{2-[(Benzyloxy)methyl]-5-oxa-6-azaspiro[3.4]oct-6-en-7-yl}-1-(4-methoxybenzyl)-N-(tetrahydro-2H-pyran-4-yl)-1H-pyrazolo[3,4-b]pyridin-4-amine (Compound No. 97), (trans or cis) 3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 98), 7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carboxylic acid (Compound No. 99), 1-(4-Methoxybenzyl)-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 100), 5-(1-Oxa-2-azaspiro[4.5]dec-2-en-3-yl)-N-(tetrahydro-2H-pyran-4-yl)-1H-pyrazolo[3,4-b]pyridin-4-amine (Compound No. 101), 1-(4-Methoxybenzyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 102), 5-{2-[(Benzyloxy)methyl]-5-oxa-6-azaspiro[3.4]oct-6-en-7-yl}-1-ethyl-N-(tetrahydro-2H-pyran-4-yl)-1H-pyrazolo[3,4-b]pyridin-4-amine (Compound No. 103), {7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-yl}methanol (Compound No. 104), 7-[4-(Cyclohexylamino)-1-ethyl-1H-pyrazolo[3,4-b]pyridin-5-yl]-5-oxa-6-azaspiro[3.4]oct-6-ene-2-carboxylic acid (Compound No. 105), cis or trans 7-[4-(Cyclohexylamino)-1-ethyl-1H-pyrazolo[3,4-b]pyridin-5-yl]-5-oxa-6-azaspiro[3.4]oct-6-ene-2-carboxamide (Compound No. 106), (trans or cis) 7-[4-(Cyclohexylamino)-1-ethyl-1H-pyrazolo[3,4-b]pyridin-5-yl]-5-oxa-6-azaspiro[3.4]oct-6-ene-2-carboxamide (Compound No. 107), (cis or trans) 3-[4-(Cyclohexylamino)-1-ethyl-1H-pyrazolo[3,4-b]pyridin-5-yl]-1-oxa-2-azaspiro[4.5]dec-2-ene-8-carboxamide (Compound No. 108), (trans or cis) 3-[4-(Cyclohexylamino)-1-ethyl-1H-pyrazolo[3,4-b]pyridin-5-yl]-1-oxa-2-azaspiro[4.5]dec-2-ene-8-carboxamide (Compound No. 109), 1-(4-Methoxybenzyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 110), 5-[2-(Benzyloxy)-5-oxa-6-azaspiro[3.4]oct-6-en-7-yl]-1-(4-methoxybenzyl)-N-(tetrahydro-2H-pyran-4-yl)-1H-pyrazolo[3,4-b]pyridin-4-amine (Compound No. 111), Ethyl (cis or trans) 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 112), Ethyl (trans or cis) 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 113), N-(1,1-dioxidotetrahydro-2H-thiopyran-4-yl)-1-ethyl-5-(1-oxa-2-azaspiro[4.5]dec-2-en-3-yl)-1H-pyrazolo[3,4-b]pyridin-4-amine ((Compound No. 114), 3-{[1-Ethyl-5-(5-oxa-6-azaspiro[3.4]oct-6-en-7-yl)-1H-pyrazolo[3,4-b]pyridin-4-yl]amino}cyclobutanecarboxylic acid (Compound No. 115), 3-{[1-Ethyl-5-(1-oxa-2-azaspiro[4.4]non-2-en-3-yl)-1H-pyrazolo[3,4-b]pyridin-4-yl]amino}cyclobutanecarboxylic acid (Compound No. 116), 3-{[1-Ethyl-5-(1-oxa-2-azaspiro[4.5]dec-2-en-3-yl)-1H-pyrazolo[3,4-b]pyridin-4-yl]amino}cyclobutanecarboxylic acid (Compound No. 117), 3-[4-(Cyclohexylamino)-1-ethyl-1H-pyrazolo[3,4-b]pyridin-5-yl]-1-oxa-2-azaspiro[4.5]dec-2-ene-8-carbonitrile (Compound No. 118), 3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carboxylic acid (Compound No. 119), 3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carbonitrile (Compound No. 120), 7-[4-(Cyclohexylamino)-1-ethyl-1H-pyrazolo[3,4-b]pyridin-5-yl]-5-oxa-6-azaspiro[3.4]oct-6-en-2-ol (Compound No. 121), 7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 122), 7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 123), 7-[4-(Cyclohexylamino)-1-ethyl-1H-pyrazolo[3,4-b]pyridin-5-yl]-N-methyl-5-oxa-6-azaspiro[3.4]oct-6-ene-2-carboxamide (Compound No. 124), 7-[1-Ethyl-4-(tetrahydro-2H-pyran-4-ylamino)-1H-pyrazolo[3,4-b]pyridin-5-yl]-N-methyl-5-oxa-6-azaspiro[3.4]oct-6-ene-2-carboxamide (Compound No. 125), 7-[4-(Cyclohexylamino)-1-ethyl-1H-pyrazolo[3,4-b]pyridin-5-yl]-N-ethyl-5-oxa-6-azaspiro[3.4]oct-6-ene-2-carboxamide (Compound No. 126), N-Ethyl-7-[1-ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 127), 5-(2-Amino-5-oxa-6-azaspiro[3.4]oct-6-en-7-yl)-1-ethyl-N-(tetrahydro-2H-pyran-4-yl)-1H-pyrazolo[3,4-b]pyridin-4-amine (Compound No. 128), 5-(2-Amino-5-oxa-6-azaspiro[3.4]oct-6-en-7-yl)-N-cyclohexyl-1-ethyl-1H-pyrazolo[3,4-b]pyridin-4-amine (Compound No. 129), N-{7-[4-(cyclohexylamino)-1-ethyl-1H-pyrazolo[3,4-b]pyridin-5-yl]-5-oxa-6-azaspiro[3.4]oct-6-en-2-yl}acetamide (Compound No. 130), N-{7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}acetamide (Compound No. 131), 4-{[1-Ethyl-5-(5-oxa-6-azaspiro[3.4]oct-6-en-7-yl)-1H-pyrazolo[3,4-b]pyridin-4-yl]amino}cyclohexanecarboxylic acid (Compound No. 132), 4-{[1-Ethyl-5-(1-oxa-2-azaspiro[4.4]non-2-en-3-yl)-1H-pyrazolo[3,4-b]pyridin-4-yl]amino}cyclohexanecarboxylic acid (Compound No. 133), 4-{[1-Ethyl-5-(1-oxa-2-azaspiro[4.5]dec-2-en-3-yl)-1H-pyrazolo[3,4-b]pyridin-4-yl]amino}cyclohexanecarboxylic acid (Compound No. 134), 4-{[5-(2-Cyano-5-oxa-6-azaspiro[3.4]oct-6-en-7-yl)-1-ethyl-1H-pyrazolo[3,4-b]pyridin-4-yl]amino}cyclohexanecarboxylic acid (Compound No. 135), 1-Ethyl-3-methyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 136), 1-Ethyl-3-methyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 137), 1-Ethyl-3-methyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 138), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 139), N-Cyclohexyl-1-ethyl-3-methyl-5-(5-oxa-6-azaspiro[3.4]oct-6-en-7-yl)-1H-pyrazolo[3,4-b]pyridin-4-amine (Compound No. 140), 7-[4-(Cyclohexylamino)-1-ethyl-3-methyl-1H-pyrazolo[3,4-b]pyridin-5-yl]-5-oxa-6-azaspiro[3.4]oct-6-ene-2-carbonitrile (Compound No. 141), 3-[4-(Cyclohexylamino)-1-ethyl-1H-pyrazolo[3,4-b]pyridin-5-yl]-N-methyl-1-oxa-2-azaspiro[4.5]dec-2-en-8-amine (Compound No. 142), 4-{[5-(2-Cyano-5-oxa-6-azaspiro[3.4]oct-6-en-7-yl)-1-ethyl-3-methyl-1H-pyrazolo[3,4-b]pyridin-4-yl]amino}cyclohexanecarboxylic acid (Compound No. 143), 4-{[1-Ethyl-5-(2-hydroxy-5-oxa-6-azaspiro[3.4]oct-6-en-7-yl)-3-methyl-1H-pyrazolo[3,4-b]pyridin-4-yl]amino}cyclohexanecarboxylic acid (Compound No. 144), 4-{[1-Ethyl-3-methyl-5-(1-oxa-2-azaspiro[4.4]non-2-en-3-yl)-1H-pyrazolo[3,4-b]pyridin-4-yl]amino}cyclohexanecarboxylic acid (Compound No. 145), 4-{[1-Ethyl-3-methyl-5-(1-oxa-2-azaspiro[4.5]dec-2-en-3-yl)-1H-pyrazolo[3,4-b]pyridin-4-yl]amino}cyclohexanecarboxylic acid (Compound No. 146), 4-{[1-Ethyl-5-(8-hydroxy-1-oxa-2-azaspiro[4.5]dec-2-en-3-yl)-1H-pyrazolo[3,4-b]pyridin-4-yl]amino}cyclohexanecarboxylic acid (Compound No. 147), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-en-8-ol (Compound No. 148), 3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 149), 4-{[5-(8-Carbamoyl-1-oxa-2-azaspiro[4.5]dec-2-en-3-yl)-1-ethyl-1H-pyrazolo[3,4-b]pyridin-4-yl]amino}cyclohexanecarboxylic acid (Compound No. 150), 3-{[5-(8-Carbamoyl-1-oxa-2-azaspiro[4.5]dec-2-en-3-yl)-1-ethyl-1H-pyrazolo[3,4-b]pyridin-4-yl]amino}cyclobutanecarboxylic acid (Compound No. 151), 3-{1-Ethyl-4-[(3-hydroxycyclobutyl)amino]-1H-pyrazolo[3,4-b]pyridin-5-yl}-N-methyl-1-oxa-2-azaspiro[4.5]dec-2-ene-8-carboxamide (Compound No. 152), 3-[4-(Cyclohexylamino)-1-ethyl-1H-pyrazolo[3,4-b]pyridin-5-yl]-N-methyl-1-oxa-2-azaspiro[4.5]dec-2-ene-8-carboxamide (Compound No. 153), 3-[1-Ethyl-4-(tetrahydro-2H-pyran-4-ylamino)-1H-pyrazolo[3,4-b]pyridin-5-yl]-N-methyl-1-oxa-2-azaspiro[4.5]dec-2-ene-8-carboxamide (Compound No. 154), 3-{4-[(1,1-Dioxidotetrahydro-2H-thiopyran-4-yl)amino]-1-ethyl-1H-pyrazolo[3,4-b]pyridin-5-yl}-N-methyl-1-oxa-2-azaspiro[4.5]dec-2-ene-8-carboxamide (Compound No. 155), 3-{4-[(1,1-Dioxidotetrahydro-2H-thiopyran-4-yl)amino]-1-ethyl-3-methyl-1H-pyrazolo[3,4-b]pyridin-5-yl}-N-methyl-1-oxa-2-azaspiro[4.5]dec-2-ene-8-carboxamide (Compound No. 156), N-(1,1-dioxidotetrahydro-2H-thiopyran-4-yl)-1-ethyl-3-methyl-5-(5-oxa-6-azaspiro[3.4]oct-6-en-7-yl)-1H-pyrazolo[3,4-b]pyridin-4-amine (Compound No. 157), N-(1,1-dioxidotetrahydro-2H-thiopyran-4-yl)-1-ethyl-3-methyl-5-(1-oxa-2-azaspiro[4.4]non-2-en-3-yl)-1H-pyrazolo[3,4-b]pyridin-4-amine (Compound No. 158), N-(1,1-dioxidotetrahydro-2H-thiopyran-4-yl)-1-ethyl-3-methyl-5-(1-oxa-2-azaspiro[4.5]dec-2-en-3-yl)-1H-pyrazolo[3,4-b]pyridin-4-amine (Compound No. 159), 3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-en-8-ol (Compound No. 160), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylic acid (Compound No. 161), 3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-ene-8-carboxylic acid (Compound No. 162), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxamide (Compound No. 163), 3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-ene-8-carboxamide (Compound No. 164), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 165), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-ene-8-carboxylic acid (Compound No. 166), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-ene-8-carbonitrile (Compound No. 167), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxylic acid (Compound No. 168), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 169), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 170), 5-(2-Amino-5-oxa-6-azaspiro[3.4]oct-6-en-7-yl)-1-ethyl-3-methyl-N-(tetrahydro-2H-pyran-4-yl)-1H-pyrazolo[3,4-b]pyridin-4-amine (Compound No. 171), 3-[4-(Cyclohexylamino)-1-ethyl-3-methyl-1H-pyrazolo[3,4-b]pyridin-5-yl]-1-oxa-2-azaspiro[4.5]dec-2-en-8-ol (Compound No. 172), 3-[4-(Cyclohexylamino)-1-ethyl-3-methyl-1H-pyrazolo[3,4-b]pyridin-5-yl]-1-oxa-2-azaspiro[4.5]dec-2-ene-8-carbonitrile (Compound No. 173), 3-[4-(Cyclohexylamino)-1-ethyl-3-methyl-1H-pyrazolo[3,4-b]pyridin-5-yl]-1-oxa-2-azaspiro[4.5]dec-2-ene-8-carboxylic acid (Compound No. 174), 7-[4-(Cyclohexylamino)-1-ethyl-3-methyl-1H-pyrazolo[3,4-b]pyridin-5-yl]-5-oxa-6-azaspiro[3.4]oct-6-ene-2-carboxylic acid (Compound No. 175), 7-[4-(Cyclohexylamino)-1-ethyl-3-methyl-1H-pyrazolo[3,4-b]pyridin-5-yl]-5-oxa-6-azaspiro[3.4]oct-6-en-2-ol (Compound No. 176), 7-[4-(Cyclohexylamino)-1-ethyl-3-methyl-1H-pyrazolo[3,4-b]pyridin-5-yl]-N-methyl-5-oxa-6-azaspiro[3.4]oct-6-ene-2-carboxamide (Compound No. 177), 5-(2-Amino-5-oxa-6-azaspiro[3.4]oct-6-en-7-yl)-N-cyclohexyl-1-ethyl-3-methyl-1H-pyrazolo[3,4-b]pyridin-4-amine (Compound No. 178), 4-{[1-Ethyl-3-methyl-5-(5-oxa-6-azaspiro[3.4]oct-6-en-7-yl)-1H-pyrazolo[3,4-b]pyridin-4-yl]amino}cyclohexanecarboxylic acid (Compound No. 179), 4-{[1-Ethyl-5-(8-hydroxy-1-oxa-2-azaspiro[4.5]dec-2-en-3-yl)-3-methyl-1H-pyrazolo[3,4-b]pyridin-4-yl]amino}cyclohexanecarboxylic acid (Compound No. 180), 3-{[1-Ethyl-3-methyl-5-(5-oxa-6-azaspiro[3.4]oct-6-en-7-yl)-1H-pyrazolo[3,4-b]pyridin-4-yl]amino}cyclobutanecarboxylic acid (Compound No. 181), 3-{[1-Ethyl-3-methyl-5-(1-oxa-2-azaspiro[4.4]non-2-en-3-yl)-1H-pyrazolo[3,4-b]pyridin-4-yl]amino}cyclobutanecarboxylic acid (Compound No. 182), 3-{[1-Ethyl-3-methyl-5-(1-oxa-2-azaspiro[4.5]dec-2-en-3-yl)-1H-pyrazolo[3,4-b]pyridin-4-yl]amino}cyclobutanecarboxylic acid (Compound No. 183), 3-{[5-(2-Cyano-5-oxa-6-azaspiro[3.4]oct-6-en-7-yl)-1-ethyl-1H-pyrazolo[3,4-b]pyridin-4-yl]amino}cyclobutanecarboxylic acid (Compound No. 184), 3-{[5-(2-Cyano-5-oxa-6-azaspiro[3.4]oct-6-en-7-yl)-1-ethyl-3-methyl-1H-pyrazolo[3,4-b]pyridin-4-yl]amino}cyclobutanecarboxylic acid (Compound No. 185), 3-{[1-Ethyl-5-(8-hydroxy-1-oxa-2-azaspiro[4.5]dec-2-en-3-yl)-3-methyl-1H-pyrazolo[3,4-b]pyridin-4-yl]amino}cyclobutanecarboxylic acid (Compound No. 186), 3-{[1-Ethyl-5-(8-hydroxy-1-oxa-2-azaspiro[4.5]dec-2-en-3-yl)-1H-pyrazolo[3,4-b]pyridin-4-yl]amino}cyclobutanecarboxylic acid (Compound No. 187), 3-{[1-Ethyl-5-(2-hydroxy-5-oxa-6-azaspiro[3.4]oct-6-en-7-yl)-1H-pyrazolo[3,4-b]pyridin-4-yl]amino}cyclobutanecarboxylic acid (Compound No. 188), 3-{[1-Ethyl-5-(2-hydroxy-5-oxa-6-azaspiro[3.4]oct-6-en-7-yl)-3-methyl-1H-pyrazolo[3,4-b]pyridin-4-yl]amino}cyclobutanecarboxylic acid (Compound No. 189), 5-(2-Amino-5-oxa-6-azaspiro[3.4]oct-6-en-7-yl)-N-(1,1-dioxidotetrahydro-2H-thiopyran-4-yl)-1-ethyl-1H-pyrazolo[3,4-b]pyridin-4-amine (Compound No. 190), 5-(2-Amino-5-oxa-6-azaspiro[3.4]oct-6-en-7-yl)-N-(1,1-dioxidotetrahydro-2H-thiopyran-4-yl)-1-ethyl-3-methyl-1H-pyrazolo[3,4-b]pyridin-4-amine (Compound No. 191), N-(7-{4-[(1,1-dioxidotetrahydro-2H-thiopyran-4-yl)amino]-1-ethyl-3-methyl-1H-pyrazolo[3,4-b]pyridin-5-yl}-5-oxa-6-azaspiro[3.4]oct-6-en-2-yl)acetamide (Compound No. 192), N-(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)acetamide (Compound No. 193), N-(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)propanamide (Compound No. 194), N-(7-{4-[(1,1-dioxidotetrahydro-2H-thiopyran-4-yl)amino]-1-ethyl-3-methyl-1H-pyrazolo[3,4-b]pyridin-5-yl}-5-oxa-6-azaspiro[3.4]oct-6-en-2-yl)propanamide (Compound No. 195), 3-{[5-(2-Amino-5-oxa-6-azaspiro[3.4]oct-6-en-7-yl)-1-ethyl-1H-pyrazolo[3,4-b]pyridin-4-yl]amino}cyclobutanecarboxylic acid (Compound No. 196), 3-{[5-(2-Amino-5-oxa-6-azaspiro[3.4]oct-6-en-7-yl)-1-ethyl-3-methyl-1H-pyrazolo[3,4-b]pyridin-4-yl]amino}cyclobutanecarboxylic acid (Compound No. 197), 3-({5-[2-(Acetylamino)-5-oxa-6-azaspiro[3.4]oct-6-en-7-yl]-1-ethyl-3-methyl-1H-pyrazolo[3,4-b]pyridin-4-yl}amino)cyclobutanecarboxylic acid (Compound No. 198), 3-({5-[2-(Acetylamino)-5-oxa-6-azaspiro[3.4]oct-6-en-7-yl]-1-ethyl-1H-pyrazolo[3,4-b]pyridin-4-yl}amino)cyclobutanecarboxylic acid (Compound No. 199), 3-({1-Ethyl-5-[2-(propanoylamino)-5-oxa-6-azaspiro[3.4]oct-6-en-7-yl]-1H-pyrazolo[3,4-b]pyridin-4-yl}amino)cyclobutanecarboxylic acid (Compound No. 200), 3-({1-Ethyl-3-methyl-5-[2-(propanoylamino)-5-oxa-6-azaspiro[3.4]oct-6-en-7-yl]-1H-pyrazolo[3,4-b]pyridin-4-yl}amino)cyclobutanecarboxylic acid (Compound No. 201), N-ethyl-7-[1-ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 202), N-{7-[4-(cyclohexylamino)-1-ethyl-1H-pyrazolo[3,4-b]pyridin-5-yl]-5-oxa-6-azaspiro[3.4]oct-6-en-2-yl}propanamide (Compound No. 203), N-{7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}propanamide (Compound No. 204), N-{7-[1-ethyl-3-methyl-4-(tetrahydro-2H-pyran-4-ylamino)-1H-pyrazolo[3,4-b]pyridin-5-yl]-5-oxa-6-azaspiro[3.4]oct-6-en-2-yl}propanamide (Compound No. 205), 4-{[5-(8-Amino-1-oxa-2-azaspiro[4.5]dec-2-en-3-yl)-1-ethyl-3-methyl-1H-pyrazolo[3,4-b]pyridin-4-yl]amino}cyclohexanecarboxylic acid (Compound No. 206), 4-{[5-(8-Amino-1-oxa-2-azaspiro[4.5]dec-2-en-3-yl)-1-ethyl-1H-pyrazolo[3,4-b]pyridin-4-yl]

amino}cyclohexanecarboxylic acid (Compound No. 207),
4-({5-[8-(Acetylamino)-1-oxa-2-azaspiro[4.5]dec-2-en-3-yl]-1-ethyl-1H-pyrazolo[3,4-b]pyridin-4-yl}amino)cyclohexanecarboxylic acid (Compound No. 208),
4-({5-[8-(Acetylamino)-1-oxa-2-azaspiro[4.5]dec-2-en-3-yl]-1-ethyl-3-methyl-1H-pyrazolo[3,4-b]pyridin-4-yl}amino)cyclohexanecarboxylic acid (Compound No. 209),
4-({1-Ethyl-3-methyl-5-[8-(propanoylamino)-1-oxa-2-azaspiro[4.5]dec-2-en-3-yl]-1H-pyrazolo[3,4-b]pyridin-4-yl}amino)cyclohexanecarboxylic acid (Compound No. 210),
4-({1-Ethyl-5-[8-(propanoylamino)-1-oxa-2-azaspiro[4.5]dec-2-en-3-yl]-1H-pyrazolo[3,4-b]pyridin-4-yl}amino)cyclohexanecarboxylic acid (Compound No. 211),
7-{4-[(4-Carboxycyclohexyl)amino]-1-ethyl-3-methyl-1H-pyrazolo[3,4-b]pyridin-5-yl}-5-oxa-6-azaspiro[3.4]oct-6-ene-2-carboxylic acid (Compound No. 212),
7-{4-[(4-Carboxycyclohexyl)amino]-1-ethyl-1H-pyrazolo[3,4-b]pyridin-5-yl}-5-oxa-6-azaspiro[3.4]oct-6-ene-2-carboxylic acid (Compound No. 213),
4-{[5-(2-Carbamoyl-5-oxa-6-azaspiro[3.4]oct-6-en-7-yl)-1-ethyl-1H-pyrazolo[3,4-b]pyridin-4-yl]amino}cyclohexanecarboxylic acid (Compound No. 214),
4-{[5-(2-Carbamoyl-5-oxa-6-azaspiro[3.4]oct-6-en-7-yl)-1-ethyl-3-methyl-1H-pyrazolo[3,4-b]pyridin-4-yl]amino}cyclohexanecarboxylic acid (Compound No. 215),
4-({1-Ethyl-3-methyl-5-[2-(methylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 216),
4-({1-Ethyl-5-[2-(methylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 217),
4-({1-Ethyl-5-[2-(ethylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 218),
4-({1-Ethyl-5-[2-(ethylcarbamoyl)-5-oxa-6-azaspiro[3.4]oct-6-en-7-yl]-3-methyl-1H-pyrazolo[3,4-b]pyridin-4-yl}amino)cyclohexanecarboxylic acid (Compound No. 219),
3-{4-[(4-Carboxycyclohexyl)amino]-1-ethyl-1H-pyrazolo[3,4-b]pyridin-5-yl}-1-oxa-2-azaspiro[4.5]dec-2-ene-8-carboxylic acid (Compound No. 220),
3-{4-[(4-Carboxycyclohexyl)amino]-1-ethyl-3-methyl-1H-pyrazolo[3,4-b]pyridin-5-yl}-1-oxa-2-azaspiro[4.5]dec-2-ene-8-carboxylic acid (Compound No. 221),
4-{[5-(8-Carbamoyl-1-oxa-2-azaspiro[4.5]dec-2-en-3-yl)-1-ethyl-3-methyl-1H-pyrazolo[3,4-b]pyridin-4-yl]amino}cyclohexanecarboxylic acid (Compound No. 222),
4-({1-Ethyl-5-[8-(methylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 223),
4-({1-Ethyl-3-methyl-5-[8-(methylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 224),
4-({1-Ethyl-5-[8-(ethylcarbamoyl)-1-oxa-2-azaspiro[4.5]dec-2-en-3-yl]-3-methyl-1H-pyrazolo[3,4-b]pyridin-4-yl}amino)cyclohexanecarboxylic acid (Compound No. 225),
4-({1-Ethyl-5-[8-(ethylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 226),
4-{[1-Ethyl-5-(8-methoxy-1-oxa-2-azaspiro[4.5]dec-2-en-3-yl)-1H-pyrazolo[3,4-b]pyridin-4-yl]amino}cyclohexanecarboxylic acid (Compound No. 227),
4-{[5-(8-Ethoxy-1-oxa-2-azaspiro[4.5]dec-2-en-3-yl)-1-ethyl-1H-pyrazolo[3,4-b]pyridin-4-yl]amino}cyclohexanecarboxylic acid (Compound No. 228),
4-({1-Ethyl-5-[8-(2-hydroxyethoxy)-1-oxa-2-azaspiro[4.5]dec-2-en-3-yl]-1H-pyrazolo[3,4-b]pyridin-4-yl}amino)cyclohexanecarboxylic acid (Compound No. 229),
1-Ethyl-5-(5-oxa-6-azaspiro[3.4]oct-6-en-7-yl)-N-pyridin-4-yl-1H-pyrazolo[3,4-b]pyridin-4-amine (Compound No. 230),
1-Ethyl-5-(5-oxa-6-azaspiro[3.4]oct-6-en-7-yl)-N-pyridin-3-yl-1H-pyrazolo[3,4-b]pyridin-4-amine (Compound No. 231),
1-Ethyl-5-(5-oxa-6-azaspiro[3.4]oct-6-en-7-yl)-N-pyridin-2-yl-1H-pyrazolo[3,4-b]pyridin-4-amine (Compound No. 232),
1-Ethyl-5-(5-oxa-6-azaspiro[3.4]oct-6-en-7-yl)-N-pyrazin-2-yl-1H-pyrazolo[3,4-b]pyridin-4-amine (Compound No. 233),
1-Ethyl-5-(5-oxa-6-azaspiro[3.4]oct-6-en-7-yl)-N-pyrimidin-2-yl-1H-pyrazolo[3,4-b]pyridin-4-amine (Compound No. 234),
1-Ethyl-5-(5-oxa-6-azaspiro[3.4]oct-6-en-7-yl)-N-1,2,4-triazin-5-yl-1H-pyrazolo[3,4-b]pyridin-4-amine (Compound No. 235),
1-Ethyl-5-(5-oxa-6-azaspiro[3.4]oct-6-en-7-yl)-N-1,3-thiazol-2-yl-1H-pyrazolo[3,4-b]pyridin-4-amine (Compound No. 236),
1-Ethyl-5-(5-oxa-6-azaspiro[3.4]oct-6-en-7-yl)-N-4H-1,2,4-triazol-4-yl-1H-pyrazolo[3,4-b]pyridin-4-amine (Compound No. 237),
1-Ethyl-5-(5-oxa-6-azaspiro[3.4]oct-6-en-7-yl)-N-2H-tetrazol-5-yl-1H-pyrazolo[3,4-b]pyridin-4-amine (Compound No. 238),
1-Ethyl-5-(5-oxa-6-azaspiro[3.4]oct-6-en-7-yl)-N-1H-tetrazol-5-yl-1H-pyrazolo[3,4-b]pyridin-4-amine (Compound No. 239),
1-Ethyl-5-(5-oxa-6-azaspiro[3.4]oct-6-en-7-yl)-N-pyrimidin-5-yl-1H-pyrazolo[3,4-b]pyridin-4-amine (Compound No. 240),
1-Ethyl-5-(1-oxa-2-azaspiro[4.5]dec-2-en-3-yl)-N-pyridin-4-yl-1H-pyrazolo[3,4-b]pyridin-4-amine (Compound No. 241),
1-Ethyl-5-(1-oxa-2-azaspiro[4.4]non-2-en-3-yl)-N-pyridin-4-yl-1H-pyrazolo[3,4-b]pyridin-4-amine (Compound No. 242),
1-Ethyl-5-(1-oxa-2-azaspiro[4.5]dec-2-en-3-yl)-N-pyridin-3-yl-1H-pyrazolo[3,4-b]pyridin-4-amine (Compound No. 243),
1-Ethyl-5-(1-oxa-2-azaspiro[4.5]dec-2-en-3-yl)-N-pyridin-2-yl-1H-pyrazolo[3,4-b]pyridin-4-amine (Compound No. 244),
1-Ethyl-5-(1-oxa-2-azaspiro[4.5]dec-2-en-3-yl)-N-pyrimidin-2-yl-1H-pyrazolo[3,4-b]pyridin-4-amine (Compound No. 245), 1-Ethyl-5-(1-oxa-2-azaspiro[4.5]dec-2-en-3-yl)-N-pyrimidin-5-yl-1H-pyrazolo[3,4-b]pyridin-4-amine (Compound No. 246),
1-Ethyl-5-(1-oxa-2-azaspiro[4.5]dec-2-en-3-yl)-N-1,2,4-triazin-5-yl-1H-pyrazolo[3,4-b]pyridin-4-amine (Compound No. 247),
1-Ethyl-5-(1-oxa-2-azaspiro[4.5]dec-2-en-3-yl)-N-1,3-thiazol-2-yl-1H-pyrazolo[3,4-b]pyridin-4-amine (Compound No. 248),
1-Ethyl-5-(1-oxa-2-azaspiro[4.5]dec-2-en-3-yl)-N-4H-1,2,4-triazol-4-yl-1H-pyrazolo[3,4-b]pyridin-4-amine (Compound No. 249), 1-Ethyl-5-(1-oxa-2-azaspiro[4.5]dec-2-en-3-yl)-N-2H-tetrazol-5-yl-1H-pyrazolo[3,4-b]pyridin-4-amine (Compound No. 250), 1-Ethyl-5-(1-oxa-2-azaspiro[4.5]dec-2-en-3-yl)-N-1H-tetrazol-5-yl-1H-pyrazolo[3,4-b]pyridin-4-amine (Compound No. 251), 1-Ethyl-5-(1-oxa-2-azaspiro[4.4]non-2-en-3-yl)-N-pyridin-3-yl-1H-pyrazolo[3,4-b]pyridin-4-amine (Compound No. 252), 1-Ethyl-5-(1-oxa-2-azaspiro[4.4]non-2-en-3-yl)-N-pyridin-2-yl-1H-pyrazolo[3,4-b]pyridin-4-amine (Compound No. 253), 1-Ethyl-5-(1-oxa-2-azaspiro[4.4]non-2-en-3-yl)-N-pyrimidin-2-yl-1H-pyrazolo[3,4-b]pyridin-4-amine (Compound No. 254), 1-Ethyl-5-(1-oxa-2-azaspiro[4.4]non-2-en-3-yl)-N-pyrimidin-5-yl-1H-pyrazolo[3,4-b]pyridin-4-amine (Compound No. 255), 1-Ethyl-5-(1-oxa-2-azaspiro[4.4]non-2-en-3-yl)-N-1,2,4-triazin-5-yl-1H-pyrazolo[3,4-b]pyridin-4-amine (Compound No. 256), 1-Ethyl-5-(1-oxa-2-azaspiro[4.4]non-2-en-3-yl)-N-1H-tetrazol-5-yl-1H-pyrazolo[3,4-b]pyridin-4-amine (Compound No. 257), 1-Ethyl-5-(1-oxa-2-azaspiro[4.4]non-2-en-3-yl)-N-2H-tetrazol-5-yl-1H-pyrazolo[3,4-b]pyridin-4-amine (Compound No. 258), 1-Ethyl-5-(1-oxa-2-azaspiro[4.4]non-2-en-3-yl)-N-4H-1,2,4-triazol-4-yl-1H-pyrazolo[3,4-b]pyridin-4-amine (Compound No. 259), 1-Ethyl-5-(1-oxa-2-azaspiro[4.4]non-2-en-3-yl)-N-1,3-thiazol-2-yl-1H-pyrazolo[3,4-b]pyridin-4-amine (Compound No. 260), 1-Ethyl-N-furan-3-yl-5-(1-oxa-2-azaspiro[4.5]dec-2-en-3-yl)-1H-pyrazolo[3,4-b]pyridin-4-amine (Compound No. 261), 1-Ethyl-N-furan-3-yl-5-(1-oxa-2-azaspiro[4.4]non-2-en-3-yl)-1H-pyrazolo[3,4-b]pyridin-4-amine (Compound No. 262), 1-Ethyl-N-furan-3-yl-5-(5-oxa-6-azaspiro[3.4]oct-6-en-7-yl)-1H-pyrazolo[3,4-b]pyridin-4-amine (Compound No. 263), 1-Ethyl-5-(1-oxa-2-azaspiro[4.4]non-2-en-3-yl)-N-pyrazin-2-yl-1H-pyrazolo[3,4-b]pyridin-4-amine (Compound No. 264), 1-Ethyl-5-(1-oxa-2-azaspiro[4.5]dec-2-en-3-yl)-N-pyrazin-2-yl-1H-pyrazolo[3,4-b]pyridin-4-amine (Compound No. 265), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carbonitrile (Compound No. 266), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylic acid (Compound No. 267), Methyl 7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylate (Compound No. 268), Ethyl 7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylate (Compound No. 269), tert-Butyl 7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylate (Compound No. 270), 7-{4-[(1,1-Dioxidotetrahydro-2H-thiopyran-4-yl)amino]-1-ethyl-1H-pyrazolo[3,4-b]pyridin-5-yl}-N-methyl-5-oxa-6-azaspiro[3.4]oct-6-ene-2-carboxamide (Compound No. 271), 7-{4-[(1,1-Dioxidotetrahydro-2H-thiopyran-4-yl)amino]-1-ethyl-1H-pyrazolo[3,4-b]pyridin-5-yl}-N-ethyl-5-oxa-6-azaspiro[3.4]oct-6-ene-2-carboxamide (Compound No. 272), N-cyclopropyl-7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxamide (Compound No. 273), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxamide (Compound No. 274), 7-[4-(Cyclohexylamino)-1-ethyl-1H-pyrazolo[3,4-b]pyridin-5-yl]-N-cyclopropyl-5-oxa-6-azaspiro[3.4]oct-6-ene-2-carboxamide (Compound No. 275), N-cyclopropyl-7-[1-ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 276), 1-Ethyl-5-(8-methoxy-1-oxa-2-azaspiro[4.5]dec-2-en-3-yl)-N-(tetrahydro-2H-pyran-4-yl)-1H-pyrazolo[3,4-b]pyridin-4-amine (Compound No. 277), 5-(8-Ethoxy-1-oxa-2-azaspiro[4.5]dec-2-en-3-yl)-1-ethyl-N-(tetrahydro-2H-pyran-4-yl)-1H-pyrazolo[3,4-b]pyridin-4-amine (Compound No. 278), N-cyclohexyl-5-(8-ethoxy-1-oxa-2-azaspiro[4.5]dec-2-en-3-yl)-1-ethyl-1H-pyrazolo[3,4-b]pyridin-4-amine (Compound No. 279), N-cyclohexyl-1-ethyl-5-(8-methoxy-1-oxa-2-azaspiro[4.5]dec-2-en-3-yl)-1H-pyrazolo[3,4-b]pyridin-4-amine (Compound No. 280), 3-{4-[(1,1-Dioxidotetrahydro-2H-thiopyran-4-yl)amino]-1-ethyl-1H-pyrazolo[3,4-b]pyridin-5-yl}-N-ethyl-1-oxa-2-azaspiro[4.5]dec-2-ene-8-carboxamide (Compound No. 281), N-cyclopropyl-3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxamide (Compound No. 282), 3-[4-(Cyclohexylamino)-1-ethyl-1H-pyrazolo[3,4-b]pyridin-5-yl]-N-cyclopropyl-1-oxa-2-azaspiro[4.5]dec-2-ene-8-carboxamide (Compound No. 283), N-cyclopropyl-3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 284), N-ethyl-3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 285), 3-[4-(Cyclohexylamino)-1-ethyl-1H-pyrazolo[3,4-b]pyridin-5-yl]-N-ethyl-1-oxa-2-azaspiro[4.5]dec-2-ene-8-carboxamide (Compound No. 286), Ethyl 3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylate (Compound No. 287), Methyl 3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylate (Compound No. 288), tert-Butyl 3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylate (Compound No. 289), N-(1,1-dioxidotetrahydro-2H-thiopyran-4-yl)-1-ethyl-5-(8-methoxy-1-oxa-2-azaspiro[4.5]dec-2-en-3-yl)-1H-pyrazolo[3,4-b]pyridin-4-amine (Compound No. 290), N-(1,1-dioxidotetrahydro-2H-thiopyran-4-yl)-5-(8-ethoxy-1-oxa-2-azaspiro[4.5]dec-2-en-3-yl)-1-ethyl-1H-pyrazolo[3,4-b]pyridin-4-amine (Compound No. 291), 1-Ethyl-5-(1-oxa-2-azaspiro[4.4]non-2-en-3-yl)-N-1,2,4-triazin-3-yl-1H-pyrazolo[3,4-b]pyridin-4-amine (Compound No. 292), 1-Ethyl-5-(5-oxa-6-azaspiro[3.4]oct-6-en-7-yl)-N-1,2,4-triazin-3-yl-1H-pyrazolo[3,4-b]pyridin-4-amine (Compound No. 293), 1-Ethyl-5-(1-oxa-2-azaspiro[4.5]dec-2-en-3-yl)-N-1,2,4-triazin-3-yl-1H-pyrazolo[3,4-b]pyridin-4-amine (Compound No. 294), 1-Ethyl-5-(2-methoxy-5-oxa-6-azaspiro[3.4]oct-6-en-7-yl)-N-(tetrahydro-2H-pyran-4-yl)-1H-pyrazolo[3,4-b]pyridin-4-amine (Compound No. 295), N-cyclohexyl-1-ethyl-5-(2-methoxy-5-oxa-6-azaspiro[3.4]oct-6-en-7-yl)-1H-pyrazolo[3,4-b]pyridin-4-amine (Compound No. 296), N-(1,1-dioxidotetrahydro-2H-thiopyran-4-yl)-1-ethyl-5-(2-methoxy-5-oxa-6-azaspiro[3.4]oct-6-en-7-yl)-1H-pyrazolo[3,4-b]pyridin-4-amine (Compound No. 297), N-(1,1-dioxidotetrahydro-2H-thiopyran-4-yl)-5-(2-ethoxy-5-oxa-6-azaspiro[3.4]oct-6-en-7-yl)-1-ethyl-1H-pyrazolo[3,4-b]pyridin-4-amine (Compound No. 298), N-cyclohexyl-5-(2-ethoxy-5-oxa-6-azaspiro[3.4]oct-6-en-7-yl)-1-ethyl-1H-pyrazolo[3,4-b]pyridin-4-amine (Compound No. 299), 5-(2-Ethoxy-5-oxa-6-azaspiro[3.4]oct-6-en-7-yl)-1-ethyl-N-(tetrahydro-2H-pyran-4-yl)-1H-pyrazolo[3,4-b]pyridin-4-amine (Compound No. 300), {7-[4-(Cyclohexylamino)-1-ethyl-1H-pyrazolo[3,4-b]pyridin-5-yl]-5-oxa-6-azaspiro[3.4]oct-6-en-2-yl}methanol (Compound No. 301), (7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methanol (Compound No. 302), N-(1,1-dioxidotetrahydro-2H-thiopyran-4-yl)-1-ethyl-5-[2-(methoxymethyl)-5-oxa-6-azaspiro[3.4]oct-6-en-7-yl]-1H-pyrazolo[3,4-b]pyridin-4-amine (Compound No. 303), N-(1,1-dioxidotetrahydro-2H-thiopyran-4-yl)-5-[2-(ethoxymethyl)-5-oxa-6-azaspiro[3.4]oct-6-en-7-yl]-1-ethyl-1H-pyrazolo[3,4-b]pyridin-4-amine (Compound No. 304), N-cyclohexyl-5-[2-(ethoxymethyl)-5-oxa-6-azaspiro[3.4]oct-6-en-7-yl]-1-ethyl-1H-pyrazolo[3,4-b]pyridin-4-amine (Compound No. 305), 5-[2-(Ethoxymethyl)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 306), 1-Ethyl-5-[2-(methoxymethyl)-5-oxa-6-azaspiro[3.4]oct-6-en-7-yl]-N-(tetrahydro-2H-pyran-4-yl)-1H-pyrazolo[3,4-b]pyridin-4-amine (Compound No. 307), N-cyclohexyl-1-ethyl-5-[2-(methoxymethyl)-5-oxa-6-azaspiro[3.4]oct-6-en-7-yl]-1H-pyrazolo[3,4-b]pyridin-4-amine (Compound No. 308), 5-[2-(Aminomethyl)-5-oxa-6-azaspiro[3.4]oct-6-en-7-yl]-N-cyclohexyl-1-ethyl-1H-pyrazolo[3,4-b]pyridin-4-amine (Compound No. 309), 5-[2-(Aminomethyl)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 310), 5-[2-(Aminomethyl)-5-oxa-6-azaspiro[3.4]oct-6-en-7-yl]-N-(1,1-dioxidotetrahydro-2H-thiopyran-4-yl)-1-ethyl-1H-pyrazolo[3,4-b]pyridin-4-amine (Compound No. 311), N-[(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methyl]acetamide (Compound No. 312), N-[(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methyl]propanamide (Compound No. 313), N-({7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}methyl)propanamide (Compound No. 314), N-({7-[4-(cyclohexylamino)-1-ethyl-1H-pyrazolo[3,4-b]pyridin-5-yl]-5-oxa-6-azaspiro[3.4]oct-6-en-2-yl}methyl)propanamide (Compound No. 315), N-({7-[4-(cyclohexylamino)-1-ethyl-1H-pyrazolo[3,4-b]pyridin-5-yl]-5-oxa-6-azaspiro[3.4]oct-6-en-2-yl}methyl)acetamide (Compound No. 316), N-({7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}methyl)acetamide (Compound No. 317), 1-Ethyl-N-(tetrahydro-2H-pyran-4-yl)-5-[2-(1H-tetrazol-5-yl)-5-oxa-6-azaspiro[3.4]oct-6-en-7-yl]-1H-pyrazolo[3,4-b]pyridin-4-amine (Compound No. 318), N-cyclohexyl-1-ethyl-5-[2-(1H-tetrazol-5-yl)-5-oxa-6-azaspiro[3.4]oct-6-en-7-yl]-1H-pyrazolo[3,4-b]pyridin-4-amine (Compound No. 319), N-(1,1-dioxidotetrahydro-2H-thiopyran-4-yl)-1-ethyl-5-[2-(1H-tetrazol-5-yl)-5-oxa-6-azaspiro[3.4]oct-6-en-7-yl]-1H-pyrazolo[3,4-b]pyridin-4-amine (Compound No. 320), 1-Ethyl-N-(tetrahydro-2H-pyran-4-yl)-5-[8-(1H-tetrazol-5-yl)-1-oxa-2-azaspiro[4.5]dec-2-en-3-yl]-1H-pyrazolo[3,4-b]pyridin-4-amine (Compound No. 321), N-cyclohexyl-1-ethyl-5-[8-(1H-tetrazol-5-yl)-1-oxa-2-azaspiro[4.5]dec-2-en-3-yl]-1H-pyrazolo[3,4-b]pyridin-4-amine (Compound No. 322), N-(1,1-dioxidotetrahydro-2H-thiopyran-4-yl)-1-ethyl-5-[8-(1H-tetrazol-5-yl)-1-oxa-2-azaspiro[4.5]dec-2-en-3-yl]-1H-pyrazolo[3,4-b]pyridin-4-amine (Compound No. 323), N-(1,1-dioxidotetrahydro-2H-thiopyran-4-yl)-1-ethyl-5-[8-(2H-tetrazol-5-yl)-1-oxa-2-azaspiro[4.5]dec-2-en-3-yl]-1H-pyrazolo[3,4-b]pyridin-4-amine (Compound No. 324), N-cyclohexyl-1-ethyl-5-[8-(2H-tetrazol-5-yl)-1-oxa-2-azaspiro[4.5]dec-2-en-3-yl]-1H-pyrazolo[3,4-b]pyridin-4-amine (Compound No. 325), 1-Ethyl-N-(tetrahydro-2H-pyran-4-yl)-5-[8-(2H-tetrazol-5-yl)-1-oxa-2-azaspiro[4.5]dec-2-en-3-yl]-1H-pyrazolo[3,4-b]pyridin-4-amine (Compound No. 326), 1-Ethyl-N-(tetrahydro-2H-pyran-4-yl)-5-[2-(2H-tetrazol-5-yl)-5-oxa-6-azaspiro[3.4]oct-6-en-7-yl]-1H-pyrazolo[3,4-b]pyridin-4-amine (Compound No. 327), N-cyclohexyl-1-ethyl-5-[2-(2H-tetrazol-5-yl)-5-oxa-6-azaspiro[3.4]oct-6-en-7-yl]-1H-pyrazolo[3,4-b]pyridin-4-amine (Compound No. 328), N-(1,1-dioxidotetrahydro-2H-thiopyran-4-yl)-1-ethyl-5-[2-(2H-tetrazol-5-yl)-5-oxa-6-azaspiro[3.4]oct-6-en-7-yl]-1H-pyrazolo[3,4-b]pyridin-4-amine (Compound No. 329), Ethyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 330), Ethyl 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 331), Methyl 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 332), Methyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 333), tert-Butyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 334), tert-Butyl 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 335), N-(1,1-dioxidotetrahydro-2H-thiopyran-4-yl)-1-ethyl-5-(5-oxa-6-azaspiro[3.4]oct-6-en-7-yl)-1H-pyrazolo[3,4-b]pyridin-4-amine (Compound No. 336), N-(1,1-dioxidotetrahydro-2H-thiopyran-4-yl)-1-ethyl-5-(1-oxa-2-azaspiro[4.4]non-2-en-3-yl)-1H-pyrazolo[3,4-b]pyridin-4-amine (Compound No. 337), 3-[4-(Cyclohexylamino)-1-ethyl-1H-pyrazolo[3,4-b]pyridin-5-yl]-1-oxa-2-azaspiro[4.5]dec-2-en-8-amine (Compound No. 338), or their pharmaceutically acceptable salts, pharmaceutically acceptable solvates, stereoisomers, tautomers, geometric isomers, racemates, regioisomers, prodrugs, metabolites, polymorphs or N-oxides, thereof.

The term "pharmaceutically acceptable" means approved by regulatory agency of the federal or a state government or listed in the U.S. Pharmacopoeia or other generally recognized pharmacopoeia for use in mammals, and more particularly in humans.

The term "pharmaceutically acceptable salts" refers to derivatives of compounds that can be modified by forming their corresponding acid or base salts. Examples of pharmaceutically acceptable salts include, but are not limited to, mineral or organic acids salts of basic residues (such as amines), or alkali or organic salts of acidic residues (such as carboxylic acids), and the like.

The term "pharmaceutically acceptable solvates" refers to solvates with water such as hydrates, hemihydrate or sesquihydrate or pharmaceutically acceptable solvents, for example solvates with common organic solvents as ethanol and the like. Such solvates are also encompassed within the scope of the disclosure.

The present invention also includes within its scope prodrugs of these agents. In general, such prodrugs will be functional derivatives of these compounds, which are readily convertible in vivo into the required compound. Conventional procedures for the selection and preparation of prodrugs are known.

The disclosed compounds may get metabolized in vivo and these metabolites are also encompassed within the scope of this invention.

The term "polymorphs" includes all crystalline form as well as amorphous form for compounds described herein and as such are intended to be included in the present invention.

All stereoisomers of the compounds of the invention are contemplated, either in admixture or in pure or substantially pure form. The compounds of the present invention can have asymmetric centers at any of the carbon atoms including all the substituents. Consequently, compounds of present invention can exist in enantiomeric or diastereomeric forms or in mixture thereof. The processes for the preparation can utilize racemates, enantiomers, or diastereomers as starting materials. When diastereomeric or enantiomeric products are prepared, they can be separated by conventional methods, for example, chromatographic or fractional crystallization.

The term "tautomer" includes one of two or more structural isomers that exist in equilibrium and are readily converted from one isomeric form to another. Certain compounds of the general Formula (I) may furthermore be present in tautomeric forms.

The term, "geometric isomers", refers to compounds, having the same molecular formula as another but a different geometric configuration, as when atoms or groups of atoms are attached in different spatial arrangements on either side of a double bond or other rigid bond.

The term "regioisomers" refers to compounds, which have the same molecular formula but differ in the connectivity of the atoms.

The term "racemate" includes a mixture of equal amounts of left- and right-handed stereoisomers of chiral molecules.

When a bond to a substituent is shown to cross a bond connecting two atoms in a ring, then such substituent may be bonded to any atom on the ring.

In another aspect, the present invention includes pharmaceutical compositions comprising, as an active ingredient, at least one of the disclosed compound or a pharmaceutically acceptable salt, a pharmaceutically acceptable solvate, stereoisomer, tautomer, geometric isomer, racemate, regioisomer, prodrug, metabolite, polymorph or N-oxide, together with a pharmaceutically acceptable carrier, excipient or diluent. Compounds disclosed herein may be administered to mammal for treatment by any route, which effectively transports the active compound to the appropriate or desired site of action such as oral, nasal, pulmonary, transdermal or parenteral (rectal, subcutaneous, intravenous, intraurethral, intramuscular, intranasal). The pharmaceutical composition of the present invention comprises a pharmaceutically effective amount of a compound of the present invention formulated together with one or more pharmaceutically acceptable carriers, excipients or diluents. The choice of pharmaceutical carrier, excipient or diluent can be made with regard to the intended route of administration and standard pharmaceutical practice.

Where desired, the compounds of the invention and/or their pharmaceutically acceptable salts, pharmaceutically acceptable solvates, stereoisomers, tautomers, geometric isomers, racemates, regioisomers, prodrugs, metabolites, polymorphs or N-oxides may be advantageously used in combination with one or more other compounds. Examples of other compounds, which may be used in combination with compounds of this invention and/or their pharmaceutically acceptable salts, pharmaceutically acceptable solvates, stereoisomers, tautomers, geometric isomers, racemates, regioisomers, prodrugs, metabolites, polymorphs or N-oxides include β2-agonists, corticosteroids, leukotriene antagonists, 5-lipoxygenase inhibitors, chemokine inhibitors, p38 kinase inhibitors, anticholinergics, antiallergics, PAF (platelet activating factor) antagonists, EGFR (epidermal growth factor receptor) kinase inhibitors, muscarinic receptor antagonists or combinations thereof.

The one or more β2-agonist as described herein may be chosen from those described in the art. The β2-agonists may include one or more compounds described in U.S. Pat. Nos. 3,705,233; 3,644,353; 3,642,896; 3,700,681; 4,579,985; 3,994,974; 3,937,838; 4,419,364; 5,126,375; 5,243,076; 4,992,474; and 4,011,258.

β2-agonists include, for example, one or more of albuterol, salbutamol, biltolterol, pirbuterol, levosalbutamol, tulobuterol, terbutaline, bambuterol, metaproterenol, fenoterol, salmeterol, carmoterol, arformoterol, formoterol, and their pharmaceutically acceptable salts or solvates thereof.

Corticosteroids as described herein may be chosen from those described in the art. Corticosteroids may include one or more compounds described in U.S. Pat. Nos. 3,312,590; 3,983,233; 3,929,768; 3,721,687; 3,436,389; 3,506,694; 3,639,434; 3,992,534; 3,928,326; 3,980,778; 3,780,177; 3,652,554; 3,947,478; 4,076,708; 4,124,707; 4,158,055; 4,298,604; 4,335,121; 4,081,541; 4,226,862; 4,290,962; 4,587,236; 4,472,392; 4,472,393; 4,242,334; 4,014,909; 4,098,803; 4,619,921; 5,482,934; 5,837,699; 5,889,015; 5,278,156; 5,015,746; 5,976,573; 6,337,324; 6,057,307; 6,723,713; 6,127,353; and 6,180,781.

Corticosteroids may include, for example, one or more of alclometasone, amcinonide, amelometasone, beclometasone, betamethasone, budesonide, ciclesonide, clobetasol, cloticasone, cyclomethasone, deflazacort, deprodone, dexbudesonide, diflorasone, difluprednate, fluticasone, flunisolide, halometasone, halopredone, hydrocortisone, hydrocortisone, methylprednisolone, mometasone, prednicarbate, prednisolone, rimexolone, tixocortol, triamcinolone, ulobetasol, rofleponide, GW 215864, KSR 592, ST-126, dexamethasone and pharmaceutically acceptable salts, solvates thereof. Preferred corticosteroids include, for example, flunisolide, beclomethasone, triamcinolone, budesonide, fluticasone, mometasone, ciclesonide, and dexamethasone. Examples of possible salts or derivatives include: sodium salts, sulfobenzoates, phosphates, isonicotinates, acetates, propionates, dihydrogen phosphates, palmitates, pivalates, or furoates. In some cases, the corticosteroids may also occur in the form of their hydrates.

The leukotriene antagonist can be selected from compounds, for example, those described in U.S. Pat. Nos. 5,565,473, 5,583,152, 4,859,692 or U.S. Pat. No. 4,780,469.

Examples of leukotriene antagonist include, but are not limited to, montelukast, zafirlukast, pranlukast and pharmaceutically acceptable salts thereof.

5-Lipoxygenase inhibitors can be selected from for example, compounds in U.S. Pat. Nos. 4,826,868, or 4,873,259, or European Patent Nos. EP 419049, EP 542356 or EP 542355. Examples may include, but are not limited to, atreleuton, zyflo (zileuton), ABT-761, fenleuton or tepoxalin.

Examples of the chemokine inhibitors include, but are not limited to, endogenous ligands of chemokine receptors or derivatives thereof, and non-peptidic low molecular compounds or antibodies for chemokine receptors.

Examples of the endogenous ligands of chemokine receptors include, but are not limited to, MIP-1α, MIP-1β, Rantes, SDF-1α, SDF-1β, MCP-1, MCP-2, MCP4, Eotaxin, MDC. Examples of the derivatives of endogenous ligands include, but are not limited to, AOP-RANTES, Met-SDF-1α, Met-SDF-1β.

Examples of the antibodies for chemokine receptors include, but are not limited to, Pro-140.

Examples of the non-peptidic low molecular compounds include, but are not limited to, antagonists and agonists for CCR1, CCR2, CCR3, CCR4, CCR5, CXCR1, CXCR2, CXCR3 and CXCR4 receptors.

p38 kinase inhibitors include compounds disclosed in WO06021848, WO06016237, WO06056863, WO06117657 and WO06082492. Any reference to the above mentioned p38 kinase inhibitors also includes any pharmaceutically acceptable salts thereof which may exist.

Anticholinergics include, for example, tiotropium salts, ipratropium salts, oxitropium salts, salts of the compounds known from WO 02/32899: tropenol N-methyl-2,2-diphenylpropionate, scopine N-methyl-2,2-diphenylpropionate, scopine N-methyl-2-fluoro-2,2-diphenylacetate and tropenol N-methyl-2-fluoro-2,2-diphenylacetate; as well as salts of the compounds known from WO 02/32898: tropenol N-methyl-3,3',4,4'-tetrafluorobenzilate, scopine N-methyl-3,3',4,4'-tetrafluorobenzilate, scopine N-methyl-4,4'-dichlorobenzilate, scopine N-methyl-4,4'-difluorobenzilate, tropenol N-methyl-3,3'-difluorobenzilate, scopine N-methyl-3,3'-difluorobenzilate, and tropenol N-ethyl-4,4'-difluorobenzilate, optionally in the form of their hydrates and solvates. By salts are meant those compounds which contain, in addition to the above mentioned cations, as counter-ion, an anion with a single negative charge selected from among the chloride, bromide, and methanesulfonate.

Preferred anticholinergics include, for example, tiotropium bromide, ipratropium bromide, oxitropium bromide, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, scopine 4,4'-dichlorobenzilate methobromide, scopine 4,4'-difluorobenzilate methobromide, tropenol 3,3'-difluorobenzilate methobromide, scopine 3,3'-difluorobenzilate methobromide, and tropenol 4,4'-difluorobenzilate ethylbromide.

Antiallergics include, for example, epinastine, cetirizine, azelastine, fexofenadine, levocabastine, loratadine, mizolastine, ketotifene, emedastine, dimetindene, clemastine, bamipine, hexachloropheniramine, pheniramine, doxylamine, chlorophenoxamine, dimenhydrinate, diphenhydramine, promethazine, ebastine, desloratadine, and meclizine. Preferred antiallergic agents include, for example, epinastine, cetirizine, azelastine, fexofenadine, levocabastine, loratadine, ebastine, desloratadine, and mizolastine. Any reference to the above-mentioned antiallergic agents also includes any pharmacologically acceptable salts thereof, which may exist.

PAF antagonists include, for example, 4-(2-chlorophenyl)-9-methyl-2-[3-(4-morpholinyl)-3-propanon-1-yl]-6H-thieno[3,2-f][1,2,4]triazolo[4,3-a][1,4]diazepine and 6-(2-chlorophenyl)-8,9-dihydro-1-methyl-8-[(4-morpholinyl)carbonyl]-4H,7H-cyclopenta[4.5]thieno[3,2-f][1,2,4]triazolo[4,3-a][1,4]diazepine.

EGFR kinase inhibitors include, for example, 4-[(3-chloro-4-fluorophenyl)amino]-7-(2-{4-[(S)-(2-oxotetrahydro furan-5-yl)carbonyl]piperazin-1-yl}-ethoxy)-6-[(vinylcarbonyl)amino]quinazoline, 4-[(3-chloro-4-fluorophenyl)amino]-7-[4-((S)-6-methyl-2-oxomorpholin-4-yl)butyloxy]-6-[(vinylcarbonyl)amino]quinazoline, 4-[(3-chloro-4-fluorophenyl)amino]-7-[4-((R)-6-methyl-2-oxomorpholin-4-yl)butyloxy]-6-[(vinylcarbonyl)amino]quinazoline, 4-[(3-chloro-4-fluorophenyl)amino]-7-[2-((S)-6-methyl-2-oxomorpholin-4-yl)ethoxy]-6-[(vinylcarbonyl)amino] quinazoline, 4-[(3-chloro-4-fluorophenyl)amino]-6-[(4-{N-[2-(ethoxycarbonyl)ethyl]-N-[(ethoxycarbonyl)methyl]-amino}-1-oxo-2-buten-1-yl)amino]-7-cyclopropylmethoxyquinazoline, 4-[(R)-(1-phenylethyl)amino]-6-{[4-(morpholin-4-yl)-1-oxo-2-buten-1-yl]amino}-7-cyclopropyl-methoxyquinazoline, and 4-[(3-chloro-4-fluorophenyl)amino]-6-[3-(morpholin-4-yl)propyloxy]-7-methoxyquinazoline. Any reference to the above-mentioned EGFR kinase inhibitors also includes any pharmacologically acceptable salts thereof which may exist.

Muscarinic receptor antagonists include substances that directly or indirectly block activation of muscarinic cholinergic receptors. Examples include, but are not limited to, quaternary amines (e.g., methantheline, ipratropium, propantheline), tertiary amines (e.g., dicyclomine, scopolamine) and tricyclic amines (e.g., telenzepine). Other muscarinic receptor antagonists include benztropine, hexahydro-sila-difenidol hydrochloride (HHSID hydrochloride), (+/−)-3-quinuclidinyl xanthene-9-carboxylate hemioxalate (QNX-hemioxalate), telenzepine dihydrochloride and tolterodine, oxybutynin, and atropine.

Examples set forth below demonstrate the synthetic procedures for the preparation of the representative compounds. The examples are provided to illustrate particular aspect of the disclosure and do not constrain the scope of the present invention as defined by the claims.

EXPERIMENTAL DETAILS

Example 1a

Preparation of 1-(4-methoxybenzyl)-1H-pyrazol-5-amine

This compound was synthesized according to procedure reported in *Bioorganic and medicinal chemistry letters,* 13, 1133-1136 (2003).

Example 1b

Preparation of 1-ethyl-3-methyl-1H-pyrazol-5-amine

This compound was synthesized according to procedure reported in *Chem. Pharm. Bull.* 52(9), 1098-1104 (2004).

Example 1c

Preparation of tetrahydro-2H-pyran-4-amine hydrochloride

This compound was synthesized according to the procedure reported in Tetrahedron letters, 42, 4257-4259, (2001).

Example 1d

Preparation of tetrahydro-2H-thiopyran-4-amine

Step a: Tetrahydro-4H-thiopyran-4-one (15 gm, 0.129 mole), hydroxylamine hydrochloride (15.27 gm, 0.219 mole) and sodium acetate trihydrate (30 gm, 0.219 mole) were taken together in a mixture of water (150 ml) and ethanol (60 ml). The reaction mixture was refluxed for about 4 hours. The solvent was evaporated under reduced pressure. Solid compound, which separated out, was filtered and dried under vacuum.
Yield: 15 gm (99%)
Step b: Lithium aluminum hydride (6.96 gm, 0.183 mole) was taken in tetrahydrofuran (80 ml) and solution of tetrahydro-4H-thiopyran-4-one oxime (8 gm, 0.0610 mole) (step a) in tetrahydrofuran (20 ml) was added to it drop wise at 0° C. The reaction mixture was refluxed for about 4 hours and quenched with saturated ammonium chloride solution. Extraction was done using ethyl acetate, organic layer was dried over anhydrous sodium sulphate and concentrated under reduced pressure to get the title compound.
Yield: 8 gm (crude) (100%)

Example 2

Preparation of diethyl {[(1-ethyl-1H-pyrazol-5-yl) amino]methylidene}propanedioate A mixture of 5-amino-1-ethylpyrazole (5 gm, 0.0448 mole) and diethylethoxy methylenemalonate (10.35 ml, 0.0448 mole) was stirred at 120° C. for about 1 hour. The reaction mixture was poured into water and extraction was done with ethyl acetate. The organic layer was dried over anhydrous sodium sulphate and concentrated under reduced pressure to give viscous oil.
Yield: 15 gm (crude) (124%)
The following compounds were prepared similarly
Diethyl {[(1,3-dimethyl-1H-pyrazol-5-yl)amino] methylidene}propanedioate
Diethyl ({[1-(4-methoxybenzyl)-1H-pyrazol-5-yl] amino}methylidene)propanedioate
The following compound can be prepared similarly
Diethyl {[(1-ethyl-3-methyl-1H-pyrazol-5-yl)amino] methylidene}propanedioate Example 2a Preparation of ethyl 4-hydroxy-1-(4-methoxybenzyl)-1H-pyrazolo[3,4-b]pyridine-5-carboxylate Diphenyl ether (180 ml) was heated to about 230° C. (Internal temperature 200-210° C.) under inert atmosphere in a round bottom flask fitted with distillation set and a solution of diethyl ({[1-(4-methoxybenzyl)-1H-pyrazol-5-yl] amino}methylidene)propanedioate (85 gm, 0.227 mol) (example 2) in absolute ethanol (130 ml) was added dropwise. The reaction mixture was heated for about 2 hours. Volatile solubles were distilled out. The mixture was cooled to 45° C. and methanol (150 ml) was added dropwise. Solid, which precipitated out was filtered and washed with methanol and hexane and dried under vacuum.
Yield: 33 gm (crude) (45%)
m/z: (M$^+$+1) 328.10

Example 3

Preparation of ethyl 4-chloro-1-ethyl-1H-pyrazolo[3,4-b]pyridine-5-carboxylate

A mixture of diethyl {[(1-ethyl-1H-pyrazol-5-yl)amino] methylidene}propanedioate (15 gm, 0.0533 mole) (example 2) and phosphorous oxy chloride (76.64 ml, 0.7998 mole) was heated at 110-120° C. under stirring for about 4 hours under argon atmosphere. The reaction mixture was cooled and then poured drop wise into ice water. A pale yellow solid separated which was filtered. The solid was first washed twice with ice cold water and then finally with hexane and dried over vacuum.
Yield: 10 gm (70%)
m/z: (M$^+$+1) 254.2
The following compound was prepared similarly
Ethyl 4-chloro-1,3-dimethyl-1H-pyrazolo[3,4-b]pyridine-5-carboxylate
The following compound can be prepared similarly
Ethyl 4-chloro-1-ethyl-3-methyl-1H-pyrazolo[3,4-b]pyridine-5-carboxylate Example 3a Preparation of ethyl 4-chloro-1-(4-methoxybenzyl)-1H-pyrazolo[3,4-b]pyridine-5-carboxylate The title compound was prepared by following the procedure of example 3 using ethyl 4-hydroxy-1-(4-methoxybenzyl)-1H-pyrazolo[3,4-b]pyridine-5-carboxylate (example 2a).
m/z: (M$^+$+1) 346.09

Example 4

Preparation of ethyl 4-(cyclohexylamino)-1-ethyl-1H-pyrazolo[3,4-b]pyridine-5-carboxylate Cyclohexyl amine (9.07 ml, 0.7905 mole) was added to a mixture of ethyl 4-chloro-1-ethyl-1H-pyrazolo[3,4-b]pyridine-5-carboxylate (10 gm, 0.0395 mole) (example 3) in acetonitrile. After stirring for about 2 h at 110° C., acetonitrile was removed under reduced pressure. Water was added and the reaction mixture was extracted with ethyl acetate. The organic layer was washed with brine, dried over anhydrous sodium sulphate and concentrated in vacuo to give brownish solid.

Yield: 9.6 gm (78%)
m/z: ($M^+$+1) 317.22
The following compounds were prepared similarly
Ethyl 1-ethyl-4-(tetrahydro-2H-pyran-4-ylamino)-1H-pyrazolo[3,4-b]pyridine-5-carboxylate
m/z: ($M^+$+1) 319.26
Ethyl 1-ethyl-4-[(4-hydroxycyclohexyl)amino]-1H-pyrazolo[3,4-b]pyridine-5-carboxylate
m/z: ($M^+$+1) 333.06
Ethyl 4-cyclopropylamino-1-ethyl-1H-pyrazolo[3,4-b]pyridine-5-carboxylate
m/z: ($M^+$+1) 275.0
Ethyl 4-(cyclopropylamino)-1,3-dimethyl-1H-pyrazolo[3,4-b]pyridine-5-carboxylate
Ethyl 4-(cyclopentylamino)-1-ethyl-1H-pyrazolo[3,4-b]pyridine-5-carboxylate
Ethyl 4-(cyclopentylamino)-1,3-dimethyl-1H-pyrazolo[3,4-b]pyridine-5-carboxylate
Ethyl 1-(4-methoxybenzyl)-4-(tetrahydro-2H-thiopyran-4-ylamino)-1H-pyrazolo[3,4-b]pyridine-5-carboxylate
m/z: ($M^+$+1) 427.14
Ethyl 4-(cyclohexylamino)-1-(4-methoxybenzyl)-1H-pyrazolo[3,4-b]pyridine-5-carboxylate
m/z: ($M^+$+1) 409.22
Ethyl 4-{[1-(tert-butoxycarbonyl)piperidin-4-yl]amino}-1-ethyl-1H-pyrazolo[3,4-b]pyridine-5-carboxylate
m/z: ($M^+$+1) 418.39
Ethyl 1-(4-methoxybenzyl)-4-[(3-methoxyphenyl)amino]-1H-pyrazolo[3,4-b]pyridine-5-carboxylate
m/z: ($M^+$+1) 433.63
Ethyl 1-(4-methoxybenzyl)-4-(tetrahydro-2H-pyran-4-ylamino)-1H-pyrazolo[3,4-b]pyridine-5-carboxylate
m/z: ($M^+$+1) 411.14
Ethyl 4-(benzylamino)-1-(4-methoxybenzyl)-1H-pyrazolo[3,4-b]pyridine-5-carboxylate
m/z: ($M^+$+1) 417.14
Ethyl 1-ethyl-4-(tetrahydro-2H-thiopyran-4-ylamino)-1H-pyrazolo[3,4-b]pyridine-5-carboxylate

Example 4a

Preparation of 4-chloro-1-ethyl-1H-pyrazolo[3,4-b]pyridine-5-carboxylic acid A solution of ethyl 4-chloro-1-ethyl-1H-pyrazolo[3,4-b]pyridine-5-carboxylate (0.013 mol) (example 3) in dioxane is treated with potassium hydroxide (0.13 mol in 30 ml water) solution. The reaction mixture is stirred for about 3-4 hrs and concentrated under reduced pressure. It is acidified with hydrochloric acid to pH of about 3-4, extracted with ethyl acetate, washed with brine and dried under vacuo

Example 4b

Preparation of 4-{[4-(tert-butoxycarbonyl)cyclohexyl]amino}-1-ethyl-1H-pyrazolo[3,4-b]pyridine-5-carboxylic acid A solution of 4-chloro-1-ethyl-1H-pyrazolo[3,4-b]pyridine-5-carboxylic acid (0.0088 mol) (example 4a) in acetonitrile is treated with tert-butyl 4-aminocyclohexanecarboxylate (0.026 mol). The reaction mixture is refluxed for about 3-4 hrs. Solvent is evaporated off and water is added and extraction is done with ethyl acetate. The organic layer is washed with brine, dried and concentrated under reduced pressure to give crude compound, which is purified by column chromatography.

The following compound can be prepared similarly
4-{[3-(tert-Butoxycarbonyl)cyclobutyl]amino}-1-ethyl-1H-pyrazolo[3,4-b]pyridine-5-carboxylic acid

Example 4c

Preparation of ethyl 4-[(1,1-dioxidotetrahydro-2H-thiopyran-4-yl)amino]-1-(4-methoxybenzyl)-1H-pyrazolo[3,4-b]pyridine-5-carboxylate Ethyl 1-(4-methoxybenzyl)-4-(tetrahydro-2H-thiopyran-4-ylamino)-1H-pyrazolo[3,4-b]pyridine-5-carboxylate (500 mg, 0.00117 mole) (example 4) was taken in dichloromethane (5 ml). At 0° C., m-chloroperbenzoic acid (600 mg, 0.00352 mole) was added and the mixture was stirred overnight. Water was added and extraction was done using dichloromethane. The organic layer was washed with saturated ammonium bicarbonate and then with brine, dried over anhydrous sodium sulphate and concentrated under reduced pressure to get the title compound.

Yield: 500 mg (93%)
m/z: ($M^+$+1) 495.16
The following compound can be prepared similarly
Ethyl 4-[(1,1-dioxidotetrahydro-2H-thiopyran-4-yl)amino]-1-ethyl-1H-pyrazolo[3,4-b]pyridine-5-carboxylate

Example 5

Preparation of 4-cyclohexylamino-1-ethyl-1H-pyrazolo[3,4-b]pyridine-5-carboxylic acid Sodium hydroxide solution (4.09 gm in 20 ml water) was added to a solution of ethyl 4-(cyclohexylamino)-1-ethyl-1H-pyrazolo[3,4-b]pyridine-5-carboxylate (9.32 gm, 0.0294 mole) (example 4) in ethanol. The reaction mixture was stirred for about 14 h at room temperature and then warmed for about 1 h at 60° C. Water was added and the reaction mixture was extracted with ethyl acetate. Aqueous layer was acidified by using hydrochloric acid (2N) to pH of about 4-5. White solid, which was obtained, was filtered and dried in vacuo.

Yield: 9 gm crude (100%)
m/z: ($M^+$+1) 289.22
The following compounds were prepared similarly
1-Ethyl-4-(tetrahydro-2H-pyran-4-ylamino)-1H-pyrazolo[3,4-b]pyridine-5-carboxylic acid
m/z: ($M^+$+1) 291.36
1-Ethyl-4-[(4-hydroxycyclohexyl)amino]-1H-pyrazolo[3,4-b]pyridine-5-carboxylic acid
m/z: ($M^+$+1) 305.10

4-Cyclopropylamino-1-ethyl-1H-pyrazolo[3,4-b]pyridine-5-carboxylic acid
m/z: (M$^+$+1) 274.2

4-(Cyclopropylamino)-1,3-dimethyl-1H-pyrazolo[3,4-b]pyridine-5-carboxylic acid 4-(Cyclopentylamino)-1-ethyl-1H-pyrazolo[3,4-b]pyridine-5-carboxylic acid 4-(Cyclopentylamino)-1,3-dimethyl-1H-pyrazolo[3,4-b]pyridine-5-carboxylic acid 4-[(1,1-Dioxidotetrahydro-2H-thiopyran-4-yl)amino]-1-ethyl-1H-pyrazolo[3,4-b]pyridine-5-carboxylic acid 4-[(1,1-Dioxidotetrahydro-2H-thiopyran-4-yl)amino]-1-(4-methoxybenzyl)-1H-pyrazolo[3,4-b]pyridine-5-carboxylic acid
m/z: (M$^+$+1) 383.28

4-(Benzylamino)-1-(4-methoxybenzyl)-1H-pyrazolo[3,4-b]pyridine-5-carboxylic acid
m/z: (M$^+$+1) 389.08

4-(Cyclohexylamino)-1-(4-methoxybenzyl)-1H-pyrazolo[3,4-b]pyridine-5-carboxylic acid 4-{[1-(tert-Butoxycarbonyl)piperidin-4-yl]amino}-1-ethyl-1H-pyrazolo[3,4-b]pyridine-5-carboxylic acid
m/z: (M$^+$+1) 390.40

1-(4-Methoxybenzyl)-4-[(3-methoxyphenyl)amino]-1H-pyrazolo[3,4-b]pyridine-5-carboxylic acid
m/z: (M$^+$+1) 405.05

1-(4-Methoxybenzyl)-4-(tetrahydro-2H-pyran-4-ylamino)-1H-pyrazolo[3,4-b]pyridine-5-carboxylic acid
m/z: (M$^+$+1) 383.28

Example 6

Preparation of 4-(cyclohexylamino)-1-ethyl-N-methoxy-N-methyl-1H-pyrazolo[3,4-b]pyridine-5-carboxamide (Intermediate No. 1)

4-Cyclohexylamino-1-ethyl-1H-pyrazolo[3,4-b]pyridine-5-carboxylic acid (0.200 gm, 0.0006 mole) (example 5) and N,O-dimethylhydroxylamine hydrochloride (0.102 gm, 0.0010 mole) were taken in dimethylformamide. At 0° C., hydroxybenzotriazole (0.162 gm, 0.0012 mole) and N-methylmorpholine (0.30 ml, 0.0027 mole) were added and the reaction mixture was stirred for about 1 h. 1-Ethyl-3-(3-dimethylaminopropyl) carbodiimide hydrochloride (0.266 gm, 0.0012 mole) was added and the reaction mixture was stirred for about 14 h. Water was added and extraction was carried out with ethyl acetate. The organic layer was washed with brine, dried over anhydrous sodium sulphate and concentrated in vacuo. The compound was purified over preparative thin layer chromatography.
Yield: 136 mg (59%)
m/z: (M$^+$+1) 332.26

The following intermediates were prepared similarly
1-Ethyl-N-methoxy-N-methyl-4-(tetrahydro-2H-pyran-4-ylamino)-1H-pyrazolo[3,4-b]pyridine-5-carboxamide (Intermediate No. 2)
m/z: (M$^+$+1) 334.11

1-Ethyl-4-[(4-hydroxycyclohexyl)amino]-N-methoxy-N-methyl-1H-pyrazolo[3,4-b]pyridine-5-carboxamide (Intermediate No. 3)
m/z: (M$^+$+1) 348.05

4-(Cyclopropylamino)-1-ethyl-N-methoxy-N-methyl-1H-pyrazolo[3,4-b]pyridine-5-carboxamide (Intermediate No. 4)
m/z: (M$^+$+1) 290.2

4-(Cyclopropylamino)-N-methoxy-N-1,3-trimethyl-1H-pyrazolo[3,4-b]pyridine-5-carboxamide (Intermediate No. 5)

4-(Cyclopentylamino)-1-ethyl-N-methoxy-N-methyl-1H-pyrazolo[3,4-b]pyridine-5-carboxamide (Intermediate No. 6)

4-(Cyclopentylamino)-N-methoxy-N-1,3-trimethyl-1H-pyrazolo[3,4-b]pyridine-5-carboxamide (Intermediate No. 7)

4-[(1,1-Dioxidotetrahydro-2H-thiopyran-4-yl)amino]-1-ethyl-N-methoxy-N-methyl-1H-pyrazolo[3,4-b]pyridine-5-carboxamide ((Intermediate No. 24),
m/z: (M$^+$+1) 382.10

4-(Benzylamino)-N-methoxy-1-(4-methoxybenzyl)-N-methyl-1H-pyrazolo[3,4-b]pyridine-5-carboxamide
m/z: (M$^+$+1) 432.10

4-[(1,1-Dioxidotetrahydro-2H-thiopyran-4-yl)amino]-N-methoxy-1-(4-methoxybenzyl)-N-methyl-1H-pyrazolo[3,4-b]pyridine-5-carboxamide
m/z: (M$^+$+1) 474.06

4-(Cyclohexylamino)-N-methoxy-1-(4-methoxybenzyl)-N-methyl-1H-pyrazolo[3,4-b]pyridine-5-carboxamide
m/z: (M$^+$+1) 332.26

1-Ethyl-N-methoxy-4-[(3-methoxyphenyl)amino]-N-methyl-1H-pyrazolo[3,4-b]pyridine-5-carboxamide (Intermediate No. 23), tert-Butyl 4-({1-ethyl-5-[methoxy(methyl)carbamoyl]-1H-pyrazolo[3,4-b]pyridin-4-yl}amino)piperidine-1-carboxylate (Intermediate No. 22),
m/z: (M$^+$+1) 433.36

N-methoxy-1-(4-methoxybenzyl)-4-[(3-methoxyphenyl)amino]-N-methyl-1H-pyrazolo[3,4-b]pyridine-5-carboxamide
m/z: (M$^+$+1) 448.15

N-methoxy-1-(4-methoxybenzyl)-N-methyl-4-(tetrahydro-2H-pyran-4-ylamino)-1H-pyrazolo[3,4-b]pyridine-5-carboxamide
m/z: (M$^+$+1) 426.38

The following compounds can be prepared similarly
tert-Butyl 3-({1-ethyl-5-[methoxy(methyl)carbamoyl]-1H-pyrazolo[3,4-b]pyridin-4-yl}amino)cyclobutanecarboxylate tert-Butyl 4-({1-ethyl-5-[methoxy(methyl)carbamoyl]-1H-pyrazolo[3,4-b]pyridin-4-yl}amino)cyclohexanecarboxylate Example 6a Preparation of 4-(benzylamino)-N-methoxy-N-methyl-1H-pyrazolo[3,4-b]pyridine-5-carboxamide Trifluoroacetic acid (5.35 ml, 69.6 mmol) was added to the solution of 4-(benzylamino)-N-methoxy-1-(4-methoxybenzyl)-N-methyl-1H-pyrazolo[3,4-b]pyridine-5-carboxamide (3 gm, 6.96 mmol) (example 6) in dichloroethane (20 ml) and the reaction mixture was refluxed for about 2 hours under inert atmosphere. It was cooled, diluted with ethyl acetate, washed with saturated sodium bicarbonate, water and brine, dried over anhydrous sodium sulphate and concentrated under reduced pressure to get the title compound.
Yield: 2 gm (92%)
The following compound was prepared similarly
4-(Cyclohexylamino)-N-methoxy-N-methyl-1H-pyrazolo[3,4-b]pyridine-5-carboxamide
m/z: (M$^+$+1) 304.12

Example 6b

Preparation of 4-(benzylamino)-1-ethyl-N-methoxy-N-methyl-1H-pyrazolo[3,4-b]pyridine-5-carboxamide (Intermediate No. 25)

Ethyl iodide (1.52 gm, 9.63 mmol) and potassium carbonate (2.214 gm, 16.05 mmol) were added to the solution 4-(benzylamino)-N-methoxy-N-methyl-1H-pyrazolo[3,4-b]pyridine-5-carboxamide (1 gm, 3.21 mmol) (example 6a) in dimethylformamide and the reaction mixture was stirred at 60° C. for about 5 hours. It was cooled, diluted with water and extracted with ethyl acetate. The organic layer was washed with brine, dried over anhydrous sodium sulphate and concentrated under reduced pressure. The crude product was purified over silica gel column.

Yield: 0.800 gm (73%)
m/z: (M$^+$+1) 340.22

Example 7

Preparation of 4-(cyclohexylamino)-1-ethyl-1H-pyrazolo[3,4-b]pyridine-5-carbaldehyde (Intermediate No. 8)

Toluene was cooled to −30 to −35° C. and vitride (0.12 ml, 0.0006 mole) was added. After about 10 min., 4-(cyclohexylamino)-1-ethyl-N-methoxy-N-methyl-1H-pyrazolo[3,4-b]pyridine-5-carboxamide (0.10 gm, 0.0003 mole) (example 6) was added and the reaction mixture was stirred for about 4 h. Citric acid (10%) solution was added dropwise to quench the reaction and the reaction mixture was extracted with ethyl acetate. The organic layer was washed with brine and dried over anhydrous sodium sulphate and concentrated in vacuo. The compound was purified over preparative thin layer chromatography.

Yield: 54 mg (65%)
m/z: 273.23

The following intermediates were prepared similarly
1-Ethyl-4-(tetrahydro-2H-pyran-4-ylamino)-1H-pyrazolo[3,4-b]pyridine-5-carbaldehyde (Intermediate No. 9)
m/z: (M$^+$+1) 275.06
1-Ethyl-4-[(4-hydroxycyclohexyl)amino]-1H-pyrazolo[3,4-b]pyridine-5-carbaldehyde (Intermediate No. 10)
m/z: (M$^+$+1) 289.06
4-Cyclopropylamino-1-ethyl-1H-pyrazolo[3,4-b]pyridine-5-carbaldehyde (Intermediate No. 11)
m/z: (M$^+$+1) 231.1
4-Cyclopropylamino-1,3-dimethyl-1H-pyrazolo[3,4-b]pyridine-5-carbaldehyde (Intermediate No. 12)
4-(Cyclopentylamino)-1-ethyl-1H-pyrazolo[3,4-b]pyridine-5-carbaldehyde (Intermediate No. 13)
4-(Cyclopentylamino)-1,3-dimethyl-1H-pyrazolo[3,4-b]pyridine-5-carbaldehyde (Intermediate No. 14)
1-Ethyl-4-[(3-methoxyphenyl)amino]-1H-pyrazolo[3,4-b]pyridine-5-carbaldehyde (Intermediate No. 26),
1-(4-Methoxybenzyl)-4-[(3-methoxyphenyl)amino]-1H-pyrazolo[3,4-b]pyridine-5-carbaldehyde
m/z: (M$^+$+1) 389.08
tert-Butyl 4-[(1-ethyl-5-formyl-1H-pyrazolo[3,4-b]pyridin-4-yl)amino]piperidine-1-carboxylate (Intermediate No. 27),
m/z: (M$^+$+1) 374.35
4-[(1,1-Dioxidotetrahydro-2H-thiopyran-4-yl)amino]-1-ethyl-1H-pyrazolo[3,4-b]pyridine-5-carbaldehyde (Intermediate No. 28),
m/z: (M$^+$+1) 323.19
4-(Benzylamino)-1-ethyl-1H-pyrazolo[3,4-b]pyridine-5-carbaldehyde (Intermediate No. 29),
m/z: (M$^+$+1) 281.11
4-(Cyclohexylamino)-1-(4-methoxybenzyl)-1H-pyrazolo[3,4-b]pyridine-5-carbaldehyde
m/z: (M$^+$+1) 365.31
1-(4-Methoxybenzyl)-4-(tetrahydro-2H-pyran-4-ylamino)-1H-pyrazolo[3,4-b]pyridine-5-carbaldehyde
m/z: (M$^+$+1) 367.10

The following compounds can be prepared similarly
tert-Butyl 4-[(1-ethyl-5-formyl-1H-pyrazolo[3,4-b]pyridin-4-yl)amino]cyclohexane carboxylate
tert-Butyl 3-[(1-ethyl-5-formyl-1H-pyrazolo[3,4-b]pyridin-4-yl)amino]cyclobutane carboxylate

Example 8

Preparation of 4-(cyclohexylamino)-1-ethyl-1H-pyrazolo[3,4-b]pyridine-5-carbaldehyde oxime (Intermediate No. 15)

Hydroxylamine hydrochloride (0.255 gm, 0.0036 mole) and sodium acetate (0.301 gm, 0.0036 mole) were added to a stirred solution of 4-(cyclohexylamino)-1-ethyl-1H-pyrazolo[3,4-b]pyridine-5-carbaldehyde (0.250 gm, 0.0009 mole) (example 7) in ethanol. The reaction mixture was allowed to stir at room temperature for about 2 h. Ethanol was removed under reduced pressure and residue was poured in water. The title compound was then filtered and washed with water twice and finally with hexane.

Yield: 0.202 gm (77%)
m/z: (M$^+$+1) 288.31

The following intermediates were prepared similarly:
1-Ethyl-4-(tetrahydro-2H-pyran-4-ylamino)-1H-pyrazolo[3,4-b]pyridine-5-carbaldehyde oxime (Intermediate No. 16)
m/z: (M$^+$+1) 290.13
1-Ethyl-4-[(4-hydroxycyclohexyl)amino]-1H-pyrazolo[3,4-b]pyridine-5-carbaldehyde oxime (Intermediate No. 17)
m/z: (M$^+$+1) 304.11
4-Cyclopropylamino-1-ethyl-1H-pyrazolo[3,4-b]pyridine-5-carbaldehyde oxime (Intermediate No. 18)
m/z: (M$^+$+1) 246.1
4-(Cyclopropylamino)-1,3-dimethyl-1H-pyrazolo[3,4-b]pyridine-5-carbaldehyde oxime (Intermediate No. 19)
4-(Cyclopentylamino)-1-ethyl-1H-pyrazolo[3,4-b]pyridine-5-carbaldehyde oxime (Intermediate No. 20)
4-(Cyclopentylamino)-1,3-dimethyl-1H-pyrazolo[3,4-b]pyridine-5-carbaldehyde oxime (Intermediate No. 21)
1-Ethyl-4-[(3-methoxyphenyl)amino]-1H-pyrazolo[3,4-b]pyridine-5-carbaldehyde oxime (intermediate No. 30)
tert-Butyl 4-[(1-ethyl-5-[(E)-(hydroxyimino)methyl-1H-pyrazolo[3,4-b]pyridin-4-yl)amino]piperidine-1-carboxylate (intermediate No. 32)
m/z: (M$^+$+1) 389.22
4-[(1,1-Dioxidotetrahydro-2H-thiopyran-4-yl)amino]-1-ethyl-1H-pyrazolo[3,4-b]pyridine-5-carbaldehyde oxime (intermediate No. 33)
m/z: (M$^+$+1) 338.22
4-(Benzylamino)-1-ethyl-1H-pyrazolo[3,4-b]pyridine-5-carb aldehyde oxime (intermediate No. 31)
4-(Cyclohexylamino)-1-(4-methoxybenzyl)-1H-pyrazolo[3,4-b]pyridine-5-carbaldehyde oxime 1-(4-Methoxybenzyl)-4-(tetrahydro-2H-pyran-4-ylamino)-1H-pyrazolo[3,4-b]pyridine-5-carbaldehyde oxime
m/z: ($M^+$+1) 382.21

1-(4-Methoxybenzyl)-4-[(3-methoxyphenyl)amino]-1H-pyrazolo[3,4-b]pyridine-5-carbaldehyde oxime
m/z: ($M^+$+1) 404.11

The following compounds can be prepared similarly tert-butyl 3-({1-ethyl-5-[(Z)-(hydroxyimino)methyl]-1H-pyrazolo[3,4-b]pyridin-4-yl}amino)cyclobutanecarboxylate tert-butyl 4-({1-ethyl-5-[(E)-(hydroxyimino)methyl]-1H-pyrazolo[3,4-b]pyridin-4-yl}amino)cyclohexanecarboxylate

Example 8(a)

Preparation of 8-methylene-1,4-dioxaspiro[4.5]decane

Potassium tert-butoxide (3.230 gm, 28.812 mmol) and triphenylphosphine methyl iodide (10.286 gm, 28.812 mmol) were dissolved in dry tetrahydrofuran (30 ml). The mixture was cooled to −78° C. and stirred at the same temperature for about 15 minutes. 1,4-Dioxaspiro[4.5]decan-8-one (3.0 gm, 19.208 mmol) in tetrahydrofuran was added drop wise and the mixture was stirred at the same temperature for about 30 minutes and then it was warmed to room temperature and stirred overnight, extaction was done with ethyl acetate and water. The organic layer was dried over sodium sulphate and concentrated. Purification was done by column chromatography.

Yield: 2.0 gm (67%)
m/z: ($M^+$+1) 155
NMR: (6, $CDCl_3$): 4.66 (s, 2H), 3.95 (s, 4H), 2.29-2.26 (t, 4H), 1.71-1.67 (t, 4H).

The following compound was prepared similarly
{[(3-Methylidenecyclobutyl)methoxy]methyl}benzene

Example 8(b)

Preparation of 2-methylidene-5,8-dioxaspiro[3.4]octane

Step a: Preparation of 3-[(benzyloxy)methyl]-2,2-dichlorocyclobutanone

The title compound was synthesized by following the procedure disclosed in WO 2006/092691.

Step b: Preparation of 3-[(benzyloxy)methyl]cyclobutanone

The title compound was synthesized by following the procedure disclosed in WO 2006/092691.

Step c: Preparation of 2-[(benzyloxy)methyl]-5,8-dioxaspiro[3.4]octane p-Toluene sulphonic acid (2.0 gm) was added to a solution of 3-[(benzyloxy)methyl]cyclobutanone (25.0 gm, 131.6 mmol) (step b) and 1,2-ethanediol (8.98 gm, 144.7 mmol) in benzene and the reaction mixture was refluxed with removal of water through dean-stark apparatus. After about 6 hours, the reaction mixture was cooled to room temperature and washed with saturated sodium bicarbonate solution, followed by water and brine. The organic layer was dried over sodium sulphate and concentrated under reduced pressure to get a crude product, which was purified by column chromatography.

Yield: 22.0 gm (71%)

Step d: Preparation of 5,8-dioxaspiro[3.4]oct-2-ylmethanol

Palladium/carbon (10%) was added to a solution of 2-[(benzyloxy)methyl]-5,8-dioxaspiro[3.4]octane (22.0 gm, 94.0 mmol) (step c) in methanol and the mixture was stirred at room temperature under hydrogen balloon for about 4 hours. It was filtered through celite bed and residue was washed with methanol. The combined filtrate was concentrated under reduced pressure.

Yield: 14.0 gm (97%)

Step e: Preparation of 2-(bromomethyl)-5,8-dioxaspiro[3.4]octane

Triphenylphosphine (6.28 gm, 24 mmol) in dichloromethane was added drop wise to a solution of 5,8-dioxaspiro[3.4]oct-2-ylmethanol (2.3 gm, 16 mmol) (step d) and tetrabromomethane (6.62 gm, 20 mmol) in dichloromethane. The reaction mixture was stirred at room temperature for about 6 hours. The solvent was removed under reduced pressure and the residue was extracted with diethyl ether. The organic layer was concentrated under reduced pressure to get a crude product, which was purified by column chromatography.

Yield: 1.3 gm (39.4%)

Step f: Preparation of 2-methylidene-5,8-dioxaspiro[3.4]octane

A mixture of 2-(bromomethyl)-5,8-dioxaspiro[3.4]octane (1.3 gm, 6.28 mmol) (step e), polyethylene glycol (PEG-600) (0.5 gm), 50% aqueous sodium hydroxide solution (5 ml) and benzene was refluxed for about 12 hours. The reaction mixture was cooled, diluted with water and extracted with diethyl ether. The organic layer was washed with brine, dried over sodium sulphate and concentrated under reduced pressure to get a crude product, which was purified by column chromatography.

Yield: 0.26 gm (33%)

Example 9

Preparation of N-cyclohexyl-1-ethyl-5-(1-oxa-2-azaspiro[4.4]non-2-en-3-yl)-1H-pyrazolo[3,4-b]pyridin-4-amine (Compound No. 1)

Methylene cyclopentane (0.073 ml, 0.0006 mole) was added to 4-(cyclohexylamino)-1-ethyl-1H-pyrazolo[3,4-b]pyridine-5-carbaldehyde oxime (0.1 gm, 0.0003 mole) (example 8) in tetrahydrofuran. The reaction mixture was stirred at room temperature for about 5 minutes. Sodium hypochlorite (5 ml) was added slowly to the reaction mixture over a period of about 5 minutes and the mixture was allowed to stir at room temperature for about 5 h. The organic solvent was evaporated and the residue was extracted in ethyl acetate. The organic layer was concentrated and the title compound obtained was purified by preparative thin layer chromatography.

Yield: 40%
m/z: ($M^+$+1) 368.36

NMR: (δ, CDCl₃): 8.93-8.91 (d, 1H), 8.11 (s, 1H), 7.97 (s, 1H), 4.49-4.44 (q, 2H), 3.92-3.89 (m, 1H), 3.44 (s, 2H), 2.20-1.66 (m, 14H), 1.51-1.48 (t, 3H).

The following compounds were prepared similarly

N-cyclohexyl-1-ethyl-5-(5-oxa-6-azaspiro[3.4]oct-6-en-7-yl)-1H-pyrazolo[3,4-b]pyridin-4-amine (Compound No. 2),
Yield: 30%
m/z: (M⁺+1) 354.38

N-cyclohexyl-1-ethyl-5-(1-oxa-2-azaspiro[4.5]dec-2-en-3-yl)-1H-pyrazolo[3,4-b]pyridin-4-amine (Compound No. 3),
Yield: 28%
m/z: (M⁺+1) 382.41

1-Ethyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 7),
Yield: 28.5%
m/z: (M⁺+1) 356.10

1-Ethyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 8),
Yield: 25.6%
m/z: (M⁺+1) 370.10

1-Ethyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 9),
Yield: 26.1%
m/z: (M⁺+1) 384.12

4-{[1-Ethyl-5-(1-oxa-2-azaspiro[4.4]non-2-en-3-yl)-1H-pyrazolo[3,4-b]pyridin-4-yl]amino}cyclohexanol (Compound No. 10),
Yield: 32.6%
m/z: (M⁺+1) 384.08

4-{[1-Ethyl-5-(1-oxa-2-azaspiro[4.5]dec-2-en-3-yl)-1H-pyrazolo[3,4-b]pyridin-4-yl]amino}cyclohexanol (Compound No. 11),
Yield: 33.4%
m/z: (M⁺+1) 398.09

4-{[1-Ethyl-5-(5-oxa-6-azaspiro[3.4]oct-6-en-7-yl)-1H-pyrazolo[3,4-b]pyridin-4-yl]amino}cyclohexanol (Compound No. 13),
Yield: 35.3%
m/z: (M⁺+1) 370.08 tert-Butyl 3-[4-(cyclohexylamino)-1-ethyl-1H-pyrazolo[3,4-b]pyridin-5-yl]-1-oxa-2,8-diazaspiro[4.5]dec-2-ene-8-carboxylate (Compound No. 15),
Yield: 56%
m/z: (M⁺-OC(CH₃)₃) 410

4-{[1-Ethyl-5-(1,9,12-trioxa-2-azadispiro[4.2.4.2]tetradec-2-en-3-yl)-1H-pyrazolo[3,4-b]pyridin-4-yl]amino}cyclohexanol (Compound No. 19),
Yield: 6.0%
m/z: (M⁺+1) 456.05

N-cyclopropyl-1-ethyl-5-(1-oxa-2-azaspiro[4.5]dec-2-en-3-yl)-1H-pyrazolo[3,4-b]pyridin-4-amine (Compound No. 29),
Yield: 21.68%
m/z: (M⁺+1) 340.2

N-cyclopropyl-1-ethyl-5-(1-oxa-2-azaspiro[4.4]non-2-en-3-yl)-1H-pyrazolo[3,4-b]pyridin-4-amine (Compound No. 30),
Yield: 28.6%
m/z: (M⁺+1) 326.2

N-cyclopropyl-1-ethyl-5-(5-oxa-6-azaspiro[3.4]oct-6-en-7-yl)-1H-pyrazolo[3,4-b]pyridin-4-amine (Compound No. 31),
Yield: 15.87%
m/z: (M⁺+1) 312.2

N-cyclopentyl-1,3-dimethyl-5-(5-oxa-6-azaspiro[3.4]oct-6-en-7-yl)-1H-pyrazolo[3,4-b]pyridin-4-amine (Compound No. 32),
Yield: 28.6%
m/z: (M⁺+1) 340.1

N-cyclopentyl-1,3-dimethyl-5-(1-oxa-2-azaspiro[4.4]non-2-en-3-yl)-1H-pyrazolo[3,4-b]pyridin-4-amine (Compound No. 33),
Yield: 22%
m/z: (M⁺+1) 354.2

N-cyclopentyl-1,3-dimethyl-5-(1-oxa-2-azaspiro[4.5]dec-2-en-3-yl)-1H-pyrazolo[3,4-b]pyridin-4-amine (Compound No. 34),
Yield: 23.29%
m/z: (M⁺+1) 368.1

N-cyclopropyl-1,3-dimethyl-5-(1-oxa-2-azaspiro[4.4]non-2-en-3-yl)-1H-pyrazolo[3,4-b]pyridin-4-amine (Compound No. 35),
Yield: 23.44%
m/z: (M⁺+1) 326.1

N-cyclopropyl-1,3-dimethyl-5-(5-oxa-6-azaspiro[3.4]oct-6-en-7-yl)-1H-pyrazolo[3,4-b]pyridin-4-amine (Compound No. 36),
Yield: 15.74%
m/z: (M⁺+1) 312.1

N-cyclopropyl-1,3-dimethyl-5-(1-oxa-2-azaspiro[4.5]dec-2-en-3-yl)-1H-pyrazolo[3,4-b]pyridin-4-amine (Compound No. 37),
Yield: 18.11%
m/z: (M⁺+1) 340.1

N-cyclopentyl-1-ethyl-5-(5-oxa-6-azaspiro[3.4]oct-6-en-7-yl)-1H-pyrazolo[3,4-b]pyridin-4-amine (Compound No. 38),
Yield: 32.3%
m/z: (M⁺+1) 340.1

N-cyclopentyl-1-ethyl-5-(1-oxa-2-azaspiro[4.4]non-2-en-3-yl)-1H-pyrazolo[3,4-b]pyridin-4-amine (Compound No. 39),
Yield: 31%
m/z: (M⁺+1) 354.2

1-(4-Methoxybenzyl)-N-(3-methoxyphenyl)-5-(1-oxa-2-azaspiro[4.4]non-2-en-3-yl)-1H-pyrazolo[3,4-b]pyridin-4-amine (Compound No. 41),
Yield: 21%
m/z: (M⁺+1) 484.06

7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 47),
Yield: 19%
m/z: (M⁺+1) 381.16

7-[4-(Cyclohexylamino)-1-ethyl-1H-pyrazolo[3,4-b]pyridin-5-yl]-5-oxa-6-azaspiro[3.4]oct-6-ene-2-carbonitrile (Compound No. 48),
Yield: 65%
m/z: (M⁺+1) 379.23

1-(4-Methoxybenzyl)-N-(tetrahydro-2H-pyran-4-yl)-5-(1,9,12-trioxa-2-azadispiro[4.2.4.2]tetradec-2-en-3-yl)-1H-pyrazolo[3,4-b]pyridin-4-amine (Compound No. 55),
Yield: 59%
m/z: (M⁺+1) 534.19

7-[1-(4-Methoxybenzyl)-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 57),
Yield: 48%
m/z: (M⁺+1) 473.22

N-Cyclohexyl-1-ethyl-5-(1,9,12-trioxa-2-azadispiro [4.2.4.2]tetradec-2-en-3-yl)-1H-pyrazolo[3,4-b]pyridin-4-amine (Compound No. 80),
Yield: 65%
m/z: (M$^+$+1) 420.21

Tert-butyl 4-{[1-ethyl-5-(1-oxa-2-azaspiro[4.4]non-2-en-3-yl)-1H-pyrazolo[3,4-b]pyridin-4-yl]amino}piperidine-1-carboxylate (Compound No. 83),
Yield: 37%
m/z: (M$^+$+1) 469.42

Tert-butyl 4-{[1-ethyl-5-(1-oxa-2-azaspiro[4.5]dec-2-en-3-yl)-1H-pyrazolo[3,4-b]pyridin-4-yl]amino}piperidine-1-carboxylate (Compound No. 87),
Yield: 26%
m/z: (M$^+$+1) 483.39

N-cyclohexyl-1-(4-methoxybenzyl)-5-(1-oxa-2-azaspiro [4.4]non-2-en-3-yl)-1H-pyrazolo[3,4-b]pyridin-4-amine (Compound No. 91),
Yield: 72%
m/z: (M$^+$+1) 460.35

1-Ethyl-N-(3-methoxyphenyl)-5-(1-oxa-2-azaspiro[4.4]non-2-en-3-yl)-1H-pyrazolo[3,4-b]pyridin-4-amine (Compound No. 94),
Yield: 16%
m/z: (M$^+$+1) 392.17

5-{2-[(Benzyloxy)methyl]-5-oxa-6-azaspiro[3.4]oct-6-en-7-yl}-1-(4-methoxybenzyl)-N-(tetrahydro-2H-pyran-4-yl)-1H-pyrazolo[3,4-b]pyridin-4-amine (Compound No. 97),
Yield: 47%
m/z: 568.19 (M$^+$+1)

1-(4-Methoxybenzyl)-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 100),
Yield: 37%
m/z: (M$^+$+1) 476.34

1-(4-Methoxybenzyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 102),
Yield: 42%
m/z: (M$^+$+1) 462.17

1-(4-Methoxybenzyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 110),
Yield: 38%

Ethyl (cis or trans) 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 112),
Yield: 20%
m/z (M$^+$+1) 454.2

Ethyl (trans or cis) 3-[4-(cyclohexylamino)-1-ethyl-1H-pyrazolo[3,4-b]pyridin-5-yl]-1-oxa-2-azaspiro[4.5]dec-2-ene-8-carboxylate Compound No. 113)
Yield: 19%
m/z (M$^+$+1) 454.2

The following compounds can be prepared similarly

N-cyclohexyl-1-ethyl-5-(1,8,11-trioxa-2-azadispiro[4.1.4.1] dodec-2-en-3-yl)-1H-pyrazolo[3,4-b]pyridin-4-amine, N-benzyl-1-ethyl-5-(5-oxa-6-azaspiro[3.4]oct-6-en-7-yl)-1H-pyrazolo[3,4-b]pyridin-4-amine, tert-Butyl 3-{[1-ethyl-5-(5-oxa-6-azaspiro[3.4]oct-6-en-7-yl)-1H-pyrazolo[3,4-b]pyridin-4-yl]amino}cyclobutanecarboxylate, N-(1,1-dioxidotetrahydro-2H-thiopyran-4-yl)-1-ethyl-5-(1-oxa-2-azaspiro[4.5]dec-2-en-3-yl)-1H-pyrazolo[3,4-b]pyridin-4-amine ((Compound No. 114), 1-Ethyl-3-methyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 136), 1-Ethyl-3-methyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 137), 1-Ethyl-3-methyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 138), 7-[1-Ethyl-3-methyl-4-(tetrahydro-2H-pyran-4-ylamino)-1H-pyrazolo[3,4-b]pyridin-5-yl]-5-oxa-6-azaspiro[3.4] oct-6-ene-2-carbonitrile (Compound No. 139), N-cyclohexyl-1-ethyl-3-methyl-5-(5-oxa-6-azaspiro[3.4] oct-6-en-7-yl)-1H-pyrazolo[3,4-b]pyridin-4-amine (Compound No. 140), 7-[4-(Cyclohexylamino)-1-ethyl-3-methyl-1H-pyrazolo[3, 4-b]pyridin-5-yl]-5-oxa-6-azaspiro[3.4]oct-6-ene-2-carbonitrile (Compound No. 141), N-(1,1-dioxidotetrahydro-2H-thiopyran-4-yl)-1-ethyl-3-methyl-5-(5-oxa-6-azaspiro[3.4]oct-6-en-7-yl)-1H-pyrazolo [3,4-b]pyridin-4-amine (Compound No. 157), N-(1,1-dioxidotetrahydro-2H-thiopyran-4-yl)-1-ethyl-3-methyl-5-(1-oxa-2-azaspiro[4.4]non-2-en-3-yl)-1H-pyrazolo [3,4-b]pyridin-4-amine (Compound No. 158), N-(1,1-dioxidotetrahydro-2H-thiopyran-4-yl)-1-ethyl-3-methyl-5-(1-oxa-2-azaspiro[4.5]dec-2-en-3-yl)-1H-pyrazolo [3,4-b]pyridin-4-amine (Compound No. 159), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro [3.4]oct-6-ene-2-carbonitrile (Compound No. 266), Methyl 7-{4-[(1,1-dioxidotetrahydro-2H-thiopyran-4-yl) amino]-1-ethyl-1H-pyrazolo[3,4-b]pyridin-5-yl}-5-oxa-6-azaspiro[3.4]oct-6-ene-2-carboxylate (Compound No. 268), Ethyl 7-{4-[(1,1-dioxidotetrahydro-2H-thiopyran-4-yl) amino]-1-ethyl-1H-pyrazolo[3,4-b]pyridin-5-yl}-5-oxa-6-azaspiro[3.4]oct-6-ene-2-carboxylate (Compound No. 269), tert-Butyl 7-{4-[(1,1-dioxidotetrahydro-2H-thiopyran-4-yl) amino]-1-ethyl-1H-pyrazolo[3,4-b]pyridin-5-yl}-5-oxa-6-azaspiro[3.4]oct-6-ene-2-carboxylate (Compound No. 270), Ethyl 3-{4-[(1,1-dioxidotetrahydro-2H-thiopyran-4-yl) amino]-1-ethyl-1H-pyrazolo[3,4-b]pyridin-5-yl}-1-oxa-2-azaspiro[4.5]dec-2-ene-8-carboxylate (Compound No. 287), Methyl 3-{4-[(1,1-dioxidotetrahydro-2H-thiopyran-4-yl) amino]-1-ethyl-1H-pyrazolo[3,4-b]pyridin-5-yl}-1-oxa-2-azaspiro[4.5]dec-2-ene-8-carboxylate (Compound No. 288), tert-Butyl 3-{4-[(1,1-dioxidotetrahydro-2H-thiopyran-4-yl) amino]-1-ethyl-1H-pyrazolo[3,4-b]pyridin-5-yl}-1-oxa-2-azaspiro[4.5]dec-2-ene-8-carboxylate (Compound No. 289), Ethyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 330), Ethyl 3-[4-(cyclohexylamino)-1-ethyl-1H-pyrazolo[3,4-b] pyridin-5-yl]-1-oxa-2-azaspiro[4.5]dec-2-ene-8-carboxylate (Compound No. 331), Methyl 3-[4-(cyclohexylamino)-1-ethyl-1H-pyrazolo[3,4-b] pyridin-5-yl]-1-oxa-2-azaspiro[4.5]dec-2-ene-8-carboxylate (Compound No. 332), Methyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 333), tert-Butyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 334), tert-Butyl 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 335), N-(1,1-dioxidotetrahydro-2H-thiopyran-4-yl)-1-ethyl-5-(5-oxa-6-azaspiro[3.4]oct-6-en-7-yl)-1H-pyrazolo[3,4-b]pyridin-4-amine (Compound No. 336), N-(1,1-dioxidotetrahydro-2H-thiopyran-4-yl)-1-ethyl-5-(1-oxa-2-azaspiro[4.4]non-2-en-3-yl)-1H-pyrazolo[3,4-b]pyridin-4-amine (Compound No. 337).

Example 10

Preparation of methyl 3-[4-(cyclohexylamino)-1-ethyl-1H-pyrazolo[3,4-b]pyridin-5-yl]-5-(2-methoxy-2-oxoethyl)-4,5-dihydroisoxazole-5-carboxylate The title compound was prepared by following the procedure of example 9.
Yield: 54%
m/z: (M$^+$+1) 444.45
The following compounds were prepared similarly
Methyl 3-[4-(cyclopentylamino)-1,3-dimethyl-1H-pyrazolo[3,4-b]pyridin-5-yl]-5-(2-methoxy-2-oxo ethyl)-4,5-dihydroisoxazole-5-carboxylate
{3-[4-(Cyclohexylamino)-1-ethyl-1H-pyrazolo[3,4-b]pyridin-5-yl]-4,5-dihydroisoxazole-5,5-diyl}dimethanol

Example 11

Preparation of 2-{3-[4-(cyclohexylamino)-1-ethyl-1H-pyrazolo[3,4-b]pyridin-5-yl]-5-(hydroxymethyl)-4,5-dihydroisoxazol-5-yl}ethanol Sodium borohydride (14 mg, 0.00036 mole) was added to methyl 3-[4-(cyclohexylamino)-1-ethyl-1H-pyrazolo[3,4-b]pyridin-5-yl]-5-(2-methoxy-2-oxoethyl)-4,5-dihydroisoxazole-5-carboxylate (80 mg, 0.00018 mole) (example 10) in tetrahydrofuran (5 ml). Methanol (2 drops) was added and the reaction mixture was stirred at room temperature overnight. It was quenched with saturated ammonium chloride solution, diluted with ethyl acetate and extracted with brine. The organic layer was dried over anhydrous sodium sulphate and concentrated in vacuo. The crude product was purified by column chromatography.
Yield: 70 mg (98%)
m/z: (M$^+$+1) 388.28
NMR (δ, CDCl$_3$): 8.77-8.75 (d, 1H), 8.13 (s, 1H), 7.97 (s, 1H), 4.47-4.44 (q, 2H), 3.95-3.74 (m, 5H), 3.60-3.37 (m, 2H), 2.11-1.36 (m, 15H)
The following compound was prepared similarly
2-{3-[4-(Cyclopentylamino)-1,3-dimethyl-1H-pyrazolo[3,4-b]pyridin-5-yl]-5-(hydroxymethyl)-4,5-dihydroisoxazol-5-yl}ethanol

Example 12

Preparation of (3-[4-(cyclohexylamino)-1-ethyl-1H-pyrazolo[3,4-b]pyridin-5-yl]-5-{2-[(methylsulfonyl)oxy]ethyl}-4,5-dihydroisoxazol-5-yl)methyl methanesulfonate 2-{3-[4-(Cyclohexylamino)-1-ethyl-1H-pyrazolo[3,4-b]pyridin-5-yl]-5-(hydroxymethyl)-4,5-dihydroisoxazol-5-yl}ethanol (150 mg, 0.00038 mole) (example 11) was taken in a mixture of dichloromethane and chloroform (10 ml: 10 ml). At 0° C., triethylamine (0.153 g, 0.001513 mole) and methane sulphonyl chloride (0.173 g, 0.001513 mole) were added. The reaction mixture was stirred at 0° C. for about 2 h. The mixture was diluted with dichloromethane and washed with sodium bicarbonate solution. The organic layer was washed with brine, dried over anhydrous sodium sulphate and concentrated in vacuo.
Yield: 280 mg (crude)
The following compound was prepared similarly
{3-[4-(Cyclohexylamino)-1-ethyl-1H-pyrazolo[3,4-b]pyridin-5-yl]-4,5-dihydroisoxazole-5,5-diyl}bis(methyl) dimethanesulfonate

Example 13

Preparation of N-cyclohexyl-1-ethyl-5-(1-oxa-7-thia-2-azaspiro[4.4]non-2-en-3-yl)-1H-pyrazolo[3,4-b]pyridin-4-amine (Compound No. 4)

(3-[4-(Cyclohexylamino)-1-ethyl-1H-pyrazolo[3,4-b]pyridin-5-yl]-5-{2-[(methylsulfonyl)oxy]ethyl}-4,5-dihydroisoxazol-5-yl)methyl methanesulfonate (280 mg, 0.00051 mole) (example 12) was taken in dimethylformamide (5 ml). Sodium sulphide nanohydrate (372 mg, 0.0015 mole) was added. The reaction mixture was refluxed at 90-100° C. overnight. Water was added, extraction was done with ethyl acetate, the organic layer was washed with brine, dried over anhydrous sodium sulphate and concentrated in vacuum. Purification was done by preparative thin layer chromatography by using ethyl acetate (40%) in hexane solvent.
Yield: 100 mg (65%)
m/z: (M$^+$+1) 386.32
NMR (δ, CDCl$_3$): 8.84-8.83 (d, 1H), 8.09 (s, 1H), 7.98 (s, 1H), 4.90-4.44 (q, 2H), 3.96 (m, 1H), 3.56-2.97 (m, 6H), 2.42-1.25 (m, 14H).
The following compound was prepared similarly
N-cyclohexyl-1-ethyl-5-(5-oxa-2-thia-6-azaspiro[3.4]oct-6-en-7-yl)-1H-pyrazolo[3,4-b]pyridin-4-amine (Compound No. 6),
Yield: 14.6%
m/z: (M$^+$+1) 372.16

Example 14

Preparation of N-cyclohexyl-1-ethyl-5-(7-oxido-1-oxa-7-thia-2-azaspiro[4.4]non-2-en-3-yl)-1H-pyrazolo[3,4-b]pyridin-4-amine (Compound No. 5)

N-cyclohexyl-1-ethyl-5-(1-oxa-7-thia-2-azaspiro[4.4]non-2-en-3-yl)-1H-pyrazolo[3,4-b]pyridin-4-amine (70 mg, 0.00018 mole) (example 13) was taken in methanol and stirring was done for about five minutes. Water (1 ml) was added. Sodium periodate (38 mg, 0.00018 mole) was added. The reaction mixture was stirred at room temperature for about 5 h. Filtration was done and the residue was washed with dichloromethane. The organic layer was dried over anhydrous sodium sulphate and concentrated in vacuo. Purification was done by preparative thin layer chromatography using ethyl acetate (60%) in hexane.
Yield: 68.5%
m/z: (M$^+$+1) 402.26
NMR (δ, CDCl$_3$) 8.69-8.67 (d, 1H), 8.05 (s, 1H), 7.98 (s, 1H), 4.48-4.45 (q, 2H), 3.98-3.92 (m, 1H), 3.78-3.74 (m, 3H), 3.15-3.11 (m, 3H), 3.04-3.01 (m, 1H), 2.8-2.7 (m, 1H), 2.14-1.46 (m, 13H).

Example 15

Preparation of N-cyclohexyl-5-(2,2-dioxido-5-oxa-2-thia-6-azaspiro[3.4]oct-6-en-7-yl)-1-ethyl-1H-pyrazolo[3,4-b]pyridin-4-amine (Compound No. 14)

N-cyclohexyl-1-ethyl-5-(5-oxa-2-thia-6-azaspiro[3.4]oct-6-en-7-yl)-1H-pyrazolo[3,4-b]pyridin-4-amine (70 mg, 0.00018 mole) (example 13) was taken in dichloromethane. m-Chloroperbenzoic acid (48 mg, 0.00028 mole) was added at 0° C. The reaction mixture was stirred at room temperature overnight. Extraction was done with water. The organic layer was washed with sodium hydroxide solution (1N, 10 ml) and brine. It was concentrated in vacuo. The title compound obtained was purified by preparative thin layer chromatography.

Yield: 28%
m/z: (M$^+$+1) 403.98
NMR (δ, CDCl$_3$): 8.96 (s, 1H), 8.12 (s, 1H), 8.02 (s, 1H), 4.68-4.64 (d, 2H), 4.60-4.55 (q, 2H), 4.45-4.42 (d, 2H), 3.97-3.93 (m, 3H), 2.15-1.45 (m, 10H), 1.42-1.08 (m, 3H).

Example 16

Preparation of N-cyclohexyl-5-(1,7-dioxa-2-azaspiro[4.4]non-2-en-3-yl)-1-ethyl-1H-pyrazolo[3,4-b]pyridin-4-amine (Compound No. 12)

2-{3-[4-(Cyclohexylamino)-1-ethyl-1H-pyrazolo[3,4-b]pyridin-5-yl]-5-(hydroxymethyl)-4,5-dihydroisoxazol-5-yl}ethanol (150 mg, 0.00038 mole) (example 11), triphenylphosphine (132 mg, 0.00050 mole) and succinimide (42 mg, 0.00042 mole) were taken in dry tetrahydrofuran. Diisopropyl azodicarboxylate (0.115 ml, 0.00058 mole) was added dropwise. The reaction mixture was stirred at room temperature overnight. The solvent was removed under reduced pressure. The crude product obtained was purified by column chromatography.

Yield: 42%
m/z: (M$^+$+1) 370.06
NMR (δ, CDCl$_3$): 10.03 (s, 1H), 8.10-8.03 (d, 2H), 4.83-4.13 (q, 2H), 4.10-3.99 (m, 3H), 3.82-3.80 (d, 1H), 3.55-3.53 (d, 2H), 2.66-2.11 (m, 2H), 1.7-1.25 (m, 10H), 0.89-0.82 (m, 3H).

The following compound was prepared similarly
N-cyclopentyl-5-(1,7-dioxa-2-azaspiro[4.4]non-2-en-3-yl)-1,3-dimethyl-1H-pyrazolo[3,4-b]pyridin-4-amine (Compound No. 40),
Yield: 26%
m/z: (M$^+$+1). 356.1

Example 17

Preparation of 4-{[1-ethyl-5-(1-oxa-2-azaspiro[4.5]dec-2-en-3-yl)-1H-pyrazolo[3,4-b]pyridin-4-yl]amino}cyclohexanone (Compound No. 16)

4-{[1-Ethyl-5-(1-oxa-2-azaspiro[4.5]dec-2-en-3-yl)-1H-pyrazolo[3,4-b]pyridin-4-yl]amino}cyclohexanol (100 mg, 0.251 mmol) (example 9) was dissolved in dichloromethane and the reaction mixture was cooled up to 5° C. Pyridinium chlorochromate (108 mg, 0.502 mmol) was added and the reaction mixture was stirred for about 5 minutes at the same temperature. It was warmed to room temperature and stirred at room temperature for about 16 h. Dilution was done with dichloromethane and filtration was done using celite. The organic layers were combined, concentrated and purified by preparative thin layer chromatography by using ethyl acetate.

Yield: 50 mg (50%)
m/z: (M$^+$+1) 396.00
NMR (δ, CDCl$_3$): 8.15 (s, 1H), 8.07 (s, 1H), 4.60-4.57 (q, 2H), 4.46-4.44 (m, 1H), 3.22 (s, 2H), 2.64-2.40 (m, 6H), 2.17-2.12 (m, 2H), 1.85-1.81 (m, 4H), 1.71-1.69 (m, 2H), 1.69-1.42 (m, 5H).

The following compounds were prepared similarly
4-{[1-Ethyl-5-(5-oxa-6-azaspiro[3.4]oct-6-en-7-yl)-1H-pyrazolo[3,4-b]pyridin-4-yl]amino}cyclohexanone (Compound No. 20),
Yield: 5.0%
m/z: (M$^+$+1) 367.97
4-{[1-Ethyl-5-(1-oxa-2-azaspiro[4.4]non-2-en-3-yl)-1H-pyrazolo[3,4-b]pyridin-4-yl]amino}cyclohexanone (Compound No. 21),
Yield: 9.6%
m/z: (M$^+$+1) 381.95

Example 18

Preparation of 4-{[1-ethyl-5-(1-oxa-2-azaspiro[4.5]dec-2-en-3-yl)-1H-pyrazolo[3,4-b]pyridin-4-yl]amino}cyclohexanone oxime (Compound No. 17)

4-{[1-Ethyl-5-(1-oxa-2-azaspiro[4.5]dec-2-en-3-yl)-1H-pyrazolo[3,4-b]pyridin-4-yl]amino}cyclohexanone (0.025 gm, 0.063 mmol) (example 17), hydroxylamine hydrochloride (0.008 gm, 0.126 mmol) and potassium carbonate (0.043 gm, 0.315 mmol) were taken in acetonitrile and the reaction mixture was stirred at room temperature for about 6 h. Excess of solvent was removed under reduced pressure and solid separated was washed with hexane and dried in vacuum.

Yield: 60%
m/z: (M$^+$+1) 411.15
NMR (δ, CDCl$_3$): 8.25 (s, 1H), 8.23 (s, 1H), 4.41-4.32 (q, 2H), 4.31-4.30 (m, 1H), 3.20-3.17 (m, 2H), 2.94-2.90 (m, 1H), 2.39-2.31 (m, 3H), 2.17-2.13 (m, 2H), 1.77-1.39 (m, 15H).

Example 19

Preparation of ethyl 5-(bromomethyl)-3-[4-(cyclohexylamino)-1-ethyl-1H-pyrazolo[3,4-b]pyridin-5-yl]-4,5-dihydroisoxazole-5-carboxylate 4-(Cyclohexylamino)-1-ethyl-1H-pyrazolo[3,4-b]pyridine-5-carbaldehyde oxime (200 mg, 0.0006 mole) (example 8) was taken in dichloromethane: chloroform mixture (10 ml: 5 ml). Ethyl 2-(bromomethyl)acrylate (0.2 ml, 0.00103 mole) was added. Sodium hypochlorite (2.5 ml) was added drop wise. The reaction mixture was stirred overnight. Water was added, the mixture was extracted with chloroform, washed with brine, dried over anhydrous sodium sulphate and concentrated in vacuo. The crude compound obtained was purified by column chromatography.

Yield: 66%
m/z: (M$^+$+1) 479.97

Example 20

Preparation of {5-(bromomethyl)-3-[4-(cyclohexylamino)-1-ethyl-1H-pyrazolo[3,4-b]pyridin-5-yl]-4,5-dihydroisoxazol-5-yl}methanol Ethyl 5-(bromomethyl)-3-[4-(cyclohexylamino)-1-ethyl-1H-pyrazolo[3,4-b]pyridin-5-yl]-4,5-dihydroisoxazole-5-carboxylate (200 mg, 0.0004 mole) (example 19) was taken in tetrahydrofuran (15 ml). Sodium borohydride (31 mg, 0.0008 mole) was added portion wise. The reaction mixture was stirred overnight. It was quenched with saturated ammonium chloride solution. The organic solvent was removed, water was added and the mixture was extracted with ethyl acetate, washed with brine, dried over anhydrous sodium sulphate and concentrated in vacuo. The crude product obtained was purified by column chromatography.

Yield: 65.7% m/z: (M$^+$+1) 437.94

Example 21

Preparation of N-cyclohexyl-5-(2,5-dioxa-6-azaspiro [3.4]oct-6-en-7-yl)-1-ethyl-1H-pyrazolo[3,4-b]pyridin-4-amine (Compound No. 28)

{5-(Bromomethyl)-3-[4-(cyclohexylamino)-1-ethyl-1H-pyrazolo[3,4-b]pyridin-5-yl]-4,5-dihydroisoxazol-5-yl}methanol (110 mg, 0.00025 mole) (example 20) was dissolved in ethanol (10 ml). Water (2 ml) was added followed by potassium hydroxide (20 mg, 0.00050 mole). The reaction mixture was stirred at refluxing temperature overnight. The solvent was removed under reduced pressure. Water was added and the mixture was extracted with ethyl acetate, washed with brine, dried over anhydrous sodium sulphate and concentrated in vacuo. The crude product obtained was purified by column chromatography.

Yield: 28% m/z: (M$^+$+1) 356.07

NMR (δ, CDCl$_3$): 8.85 (s, 1H), 8.12 (s, 1H), 7.99 (s, 1H), 5.06-5.04 (d, 2H), 4.80-4.78 (d, 2H), 4.55-4.49 (q, 2H), 3.95-3.93 (m, 1H), 3.84 (s, 2H), 2.15-1.26 (m, 13H).

Example 22

Preparation of N-cyclohexyl-1-ethyl-5-(1-oxa-2,8-diazaspiro[4.5]dec-2-en-3-yl)-1H-pyrazolo[3,4-b] pyridin-4-amine hydrochloride salt (Compound No. 18)

Ethanolic hydrochloric acid (25 ml) was added to tert-butyl 3-[4-(cyclohexylamino)-1-ethyl-1H-pyrazolo[3,4-b]pyridin-5-yl]-1-oxa-2,8-diazaspiro[4.5]dec-2-ene-8-carboxylate (700 mg, 0.00148 mole) (example 9) The reaction mixture was stirred at room temperature overnight. The solvent was removed under reduced pressure. White solid precipitated, which was dried under vacuum.

Yield: 96% m/z: (M$^+$+1) 383.02

NMR (δ, D$_2$O): 8.18 (s, 1H), 7.99 (s, 1H), 4.33-4.27 (q, 2H), 4.05 (s, 1H), 3.40 (s, 2H), 3.34-3.22 (m, 4H), 2.11-1.41-(m, 14H), 1.36-1.32 (m, 3H).

Example 23

Preparation of N-cyclohexyl-5-[8-(2,2-dimethylpropanoyl)-1-oxa-2,8-diazaspiro[4.5]dec-2-en-3-yl]-1-ethyl-1H-pyrazolo[3,4-b]pyridin-4-amine (Compound No. 23)

N-Cyclohexyl-1-ethyl-5-(1-oxa-2,8-diazaspiro[4.5]dec-2-en-3-yl)-1H-pyrazolo[3,4-b]pyridin-4-amine hydrochloride salt (70 mg, 0.00016 mole) (example 22) was taken in dichloromethane (10 ml). Triethyl amine (0.07 ml, 0.00050 mole) and pivaloyl chloride (0.030 ml, 0.00025 mole) were added at 0° C. The reaction mixture was stirred at room temperature overnight. It was diluted with dichloromethane, washed with sodium bicarbonate solution, extracted with brine, dried over anhydrous sodium sulphate and concentrated in vacuo. The crude product obtained was purified by preparative thin layer chromatography.

Yield: 66% m/z: (M$^+$+1) 467.15

NMR (δ, CDCl$_3$): 9.1 (s, 1H), 8.0 (s, 1H), 7.9 (s, 1H), 4.56-4.50 (q, 2H), 4.11-4.08 (d, 2H), 3.9 (s, 1H), 3.53-3.4 (m, 2H), 3.2 (s, 2H), 2.14-1.7 (m, 4H) 1.6-1.5 (m, 13H), 1.51-1.2 (m, 9H).

The following compounds were prepared similarly

N-cyclohexyl-1-ethyl-5-{8-[(trifluoromethyl)sulfonyl]-1-oxa-2,8-diazaspiro[4.5]dec-2-en-3-yl}-1H-pyrazolo[3,4-b]pyridin-4-amine (Compound No. 24), Yield: 29% m/z: (M$^+$+1) 515.02

N-cyclohexyl-1-ethyl-5-[8-(ethylsulfonyl)-1-oxa-2,8-diazaspiro[4.5]dec-2-en-3-yl]-1H-pyrazolo[3,4-b]pyridin-4-amine (Compound No. 25), Yield: 50% m/z: (M$^+$+1) 475.12

5-(8-Acetyl-1-oxa-2,8-diazaspiro[4.5]dec-2-en-3-yl)-N-cyclohexyl-1-ethyl-1H-pyrazolo[3,4-b]pyridin-4-amine (Compound No. 27), Yield: 70% m/z: (M$^+$+1) 425.11

Example 24

Preparation of N-cyclohexyl-5-[8-(cyclopropylmethyl)-1-oxa-2,8-diazaspiro[4.5]dec-2-en-3-yl]-1-ethyl-1H-pyrazolo[3,4-b]pyridin-4-amine (Compound No. 26)

N-cyclohexyl-1-ethyl-5-(1-oxa-2,8-diazaspiro[4.5]dec-2-en-3-yl)-1H-pyrazolo[3,4-b]pyridin-4-amine hydrochloride salt (70 mg, 0.00016 mole) (example 22) was taken in dimethylformamide (5 ml). Potassium carbonate (69 mg, 0.00050 mole) and cyclopropane methyl chloride (0.20 ml, 0.000021 mole) were added. The reaction mixture was stirred at 70-80° C. overnight. Water was added and the mixture was extracted with ethyl acetate, washed with brine, dried over anhydrous sodium sulphate and concentrated in vacuum. The crude product obtained was purified by preparative thin layer chromatography.

Yield: 27% m/z: (M$^+$+1) 437.16

NMR (δ, CDCl$_3$): 8.72 (s, 1H), 8.1 (s, 1H), 7.9 (s, 1H), 4.50-4.44 (q, 2H), 3.9 (s, 1H), 3.34-3.31 (d, 2H), 3.0 (bs, 2H), 2.7 (bs, 2H), 2.25-1.25 (m, 20H), 0.72 (s, 2H), 0.34 (s, 2H).

Example 25

Preparation of 3-{1-ethyl-4-[4-hydroxycyclohexyl) amino]-1H-pyrazolo[3,4-b]pyridin-5-yl}-1-oxa-2-azaspiro[4.5]dec-2-en-8-one (Compound No. 22)

4-{[1-Ethyl-5-(1,9,12-trioxa-2-azadispiro[4.2.4.2]tetradec-2-en-3-yl)-1H-pyrazolo[3,4-b]pyridin-4-yl] amino}cyclohexanol (0.040 g, 0.087 mole) (example 9) was dissolved in dichloromethane and the mixture was cooled to 5° C. Trifluoroacetic acid (0.050 g, 0.439 mmol) was added drop wise in about 1 h. Water (0.1 ml) was added and the mixture was stirred vigorously for about 6 h at room temperature. It was diluted with dichloromethane and washed with sodium bicarbonate, dried over sodium sulphate, concentrated and purified by column chromatography.

Yield: 57.5% m/z: (M$^+$+1) 411.98

NMR (δ, CDCl$_3$): 9.47 (bs, 1H), 8.13 (s, 1H), 8.05 (s, 1H), 4.58-4.52 (m, 2H) 4.00 (s, 1H), 3.84-3.83 (d, 1H), 3.64 (s, 1H), 3.37 (s, 2H), 2.86-2.77 (m, 2H), 2.44-2.40 (d, 2H), 2.33-2.29 (d, 4H), 2.15-2.08 (m, 5H), 168-1.53 (m, 6H).

The following compounds were prepared similarly

3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-one (Compound No. 46), Yield: 28% m/z: (M$^+$+1) 398.14

3-[4-(Cyclohexylamino)-1-ethyl-1H-pyrazolo[3,4-b]pyridin-5-yl]-1-oxa-2-azaspiro[4.5]dec-2-en-8-one (Compound No. 81), Yield: 69% m/z: (M$^+$+1) 396.24

3-[1-(4-Methoxybenzyl)-4-(tetrahydro-2H-pyran-4-ylamino)-1H-pyrazolo[3,4-b]pyridin-5-yl]-1-oxa-2-azaspiro[4.5]dec-2-en-8-one (Compound No. 92), Yield: 48% m/z: (M$^+$+1) 490.10

Example 26

Preparation of (cis or trans)) 3-[4-(Cyclohexylamino)-1-ethyl-1H-pyrazolo[3,4-b]pyridin-5-yl]-1-oxa-2-azaspiro[4.5]dec-2-en-8-ol (Compound No. 42) and (trans or cis) 3-[4-(cyclohexylamino)-1-ethyl-1H-pyrazolo[3,4-b]pyridin-5-yl]-1-oxa-2-azaspiro[4.5]dec-2-en-8-ol (Compound No. 43)

3-[4-(Cyclohexylamino)-1-ethyl-1H-pyrazolo[3,4-b]pyridin-5-yl]-1-oxa-2-azaspiro[4.5]dec-2-en-8-one (100 mg, 0.000253 mole) (example 25) in methanol was cooled to −78° C. and cerium chloride (187 mg, 0.00075 mole) and sodium borohydride (28 mg, 0.00075 mole) were added sequentially. The reaction mixture was stirred at −78° C. for about 2-3 hours. It was quenched with 5% hydrochloric acid and brine. The reaction mixture was extracted with ethyl acetate, organic layer was dried over anhydrous sodium sulphate and concentrated under reduced pressure to get crude product. The title compounds were separated by preparative thin layer chromatography.

Compound No. 42, Yield: 15%, HPLC purity-97.81%

Compound No. 43, Yield: 10%, HPLC purity-93.86% m/z: (M$^+$+1) 398.21

Compound No. 42, NMR (δ, CDCl$_3$) 8.90-8.88 (d, 1H), 8.09 (s, 1H), 7.98 (s, 1H), 4.49-4.44 (m, 2H), 3.92-3.90 (m, 1H), 3.79-3.73 (m, 1H), 3.24 (s, 2H), 2.26-1.42 (m, 21H)

Compound No. 43, NMR (δ, CDCl$_3$) 8.91-8.90 (d, 1H), 8.12 (s, 1H), 7.97 (s, 1H), 4.50-4.44 (m, 2H), 4.00-3.89 (m, 1H) 3.89-3.64 (m, 1H), 3.28 (s, 2H), 2.16-1.25 (m, 21H)

The following compounds were prepared similarly (cis or trans) 3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 45)

Yield: 28%

HPLC purity: 99.59% m/z: (M$^+$+1) 400.22

(trans or cis) 3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 98)

Yield: 35%

HPLC purity: 96.94 m/z: (M$^+$+1) 400.22

The following compounds can be prepared similarly

3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-en-8-ol (Compound No. 148)

3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-en-8-ol (Compound No. 160)

3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 165)

3-[4-(Cyclohexylamino)-1-ethyl-3-methyl-1H-pyrazolo[3,4-b]pyridin-5-yl]-1-oxa-2-azaspiro[4.5]dec-2-en-8-ol (Compound No. 172)

Example 27

Preparation of 9-[4-(cyclohexylamino)-1-ethyl-1H-pyrazolo[3,4-b]pyridin-5-yl]-1,7-dioxa-8-azadispiro[2.2.4.2]dodec-8-ene-2-carbonitrile Benzyltriethyl ammonium chloride (23 mg, 0.00001 mole) was added to a mixture of 50% potassium hydroxide solution and tetrahydrofuran (10 ml) and the mixture was cooled to 0° C. Chloroacetonitrile (0.020 ml, 0.00026 mole) and 3-[4-(cyclohexylamino)-1-ethyl-1H-pyrazolo[3,4-b]pyridin-5-yl]-1-oxa-2-azaspiro[4.5]dec-2-en-8-one (100 mg, 0.00025 mole) (example 25) in tetrahydrofuran were added to the reaction mixture. It was stirred for about 4 hours at room temperature and water was added. The reaction mixture was extracted with ethyl acetate, organic layer was washed with brine, dried over anhydrous sodium sulphate and concentrated under reduced pressure. The crude product was purified by preparative thin layer chromatography.

Yield: 80 mg (72%)

m/z: (M$^+$+1) 435.12

Example 28

Preparation of (cis or trans) 3-[4-(cyclohexylamino)-1-ethyl-1H-pyrazolo[3,4-b]pyridin-5-yl]-1-oxa-2-azaspiro[4.5]dec-2-ene-8-carboxylic acid (Compound No. 95) and (trans or cis) 3-[4-(cyclohexylamino)-1-ethyl-1H-pyrazolo[3,4-b]pyridin-5-yl]-1-oxa-2-azaspiro[4.5]dec-2-ene-8-carboxylic acid (Compound No. 96)

Lithium bromide (23 mg, 0.0002 mole) was added to a mixture of dimethylformamide (0.17 ml), acetonitrile (0.17 ml) and water (1.2 ml). 9-[4-(Cyclohexylamino)-1-ethyl-1H-pyrazolo[3,4-b]pyridin-5-yl]-1,7-dioxa-8-azadispiro[2.2.4.2]dodec-8-ene-2-carbonitrile (80 mg, 0.00018 mole) (example 27) was added after about 15 minutes and the reaction mixture was heated at 90° C. for about 10-12 hours. Acetonitrile was evaporated, water was added and the reaction mixture was extracted with ethyl acetate. The organic layer was dried over anhydrous sodium sulphate and concentrated under reduced pressure to get crude product. The title compounds were separated by preparative thin layer chromatography.

Compound No. 95 Yield: 10.25% Chiral purity 99.69%

Compound No. 96 Yield: 13% Chiral purity 99.81% m/z: (M$^+$+1) 426.20

Compound No. 95 (δ, CDCl$_3$) NMR 8.95-8.94 (d, 1H), 8.17 (s, 1H), 7.98 (s, 1H), 4.51-4.45 (q, 2H), 3.93-3.92 (m, 1H), 3.31 (s, 2H), 2.56 (m, 1H), 2.20-2.13 (m, 4H), 1.95-1.89 (m, 2H), 1.84-1.7 (m, 6H), 1.70-1.55 (m, 6H), 1.51-1.48 (t, 3H)

Compound No. 96 (δ, CDCl$_3$) NMR 8.91-8.89 (d, 1H), 8.11 (s, 1H), 7.97 (s, 1H), 4.49-4.439 (q, 2H), 3.92 (m, 1H), 3.25 (s, 1H), 2.42 (m, 1H), 2.17-2.66 (m, 4H), 1.85-1.82 (m, 2H), 1.68-1.61 (m, 6H), 1.54-1.49 (m, 6H), 1.47-1.41 (t, 3H)

Example 29

Preparation of 5-(5-oxa-6-azaspiro[3.4]oct-6-en-7-yl)-N-(tetrahydro-2H-pyran-4-yl)-1H-pyrazolo[3,4-b]pyridin-4-amine (Compound No. 49)

1-(4-Methoxybenzyl)-5-(5-oxa-6-azaspiro[3.4]oct-6-en-7-yl)-N-(tetrahydro-2H-pyran-4-yl)-1H-pyrazolo[3,4-b]pyridin-4-amine (1.8 gm, 4 mmol) (example 9) was dissolved in trifluoroacetic acid (4.56 gm, 40 mmol) and the reaction mixture was stirred for about 4 hours at room temperature under nitrogen atmosphere. The reaction mixture was diluted with ethyl acetate and sodium bicarbonate solution was added drop wise. It was extracted with ethyl acetate, organic layer was washed with water, brine, dried over anhydrous sodium sulphate and concentrated under reduced pressure. The crude product was purified by column chromatography.

Yield: 1.5 gm (87%)
m/z: (M$^+$+1) 328.56
NMR: (δ, CDCl$_3$) 9.14 (d, 1H), 8.24 (s, 1H), 8.06 (s, 1H), 4.22 (s, 1H), 3.68-3.65 (t, 2H), 3.61 (s, 2H), 2.63-2.55 (m, 2H), 2.19-2.16 (m, 2H), 1.92-1.89 (d, 1H), 1.65-115 (m, 8H)

The following compound was prepared similarly
5-(1-Oxa-2-azaspiro[4.5]dec-2-en-3-yl)-N-(tetrahydro-2H-pyran-4-yl)-1H-pyrazolo[3,4-b]pyridin-4-amine (Compound No. 101)
Yield: 32%
m/z: 356.14 (M$^+$+1)

Example 30

Preparation of 5-(5-oxa-6-azaspiro[3.4]oct-6-en-7-yl)-N-(tetrahydro-2H-pyran-4-yl)-1-(2,2,2-trifluoroethyl)-1H-pyrazolo[3,4-b]pyridin-4-amine (Compound No. 56)

1,1,1-Trifluoro-2-iodoethane (0.07 gm, 0.33 mmol) and potassium carbonate (0.125 gm, 0.9 mmol) were added to the solution of 5-(5-oxa-6-azaspiro[3.4]oct-6-en-7-yl)-N-(tetrahydro-2H-pyran-4-yl)-1H-pyrazolo[3,4-b]pyridin-4-amine (0.1 gm, 0.3 mmol) (example 29) in dimethylformamide and the reaction mixture was heated at 80° C. for about 3 hours. It was diluted with water and extracted with ethyl acetate. The organic layer was washed with brine, dried over anhydrous sodium sulphate and concentrated under reduced pressure. The crude product was purified by column chromatography.

Yield: 0.046 gm (37%)
m/z: (M$^+$+1) 410.18
NMR (δ, CDCl$_3$) 9.11 (s, 1H), 8.11 (s, 1H), 8.05 (s, 1H), 5.07-5.01 (m, 2H), 4.15 (s, 1H), 4.05-4.02 (d, 2H), 3.66-3.63 (d, 2H), 3.61-3.58 (d, 2H), 2.60-2.54 (m, 2H), 2.28-2.23 (m, 2H), 1.89-1.25 (m, 6H).

The following compounds were prepared similarly
1-Methyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 50),
Yield: 21%
m/z: (M$^+$+1) 342.18

5-(1-Oxa-2-azaspiro[4.4]non-2-en-3-yl)-N-(tetrahydro-2H-pyran-4-yl)-1-(2,2,2-trifluoroethyl)-1H-pyrazolo[3,4-b]pyridin-4-amine (Compound No. 51),
Yield: 26%
m/z: (M$^+$+1) 424.56
1-(Cyclopropylmethyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 58),
Yield: 22%
m/z: (M$^+$+1) 382.18
1-Butyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 59),
Yield: 20%
m/z: (M$^+$+1) 384.20
1-(1-Methylethyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 60),
Yield: 24%
m/z: (M$^+$+1) 370.17
5-(5-Oxa-6-azaspiro[3.4]oct-6-en-7-yl)-1-propyl-N-(tetrahydro-2H-pyran-4-yl)-1H-pyrazolo[3,4-b]pyridin-4-amine (Compound No. 61),
Yield: 20%
m/z: (M$^+$+1) 370.17
5-(1-Oxa-2-azaspiro[4.5]dec-2-en-3-yl)-N-(tetrahydro-2H-pyran-4-yl)-1-(2,2,2-trifluoroethyl)-1H-pyrazolo[3,4-b]pyridin-4-amine (Compound No. 62),
Yield: 38%
m/z: (M$^+$+1) 438.17
1-Cyclopentyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 71),
Yield: 17%
m/z: (M$^+$+1) 424.23
1-(Cyclopropylmethyl)-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 72),
Yield: 18%
m/z: (M$^+$+1) 410.20
1-(1-Methylethyl)-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 73),
Yield: 20%
m/z: (M$^+$+1) 398.25
5-(1-Oxa-2-azaspiro[4.5]dec-2-en-3-yl)-1-propyl-N-(tetrahydro-2H-pyran-4-yl)-1H-pyrazolo[3,4-b]pyridin-4-amine (Compound No. 74),
Yield: 20%
m/z: (M$^+$+1) 398.18
1-Cyclopentyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 75),
Yield: 28%
m/z: (M$^+$+1) 410.20
1-(Cyclopropylmethyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 76),
Yield: 32%
m/z: (M$^+$+1) 396.17
1-(1-Methylethyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 77),
Yield: 25%
m/z: (M$^+$+1) 384.22

5-(1-Oxa-2-azaspiro[4.4]non-2-en-3-yl)-1-propyl-N-(tetrahydro-2H-pyran-4-yl)-1H-pyrazolo[3,4-b]pyridin-4-amine (Compound No. 78),
Yield: 28%
m/z: (M$^+$+1) 384.22
1-Methyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 79),
Yield: 17%
m/z: (M$^+$+1) 356.16
5-{2-[(Benzyloxy)methyl]-5-oxa-6-azaspiro[3.4]oct-6-en-7-yl}-1-ethyl-N-(tetrahydro-2H-pyran-4-yl)-1H-pyrazolo[3,4-b]pyridin-4-amine (Compound No. 103),
Yield: 52%
m/z: 476.14 (M$^+$+1).

Example 31

Preparation of 1-ethyl-5-(1-oxa-2-azaspiro[4.4]non-2-en-3-yl)-N-piperidin-4-yl-1H-pyrazolo[3,4-b]pyridin-4-amine (Compound No. 82)

Tert-butyl 4-{[1-ethyl-5-(1-oxa-2-azaspiro[4.4]non-2-en-3-yl)-1H-pyrazolo[3,4-b]pyridin-4-yl]amino}piperidine-1-carboxylate (950 mg, 0.00196 mole) (example 9) was taken in dichloromethane. At 0° C., trifluoroacetic acid (10 ml) was added and the reaction mixture was stirred at room temperature for about 2 hours. It was diluted with dichloromethane and basified with saturated sodium bicarbonate solution. The organic layer was separated, washed with brine, dried over anhydrous sodium sulphate and concentrated under reduced pressure to get the title compound.
Yield: 550 mg (74%)
m/z: (M$^+$+1) 369.18
NMR (δ, CDCl$_3$) 9.03-9.015 (d, 1H), 8.13 (s, 1H), 7.966 (s, 1H), 4.50-4.45 (q, 2H), 4.12 (s, 1H), 3.45 (s, 2H), 3.24-3.21 (2H, d), 2.93-1.72 (m, 14H), 1.52-1.48 (t, 3H)
The following compound was prepared similarly 1-Ethyl-5-(1-oxa-2-azaspiro[4.5]dec-2-en-3-yl)-N-piperidin-4-yl-1H-pyrazolo[3,4-b]pyridin-4-amine (Compound No. 86)
Yield: 65%
m/z: (M$^+$+1) 383.35

Example 32

Preparation of N-(1-cyclopentylpiperidin-4-yl)-1-ethyl-5-(1-oxa-2-azaspiro[4.4]non-2-en-3-yl)-1H-pyrazolo[3,4-b]pyridin-4-amine (Compound No. 63)

1-Ethyl-5-(1-oxa-2-azaspiro[4.4]non-2-en-3-yl)-N-piperidin-4-yl-1H-pyrazolo[3,4-b]pyridin-4-amine (70 mg, 0.0018 mole) (example 31) was taken in acetonitrile and potassium carbonate (126 mg, 0.0009 mole) and cyclopentyl bromide (0.020 ml, 0.0002 mole) were added. The reaction mixture was stirred at refluxing temperature overnight. Acetonitrile was removed and water was added to the residue. Extraction was done with ethyl acetate and washings were done with brine. The organic layer was dried over anhydrous sodium sulphate and concentrated under reduced pressure and the crude product was purified by preparative thin layer chromatography.
Yield: 25 mg (32%)
m/z: (M$^+$+1) 437.23
NMR (δ, CDCl$_3$) 9.06 (d, 1H), 8.13 (1H, s), 7.95 (s, 1H), 4.50-4.45 (q, 2H), 3.22 (s, 2H), 3.01 (m, 1H), 1.97-1.25 (m, 27H), 1.51-1.48 (t, 3H)

The following compounds were prepared similarly
1-Ethyl-N-[1-(methylsulfonyl)piperidin-4-yl]-5-(1-oxa-2-azaspiro[4.4]non-2-en-3-yl)-1H-pyrazolo[3,4-b]pyridin-4-amine (Compound No. 52)
Yield: 24%
m/z: (M$^+$+1) 447.17
N-(1-acetylpiperidin-4-yl)-1-ethyl-5-(1-oxa-2-azaspiro[4.5]dec-2-en-3-yl)-1H-pyrazolo[3,4-b]pyridin-4-amine (Compound No. 53)
Yield: 28%
m/z: (M$^+$+1) 425.21
N-(1-acetylpiperidin-4-yl)-1-ethyl-5-(1-oxa-2-azaspiro[4.4]non-2-en-3-yl)-1H-pyrazolo[3,4-b]pyridin-4-amine (Compound No. 54)
Yield: 28%
m/z: (M$^+$+1) 411.18
N-(1-butylpiperidin-4-yl)-1-ethyl-5-(1-oxa-2-azaspiro[4.4]non-2-en-3-yl)-1H-pyrazolo[3,4-b]pyridin-4-amine (Compound No. 64)
Yield: 32%
m/z: (M$^+$+1) 425.28
2-(4-{[1-Ethyl-5-(1-oxa-2-azaspiro[4.4]non-2-en-3-yl)-1H-pyrazolo[3,4-b]pyridin-4-yl]amino}piperidin-1-yl)ethanol (Compound No. 65)
Yield: 22%
m/z: (M$^+$+1) 413.20
N-[1-(cyclopropylmethyl)piperidin-4-yl]-1-ethyl-5-(1-oxa-2-azaspiro[4.4]non-2-en-3-yl)-1H-pyrazolo[3,4-b]pyridin-4-amine (Compound No. 66)
Yield: 38%
m/z: (M$^+$+1) 423.20
1-Ethyl-N-[1-(1-methylethyl)piperidin-4-yl]-5-(1-oxa-2-azaspiro[4.4]non-2-en-3-yl)-1H-pyrazolo[3,4-b]pyridin-4-amine (Compound No. 67)
Yield: 34%
m/z: (M$^+$+1) 411.25
1-Ethyl-5-(1-oxa-2-azaspiro[4.4]non-2-en-3-yl)-N-(1-propylpiperidin-4-yl)-1H-pyrazolo[3,4-b]pyridin-4-amine (Compound No. 68)
Yield: 34%
m/z: (M$^+$+1) 411.25
N-(1-cyclopentylpiperidin-4-yl)-1-ethyl-5-(1-oxa-2-azaspiro[4.5]dec-2-en-3-yl)-1H-pyrazolo[3,4-b]pyridin-4-amine (Compound No. 69)
Yield: 30%
m/z: (M$^+$+1) 451.27
1-Ethyl-N-[1-(1-methylethyl)piperidin-4-yl]-5-(1-oxa-2-azaspiro[4.5]dec-2-en-3-yl)-1H-pyrazolo[3,4-b]pyridin-4-amine (Compound No. 70)
Yield: 32%
m/z: (M$^+$+1) 425.21
1-Ethyl-N-(1-ethylpiperidin-4-yl)-5-(1-oxa-2-azaspiro[4.5]dec-2-en-3-yl)-1H-pyrazolo[3,4-b]pyridin-4-amine (Compound No. 84)
Yield: 9%
m/z: (M$^+$+1) 411.41
1-Ethyl-N-(1-methylpiperidin-4-yl)-5-(1-oxa-2-azaspiro[4.5]dec-2-en-3-yl)-1H-pyrazolo[3,4-b]pyridin-4-amine (Compound No. 85)
Yield: 7%
m/z: (M$^+$+1) 397.24
1-Ethyl-5-(1-oxa-2-azaspiro[4.5]dec-2-en-3-yl)-N-(1-propylpiperidin-4-yl)-1H-pyrazolo[3,4-b]pyridin-4-amine (Compound No. 88)
Yield: 32%
m/z: (M$^+$+1) 425.24

N-[1-(cyclopropylmethyl)piperidin-4-yl]-1-ethyl-5-(1-oxa-2-azaspiro[4.5]dec-2-en-3-yl)-1H-pyrazolo[3,4-b]pyridin-4-amine (Compound No. 89)

Yield: 37% m/z: (M$^+$+1) 437.26

2-(4-{[1-Ethyl-5-(1-oxa-2-azaspiro[4.5]dec-2-en-3-yl)-1H-pyrazolo[3,4-b]pyridin-4-yl]amino}piperidin-1-yl)ethanol (Compound No. 90)

Yield: 38% m/z: (M$^+$+1) 427.25

Example 33

Preparation of Benzyl 3-methylidenecyclobutyl ether

Step a: Preparation of [3-(benzyloxy)cyclobutyl]methanol

A tetrahydrofuran solution of 3-(benzyloxy)cyclobutanecarboxylic acid (2.5 gm, 11.36 mmol) was added to a solution of sodium borohydride (0.52 gm, 13.63 mmol) in tetrahydrofuran. Iodine (1.44 gm, 5.68 mmol) in tetrahydrofuran solution was added to solution at 0° C., after about 15 minutes, and the mixture was stirred at room temperature for about 2 hours. It was quenched with dilute hydrochloric acid and extracted with ethyl acetate. The organic layer was washed with dilute sodium hydroxide solution and brine, dried over anhydrous sodium sulphate and concentrated under reduced pressure to get the title compound.

Yield: 1.1 gm (50%)

Step b: Preparation of [3-(benzyloxy)cyclobutyl]methyl methanesulfonate

Methane sulphonyl chloride (0.16 gm, 1.1 mmol) and triethylamine (0.26 gm, 2.6 mmol) were added to a solution of [3-(benzyloxy)cyclobutyl]methanol (0.25 gm, 1.3 mmol) (step a) in dichloromethane at 0° C. and the reaction mixture was stirred at room temperature for about 2 hours. It was diluted with dichloromethane, washed with water and brine, dried over anhydrous sodium sulphate and concentrated under reduced pressure to get the title compound.

Yield: 0.27 gm (14%)

Step c: Preparation of Benzyl 3-methylidenecyclobutyl ether

Sodium iodide (0.45 gm, 3 mmol) and 1,8-diazabicyclo(5.4.0)undec-7-ene (0.304 gm, 2 mmol) were added to a stirred solution of [3-(benzyloxy)cyclobutyl]methyl methanesulfonate (0.27 gm, 1 mmol) (step b) in dimethoxyethane and the reaction mixture was refluxed for about 2 hours. It was allowed to come to room temperature and then was stirred with diethyl ether and water for about 10 minutes. The ether layer was separated and aqueous layer was washed with ether. The combined organic layer was washed with brine, dried over anhydrous sodium sulphate and concentrated under reduced pressure. The crude compound was purified over silica gel.

Yield: 0.050 gm (39.6%)

Example 34

Preparation of 5-[2-(benzyloxy)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 44)

Step a: Preparation of 5-[2-(benzyloxy)-5-oxa-6-azaspiro[3.4]oct-6-en-7-yl]-1-(4-methoxybenzyl)-N-(tetrahydro-2H-pyran-4-yl)-1H-pyrazolo[3,4-b]pyridin-4-amine (Compound No. 111)

The title compound was prepared by following the procedure of example 9.

Yield: 0.40 gm (75%)

m/z: (M$^+$+1) 554.0

Step b: Preparation of 5-[2-(benzyloxy)-5-oxa-6-azaspiro[3.4]oct-6-en-7-yl]-N-(tetrahydro-2H-pyran-4-yl)-1H-pyrazolo[3,4-b]pyridin-4-amine Trifluoroacetic acid (0.41 gm, 3.61 mmol) was added to the solution of 5-[2-(benzyloxy)-5-oxa-6-azaspiro[3.4]oct-6-en-7-yl]-1-(4-methoxybenzyl)-N-(tetrahydro-2H-pyran-4-yl)-1H-pyrazolo[3,4-b]pyridin-4-amine (0.4 gm, 0.72 mmol) (step a) in dichloroethane (5 ml) and the reaction mixture was refluxed for about 2 hours under inert atmosphere. It was cooled, diluted with ethyl acetate, washed with saturated sodium bicarbonate, water and brine, dried over anhydrous sodium sulphate and concentrated under reduced pressure to get the title compound.

Yield: 0.21 gm (45%)

Step c: Preparation of 5-[2-(benzyloxy)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 44)

Ethyl iodide (0.227 gm, 1.45 mmol) and potassium carbonate (0.2 gm, 1.45 mmol) were added to the solution of 5-[2-(benzyloxy)-5-oxa-6-azaspiro[3.4]oct-6-en-7-yl]-N-(tetrahydro-2H-pyran-4-yl)-1H-pyrazolo[3,4-b]pyridin-4-amine (0.21 gm, 0.48 mmol) (step b) in dimethylformamide and the reaction mixture was stirred at 60° C. for about 5 hours. It was cooled, diluted with water and extracted with ethyl acetate. The organic layer was washed with brine, dried over anhydrous sodium sulphate and concentrated under reduced pressure. The crude product was purified over silica gel column.

Yield: 0.055 gm (25%)

m/z: (M$^+$+1) 462.18

NMR: (δ, CDCl$_3$) 8.30 (s, 1H), 8.13 (s, 1H), 7.96 (d, 1H), 7.37-7.29 (m, 5H), 4.52-4.48 (m, 4H), 4.3-4.03 (m, 1H), 4.17 (s, 1H), 4.07-4.01 (m, 2H), 3.63-3.58 (m, 4H), 1.50-1.28 (m, 11H)

Example 35

Preparation of 7-[1-ethyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 93)

Palladium/carbon (10%, 0.010 gm) was added to a solution of 5-[2-(benzyloxy)-5-oxa-6-azaspiro[3.4]oct-6-en-7-yl]-1-ethyl-N-(tetrahydro-2H-pyran-4-yl)-1H-pyrazolo[3,4-b]pyridin-4-amine (0.055 gm, 0.12 mmol) (example 34) in methanol and the reaction mixture was stirred under hydrogen balloon for about 12 hours. It was filtered through a bed of celite and residue was washed with methanol. The combined filtrate was concentrated under reduced pressure to get the title compound.

Yield: 0.021 gm (47%)

m/z: (M$^+$+1) 372.10.

NMR: (δ, CDCl$_3$) 8.14 (s, 1H), 7.96 (s, 1H), 7.88 (s, 1H), 4.63-4.49 (m, 3H), 4.03-4.01 (m, 4H), 3.63-3.61 (m, 4H), 2.15-2.03 (m, 4H), 1.79-1.28 (m, 7H).

The following compound was prepared similarly

{7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-yl}methanol (Compound No. 104)

Yield: 39% m/z: 387.13 (M$^+$+1)

The following compounds can be prepared similarly

7-[4-(Cyclohexylamino)-1-ethyl-1H-pyrazolo[3,4-b]pyridin-5-yl]-5-oxa-6-azaspiro[3.4]oct-6-en-2-ol (Compound No. 121), 7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 122), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 169), 7-[4-(Cyclohexylamino)-1-ethyl-3-methyl-1H-pyrazolo[3,4-b]pyridin-5-yl]-5-oxa-6-azaspiro[3.4]oct-6-en-2-ol (Compound No. 176), 7-[4-(Cyclohexylamino)-1-ethyl-1H-pyrazolo[3,4-b]pyridin-5-yl]-5-oxa-6-azaspiro[3.4]oct-6-en-2-yl}methanol (Compound No. 301), (7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methanol (Compound No. 302), Example 36

Preparation of 1-ethyl-5-(5-oxa-6-azaspiro[3.4]oct-6-en-7-yl)-1H-pyrazolo[3,4-b]pyridin-4-amine Palladium hydroxide/carbon (1 gm) is added to a solution of N-benzyl-1-ethyl-5-(5-oxa-6-azaspiro[3.4]oct-6-en-7-yl)-1H-pyrazolo[3,4-b]pyridin-4-amine (1 gm, 0.0022 mole) (example 9) in methanol and the reaction mixture is stirred under hydrogen balloon for about 12 hours. It is filtered through a bed of celite and residue is washed with methanol. The combined filtrate is concentrated under reduced pressure to get the title compound.

Example 37

Preparation of 1-ethyl-5-(5-oxa-6-azaspiro[3.4]oct-6-en-7-yl)-N-pyridin-4-yl-1H-pyrazolo[3,4-b]pyridin-4-amine (Compound No. 230)

2,2'-Bis(diphenylphosphino)-1,1'-binaphthyl (0.3 equivalent), palladium acetate (0.09 equivalent) and cesium carbonate (1.5 equivalent) is added to 4-bromo pyridine (1 equivalent) in anhydrous dioxane under inert atmosphere. 1-Ethyl-5-(5-oxa-6-azaspiro[3.4]oct-6-en-7-yl)-1H-pyrazolo[3,4-b]pyridin-4-amine (1.3 equivalent) (example 36) is added and the reaction mixture is stirred at reflux for about 10-12 hours. It is cooled to room temperature and filtered through celite. The reaction mixture is extracted with ethyl acetate. The organic layer is washed with water, dried over anhydrous sodium sulphate and concentrated in vacuo. The crude compound is purified by column chromatography.

The following compounds can be prepared similarly

1-Ethyl-5-(5-oxa-6-azaspiro[3.4]oct-6-en-7-yl)-N-pyridin-3-yl-1H-pyrazolo[3,4-b]pyridin-4-amine (Compound No. 231), 1-Ethyl-5-(5-oxa-6-azaspiro[3.4]oct-6-en-7-yl)-N-pyridin-2-yl-1H-pyrazolo[3,4-b]pyridin-4-amine (Compound No. 232), 1-Ethyl-5-(5-oxa-6-azaspiro[3.4]oct-6-en-7-yl)-N-pyrazin-2-yl-1H-pyrazolo[3,4-b]pyridin-4-amine (Compound No. 233), 1-Ethyl-5-(5-oxa-6-azaspiro[3.4]oct-6-en-7-yl)-N-pyrimidin-2-yl-1H-pyrazolo[3,4-b]pyridin-4-amine (Compound No. 234), 1-Ethyl-5-(5-oxa-6-azaspiro[3.4]oct-6-en-7-yl)-N-1,2,4-triazin-5-yl-1H-pyrazolo[3,4-b]pyridin-4-amine (Compound No. 235), 1-Ethyl-5-(5-oxa-6-azaspiro[3.4]oct-6-en-7-yl)-N-1,3-thiazol-2-yl-1H-pyrazolo[3,4-b]pyridin-4-amine (Compound No. 236), 1-Ethyl-5-(5-oxa-6-azaspiro[3.4]oct-6-en-7-yl)-N-4H-1,2,4-triazol-4-yl-1H-pyrazolo[3,4-b]pyridin-4-amine (Compound No. 237), 1-Ethyl-5-(5-oxa-6-azaspiro[3.4]oct-6-en-7-yl)-N-2H-tetrazol-5-yl-1H-pyrazolo[3,4-b]pyridin-4-amine (Compound No. 238), 1-Ethyl-5-(5-oxa-6-azaspiro[3.4]oct-6-en-7-yl)-N-1H-tetrazol-5-yl-1H-pyrazolo[3,4-b]pyridin-4-amine (Compound No. 239), 1-Ethyl-5-(5-oxa-6-azaspiro[3.4]oct-6-en-7-yl)-N-pyrimidin-5-yl-1H-pyrazolo[3,4-b]pyridin-4-amine (Compound No. 240), 1-Ethyl-5-(1-oxa-2-azaspiro[4.5]dec-2-en-3-yl)-N-pyridin-4-yl-1H-pyrazolo[3,4-b]pyridin-4-amine (Compound No. 241), 1-Ethyl-5-(1-oxa-2-azaspiro[4.4]non-2-en-3-yl)-N-pyridin-4-yl-1H-pyrazolo[3,4-b]pyridin-4-amine (Compound No. 242), 1-Ethyl-5-(1-oxa-2-azaspiro[4.5]dec-2-en-3-yl)-N-pyridin-3-yl-1H-pyrazolo[3,4-b]pyridin-4-amine (Compound No. 243), 1-Ethyl-5-(1-oxa-2-azaspiro[4.5]dec-2-en-3-yl)-N-pyridin-2-yl-1H-pyrazolo[3,4-b]pyridin-4-amine (Compound No. 244), 1-Ethyl-5-(1-oxa-2-azaspiro[4.5]dec-2-en-3-yl)-N-pyrimidin-2-yl-1H-pyrazolo[3,4-b]pyridin-4-amine (Compound No. 245), 1-Ethyl-5-(1-oxa-2-azaspiro[4.5]dec-2-en-3-yl)-N-pyrimidin-5-yl-1H-pyrazolo[3,4-b]pyridin-4-amine (Compound No. 246), 1-Ethyl-5-(1-oxa-2-azaspiro[4.5]dec-2-en-3-yl)-N-1,2,4-triazin-5-yl-1H-pyrazolo[3,4-b]pyridin-4-amine (Compound No. 247), 1-Ethyl-5-(1-oxa-2-azaspiro[4.5]dec-2-en-3-yl)-N-1,3-thiazol-2-yl-1H-pyrazolo[3,4-b]pyridin-4-amine (Compound No. 248), 1-Ethyl-5-(1-oxa-2-azaspiro[4.5]dec-2-en-3-yl)-N-4H-1,2,4-triazol-4-yl-1H-pyrazolo[3,4-b]pyridin-4-amine (Compound No. 249), 1-Ethyl-5-(1-oxa-2-azaspiro[4.5]dec-2-en-3-yl)-N-2H-tetrazol-5-yl-1H-pyrazolo[3,4-b]pyridin-4-amine (Compound No. 250), 1-Ethyl-5-(1-oxa-2-azaspiro[4.5]dec-2-en-3-yl)-N-1H-tetrazol-5-yl-1H-pyrazolo[3,4-b]pyridin-4-amine (Compound No. 251), 1-Ethyl-5-(1-oxa-2-azaspiro[4.4]non-2-en-3-yl)-N-pyridin-3-yl-1H-pyrazolo[3,4-b]pyridin-4-amine (Compound No. 252), 1-Ethyl-5-(1-oxa-2-azaspiro[4.4]non-2-en-3-yl)-N-pyridin-2-yl-1H-pyrazolo[3,4-b]pyridin-4-amine (Compound No. 253), 1-Ethyl-5-(1-oxa-2-azaspiro[4.4]non-2-en-3-yl)-N-pyrimidin-2-yl-1H-pyrazolo[3,4-b]pyridin-4-amine (Compound No. 254), 1-Ethyl-5-(1-oxa-2-azaspiro[4.4]non-2-en-3-yl)-N-pyrimidin-5-yl-1H-pyrazolo[3,4-b]pyridin-4-amine (Compound No. 255), 1-Ethyl-5-(1-oxa-2-azaspiro[4.4]non-2-en-3-yl)-N-1,2,4-triazin-5-yl-1H-pyrazolo[3,4-b]pyridin-4-amine (Compound No. 256), 1-Ethyl-5-(1-oxa-2-azaspiro[4.4]non-2-en-3-yl)-N-1H-tetrazol-5-yl-1H-pyrazolo[3,4-b]pyridin-4-amine (Compound No. 257), 1-Ethyl-5-(1-oxa-2-azaspiro[4.4]non-2-en-3-yl)-N-2H-tetrazol-5-yl-1H-pyrazolo[3,4-b]pyridin-4-amine (Compound No. 258), 1-Ethyl-5-(1-oxa-2-azaspiro[4.4]non-2-en-3-yl)-N-4H-1,2,4-triazol-4-yl-1H-pyrazolo[3,4-b]pyridin-4-amine (Compound No. 259), 1-Ethyl-5-(1-oxa-2-azaspiro[4.4]non-2-en-3-yl)-N-1,3-thiazol-2-yl-1H-pyrazolo[3,4-b]pyridin-4-amine (Compound No. 260), 1-Ethyl-N-furan-3-yl-5-(1-oxa-2-azaspiro[4.5]dec-2-en-3-yl)-1H-pyrazolo[3,4-b]pyridin-4-amine (Compound No. 261), 1-Ethyl-N-furan-3-yl-5-(1-oxa-2-azaspiro[4.4]non-2-en-3-yl)-1H-pyrazolo[3,4-b]pyridin-4-amine (Compound No. 262), 1-Ethyl-N-furan-3-yl-5-(5-oxa-6-azaspiro[3.4]oct-6-en-7-yl)-1H-pyrazolo[3,4-b]pyridin-4-amine (Compound No. 263), 1-Ethyl-5-(1-oxa-2-azaspiro[4.4]non-2-en-3-yl)-N-pyrazin-2-yl-1H-pyrazolo[3,4-b]pyridin-4-amine (Compound No. 264), 1-Ethyl-5-(1-oxa-2-azaspiro[4.5]dec-2-en-3-yl)-N-pyrazin-2-yl-1H-pyrazolo[3,4-b]pyridin-4-amine (Compound No. 265), 1-Ethyl-5-(1-oxa-2-azaspiro[4.4]non-2-en-3-yl)-N-1,2,4-triazin-3-yl-1H-pyrazolo[3,4-b]pyridin-4-amine (Compound No. 292), 1-Ethyl-5-(5-oxa-6-azaspiro[3.4]oct-6-en-7-yl)-N-1,2,4-triazin-3-yl-1H-pyrazolo[3,4-b]pyridin-4-amine (Compound No. 293), 1-Ethyl-5-(1-oxa-2-azaspiro[4.5]dec-2-en-3-yl)-N-1,2,4-triazin-3-yl-1H-pyrazolo[3,4-b]pyridin-4-amine (Compound No. 294).

Example 38

Preparation of 3-{[1-ethyl-5-(5-oxa-6-azaspiro[3.4]oct-6-en-7-yl)-1H-pyrazolo[3,4-b]pyridin-4-yl]amino}cyclobutanecarboxylic acid (Compound No. 115)

Trifluoroacetic acid (4 equivalent) is added to the solution of tert-butyl 3-{[1-ethyl-5-(5-oxa-6-azaspiro[3.4]oct-6-en-7-yl)-1H-pyrazolo[3,4-b]pyridin-4-yl]amino}cyclobutanecarboxylate (1 equivalent) (example 9) in dichloroethane and the reaction mixture is stirred at room temperature for about 2 hours under inert atmosphere. It is cooled and diluted with ethyl acetate. The organic layer is washed with saturated sodium bicarbonate, water and brine, dried over anhydrous sodium sulphate and concentrated under reduced pressure to get the title compound.

The following compounds can be prepared similarly

3-{[1-Ethyl-5-(1-oxa-2-azaspiro[4.4]non-2-en-3-yl)-1H-pyrazolo[3,4-b]pyridin-4-yl]amino}cyclobutane carboxylic acid (Compound No. 116), 3-{[1-Ethyl-5-(1-oxa-2-azaspiro[4.5]dec-2-en-3-yl)-1H-pyrazolo[3,4-b]pyridin-4-yl]amino}cyclobutane carboxylic acid (Compound No. 117), 4-{[1-Ethyl-5-(5-oxa-6-azaspiro[3.4]oct-6-en-7-yl)-1H-pyrazolo[3,4-b]pyridin-4-yl]amino}cyclohexanecarboxylic acid (Compound No. 132), 4-{[1-Ethyl-5-(1-oxa-2-azaspiro[4.4]non-2-en-3-yl)-1H-pyrazolo[3,4-b]pyridin-4-yl]amino}cyclohexanecarboxylic acid (Compound No. 133), 4-{[1-Ethyl-5-(1-oxa-2-azaspiro[4.5]dec-2-en-3-yl)-1H-pyrazolo[3,4-b]pyridin-4-yl]amino}cyclohexanecarboxylic acid (Compound No. 134), 4-{[5-(2-Cyano-5-oxa-6-azaspiro[3.4]oct-6-en-7-yl)-1-ethyl-1H-pyrazolo[3,4-b]pyridin-4-yl]amino}cyclohexanecarboxylic acid (Compound No. 135), 4-{[5-(2-Cyano-5-oxa-6-azaspiro[3.4]oct-6-en-7-yl)-1-ethyl-3-methyl-1H-pyrazolo[3,4-b]pyridin-4-yl]amino}cyclohexanecarboxylic acid (Compound No. 143), 4-{[1-Ethyl-5-(2-hydroxy-5-oxa-6-azaspiro[3.4]oct-6-en-7-yl)-3-methyl-1H-pyrazolo[3,4-b]pyridin-4-yl]amino}cyclohexanecarboxylic acid (Compound No. 144), 4-{[1-Ethyl-3-methyl-5-(1-oxa-2-azaspiro[4.4]non-2-en-3-yl)-1H-pyrazolo[3,4-b]pyridin-4-yl]amino}cyclohexanecarboxylic acid (Compound No. 145), 4-{[1-Ethyl-3-methyl-5-(1-oxa-2-azaspiro[4.5]dec-2-en-3-yl)-1H-pyrazolo[3,4-b]pyridin-4-yl]amino}cyclohexanecarboxylic acid (Compound No. 146), 4-{[1-Ethyl-5-(8-hydroxy-1-oxa-2-azaspiro[4.5]dec-2-en-3-yl)-1H-pyrazolo[3,4-b]pyridin-4-yl]amino}cyclohexanecarboxylic acid (Compound No. 147), 4-{[5-(8-Carbamoyl-1-oxa-2-azaspiro[4.5]dec-2-en-3-yl)-1-ethyl-1H-pyrazolo[3,4-b]pyridin-4-yl]amino}cyclohexanecarboxylic acid (Compound No. 150), 3-{[5-(8-Carbamoyl-1-oxa-2-azaspiro[4.5]dec-2-en-3-yl)-1-ethyl-1H-pyrazolo[3,4-b]pyridin-4-yl]amino}cyclobutanecarboxylic acid (Compound No. 151), 4-{[1-Ethyl-3-methyl-5-(5-oxa-6-azaspiro[3.4]oct-6-en-7-yl)-1H-pyrazolo[3,4-b]pyridin-4-yl]amino}cyclohexanecarboxylic acid (Compound No. 179), 4-{[1-Ethyl-5-(8-hydroxy-1-oxa-2-azaspiro[4.5]dec-2-en-3-yl)-3-methyl-1H-pyrazolo[3,4-b]pyridin-4-yl]amino}cyclohexanecarboxylic acid (Compound No. 180), 3-{[1-Ethyl-3-methyl-5-(5-oxa-6-azaspiro[3.4]oct-6-en-7-yl)-1H-pyrazolo[3,4-b]pyridin-4-yl]amino}cyclobutanecarboxylic acid (Compound No. 181), 3-{[1-Ethyl-3-methyl-5-(1-oxa-2-azaspiro[4.4]non-2-en-3-yl)-1H-pyrazolo[3,4-b]pyridin-4-yl]amino}cyclobutanecarboxylic acid (Compound No. 182), 3-{[1-Ethyl-3-methyl-5-(1-oxa-2-azaspiro[4.5]dec-2-en-3-yl)-1H-pyrazolo[3,4-b]pyridin-4-yl]amino}cyclobutanecarboxylic acid (Compound No. 183), 3-{[5-(2-Cyano-5-oxa-6-azaspiro[3.4]oct-6-en-7-yl)-1-ethyl-1H-pyrazolo[3,4-b]pyridin-4-yl]amino}cyclobutanecarboxylic acid (Compound No. 184), 3-{[5-(2-Cyano-5-oxa-6-azaspiro[3.4]oct-6-en-7-yl)-1-ethyl-3-methyl-1H-pyrazolo[3,4-b]pyridin-4-yl]amino}cyclobutanecarboxylic acid (Compound No. 185), 3-{[1-Ethyl-5-(8-hydroxy-1-oxa-2-azaspiro[4.5]dec-2-en-3-yl)-3-methyl-1H-pyrazolo[3,4-b]pyridin-4-yl]amino}cyclobutanecarboxylic acid (Compound No. 186), 3-{[1-Ethyl-5-(8-hydroxy-1-oxa-2-azaspiro[4.5]dec-2-en-3-yl)-1H-pyrazolo[3,4-b]pyridin-4-yl]amino}cyclobutanecarboxylic acid (Compound No. 187), 3-{[1-Ethyl-5-(2-hydroxy-5-oxa-6-azaspiro[3.4]oct-6-en-7-yl)-1H-pyrazolo[3,4-b]pyridin-4-yl]amino}cyclobutanecarboxylic acid (Compound No. 188), 3-{[1-Ethyl-5-(2-hydroxy-5-oxa-6-azaspiro[3.4]oct-6-en-7-yl)-3-methyl-1H-pyrazolo[3,4-b]pyridin-4-yl]amino}cyclobutanecarboxylic acid (Compound No. 189), 3-{[5-(2-Amino-5-oxa-6-azaspiro[3.4]oct-6-en-7-yl)-1-ethyl-1H-pyrazolo[3,4-b]pyridin-4-yl]amino}cyclobutanecarboxylic acid (Compound No. 196), 3-{[5-(2-Amino-5-oxa-6-azaspiro[3.4]oct-6-en-7-yl)-1-ethyl-3-methyl-1H-pyrazolo[3,4-b]pyridin-4-yl]amino}cyclobutanecarboxylic acid (Compound No. 197), 3-({5-[2-(Acetylamino)-5-oxa-6-azaspiro[3.4]oct-6-en-7-yl]-1-ethyl-3-methyl-1H-pyrazolo[3,4-b]pyridin-4-yl}amino)cyclobutanecarboxylic acid (Compound No. 198), 3-({5-[2-(Acetylamino)-5-oxa-6-azaspiro[3.4]oct-6-en-7-yl]-1-ethyl-1H-pyrazolo[3,4-b]pyridin-4-yl}amino)cyclobutanecarboxylic acid (Compound No. 199), 3-({1-Ethyl-5-[2-(propanoylamino)-5-oxa-6-azaspiro[3.4]oct-6-en-7-yl]-1H-pyrazolo[3,4-b]pyridin-4-yl}amino)cyclobutanecarboxylic acid (Compound No. 200), 3-({1-Ethyl-3-methyl-5-[2-(propanoylamino)-5-oxa-6-azaspiro[3.4]oct-6-en-7-yl]-1H-pyrazolo[3,4-b]pyridin-4-yl}amino)cyclobutanecarboxylic acid (Compound No. 201), 4-{[5-(8-Amino-1-oxa-2-azaspiro[4.5]dec-2-en-3-yl)-1-ethyl-3-methyl-1H-pyrazolo[3,4-b]pyridin-4-yl]amino}cyclohexanecarboxylic acid (Compound No. 206), 4-{[5-(8-Amino-1-oxa-2-azaspiro[4.5]dec-2-en-3-yl)-1-ethyl-1H-pyrazolo[3,4-b]pyridin-4-yl]amino}cyclohexanecarboxylic acid (Compound No. 207), 4-({5-[8-(Acetylamino)-1-oxa-2-azaspiro[4.5]dec-2-en-3-yl]-1-ethyl-1H-pyrazolo[3,4-b]pyridin-4-yl}amino)cyclohexanecarboxylic acid (Compound No. 208), 4-({5-[8-(Acetylamino)-1-oxa-2-azaspiro[4.5]dec-2-en-3-yl]-1-ethyl-3-methyl-1H-pyrazolo[3,4-b]pyridin-4-yl}amino)cyclohexanecarboxylic acid (Compound No. 209), 4-({1-Ethyl-3-methyl-5-[8-(propanoylamino)-1-oxa-2-azaspiro[4.5]dec-2-en-3-yl]-1H-pyrazolo[3,4-b]pyridin-4-yl}amino)cyclohexanecarboxylic acid (Compound No. 210), 4-({1-Ethyl-5-[8-(propanoylamino)-1-oxa-2-azaspiro[4.5]dec-2-en-3-yl]-1H-pyrazolo[3,4-b]pyridin-4-yl}amino)cyclohexanecarboxylic acid (Compound No. 211), 7-{4-[(4-Carboxycyclohexyl)amino]-1-ethyl-3-methyl-1H-pyrazolo[3,4-b]pyridin-5-yl}-5-oxa-6-azaspiro[3.4]oct-6-ene-2-carboxylic acid (Compound No. 212), 7-{4-[(4-Carboxycyclohexyl)amino]-1-ethyl-1H-pyrazolo[3,4-b]pyridin-5-yl}-5-oxa-6-azaspiro[3.4]oct-6-ene-2-carboxylic acid (Compound No. 213), 4-{[5-(2-Carbamoyl-5-oxa-6-azaspiro[3.4]oct-6-en-7-yl)-1-ethyl-1H-pyrazolo[3,4-b]pyridin-4-yl]amino}cyclohexanecarboxylic acid (Compound No. 214), 4-{[5-(2-Carbamoyl-5-oxa-6-azaspiro[3.4]oct-6-en-7-yl)-1-ethyl-3-methyl-1H-pyrazolo[3,4-b]pyridin-4-yl]amino}cyclohexanecarboxylic acid (Compound No. 215), 4-({1-Ethyl-3-methyl-5-[2-(methylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 216), 4-({1-Ethyl-5-[2-(methylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 217), 4-({1-Ethyl-5-[2-(ethylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 218), 4-({1-Ethyl-5-[2-(ethylcarbamoyl)-5-oxa-6-azaspiro[3.4]oct-6-en-7-yl]-3-methyl-1H-pyrazolo[3,4-b]pyridin-4-yl}amino)cyclohexanecarboxylic acid (Compound No. 219), 3-{4-[(4-Carboxycyclohexyl)amino]-1-ethyl-1H-pyrazolo[3,4-b]pyridin-5-yl}-1-oxa-2-azaspiro[4.5]dec-2-ene-8-carboxylic acid (Compound No. 220), 3-{4-[(4-Carboxycyclohexyl)amino]-1-ethyl-3-methyl-1H-pyrazolo[3,4-b]pyridin-5-yl}-1-oxa-2-azaspiro[4.5]dec-2-ene-8-carboxylic acid (Compound No. 221), 4-{[5-(8-Carbamoyl-1-oxa-2-azaspiro[4.5]dec-2-en-3-yl)-1-ethyl-3-methyl-1H-pyrazolo[3,4-b]pyridin-4-yl]amino}cyclohexanecarboxylic acid (Compound No. 222), 4-({1-Ethyl-5-[8-(methylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 223), 4-({1-Ethyl-3-methyl-5-[8-(methylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 224), 4-({1-Ethyl-5-[8-(ethylcarbamoyl)-1-oxa-2-azaspiro[4.5]dec-2-en-3-yl]-3-methyl-1H-pyrazolo[3,4-b]pyridin-4-yl}amino)cyclohexanecarboxylic acid (Compound No. 225), 4-({1-Ethyl-5-[8-(ethylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 226), 4-{[1-Ethyl-5-(8-methoxy-1-oxa-2-azaspiro[4.5]dec-2-en-3-yl)-1H-pyrazolo[3,4-b]pyridin-4-yl]amino}cyclohexanecarboxylic acid (Compound No. 227), 4-{[5-(8-Ethoxy-1-oxa-2-azaspiro[4.5]dec-2-en-3-yl)-1-ethyl-1H-pyrazolo[3,4-b]pyridin-4-yl]amino}cyclohexanecarboxylic acid (Compound No. 228), 4-({1-Ethyl-5-[8-(2-hydroxyethoxy)-1-oxa-2-azaspiro[4.5]dec-2-en-3-yl]-1H-pyrazolo[3,4-b]pyridin-4-yl}amino)cyclohexanecarboxylic acid (Compound No. 229).

Example 39

Preparation of 3-[4-(cyclohexylamino)-1-ethyl-3-methyl-1H-pyrazolo[3,4-b]pyridin-5-yl]-1-oxa-2-azaspiro[4.5]dec-2-en-8-yl 4-methylbenzenesulfonate 3-[4-(Cyclohexylamino)-1-ethyl-3-methyl-1H-pyrazolo[3,4-b]pyridin-5-yl]-1-oxa-2-azaspiro[4.5]dec-2-en-8-ol (0.0025 mole) (example 26) is dissolved in dichloromethane. Triethyl amine (0.0050 mol) is added at 0° and p-toluene sulphonyl chloride (0.0050 mole) is added. The reaction mixture is stirred for about 5 hrs. Water is added and extraction is done with dichloromethane. The organic layer is washed with brine, dried and concentrated under reduced pressure to give crude product, which is purified by column chromatography.

The following compound can be prepared similarly

3-[4-(Cyclohexylamino)-1-ethyl-1H-pyrazolo[3,4-b]pyridin-5-yl]-1-oxa-2-azaspiro[4.5]dec-2-en-8-yl 4-methylbenzenesulfonate Example 40

Preparation of 3-[4-(Cyclohexylamino)-1-ethyl-3-methyl-1H-pyrazolo[3,4-b]pyridin-5-yl]-1-oxa-2-azaspiro[4.5]dec-2-ene-8-carbonitrile (Compound No. 173)

3-[4-(Cyclohexylamino)-1-ethyl-3-methyl-1H-pyrazolo[3,4-b]pyridin-5-yl]-1-oxa-2-azaspiro[4.5]dec-2-en-8-yl 4-methylbenzenesulfonate (0.0018 mole) (example 39) is taken in dimethylformamide. Sodium cyanide (0.0036 mole) is added and the reaction mixture is stirred at 60-65° C. overnight. Water is added and extraction is done with ethyl acetate. The organic layer is washed with brine, dried and concentrated under reduced pressure to give crude compound, which is purified by column chromatography.

The following compounds can be prepared similarly

3-[4-(Cyclohexylamino)-1-ethyl-1H-pyrazolo[3,4-b]pyridin-5-yl]-1-oxa-2-azaspiro[4.5]dec-2-ene-8-carbonitrile (Compound No. 118), 3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carbonitrile (Compound No. 120), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-ene-8-carbonitrile (Compound No. 167).

Example 41

Preparation of N-cyclohexyl-1-ethyl-5-[8-(1H-tetrazol-5-yl)-1-oxa-2-azaspiro[4.5]dec-2-en-3-yl]-1H-pyrazolo[3,4-b]pyridin-4-amine (Compound No. 322)

3-[4-(Cyclohexylamino)-1-ethyl-1H-pyrazolo[3,4-b]pyridin-5-yl]-1-oxa-2-azaspiro[4.5]dec-2-ene-8-carbonitrile (0.00098 mole) (example 40), sodium azide (0.00147 mole) and triethyl amine hydrochloride (0.00147 mol) is taken in toluene. The reaction mixture is refluxed overnight. Toluene is removed and water is added. The extraction is done with ethyl acetate. The organic layer is washed with brine, dried and concentrated under reduced pressure to give crude compound, which is purified by column chromatography The following compounds can be prepared similarly 1-Ethyl-N-(tetrahydro-2H-pyran-4-yl)-5-[2-(1H-tetrazol-5-yl)-5-oxa-6-azaspiro[3.4]oct-6-en-7-yl]-1H-pyrazolo[3,4-b]pyridin-4-amine (Compound No. 318), N-cyclohexyl-1-ethyl-5-[2-(1H-tetrazol-5-yl)-5-oxa-6-azaspiro[3.4]oct-6-en-7-yl]-1H-pyrazolo[3,4-b]pyridin-4-amine (Compound No. 319), N-(1,1-dioxidotetrahydro-2H-thiopyran-4-yl)-1-ethyl-5-[2-(1H-tetrazol-5-yl)-5-oxa-6-azaspiro[3.4]oct-6-en-7-yl]-1H-pyrazolo[3,4-b]pyridin-4-amine (Compound No. 320), 1-Ethyl-N-(tetrahydro-2H-pyran-4-yl)-5-[8-(1H-tetrazol-5-yl)-1-oxa-2-azaspiro[4.5]dec-2-en-3-yl]-1H-pyrazolo[3,4-b]pyridin-4-amine (Compound No. 321), N-(1,1-dioxidotetrahydro-2H-thiopyran-4-yl)-1-ethyl-5-[8-(1H-tetrazol-5-yl)-1-oxa-2-azaspiro[4.5]dec-2-en-3-yl]-1H-pyrazolo[3,4-b]pyridin-4-amine (Compound No. 323), N-(1,1-dioxidotetrahydro-2H-thiopyran-4-yl)-1-ethyl-5-[8-(2H-tetrazol-5-yl)-1-oxa-2-azaspiro[4.5]dec-2-en-3-yl]-1H-pyrazolo[3,4-b]pyridin-4-amine (Compound No. 324), N-cyclohexyl-1-ethyl-5-[8-(2H-tetrazol-5-yl)-1-oxa-2-azaspiro[4.5]dec-2-en-3-yl]-1H-pyrazolo[3,4-b]pyridin-4-amine (Compound No. 325), 1-Ethyl-N-(tetrahydro-2H-pyran-4-yl)-5-[8-(2H-tetrazol-5-yl)-1-oxa-2-azaspiro[4.5]dec-2-en-3-yl]-1H-pyrazolo[3,4-b]pyridin-4-amine (Compound No. 326), 1-Ethyl-N-(tetrahydro-2H-pyran-4-yl)-5-[2-(2H-tetrazol-5-yl)-5-oxa-6-azaspiro[3.4]oct-6-en-7-yl]-1H-pyrazolo[3,4-b]pyridin-4-amine (Compound No. 327), N-cyclohexyl-1-ethyl-5-[2-(2H-tetrazol-5-yl)-5-oxa-6-azaspiro[3.4]oct-6-en-7-yl]-1H-pyrazolo[3,4-b]pyridin-4-amine (Compound No. 328), N-(1,1-dioxidotetrahydro-2H-thiopyran-4-yl)-1-ethyl-5-[2-(2H-tetrazol-5-yl)-5-oxa-6-azaspiro[3.4]oct-6-en-7-yl]-1H-pyrazolo[3,4-b]pyridin-4-amine (Compound No. 329).

Example 42

Preparation of N-(1,1-dioxidotetrahydro-2H-thiopyran-4-yl)-1-ethyl-5-(8-methoxy-1-oxa-2-azaspiro[4.5]dec-2-en-3-yl)-1H-pyrazolo[3,4-b]pyridin-4-amine (Compound No. 290)

3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-en-8-ol (0.00025 mole) (example 26) and potassium carbonate (0.00050 mole) is taken in dimethylformamide and methyl iodide (0.0010 mole) is added. The reaction mixture is stirred at room temperature overnight. Water is added and the extraction is done with ethyl acetate. The organic layer is washed with brine, dried and concentrated under reduced pressure to give crude compound, which is purified by column chromatography.

The following compounds can be prepared similarly

1-Ethyl-5-(8-methoxy-1-oxa-2-azaspiro[4.5]dec-2-en-3-yl)-N-(tetrahydro-2H-pyran-4-yl)-1H-pyrazolo[3,4-b]pyridin-4-amine (Compound No. 277), 5-(8-Ethoxy-1-oxa-2-azaspiro[4.5]dec-2-en-3-yl)-1-ethyl-N-(tetrahydro-2H-pyran-4-yl)-1H-pyrazolo[3,4-b]pyridin-4-amine (Compound No. 278)

N-cyclohexyl-5-(8-ethoxy-1-oxa-2-azaspiro[4.5]dec-2-en-3-yl)-1-ethyl-1H-pyrazolo[3,4-b]pyridin-4-amine (Compound No. 279)

N-cyclohexyl-1-ethyl-5-(8-methoxy-1-oxa-2-azaspiro[4.5]dec-2-en-3-yl)-1H-pyrazolo[3,4-b]pyridin-4-amine (Compound No. 280), N-(1,1-dioxidotetrahydro-2H-thiopyran-4-yl)-5-(8-ethoxy-1-oxa-2-azaspiro[4.5]dec-2-en-3-yl)-1-ethyl-1H-pyrazolo[3,4-b]pyridin-4-amine (Compound No. 291), 1-Ethyl-5-(2-methoxy-5-oxa-6-azaspiro[3.4]oct-6-en-7-yl)-N-(tetrahydro-2H-pyran-4-yl)-1H-pyrazolo[3,4-b]pyridin-4-amine (Compound No. 295), N-cyclohexyl-1-ethyl-5-(2-methoxy-5-oxa-6-azaspiro[3.4]oct-6-en-7-yl)-1H-pyrazolo[3,4-b]pyridin-4-amine (Compound No. 296), N-(1,1-dioxidotetrahydro-2H-thiopyran-4-yl)-1-ethyl-5-(2-methoxy-5-oxa-6-azaspiro[3.4]oct-6-en-7-yl)-1H-pyrazolo[3,4-b]pyridin-4-amine (Compound No. 297), N-(1,1-dioxidotetrahydro-2H-thiopyran-4-yl)-5-(2-ethoxy-5-oxa-6-azaspiro[3.4]oct-6-en-7-yl)-1-ethyl-1H-pyrazolo[3,4-b]pyridin-4-amine (Compound No. 298), N-cyclohexyl-5-(2-ethoxy-5-oxa-6-azaspiro[3.4]oct-6-en-7-yl)-1-ethyl-1H-pyrazolo[3,4-b]pyridin-4-amine (Compound No. 299), 5-(2-Ethoxy-5-oxa-6-azaspiro[3.4]oct-6-en-7-yl)-1-ethyl-N-(tetrahydro-2H-pyran-4-yl)-1H-pyrazolo[3,4-b]pyridin-4-amine (Compound No. 300), N-(1,1-dioxidotetrahydro-2H-thiopyran-4-yl)-1-ethyl-5-[2-(methoxymethyl)-5-oxa-6-azaspiro[3.4]oct-6-en-7-yl]-1H-pyrazolo[3,4-b]pyridin-4-amine (Compound No. 303), N-(1,1-dioxidotetrahydro-2H-thiopyran-4-yl)-5-[2-(ethoxymethyl)-5-oxa-6-azaspiro[3.4]oct-6-en-7-yl]-1-ethyl-1H-pyrazolo[3,4-b]pyridin-4-amine (Compound No. 304), N-cyclohexyl-5-[2-(ethoxymethyl)-5-oxa-6-azaspiro[3.4]oct-6-en-7-yl]-1-ethyl-1H-pyrazolo[3,4-b]pyridin-4-amine (Compound No. 305), 5-[2-(Ethoxymethyl)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 306), 1-Ethyl-5-[2-(methoxymethyl)-5-oxa-6-azaspiro[3.4]oct-6-en-7-yl]-N-(tetrahydro-2H-pyran-4-yl)-1H-pyrazolo[3,4-b]pyridin-4-amine (Compound No. 307), N-cyclohexyl-1-ethyl-5-[2-(methoxymethyl)-5-oxa-6-azaspiro[3.4]oct-6-en-7-yl]-1H-pyrazolo[3,4-b]pyridin-4-amine (Compound No. 308).

Example 43

Preparation of 7-[4-(cyclohexylamino)-1-ethyl-1H-pyrazolo[3,4-b]pyridin-5-yl]-5-oxa-6-azaspiro[3.4]oct-6-ene-2-carboxylic acid (Compound No. 105)

7-[4-(Cyclohexylamino)-1-ethyl-1H-pyrazolo[3,4-b]pyridin-5-yl]-5-oxa-6-azaspiro[3.4]oct-6-ene-2-carbonitrile (300 mg, 0.00079 mole) (example 9) was dissolved in ethanol (10 ml). Aqueous potassium hydroxide (178 mg, 0.0031 mole) was added and reaction mixture was refluxed for about 3-4 hrs. Ethanol was evaporated off and reaction mixture was diluted with water, acidifed with dilute hydrochloric acid to pH of about 6. It was extracted with ethyl acetate. The organic layer was washed with brine, dried and concentrated under reduced pressure to give crude compound. The title compound was purified by preparative thin layer chromatography.

Yield: 2% m/z: (M$^+$+1) 398.14

NMR: NMR: ($\delta$, CDCl$_3$) 9.05-9.03 (d, 1H), 8.67 (s, 1H), 7.9 (s, 1H), 4.44-4.39 (m, 2H), 4.03 (s, 2H), 3.95 (s, 1H), 3.17-3.12 (m, 1H), 2.90 (m, 2H), 2.6-2.68 (m, 2H), 2.15-2.11 (m, 4H), 1.70-1.57 (m, 6H), 1.52-1.35 (m, 3H).

The following compound was prepared similarly

7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carboxylic acid (Compound No. 99)

Yield: 50% m/z: (M$^+$+1) 400.09

The following compounds can be prepared similarly

7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxylic acid (Compound No. 168)

7-[4-(Cyclohexylamino)-1-ethyl-3-methyl-1H-pyrazolo[3,4-b]pyridin-5-yl]-5-oxa-6-azaspiro[3.4]oct-6-ene-2-carboxylic acid (Compound No. 175)

7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylic acid (Compound No. 267)

Example 44

Preparation of (cis or trans) 3-[4-(cyclohexylamino)-1-ethyl-1H-pyrazolo[3,4-b]pyridin-5-yl]-1-oxa-2-azaspiro[4.5]dec-2-ene-8-carboxylic acid (Compound No. 95)

Ethyl (cis or trans) 3-[4-(cyclohexylamino)-1-ethyl-1H-pyrazolo[3,4-b]pyridin-5-yl]-1-oxa-2-azaspiro[4.5]dec-2-ene-8-carboxylate (130 mg, 0.000286 mole) (example 9) was taken in tetrahydrofuran (5 ml). Aqueous lithium hydroxide (48 mg, 0.00147 mole) in 2 ml water was added to it. The reaction mixture was stirred at room temperature overnight. The solvent was removed under reduced pressure. The mixture was acidified with 3N hydrochloric acid to about pH of 6. The extraction was done with ethyl acetate. The organic layer was washed with water and brine, dried and concentrated under reduced pressure to get crude product. The title compound was purified by preparative thin layer chromatography.

Yield: 53% m/z: (M+1) 426.20

The following compound was prepared similarly (trans or cis) 3-[4-(Cyclohexylamino)-1-ethyl-1H-pyrazolo[3,4-b]pyridin-5-yl]-1-oxa-2-azaspiro[4.5]dec-2-ene-8-carboxylic acid (Compound No. 96)

Yield 62% m/z: (M+1) 426.20

The following compounds can be prepared similarly

3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carboxylic acid (Compound No. 119), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylic acid (Compound No. 161), 3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-ene-8-carboxylic acid (Compound No. 162), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-ene-8-carboxylic acid (Compound No. 166), 3-[4-(Cyclohexylamino)-1-ethyl-3-methyl-1H-pyrazolo[3,4-b]pyridin-5-yl]-1-oxa-2-azaspiro[4.5]dec-2-ene-8-carboxylic acid (Compound No. 174).

Example 45

Preparation of cis or trans 3-[4-(cyclohexylamino)-1-ethyl-1H-pyrazolo[3,4-b]pyridin-5-yl]-1-oxa-2-azaspiro[4.5]dec-2-ene-8-carboxamide (Compound No. 108)

(cis or trans) 3-[4-(Cyclohexylamino)-1-ethyl-1H-pyrazolo[3,4-b]pyridin-5-yl]-1-oxa-2-azaspiro[4.5]dec-2-ene-8-carboxylic acid (70 mg, 0.00016 mole) (example 44), ammonium carbonate (47 mg, 0.00049 mg), hydroxybenzotriazole (24 mg, 0.00018 mole) were taken in dimethylformamide. N-methylmorpholine (0.03 ml, 0.00032 mole) was added at 0° C. The reaction mixture was stirred for about an hour at this temperature. 1-Ethyl-3-(3-dimethylaminopropyl) carbodiimide hydrochloride (34 mg, 0.00018 mole) was added and the mixture was stirred at room temperature overnight. Water was added and extraction was done with ethyl acetate. The organic layer was washed with brine, dried and concentrated under reduced pressure to give crude compound, which was purified by column chromatography.

Yield 28.9%
m/z: M+1 425.15
NMR: ($\delta$, CDCl$_3$) 8.82-8.80 (m 1H), 8.03 (s, 1H), 7.90 (s, 1H), 5.45 (s, 2H), 4.43-4.37 (m, 2H), 3.86 (s, 1H), 3.23 (s, 2H), 2.25 (s, 1H), 2.20-1.59 (m 18H)
Chiral purity: 99.73%
(trans or cis) 3-[4-(Cyclohexylamino)-1-ethyl-1H-pyrazolo[3,4-b]pyridin-5-yl]-1-oxa-2-azaspiro[4.5]dec-2-ene-8-carboxamide (Compound No. 109)
Yield 43.4%
m/z: M+1 425.15
NMR: ($\delta$, CDCl$_3$) 8.79-8.77 (m 1H), 8.00 (s, 1H), 7.90 (s, 1H), 5.48 (s, 2H), 4.42-4.38 (m, 2H), 3.85 (s, 1H), 3.16 (s, 2H), 2.19-2.17 (m, 1H), 2.08-1.40 (m, 18H)
Chiral purity 97.81%
The following compounds were prepared similarly
(cis or trans) 7-[4-(Cyclohexylamino)-1-ethyl-1H-pyrazolo[3,4-b]pyridin-5-yl]-5-oxa-6-azaspiro[3.4]oct-6-ene-2-carboxamide (Compound No. 106)
Yield: 2%
m/z: M+1 397.13
(trans or cis) 7-[4-(Cyclohexylamino)-1-ethyl-1H-pyrazolo[3,4-b]pyridin-5-yl]-5-oxa-6-azaspiro[3.4]oct-6-ene-2-carboxamide (Compound No. 107)
Yield: 2%
m/z: M+1 397.13
The following compounds can be prepared similarly
7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 123), 7-[4-(Cyclohexylamino)-1-ethyl-1H-pyrazolo[3,4-b]pyridin-5-yl]-N-methyl-5-oxa-6-azaspiro[3.4]oct-6-ene-2-carboxamide (Compound No. 124), 7-[1-Ethyl-4-(tetrahydro-2H-pyran-4-ylamino)-1H-pyrazolo[3,4-b]pyridin-5-yl]-N-methyl-5-oxa-6-azaspiro[3.4]oct-6-ene-2-carboxamide (Compound No. 125), 7-[4-(Cyclohexylamino)-1-ethyl-1H-pyrazolo[3,4-b]pyridin-5-yl]-N-ethyl-5-oxa-6-azaspiro[3.4]oct-6-ene-2-carboxamide (Compound No. 126), N-ethyl-7-[1-ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 127), 3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 149), 3-{1-Ethyl-4-[(3-hydroxycyclobutyl)amino]-1H-pyrazolo[3,4-b]pyridin-5-yl}-N-methyl-1-oxa-2-azaspiro[4.5]dec-2-ene-8-carboxamide (Compound No. 152), 3-[4-(Cyclohexylamino)-1-ethyl-1H-pyrazolo[3,4-b]pyridin-5-yl]-N-methyl-1-oxa-2-azaspiro[4.5]dec-2-ene-8-carboxamide (Compound No. 153), 3-[1-Ethyl-4-(tetrahydro-2H-pyran-4-ylamino)-1H-pyrazolo[3,4-b]pyridin-5-yl]-N-methyl-1-oxa-2-azaspiro[4.5]dec-2-ene-8-carboxamide (Compound No. 154), 3-{4-[(1,1-Dioxidotetrahydro-2H-thiopyran-4-yl)amino]-1-ethyl-1H-pyrazolo[3,4-b]pyridin-5-yl}-N-methyl-1-oxa-2-azaspiro[4.5]dec-2-ene-8-carboxamide (Compound No. 155), 3-{4-[(1,1-Dioxidotetrahydro-2H-thiopyran-4-yl)amino]-1-ethyl-3-methyl-1H-pyrazolo[3,4-b]pyridin-5-yl}-N-methyl-1-oxa-2-azaspiro[4.5]dec-2-ene-8-carboxamide (Compound No. 156), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxamide (Compound No. 163), 3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-ene-8-carboxamide (Compound No. 164), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 170), 7-[4-(Cyclohexylamino)-1-ethyl-3-methyl-1H-pyrazolo[3,4-b]pyridin-5-yl]-N-methyl-5-oxa-6-azaspiro[3.4]oct-6-ene-2-carboxamide (Compound No. 177), N-ethyl-7-[1-ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 202), 7-{4-[(1,1-Dioxidotetrahydro-2H-thiopyran-4-yl)amino]-1-ethyl-1H-pyrazolo[3,4-b]pyridin-5-yl}-N-methyl-5-oxa-6-azaspiro[3.4]oct-6-ene-2-carboxamide (Compound No. 271), 7-{4-[(1,1-Dioxidotetrahydro-2H-thiopyran-4-yl)amino]-1-ethyl-1H-pyrazolo[3,4-b]pyridin-5-yl}-N-ethyl-5-oxa-6-azaspiro[3.4]oct-6-ene-2-carboxamide (Compound No. 272), N-cyclopropyl-7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxamide (Compound No. 273), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxamide (Compound No. 274), 7-[4-(Cyclohexylamino)-1-ethyl-1H-pyrazolo[3,4-b]pyridin-5-yl]-N-cyclopropyl-5-oxa-6-azaspiro[3.4]oct-6-ene-2-carboxamide (Compound No. 275), N-cyclopropyl-7-[1-ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 276),
3-{4-[(1,1-Dioxidotetrahydro-2H-thiopyran-4-yl)amino]-1-ethyl-1H-pyrazolo[3,4-b]pyridin-5-yl}-N-ethyl-1-oxa-2-azaspiro[4.5]dec-2-ene-8-carboxamide (Compound No. 281),
N-cyclopropyl-3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxamide (Compound No. 282),
3-[4-(Cyclohexylamino)-1-ethyl-1H-pyrazolo[3,4-b]pyridin-5-yl]-N-cyclopropyl-1-oxa-2-azaspiro[4.5]dec-2-ene-8-carboxamide (Compound No. 283),
N-cyclopropyl-3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 284),
N-ethyl-3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 285),
3-[4-(Cyclohexylamino)-1-ethyl-1H-pyrazolo[3,4-b]pyridin-5-yl]-N-ethyl-1-oxa-2-azaspiro[4.5]dec-2-ene-8-carboxamide (Compound No. 286).

Example 46

Preparation of 5-(8-azido-1-oxa-2-azaspiro[4.5]dec-2-en-3-yl)-N-cyclohexyl-1-ethyl-1H-pyrazolo[3,4-b]pyridin-4-amine 3-[4-(Cyclohexylamino)-1-ethyl-1H-pyrazolo[3,4-b]pyridin-5-yl]-1-oxa-2-azaspiro[4.5]dec-2-en-8-yl 4-methylbenzenesulfonate (0.00090 mole) (example 39) is taken in dimethylformamide. Sodium azide (0.0027 mole) is added. The reaction mixture is stirred at 60-70° C. overnight. It is cooled and water is added and extraction is done with ethyl acetate. The organic layer is washed with brine, dried and concentrated under reduced pressure to give crude compound, which is purified by column chromatography.

Example 47

Preparation of 3-[4-(cyclohexylamino)-1-ethyl-1H-pyrazolo[3,4-b]pyridin-5-yl]-1-oxa-2-azaspiro[4.5]dec-2-en-8-amine (Compound No. 338)

Lithium aluminium hydride (0.0018 mole) is taken in tetrahydrofuran. 5-(8-Azido-1-oxa-2-azaspiro[4.5]dec-2-en-3-yl)-N-cyclohexyl-1-ethyl-1H-pyrazolo[3,4-b]pyridin-4-amine (0.00047 mole) (example 46) is added. The reaction mixture is stirred at room temperature overnight. It is quenched with aqueous sodium sulphate solution followed by ethyl acetate. The filtration is done through celite pad and extraction is done with ethyl acetate. The organic layer is washed with brine, dried and concentrated under reduced pressure to give crude compound, which is purified by column chromatography.
The following compounds can be prepared similarly
5-(2-Amino-5-oxa-6-azaspiro[3.4]oct-6-en-7-yl)-1-ethyl-N-(tetrahydro-2H-pyran-4-yl)-1H-pyrazolo[3,4-b]pyridin-4-amine (Compound No. 128),
5-(2-Amino-5-oxa-6-azaspiro[3.4]oct-6-en-7-yl)-N-cyclohexyl-1-ethyl-1H-pyrazolo[3,4-b]pyridin-4-amine (Compound No. 129),
5-(2-Amino-5-oxa-6-azaspiro[3.4]oct-6-en-7-yl)-1-ethyl-3-methyl-N-(tetrahydro-2H-pyran-4-yl)-1H-pyrazolo[3,4-b]pyridin-4-amine (Compound No. 171),
5-(2-Amino-5-oxa-6-azaspiro[3.4]oct-6-en-7-yl)-N-cyclohexyl-1-ethyl-3-methyl-1H-pyrazolo[3,4-b]pyridin-4-amine (Compound No. 178),
5-(2-Amino-5-oxa-6-azaspiro[3.4]oct-6-en-7-yl)-N-(1,1-dioxidotetrahydro-2H-thiopyran-4-yl)-1-ethyl-1H-pyrazolo[3,4-b]pyridin-4-amine (Compound No. 190),
5-(2-Amino-5-oxa-6-azaspiro[3.4]oct-6-en-7-yl)-N-(1,1-dioxidotetrahydro-2H-thiopyran-4-yl)-1-ethyl-3-methyl-1H-pyrazolo[3,4-b]pyridin-4-amine (Compound No. 191),
5-[2-(Aminomethyl)-5-oxa-6-azaspiro[3.4]oct-6-en-7-yl]-N-cyclohexyl-1-ethyl-1H-pyrazolo[3,4-b]pyridin-4-amine (Compound No. 309),
5-[2-(Aminomethyl)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 310),
5-[2-(Aminomethyl)-5-oxa-6-azaspiro[3.4]oct-6-en-7-yl]-N-(1,1-dioxidotetrahydro-2H-thiopyran-4-yl)-1-ethyl-1H-pyrazolo[3,4-b]pyridin-4-amine (Compound No. 311).

Example 48

Preparation of 3-[4-(cyclohexylamino)-1-ethyl-1H-pyrazolo[3,4-b]pyridin-5-yl]-N-methyl-1-oxa-2-azaspiro[4.5]dec-2-en-8-amine (Compound No. 142)

The title compound is prepared by following the procedure of example 24.

Example 49

Preparation of N-{7-[4-(cyclohexylamino)-1-ethyl-1H-pyrazolo[3,4-b]pyridin-5-yl]-5-oxa-6-azaspiro[3.4]oct-6-en-2-yl}acetamide (Compound No. 130)

The title compound is prepared by following the procedure of example 23.
The following compounds can be prepared similarly
N-{7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}acetamide (Compound No. 131),
N-(7-{4-[(1,1-dioxidotetrahydro-2H-thiopyran-4-yl)amino]-1-ethyl-3-methyl-1H-pyrazolo[3,4-b]pyridin-5-yl}-5-oxa-6-azaspiro[3.4]oct-6-en-2-yl)acetamide (Compound No. 192),
N-(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)acetamide (Compound No. 193),
N-(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)propanamide (Compound No. 194),
N-(7-{4-[(1,1-dioxidotetrahydro-2H-thiopyran-4-yl)amino]-1-ethyl-3-methyl-1H-pyrazolo[3,4-b]pyridin-5-yl}-5-oxa-6-azaspiro[3.4]oct-6-en-2-yl)propanamide (Compound No. 195),
N-{7-[4-(cyclohexylamino)-1-ethyl-1H-pyrazolo[3,4-b]pyridin-5-yl]-5-oxa-6-azaspiro[3.4]oct-6-en-2-yl}propanamide (Compound No. 203),
N-{7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}propanamide (Compound No. 204),
N-{7-[1-ethyl-3-methyl-4-(tetrahydro-2H-pyran-4-ylamino)-1H-pyrazolo[3,4-b]pyridin-5-yl]-5-oxa-6-azaspiro[3.4]oct-6-en-2-yl}propanamide (Compound No. 205), N-[(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methyl]acetamide (Compound No. 312), N-[(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methyl]propanamide (Compound No. 313), N-({7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}methyl)propanamide (Compound No. 314), N-({7-[4-(cyclohexylamino)-1-ethyl-1H-pyrazolo[3,4-b]pyridin-5-yl]-5-oxa-6-azaspiro[3.4]oct-6-en-2-yl}methyl)propanamide (Compound No. 315), N-({7-[4-(cyclohexylamino)-1-ethyl-1H-pyrazolo[3,4-b]pyridin-5-yl]-5-oxa-6-azaspiro[3.4]oct-6-en-2-yl}methyl)acetamide (Compound No. 316), N-({7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}methyl)acetamide (Compound No. 317).

Example 50

Efficacy of Compounds (a)(i) PDE4B Enzyme Assay

The efficacy of compounds as PDE4 inhibitors was determined by an enzyme assay using cell lysate of HEK293 cells transfected with PDE4B2 plasmids as PDE4B source. The enzyme reaction was carried out in the presence of cAMP (1 µM) at 30° C. in the presence or absence of test compound for 45-60 min. An aliquot of this reaction mixture was taken further for the ELISA assay and the protocol of the kit followed to determine level of cAMP in the sample. The concentration of the cAMP in the sample directly correlated with the degree of PDE4 enzyme inhibition. Results were expressed as percent control and the $IC_{50}$ values of test compounds were reported. $IC_{50}$ values of test compounds were found to be in the range of 3 nM to 10 µM concentration.

(a)(ii) PDE7 Enzyme Assay

The efficacy of compounds as PDE7 inhibitors was determined by an enzyme assay using recombinant human PDE7A enzyme (*J. Med.* Chem. (2000) 43, 683-689). The enzyme reaction was carried out in the presence of cAMP (1 µM) at 37° C. in the presence or absence of test compound for 60 min. An aliquot of this reaction mixture was taken further for the ELISA assay and the protocol of the kit was followed to determine level of cAMP in the sample. The concentration of the cAMP in the sample directly correlated with the degree of PDE7 enzyme inhibition. Results were expressed as percent control and the $IC_{50}$ values of test compounds, calculated using Graph pad prism, were found to be in the range of 3 NM to 10 µM concentration.

(b) Cell based Assay for TNF-α Release

Method of Isolation of Human Peripheral Blood Mononuclear Cells (PBMNC's)

Human whole blood was collected in vacutainer tubes containing heparin or EDTA as an anti coagulant. The blood was diluted (1:1) in sterile phosphate buffered saline and 10 ml was carefully layered over 5 ml Ficoll Hypaque gradient (density 1.077 g/ml) in a 15 ml conical centrifuge tube. The sample was centrifuged at 3000 rpm for 25 minutes in a swing-out rotor at room temperature. After centrifugation, interface of cells were collected, diluted at least 1:5 with PBS (phosphate buffered saline) and washed three times by centrifugation at 2500 rpm for 10 minutes at room temperature.

The cells were resuspended in serum free RPMI 1640 medium at a concentration of 2 million cells/ml.

LPS (Lipopolysaccharide) Stimulation of Human PBMNC's

PBMN cells (0.1 ml; 2 million/ml) were co-incubated with 20 µl of compound (final DMSO concentration of 0.2%) for 10 min in a flat bottom 96 well microtiter plate. Compounds were dissolved in DMSO initially and diluted in medium for a final concentration of 0.2% DMSO. LPS (1 µg/ml, final concentration) was then added at a volume of 10 µl per well. After 30 min, 20 µl of fetal calf serum (final concentration of 10%) was added to each well. Cultures were incubated overnight at 37° C. in an atmosphere of 5% $CO_2$ and 95% air. Supernatant were then removed and tested by ELISA for TNF-α release using a commercial kit (e.g. BD Biosciences). For whole blood, the plasma samples were diluted 1:20 for ELISA. The level of TNF-α in treated wells was compared with the vehicle (0.2% DMSO in RPMI medium) treated controls and inhibitory potency of compound was expressed as $IC_{50}$ values calculated by using Graph pad prism. $IC_{50}$ values of test compounds were found to be in the range of 5 nM to 2.5 µM concentration.

$$\text{Percent inhibition} = 100 - \frac{\text{Percent } TNF\text{-}\alpha \text{ in drug treated}}{\text{Percent } TNF\text{-}\alpha \text{ in vehicle treated}} \times 100$$

(c) In-Vitro Assay to Evaluate Efficacy of Compounds in Combination with p38 MAP Kinase Inhibitors Perform the assay as described in (b) above, with individual compounds and their combinations tested at sub-optimal doses.

(d) In-Vitro Assay to Evaluate Efficacy of Compounds in Combination with β2-Agonists Measurement of Intracellular cAMP Elevation in U937 Cells Grow U937 cells (human promonocytic cell line) in endotoxin-free RPMI 1640+HEPES medium containing 10% (v/v) heat-inactivated foetal bovine serum and 1% (v/v) of an antibiotic solution (5000 IU/ml penicillin, 5000 µg/ml streptomycin). Resuspend cells ($0.25 \times 10^6$/200 µA) in Krebs' buffer solution and incubate at 37° C. for 15 min in the presence of test compounds or vehicle (0.2% DMSO in RPMI medium). Initiate generation of cAMP by adding 50 µl of 10 µM prostaglandin (PGE2). Stop the reaction after 15 min, by adding 1 N HCl (50 µA) and place on ice for 30 min. Centrifuge the sample (450 g, 3 min), and measure levels of cAMP in the supernatant using cAMP enzyme-linked immunosorbent assay kit (Assay Designs). Calculate percent inhibition by the following formula and calculate $IC_{50}$ value using Graph pad prism.

$$\text{Percent inhibition} = 100 - \frac{\text{Percent conversion in drug treated}}{\text{Percent conversion in vehicle treated}} \times 100$$

We claim:

1. A compound having the structure of Formula I:

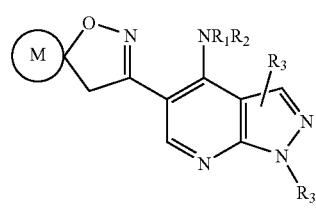

Formula I or its pharmaceutically acceptable salts, wherein
R₁ and R₂ independently are hydrogen, aryl, heteroaryl, —COR₄, —S(O)ₘR₄ (wherein R₄ is hydrogen, alkyl, cycloalkyl, aryl, aralkyl, heteroaryl or heterocyclyl and m is an integer from 0-2),

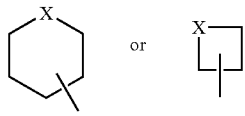

wherein X is —O—, S(O)ₘ (wherein m is an integer from 0-2), C(=O), C=NOH, CR_fR_q (wherein R_f and R_q independently are hydrogen, hydroxy, carboxy or cyano) or NR₅ {wherein R₅ is hydrogen, alkyl, alkenyl, alkynyl, cycloalkyl, cycloalkylalkyl, aryl, heteroaryl, heterocyclyl, —COR₄, —S(O)ₘR₄, —COOR₄ or —CONR₄R'₄ (wherein R₄ and R'₄ independently are hydrogen, alkyl, cycloalkyl, aryl, aralkyl, heteroaryl or heterocyclyl and m is an integer from 0-2)};

R₃ is hydrogen, alkyl, alkenyl, alkynyl, cycloalkyl, aryl, aralkyl, aralkenyl, cycloalkylalkyl, heterocyclyl, heteroaryl, heterocyclylalkyl or heteroarylalkyl;

M is a 3-7 membered saturated, partially saturated or unsaturated ring containing carbon atoms wherein one or more carbon atoms optionally are replaced by heteroatoms selected from O, S(O)ₘ {wherein m is an integer from 0-2} or NR₆ {wherein R₆ is hydrogen, alkyl, alkenyl, alkynyl, cycloalkyl, cycloalkylalkyl, aryl, heteroaryl, heterocyclyl, —COR₄, —S(O)ₘR₄, —COOR₄ or —CONR₄R'₄ (wherein R₄ and R'₄ independently are hydrogen, alkyl, cycloalkyl, aryl, aralkyl, heteroaryl or heterocyclyl and m is an integer from 0-2)}, or one or more carbon atoms optionally are substituted with oxo, halogen, spiro-attached heterocyclyl, hydroxy, cyano, alkyl, heteroaryl, heteroarylalkyl, —(CH₂)ₘNR₄R'₄, —(CH₂)ₘOR₄, —(CH₂)ₘCONR₄R'₄, —(CH₂)ₘNR₄COR₄, or —(CH₂)ₘCOOR₄ (wherein m, R₄ and R'₄ are the same as defined above).

2. A compound, which is selected from
N-cyclohexyl-1-ethyl-5-(1-oxa-2-azaspiro[4.4]non-2-en-3-yl)-1H-pyrazolo[3,4-b]pyridin-4-amine (Compound No. 1),
N-cyclohexyl-1-ethyl-5-(5-oxa-6-azaspiro[3.4]oct-6-en-7-yl)-1H-pyrazolo[3,4-b]pyridin-4-amine (Compound No. 2),
N-cyclohexyl-1-ethyl-5-(1-oxa-2-azaspiro[4.5]dec-2-en-3-yl)-1H-pyrazolo[3,4-b]pyridin-4-amine (Compound No. 3),
N-cyclohexyl-1-ethyl-5-(1-oxa-7-thia-2-azaspiro[4.4]non-2-en-3-yl)-1H-pyrazolo[3,4-b]pyridin-4-amine (Compound No. 4),
N-cyclohexyl-1-ethyl-5-(7-oxido-1-oxa-7-thia-2-azaspiro[4.4]non-2-en-3-yl)-1H-pyrazolo[3,4-b]pyridin-4-amine (Compound No. 5),
N-cyclohexyl-1-ethyl-5-(5-oxa-2-thia-6-azaspiro[3.4]oct-6-en-7-yl)-1H-pyrazolo[3,4-b]pyridin-4-amine (Compound No. 6),
1-Ethyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 7),
1-Ethyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 8),
1-Ethyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 9),
4-{[1-Ethyl-5-(1-oxa-2-azaspiro[4.4]non-2-en-3-yl)-1H-pyrazolo[3,4-b]pyridin-4-yl]amino}cyclohexanol (Compound No. 10),
4-{[1-Ethyl-5-(1-oxa-2-azaspiro[4.5]dec-2-en-3-yl)-1H-pyrazolo[3,4-b]pyridin-4-yl]amino}cyclohexanol (Compound No. 11),
N-cyclohexyl-5-(1,7-dioxa-2-azaspiro[4.4]non-2-en-3-yl)-1-ethyl-1H-pyrazolo[3,4-b]pyridin-4-amine (Compound No. 12),
4-{[1-Ethyl-5-(5-oxa-6-azaspiro[3.4]oct-6-en-7-yl)-1H-pyrazolo[3,4-b]pyridin-4-yl]amino}cyclohexanol (Compound No. 13),
N-cyclohexyl-5-(2,2-dioxido-5-oxa-2-thia-6-azaspiro[3.4]oct-6-en-7-yl)-1-ethyl-1H-pyrazolo[3,4-b]pyridin-4-amine (Compound No. 14),
tert-Butyl 3-[4-(cyclohexylamino)-1-ethyl-1H-pyrazolo[3,4-b]pyridin-5-yl]-1-oxa-2,8-diazaspiro[4.5]dec-2-ene-8-carboxylate (Compound No. 15),
4-{[1-Ethyl-5-(1-oxa-2-azaspiro[4.5]dec-2-en-3-yl)-1H-pyrazolo[3,4-b]pyridin-4-yl]amino}cyclohexanone (Compound No. 16),
4-{[1-Ethyl-5-(1-oxa-2-azaspiro[4.5]dec-2-en-3-yl)-1H-pyrazolo[3,4-b]pyridin-4-yl]amino}cyclohexanone oxime (Compound No. 17),
N-cyclohexyl-1-ethyl-5-(1-oxa-2,8-diazaspiro[4.5]dec-2-en-3-yl)-1H-pyrazolo[3,4-b]pyridin-4-amine hydrochloride salt (Compound No. 18),
4-{[1-Ethyl-5-(1,9,12-trioxa-2-azadispiro[4.2.4.2]tetradec-2-en-3-yl)-1H-pyrazolo[3,4-b]pyridin-4-yl]amino}cyclohexanol (Compound No. 19),
4-{[1-Ethyl-5-(5-oxa-6-azaspiro[3.4]oct-6-en-7-yl)-1H-pyrazolo[3,4-b]pyridin-4-yl]amino}cyclohexanone (Compound No. 20),
4-{[1-Ethyl-5-(1-oxa-2-azaspiro[4.4]non-2-en-3-yl)-1H-pyrazolo[3,4-b]pyridin-4-yl]amino}cyclohexanone (Compound No. 21),
3-{1-Ethyl-4-[(4-hydroxycyclohexyl)amino]-1H-pyrazolo[3,4-b]pyridin-5-yl}-1-oxa-2-azaspiro[4.5]dec-2-en-8-one (Compound No. 22),
N-cyclohexyl-5-[8-(2,2-dimethylpropanoyl)-1-oxa-2,8-diazaspiro[4.5]dec-2-en-3-yl]-1-ethyl-1H-pyrazolo[3,4-b]pyridin-4-amine (Compound No. 23),
N-cyclohexyl-1-ethyl-5-{8-[(trifluoromethyl)sulfonyl]-1-oxa-2,8-diazaspiro[4.5]dec-2-en-3-yl}-1H-pyrazolo[3,4-b]pyridin-4-amine (Compound No. 24),
N-cyclohexyl-1-ethyl-5-[8-(ethyl sulfonyl)-1-oxa-2,8-diazaspiro[4.5]dec-2-en-3-yl]-1H-pyrazolo[3,4-b]pyridin-4-amine (Compound No. 25),
N-cyclohexyl-5-[8-(cyclopropylmethyl)-1-oxa-2,8-diazaspiro[4.5]dec-2-en-3-yl]-1-ethyl-1H-pyrazolo[3,4-b]pyridin-4-amine (Compound No. 26),
5-(8-Acetyl-1-oxa-2,8-diazaspiro[4.5]dec-2-en-3-yl)-N-cyclohexyl-1-ethyl-1H-pyrazolo[3,4-b]pyridin-4-amine (Compound No. 27),
N-cyclohexyl-5-(2,5-dioxa-6-azaspiro[3.4]oct-6-en-7-yl)-1-ethyl-1H-pyrazolo[3,4-b]pyridin-4-amine (Compound No. 28),
1-(4-Methoxybenzyl)-N-(3-methoxyphenyl)-5-(1-oxa-2-azaspiro[4.4]non-2-en-3-yl)-1H-pyrazolo[3,4-b]pyridin-4-amine (Compound No. 41),
(cis or trans) 3-[4-(Cyclohexylamino)-1-ethyl-1H-pyrazolo[3,4-b]pyridin-5-yl]-1-oxa-2-azaspiro[4.5]dec-2-en-8-ol (Compound No. 42), (trans or cis) 3-[4-(Cyclohexylamino)-1-ethyl-1H-pyrazolo[3,4-b]pyridin-5-yl]-1-oxa-2-azaspiro[4.5]dec-2-en-8-ol (Compound No. 43),
5-[2-(Benzyloxy)-5-oxa-6-azaspiro[3.4]oct-6-en-7-yl]-1-ethyl-N-(tetrahydro-2H-pyran-4-yl)-1H-pyrazolo[3,4-b]pyridin-4-amine (Compound No. 44),
(cis or trans) 3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 45),
3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-one (Compound No. 46),
7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 47),
7-[4-(Cyclohexylamino)-1-ethyl-1H-pyrazolo[3,4-b]pyridin-5-yl]-5-oxa-6-azaspiro[3.4]oct-6-ene-2-carbonitrile (Compound No. 48),
5-(5-Oxa-6-azaspiro[3.4]oct-6-en-7-yl)-N-(tetrahydro-2H-pyran-4-yl)-1H -pyrazolo[3,4-b]pyridin-4-amine (Compound No. 49),
1-Methyl-5-(5-oxa-6-azaspiro[3.4]oct-6-en-7-yl)-N-(tetrahydro-2H-pyran-4-yl)-1H -pyrazolo[3,4-b]pyridin-4-amine (Compound No. 50),
5-(1-Oxa-2-azaspiro[4.4]non-2-en-3-yl)-N-(tetrahydro-2H-pyran-4-yl)-1-(2,2,2-trifluoroethyl)-1H-pyrazolo[3,4-b]pyridin-4-amine (Compound No. 51),
1-Ethyl-N-[1-(methylsulfonyl)piperidin-4-yl]-5-(1-oxa-2-azaspiro[4.4]non-2-en-3-yl)-1H-pyrazolo[3,4-b]pyridin-4-amine (Compound No. 52),
N-(1-acetylpiperidin-4-yl)-1-ethyl-5-(1-oxa-2-azaspiro[4.5]dec-2-en-3-yl)-1H -pyrazolo[3,4-b]pyridin-4-amine (Compound No. 53),
N-(1-acetylpiperidin-4-yl)-1-ethyl-5-(1-oxa-2-azaspiro[4.4]non-2-en-3-yl)-1H-pyrazolo[3,4-b]pyridin-4-amine (Compound No. 54),
1-(4-Methoxybenzyl)-N-(tetrahydro-2H-pyran-4-yl)-5-(1,9,12-trioxa-2-azadispiro[4.2.4.2]tetradec-2-en-3-yl)-1H-pyrazolo[3,4-b]pyridin-4-amine (Compound No. 55),
5-(5-Oxa-6-azaspiro[3.4]oct-6-en-7-yl)-N-(tetrahydro-2H-pyran-4-yl)-1-(2,2,2-trifluoroethyl)-1H-pyrazolo[3,4-b]pyridin-4-amine (Compound No. 56),
7-[1-(4-Methoxybenzyl)-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 57),
1-(Cyclopropylmethyl)-5-(5-oxa-6-azaspiro[3.4]oct-6-en-7-yl)-N-(tetrahydro-2H -pyran-4-yl)-1H-pyrazolo[3,4-b]pyridin-4-amine (Compound No. 58),
1-Butyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 59),
1-(1-Methylethyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 60),
5-(5-Oxa-6-azaspiro[3.4]oct-6-en-7-yl)-1-propyl-N-(tetrahydro-2H-pyran-4-yl)-1H-pyrazolo[3,4-b]pyridin-4-amine (Compound No. 61),
5-(1-Oxa-2-azaspiro[4.5]dec-2-en-3-yl)-N-(tetrahydro-2H-pyran-4-yl)-1-(2,2,2-trifluoroethyl)-1H-pyrazolo[3,4-b]pyridin-4-amine (Compound No. 62),
N-(1-Cyclopentylpiperidin-4-yl)-1-ethyl-5-(1-oxa-2-azaspiro[4.4]non-2-en-3-yl)-1H-pyrazolo[3,4-b]pyridin-4-amine (Compound No. 63),
N-(1-butylpiperidin-4-yl)-1-ethyl-5-(1-oxa-2-azaspiro[4.4]non-2-en-3-yl)-1H-107 pyrazolo[3,4-b]pyridin-4-amine (Compound No. 64),
2-(4-{[1-Ethyl-5-(1-oxa-2-azaspiro[4.4]non-2-en-3-yl)-1H-pyrazolo[3,4-b]pyridin-4-yl]amino}piperidin-1-yl)ethanol (Compound No. 65),
N-[1-(cyclopropylmethyl)piperidin-4-yl]-1-ethyl-5-(1-oxa-2-azaspiro[4.4]non-2-en-3-yl)-1H-pyrazolo[3,4-b]pyridin-4-amine (Compound No. 66),
1-Ethyl-N-[1-(1-methylethyl)piperidin-4-yl]-5-(1-oxa-2-azaspiro[4.4]non-2-en-3-yl)-1H-pyrazolo[3,4-b]pyridin-4-amine (Compound No. 67),
1-Ethyl-5-(1-oxa-2-azaspiro[4.4]non-2-en-3-yl)-N-(1-propylpiperidin-4-yl)-1H -pyrazolo[3,4-b]pyridin-4-amine (Compound No. 68),
N-(1-cyclopentylpiperidin-4-yl)-1-ethyl-5-(1-oxa-2-azaspiro[4.5]dec-2-en-3-yl)-1H -pyrazolo[3,4-b]pyridin-4-amine (Compound No. 69),
1-Ethyl-N-[1-(1-methylethyl)piperidin-4-yl]-5-(1-oxa-2-azaspiro[4.5]dec-2-en-3-yl)-1H-pyrazolo[3,4-b]pyridin-4-amine (Compound No. 70),
1-Cyclopentyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 71),
1-(Cyclopropylmethyl)-5-(1-oxa-2-azaspiro[4.5]dec-2-en-3-yl)-N-(tetrahydro-2H -pyran-4-yl)-1H-pyrazolo[3,4-b]pyridin-4-amine (Compound No. 72),
1-(1-Methylethyl)-5-(1-oxa-2-azaspiro[4.5]dec-2-en-3-yl)-N-(tetrahydro-2H-pyran-4-yl) -1H-pyrazolo[3,4-b]pyridin-4-amine (Compound No. 73),
5-(1-Oxa-2-azaspiro[4.5]dec-2-en-3-yl)-1-propyl-N-(tetrahydro-2H-pyran-4-yl)-1H-pyrazolo[3,4-b]pyridin-4-amine (Compound No. 74),
1-Cyclopentyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 75),
1-(Cyclopropylmethyl)-5-(1-oxa-2-azaspiro[4.4]non-2-en-3-yl)-N-(tetrahydro-2H-131 pyran-4-yl)-1H-pyrazolo[3,4-b]pyridin-4-amine (Compound No. 76),
1-(1-Methylethyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 77),
5-(1-Oxa-2-azaspiro[4.4]non-2-en-3-yl)-1-propyl-N-(tetrahydro-2H-pyran-4-yl)-1H -pyrazolo[3,4-b]pyridin-4-amine (Compound No. 78),
1-Methyl-5-(1-oxa-2-azaspiro[4.4]non-2-en-3-yl)-N-(tetrahydro-2H-pyran-4-yl)-1H -pyrazolo[3,4-b]pyridin-4-amine (Compound No. 79),
N-Cyclohexyl-1-ethyl-5-(1,9,12-trioxa-2-azadispiro[4.2.4.2]tetradec-2-en-3-yl)-1H-pyrazolo[3,4-b]pyridin-4-amine (Compound No. 80),
3-[4-(Cyclohexylamino)-1-ethyl-1H-pyrazolo[3,4-b]pyridin-5-yl]-1-oxa-2-azaspiro[4.5]dec-2-en-8-one (Compound No. 81),
1-Ethyl-5-(1-oxa-2-azaspiro[4.4]non-2-en-3-yl)-N-piperidin-4-yl-1H-pyrazolo[3,4-b]pyridin-4-amine (Compound No. 82),
Tert-butyl 4-{[1-ethyl-5-(1-oxa-2-azaspiro[4.4]non-2-en-3-yl)-1H-pyrazolo[3,4-b]pyridin-4-yl]amino}piperidine-1-carboxylate (Compound No. 83),
1-Ethyl-N-(1-ethylpiperidin-4-yl)-5-(1-oxa-2-azaspiro[4.5]dec-2-en-3-yl)-1H-pyrazolo[3,4-b]pyridin-4-amine (Compound No. 84),
1-Ethyl-N-(1-methylpiperidin-4-yl)-5-(1-oxa-2-azaspiro[4.5]dec-2-en-3-yl)-1H-pyrazolo[3,4-b]pyridin-4-amine (Compound No. 85), 1-Ethyl-5-(1-oxa-2-azaspiro[4.5]dec-2-en-3-yl)-N-piperidin-4-yl-1H-pyrazolo[3,4-b]pyridin-4-amine (Compound No. 86),
Tert-butyl 4-{[1-ethyl-5-(1-oxa-2-azaspiro[4.5]dec-2-en-3-yl)-1H-pyrazolo[3,4-b]pyridin-4-yl]amino}piperidine-1-carboxylate (Compound No. 87),
1-Ethyl-5-(1-oxa-2-azaspiro[4.5]dec-2-en-3-yl)-N-(1-propylpiperidin-4-yl)-1H-pyrazolo[3,4-b]pyridin-4-amine (Compound No. 88),
N-[1-(cyclopropylmethyl)piperidin-4-yl]-1-ethyl-5-(1-oxa-2-azaspiro[4.5]dec-2-en-3-yl)-1H-pyrazolo[3,4-b]pyridin-4-amine (Compound No. 89),
2-(4-{[1-Ethyl-5-(1-oxa-2-azaspiro[4.5]dec-2-en-3-yl)-1H-pyrazolo[3,4-b]pyridin-4-yl]amino}piperidin-1-yl)ethanol (Compound No. 90),
N-cyclohexyl-1-(4-methoxybenzyl)-5-(1-oxa-2-azaspiro[4.4]non-2-en-3-yl)-1H-pyrazolo[3,4-b]pyridin-4-amine (Compound No. 91),
3-[1-(4-Methoxybenzyl)-4-(tetrahydro-2H-pyran-4-ylamino)-1H-pyrazolo[3,4-b]pyridin-5-yl]-1-oxa-2-azaspiro[4.5]dec-2-en-8-one (Compound No. 92),
7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 93),
1-Ethyl-N-(3-methoxyphenyl)-5-(1-oxa-2-azaspiro[4.4]non-2-en-3-yl)-1H-pyrazolo[3,4-b]pyridin-4-amine (Compound No. 94),
(cis or trans) 3-[4-(Cyclohexylamino)-1-ethyl-1H-pyrazolo[3,4-b]pyridin-5-yl]-1-oxa-2-azaspiro[4.5]dec-2-ene-8-carboxylic acid (Compound No. 95),
(trans or cis) 3-[4-(Cyclohexylamino)-1-ethyl-1H-pyrazolo[3,4-b]pyridin-5-yl]-1-oxa-2-azaspiro[4.5]dec-2-ene-8-carboxylic acid (Compound No. 96),
5-{2-[(Benzyloxy)methyl]-5-oxa-6-azaspiro[3.4]oct-6-en-7-yl}-1-(4-methoxybenzyl)-N-(tetrahydro-2H-pyran-4-yl)-1H-pyrazolo[3,4-b]pyridin-4-amine (Compound No. 97),
(trans or cis) 3-[1-Ethyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 98),
7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carboxylic acid (Compound No. 99),
1-(4-Methoxybenzyl)-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 100),
5-(1-Oxa-2-azaspiro[4.5]dec-2-en-3-yl)-N-(tetrahydro-2H-pyran-4-yl)-1H-pyrazolo[3,4-b]pyridin-4-amine (Compound No. 101),
1-(4-Methoxybenzyl)-5-(1-oxa-2-azaspiro[4.4]non-2-en-3-yl)-N-(tetrahydro-2H-pyran-4-yl)-1H-pyrazolo[3,4-b]pyridin-4-amine (Compound No. 102),
5-{2-[(Benzyloxy)methyl]-5-oxa-6-azaspiro[3.4]oct-6-en-7-yl}-1-ethyl-N-(tetrahydro-2H-pyran-4-yl)-1H-pyrazolo[3,4-b]pyridin-4-amine (Compound No. 103),
{7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-yl}methanol (Compound No. 104),
7-[4-(Cyclohexylamino)-1-ethyl-1H-pyrazolo[3,4-b]pyridin-5-yl]-5-oxa-6-azaspiro[3.4]oct-6-ene-2-carboxylic acid (Compound No. 105),
cis or trans 7-[4-(Cyclohexylamino)-1-ethyl-1H-pyrazolo[3,4-b]pyridin-5-yl]-5-oxa-6-azaspiro[3.4]oct-6-ene-2-carboxamide (Compound No. 106),
(trans or cis) 7-[4-(Cyclohexylamino)-1-ethyl-1H-pyrazolo[3,4-b]pyridin-5-yl]-5-oxa-6-azaspiro[3.4]oct-6-ene-2-carboxamide (Compound No. 107),
(cis or trans) 3-[4-(Cyclohexylamino)-1-ethyl-1H-pyrazolo[3,4-b]pyridin-5-yl]-1-oxa-2-azaspiro[4.5]dec-2-ene-8-carboxamide (Compound No. 108),
(trans or cis) 3-[4-(Cyclohexylamino)-1-ethyl-1H-pyrazolo[3,4-b]pyridin-5-yl]-1-oxa-2-azaspiro[4.5]dec-2-ene-8-carboxamide (Compound No. 109),
1-(4-Methoxybenzyl)-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 110),
5-[2-(Benzyloxy)-5-oxa-6-azaspiro[3.4]oct-6-en-7-yl]-1-(4-methoxybenzyl)-N-(tetrahydro-2H-pyran-4-yl)-1H-pyrazolo[3,4-b]pyridin-4-amine (Compound No. 111),
Ethyl (cis or trans) 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 112),
Ethyl (trans or cis) 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 113),
N-(1,1-dioxidotetrahydro-2H-thiopyran-4-yl)-1-ethyl-5-(1-oxa-2-azaspiro[4.5]dec-2-en-3-yl)-1H-pyrazolo[3,4-b]pyridin-4-amine ((Compound No. 114),
3-{[1-Ethyl-5-(5-oxa-6-azaspiro[3.4]oct-6-en-7-yl)-1H-pyrazolo[3,4-b]pyridin-4-yl]amino}cyclobutanecarboxylic acid (Compound No. 115),
3-{[1-Ethyl-5-(1-oxa-2-azaspiro[4.4]non-2-en-3-yl)-1H-pyrazolo[3,4-b]pyridin-4-yl]amino}cyclobutanecarboxylic acid (Compound No. 116),
3-{[1-Ethyl-5-(1-oxa-2-azaspiro[4.5]dec-2-en-3-yl)-1H-pyrazolo[3,4-b]pyridin-4-yl]amino}cyclobutanecarboxylic acid (Compound No. 117),
3-[4-(Cyclohexylamino)-1-ethyl-1H-pyrazolo[3,4-b]pyridin-5-yl]-1-oxa-2-azaspiro[4.5]dec-2-ene-8-carbonitrile (Compound No. 118),
3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carboxylic acid (Compound No. 119),
3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carbonitrile (Compound No. 120),
7-[4-(Cyclohexylamino)-1-ethyl-1H-pyrazolo[3,4-b]pyridin-5-yl]-5-oxa-6-azaspiro[3.4]oct-6-en-2-ol (Compound No. 121),
7-[1-Ethyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 122),
7-[1-Ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 123),
7-[4-(Cyclohexylamino)-1-ethyl-1H-pyrazolo[3,4-b]pyridin-5-yl]-N-methyl-5-oxa-6-azaspiro[3.4]oct-6-ene-2-carboxamide (Compound No. 124),
7-[1-Ethyl-4-(tetrahydro-2H-pyran-4-ylamino)-1H-pyrazolo[3,4-b]pyridin-5-yl]-N-methyl-5-oxa-6-azaspiro[3.4]oct-6-ene-2-carboxamide (Compound No. 125),
7-[4-(Cyclohexylamino)-1-ethyl-1H-pyrazolo[3,4-b]pyridin-5-yl]-N-ethyl-5-oxa-6-azaspiro[3.4]oct-6-ene-2-carboxamide (Compound No. 126),
N-Ethyl-7-[1-ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 127),
5-(2-Amino-5-oxa-6-azaspiro[3.4]oct-6-en-7-yl)-1-ethyl-N-(tetrahydro-2H-pyran-4-yl)-1H-pyrazolo[3,4-b]pyridin-4-amine (Compound No. 128), 5-(2-Amino-5-oxa-6-azaspiro[3.4]oct-6-en-7-yl)-N-cyclohexyl-1-ethyl-1H-pyrazolo[3,4-b]pyridin-4-amine (Compound No. 129), N-{7-[4-(cyclohexylamino)-1-ethyl-1H-pyrazolo[3,4-b]pyridin-5-yl]-5-oxa-6-azaspiro[3.4]oct-6-en-2-yl}acetamide (Compound No. 130), N-{7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}acetamide (Compound No. 131), 4-{[1-Ethyl-5-(5-oxa-6-azaspiro[3.4]oct-6-en-7-yl)-1H-pyrazolo[3,4-b]pyridin-4-yl]amino}cyclohexanecarboxylic acid (Compound No. 132), 4-{[1-Ethyl-5-(1-oxa-2-azaspiro[4.4]non-2-en-3-yl)-1H-pyrazolo[3,4-b]pyridin-4-yl]amino}cyclohexanecarboxylic acid (Compound No. 133), 4-{[1-Ethyl-5-(1-oxa-2-azaspiro[4.5]dec-2-en-3-yl)-1H-pyrazolo[3,4-b]pyridin-4-yl]amino}cyclohexanecarboxylic acid (Compound No. 134), 4-{[5-(2-Cyano-5-oxa-6-azaspiro[3.4]oct-6-en-7-yl)-1-ethyl-1H-pyrazolo[3,4-b]pyridin-4-yl]amino}cyclohexanecarboxylic acid (Compound No. 135), 1-Ethyl-3-methyl-5-(5-oxa-6-azaspiro[3.4]oct-6-en-7-yl)-N-(tetrahydro-2H-pyran-4-yl)-1H-pyrazolo[3,4-b]pyridin-4-amine (Compound No. 136), 1-Ethyl-3-methyl-5-(1-oxa-2-azaspiro[4.4]non-2-en-3-yl)-N-(tetrahydro-2H-pyran-4-yl)-1H-pyrazolo[3,4-b]pyridin-4-amine (Compound No. 137), 1-Ethyl-3-methyl-5-(1-oxa-2-azaspiro[4.5]dec-2-en-3-yl)-N-(tetrahydro-2H-pyran-4-yl)-1H-pyrazolo[3,4-b]pyridin-4-amine (Compound No. 138), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carbonitrile (Compound No. 139), N-Cyclohexyl-1-ethyl-3-methyl-5-(5-oxa-6-azaspiro[3.4]oct-6-en-7-yl)-1H-pyrazolo[3,4-b]pyridin-4-amine (Compound No. 140), 7-[4-(Cyclohexylamino)-1-ethyl-3-methyl-1H-pyrazolo[3,4-b]pyridin-5-yl]-5-oxa-6-azaspiro[3.4]oct-6-ene-2-carbonitrile (Compound No. 141), 3-[4-(Cyclohexylamino)-1-ethyl-1H-pyrazolo[3,4-b]pyridin-5-yl]-N-methyl-1-oxa-2-azaspiro[4.5]dec-2-en-8-amine (Compound No. 142), 4-{[5-(2-Cyano-5-oxa-6-azaspiro[3.4]oct-6-en-7-yl)-1-ethyl-3-methyl-1H-pyrazolo[3,4-b]pyridin-4-yl]amino}cyclohexanecarboxylic acid (Compound No. 143), 4-{[1-Ethyl-5-(2-hydroxy-5-oxa-6-azaspiro[3.4]oct-6-en-7-yl)-3-methyl-1H-pyrazolo[3,4-b]pyridin-4-yl]amino}cyclohexanecarboxylic acid (Compound No. 144), 4-{[1-Ethyl-3-methyl-5-(1-oxa-2-azaspiro[4.4]non-2-en-3-yl)-1H-pyrazolo[3,4-b]pyridin-4-yl]amino}cyclohexanecarboxylic acid (Compound No. 145), 4-{[1-Ethyl-3-methyl-5-(1-oxa-2-azaspiro[4.5]dec-2-en-3-yl)-1H-pyrazolo[3,4-b]pyridin-4-yl]amino}cyclohexanecarboxylic acid (Compound No. 146), 4-{[1-Ethyl-5-(8-hydroxy-1-oxa-2-azaspiro[4.5]dec-2-en-3-yl)-1H-pyrazolo[3,4-b]pyridin-4-yl]amino}cyclohexanecarboxylic acid (Compound No. 147), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-en-8-ol (Compound No. 148), 3-[1-Ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 149), 4-{[5-(8-Carbamoyl-1-oxa-2-azaspiro[4.5]dec-2-en-3-yl)-1-ethyl-1H-pyrazolo[3,4-b]pyridin-4-yl]amino}cyclohexanecarboxylic acid (Compound No. 150), 3-{[5-(8-Carbamoyl-1-oxa-2-azaspiro[4.5]dec-2-en-3-yl)-1-ethyl-1H-pyrazolo[3,4-b.]pyridin-4-yl]amino}cyclobutanecarboxylic acid (Compound No. 151), 3-{1-Ethyl-4-[(3-hydroxycyclobutyl)amino]-1H-pyrazolo[3,4-b]pyridin-5-yl}-N-methyl-1-oxa-2-azaspiro[4.5]dec-2-ene-8-carboxamide (Compound No. 152), 3-[4-(Cyclohexylamino)-1-ethyl-1H-pyrazolo[3,4-b]pyridin-5-yl]-N-methyl-1-oxa-2-azaspiro[4.5]dec-2-ene-8-carboxamide (Compound No. 153), 3-[1-Ethyl-4-(tetrahydro-2H-pyran-4-ylamino)-1H-pyrazolo[3,4-b]pyridin-5-yl]-N-methyl-1-oxa-2-azaspiro[4.5]dec-2-ene-8-carboxamide (Compound No. 154), 3-{4-[(1,1-Dioxidotetrahydro-2H-thiopyran-4-yl)amino]-1-ethyl-1H-pyrazolo[3,4-b]pyridin-5-yl}-N-methyl-1-oxa-2-azaspiro[4.5]dec-2-ene-8-carboxamide (Compound No. 155), 3-{4-[(1,1-Dioxidotetrahydro-2H-thiopyran-4-yl)amino]-1-ethyl-3-methyl-1H-pyrazolo[3,4-b]pyridin-5-yl}-N-methyl-1-oxa-2-azaspiro[4.5]dec-2-ene-8-carboxamide (Compound No. 156), N-(1,1-dioxidotetrahydro-2H-thiopyran-4-yl)-1-ethyl-3-methyl-5-(5-oxa-6-azaspiro[3.4]oct-6-en-7-yl)-1H-pyrazolo[3,4-b]pyridin-4-amine (Compound No. 157), N-(1,1-dioxidotetrahydro-2H-thiopyran-4-yl)-1-ethyl-3-methyl-5-(1-oxa-2-azaspiro[4.4]non-2-en-3-yl)-1H-pyrazolo[3,4-b]pyridin-4-amine (Compound No. 158), N-(1,1-dioxidotetrahydro-2H-thiopyran-4-yl)-1-ethyl-3-methyl-5-(1-oxa-2-azaspiro[4.5]dec-2-en-3-yl)-1H-pyrazolo[3,4-b]pyridin-4-amine (Compound No. 159), 3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-en-8-ol (Compound No. 160), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylic acid (Compound No. 161), 3-{4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-ene-8-carboxylic acid (Compound No. 162), 3-{4-[(1,1-Dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxamide (Compound No. 163), 3-{-4-[(1,1-Dioxidotetrahydro-2H-thiopyran-4-yl)amino]-1-ethyl-3-methyl-1H-pyrazolo[3,4-b]pyridin-5-yl}-1-oxa-2-azaspiro[4.5]dec-2-ene-8-carboxamide (Compound No. 164), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-en-8-ol (Compound No. 165), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-ene-8-carboxylic acid (Compound No. 166), 3-[1-Ethyl-3-methyl-4-(tetrahydro-2H-pyran-4-ylamino)-1H-pyrazolo[3,4-b]pyridin-5-yl]-1-oxa-2-azaspiro[4.5]dec-2-ene-8-carbonitrile (Compound No. 167), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxylic acid (Compound No. 168), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-en-2-ol (Compound No. 169), 7-[1-Ethyl-3-methyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 170), 5-(2-Amino-5-oxa-6-azaspiro[3.4]oct-6-en-7-yl)-1-ethyl-3-methyl-N-(tetrahydro-2H-pyran-4-yl)-1H-pyrazolo[3,4-b]pyridin-4-amine (Compound No. 171), 3-[4-(Cyclohexylamino)-1-ethyl-3-methyl-1H-pyrazolo[3,4-b]pyridin-5-yl]-1-oxa-2-azaspiro[4.5]dec-2-en-8-ol (Compound No. 172), 3-[4-(Cyclohexylamino)-1-ethyl-3-methyl-1H-pyrazolo[3,4-b]pyridin-5-yl]-1-oxa-2-azaspiro[4.5]dec-2-ene-8-carbonitrile (Compound No. 173), 3-[4-(Cyclohexylamino)-1-ethyl-3-methyl-1H-pyrazolo[3,4-b]pyridin-5-yl]-1-oxa-2-azaspiro[4.5]dec-2-ene-8-carboxylic acid (Compound No. 174), 7-[4-(Cyclohexylamino)-1-ethyl-3-methyl-1H-pyrazolo[3,4-b]pyridin-5-yl]-5-oxa-6-azaspiro[3.4]oct-6-ene-2-carboxylic acid (Compound No. 175), 7-[4-(Cyclohexylamino)-1-ethyl-3-methyl-1H-pyrazolo[3,4-b]pyridin-5-yl]-5-oxa-6-azaspiro[3.4]oct-6-en-2-ol (Compound No. 176), 7-[4-(Cyclohexylamino)-1-ethyl-3-methyl-1H-pyrazolo[3,4-b]pyridin-5-yl]-N-methyl-5-oxa-6-azaspiro[3.4]oct-6-ene-2-carboxamide (Compound No. 177), 5-(2-Amino-5-oxa-6-azaspiro[3.4]oct-6-en-7-yl)-N-cyclohexyl-1-ethyl-3-methyl-1H-pyrazolo[3,4-b]pyridin-4-amine (Compound No. 178), 4-{[1-Ethyl-3-methyl-5-(5-oxa-6-azaspiro[3.4]oct-6-en-7-yl)-1H-pyrazolo[3,4-b]pyridin-4-yl]amino}cyclohexanecarboxylic acid (Compound No. 179), 4-{[1-Ethyl-5-(8-hydroxy-1-oxa-2-azaspiro[4.5]dec-2-en-3-yl)-3-methyl-1H-pyrazolo[3,4-b]pyridin-4-yl]amino}cyclohexanecarboxylic acid (Compound No. 180), 3-{[1-Ethyl-3-methyl-5-(5-oxa-6-azaspiro[3.4]oct-6-en-7-yl)-1H-pyrazolo[3,4-b]pyridin-4-yl]amino}cyclobutanecarboxylic acid (Compound No. 181), 3-{[1-Ethyl-3-methyl-5-(1-oxa-2-azaspiro[4.4]non-2-en-3-yl)-1H-pyrazolo[3,4-b]pyridin-4-yl]amino}cyclobutanecarboxylic acid (Compound No. 182), 3-{[1-Ethyl-3-methyl-5-(1-oxa-2-azaspiro[4.5]dec-2-en-3-yl)-1H-pyrazolo[3,4-b]pyridin-4-yl]amino}cyclobutanecarboxylic acid (Compound No. 183), 3-{[5-(2-Cyano-5-oxa-6-azaspiro[3.4]oct-6-en-7-yl)-1-ethyl-1H-pyrazolo[3,4-b]pyridin-4-yl]amino}cyclobutanecarboxylic acid (Compound No. 184), 3-{[5-(2-Cyano-5-oxa-6-azaspiro[3.4]oct-6-en-7-yl)-1-ethyl-3-methyl-1H-pyrazolo[3,4-b]pyridin-4-yl]amino}cyclobutanecarboxylic acid (Compound No. 185), 3-{[1-Ethyl-5-(8-hydroxy-1-oxa-2-azaspiro[4.5]dec-2-en-3-yl)-3-methyl-1H-pyrazolo[3,4-b]pyridin-4-yl]amino}cyclobutanecarboxylic acid (Compound No. 186), 3-{[1-Ethyl-5-(8-hydroxy-1-oxa-2-azaspiro[4.5]dec-2-en-3-yl)-1H-pyrazolo[3,4-b]pyridin-4-yl]amino}cyclobutanecarboxylic acid (Compound No. 187), 3-{[1-Ethyl-5-(2-hydroxy-5-oxa-6-azaspiro[3.4]oct-6-en-7-yl)-1H-pyrazolo[3,4-b]pyridin-4-yl]amino}cyclobutanecarboxylic acid (Compound No. 188), 3-{[1-Ethyl-5-(2-hydroxy-5-oxa-6-azaspiro[3.4]oct-6-en-7-yl)-3-methyl-1H-pyrazolo[3,4-b]pyridin-4-yl]amino}cyclobutanecarboxylic acid (Compound No. 189), 5-(2-Amino-5-oxa-6-azaspiro[3.4]oct-6-en-7-yl)-N-(1,1-dioxidotetrahydro-2H-thiopyran-4-yl)-1-ethyl-1H-pyrazolo[3,4-b]pyridin-4-amine (Compound No. 190), 5-(2-Amino-5-oxa-6-azaspiro[3.4]oct-6-en-7-yl)-N-(1,1-dioxidotetrahydro-2H-thiopyran-4-yl)-1-ethyl-3-methyl-1H-pyrazolo[3,4-b]pyridin-4-amine (Compound No. 191), N-(7-{4-[(1,1-dioxidotetrahydro-2H-thiopyran-4-yl)amino]-1-ethyl-3-methyl-1H-pyrazolo[3,4-b]pyridin-5-yl}-5-oxa-6-azaspiro[3.4]oct-6-en-2-yl)acetamide (Compound No. 192), N-(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)acetamide (Compound No. 193), N-(7-{4-[(1,1-dioxidotetrahydro-2H-thiopyran-4-yl)-amino]-1-ethyl-1H-pyrazolo[3,4-b]pyridin-5-yl}-5-oxa-6-azaspiro[3.4]oct-6-en-2-yl)propanamide (Compound No. 194), N-(7-{4-[(1,1-dioxidotetrahydro-2H-thiopyran-4-yl)amino]-1-ethyl-3-methyl-1H-pyrazolo[3,4-b]pyridin-5-yl}-5-oxa-6-azaspiro[3.4]oct-6-en-2-yl)propanamide (Compound No. 195), 3-{[5-(2-Amino-5-oxa-6-azaspiro[3.4]oct-6-en-7-yl)-1-ethyl-1H-pyrazolo[3,4-b]pyridin-4-yl]amino}cyclobutanecarboxylic acid (Compound No. 196), 3-{[5-(2-Amino-5-oxa-6-azaspiro[3.4]oct-6-en-7-yl)-1-ethyl-3-methyl-1H-pyrazolo[3,4-b]pyridin-4-yl]amino}cyclobutanecarboxylic acid (Compound No. 197), 3-({5-[2-(Acetylamino)-5-oxa-6-azaspiro[3.4]oct-6-en-7-yl]-1-ethyl-3-methyl-1H-pyrazolo[3,4-b]pyridin-4-yl}amino)cyclobutanecarboxylic acid (Compound No. 198), 3-({5-[2-(Acetylamino)-5-oxa-6-azaspiro[3.4]oct-6-en-7-yl]-1-ethyl-1H-pyrazolo[3,4-b]pyridin-4-yl}amino)cyclobutanecarboxylic acid (Compound No. 199), 3-({1-Ethyl-5-[2-(propanoylamino)-5-oxa-6-azaspiro[3.4]oct-6-en-7-yl]-1H-pyrazolo[3,4-b]pyridin-4-yl}amino)cyclobutanecarboxylic acid (Compound No. 200), 3-({1-Ethyl-3-methyl-5-[2-(propanoylamino)-5-oxa-6-azaspiro[3.4]oct-6-en-7-yl]-1H-pyrazolo[3,4-b]pyridin-4-yl}amino)cyclobutanecarboxylic acid (Compound No. 201), N-ethyl-7-[1-ethyl-3-methyl-4-(tetrahydro-2H-pyran-4-ylamino)-1H-pyrazolo[3,4-b)]pyridin-5-yl]-5-oxa-6-azaspiro[3.4]oct-6-ene-2-carboxamide (Compound No. 202), N-{7-[4-(cyclohexylamino)-1-ethyl-1H-pyrazolo[3,4-b]pyridin-5-yl]-5-oxa-6-azaspiro[3.4]oct-6-en-2-yl}propanamide (Compound No. 203), N-{7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}propanamide (Compound No. 204), N-{7-[1-ethyl-3-methyl-4-(tetrahydro-2H-pyran-4-ylamino)-1H-pyrazolo[3,4-b]pyridin-5-yl]-5-oxa-6-azaspiro[3.4]oct-6-en-2-yl}propanamide (Compound No. 205), 4-{[5-(8-Amino-1-oxa-2-azaspiro[4.5]dec-2-en-3-yl)-1-ethyl-3-methyl-1H-pyrazolo[3,4-b]pyridin-4-yl]amino}cyclohexanecarboxylic acid (Compound No. 206), 4-{[5-(8-Amino-1-oxa-2-azaspiro[4.5]dec-2-en-3-yl)-1-ethyl-1H-pyrazolo[3,4-b]pyridin-4-yl]amino}cyclohexanecarboxylic acid (Compound No. 207), 4-({5-[8-(Acetylamino)-1-oxa-2-azaspiro[4.5]dec-2-en-3-yl]-1-ethyl-1H-pyrazolo[3,4-b]pyridin-4-yl}amino)cyclohexanecarboxylic acid (Compound No. 208), 4-({5-[8-(Acetylamino)-1-oxa-2-azaspiro[4.5]dec-2-en-3-yl]-1-ethyl-3-methyl-1H-pyrazolo[3,4-b]pyridin-4-yl}amino)cyclohexanecarboxylic acid (Compound No. 209), 4-({1-Ethyl-3-methyl-5-[8-(propanoylamino)-1-oxa-2-azaspiro[4.5]dec-2-en-3-yl]-1H-pyrazolo[3,4-b]pyridin-4-yl}amino)cyclohexanecarboxylic acid (Compound No. 210), 4-({1-Ethyl-5-[8-(propanoylamino)-1-oxa-2-azaspiro[4.5]dec-2-en-3-yl]-1H-pyrazolo[3,4-b]pyridin-4-yl}amino)cyclohexanecarboxylic acid (Compound No. 211), 7-{4-[(4-Carboxycyclohexyl)amino]-1-ethyl-3-methyl-1H-pyrazolo[3,4-b]pyridin-5-yl}-5-oxa-6-azaspiro[3.4]oct-6-ene-2-carboxylic acid (Compound No. 212), 7-{4-[(4-Carboxycyclohexyl)amino]-1-ethyl-1H-pyrazolo[3,4-b]pyridin-5-yl}-5-oxa-6-azaspiro[3.4]oct-6-ene-2-carboxylic acid (Compound No. 213), 4-{[5-(2-Carbamoyl-5-oxa-6-azaspiro[3.4]oct-6-en-7-yl)-1-ethyl-1H-pyrazolo[3,4-b]pyridin-4-yl]amino}cyclohexanecarboxylic acid (Compound No. 214), 4-{[5-(2-Carbamoyl-5-oxa-6-azaspiro[3.4]oct-6-en-7-yl)-1-ethyl-3-methyl-1H-pyrazolo[3,4-b]pyridin-4-yl]amino}cyclohexanecarboxylic acid (Compound No. 215), 4-({1-Ethyl-3-methyl-5-[2-(methylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 216), 4-({1-Ethyl-5-[2-(methylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 217), 4-({1-Ethyl-5-[2-(ethylcarbamoyl)-5-oxa-6-azaspiro[3.4]oct-6-en-7-yl]-1H-pyrazolo[3,4-b]pyridin-4-yl}amino)cyclohexanecarboxylic acid (Compound No. 218), 4-({1-Ethyl-5-[2-(ethylcarbamoyl)-5-oxa-6-azaspiro[3.4]oct-6-en-7-yl]-3-methyl-1H-pyrazolo[3,4-b]pyridin-4-yl}amino)cyclohexanecarboxylic acid (Compound No. 219), 3-{4-[(4-Carboxycyclohexyl)amino]-1-ethyl-1H-pyrazolo[3,4-b]pyridin-5-yl}-1-oxa-2-azaspiro[4.5]dec-2-ene-8-carboxylic acid (Compound No. 220), 3-{4-[(4-Carboxycyclohexyl)amino]-1-ethyl-3-methyl-1H-pyrazolo[3,4-b]pyridin-5-yl}-1-oxa-2-azaspiro[4.5]dec-2-ene-8-carboxylic acid (Compound No. 221), 4-{[5-(8-Carbamoyl-1-oxa-2-azaspiro[4.5]dec-2-en-3-yl)-1-ethyl-3-methyl-1H-pyrazolo[3,4-b]pyridin-4-yl]amino}cyclohexanecarboxylic acid (Compound No. 222), 4-({1-Ethyl-5-[8-(methylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 223), 4-({1-Ethyl-3-methyl-5-[8-(methylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 224), 4-({1-Ethyl-5-[8-(ethylcarbamoyl)-1-oxa-2-azaspiro[4.5]dec-2-en-3-yl]-3-methyl-1H-pyrazolo[3,4-b]pyridin-4-yl}amino)cyclohexanecarboxylic acid (Compound No. 225), 4-({1-Ethyl-5-[8-(ethylcarbamoyl)-1-oxa-2-azaspiro[4.5]dec-2-en-3-yl]-1H-pyrazolo[3,4-b]pyridin-4-yl}amino)cyclohexanecarboxylic acid (Compound No. 226), 4-{[1-Ethyl-5-(8-methoxy-1-oxa-2-azaspiro[4.5]dec-2-en-3-yl)-1H-pyrazolo[3,4-b]pyridin-4-yl]amino}cyclohexanecarboxylic acid (Compound No. 227), 4-{[5-(8-Ethoxy-1-oxa-2-azaspiro[4.5]dec-2-en-3-yl)-1-ethyl-1H-pyrazolo[3,4-b]pyridin-4-yl]amino}cyclohexanecarboxylic acid (Compound No. 228), 4-({1-Ethyl-5-[8-(2-hydroxyethoxy)-1-oxa-2-azaspiro[4.5]dec-2-en-3-yl]-1H-pyrazolo[3,4-b]pyridin-4-yl}amino)cyclohexanecarboxylic acid (Compound No. 229), 1-Ethyl-5-(5-oxa-6-azaspiro[3.4]oct-6-en-7-yl)-N-pyridin-4-yl-1H-pyrazolo[3,4-b]pyridin-4-amine (Compound No. 230), 1-Ethyl-5-(5-oxa-6-azaspiro[3.4]oct-6-en-7-yl)-N-pyridin-3-yl-1H-pyrazolo[3,4-b]pyridin-4-amine (Compound No. 231), 1-Ethyl-5-(5-oxa-6-azaspiro[3.4]oct-6-en-7-yl)-N-pyridin-2-yl-1H-pyrazolo[3,4-b]pyridin-4-amine (Compound No. 232), 1-Ethyl-5-(5-oxa-6-azaspiro[3.4]oct-6-en-7-yl)-N-pyrazin-2-yl-1H-pyrazolo[3,4-b]pyridin-4-amine (Compound No. 233), 1-Ethyl-5-(5-oxa-6-azaspiro[3.4]oct-6-en-7-yl)-N-pyrimidin-2-yl-1H-pyrazolo[3,4-b]pyridin-4-amine (Compound No. 234), 1-Ethyl-5-(5-oxa-6-azaspiro[3.4]oct-6-en-7-yl)-N-1,2,4-triazin-5-yl-1H-pyrazolo[3,4-b]pyridin-4-amine (Compound No. 235), 1-Ethyl-5-(5-oxa-6-azaspiro[3.4]oct-6-en-7-yl)-N-1,3-thiazol-2-yl-1H-pyrazolo[3,4-b]pyridin-4-amine (Compound No. 236), 1-Ethyl-5-(5-oxa-6-azaspiro[3.4]oct-6-en-7-yl)-N-4H-1,2,4-triazol-4-yl-1H-pyrazolo[3,4-b]pyridin-4-amine (Compound No. 237), 1-Ethyl-5-(5-oxa-6-azaspiro[3.4]oct-6-en-7-yl)-N-2H-tetrazol-5-yl-1H-pyrazolo[3,4-b]pyridin-4-amine (Compound No. 238), 1-Ethyl-5-(5-oxa-6-azaspiro[3.4]oct-6-en-7-yl)-N-1H-tetrazol-5-yl-1H-pyrazolo[3,4-b]pyridin-4-amine (Compound No. 239), 1-Ethyl-5-(5-oxa-6-azaspiro[3.4]oct-6-en-7-yl)-N-pyrimidin-5-yl-1H-pyrazolo[3,4-b]pyridin-4-amine (Compound No. 240), 1-Ethyl-5-(1-oxa-2-azaspiro[4.5]dec-2-en-3-yl)-N-pyridin-4-yl-1H-pyrazolo[3,4-b]pyridin-4-amine (Compound No. 241), 1-Ethyl-5-(1-oxa-2-azaspiro[4.4]non-2-en-3-yl)-N-pyridin-4-yl-1H-pyrazolo[3,4-b]pyridin-4-amine (Compound No. 242), 1-Ethyl-5-(1-oxa-2-azaspiro[4.5]dec-2-en-3-yl)-N-pyridin-3-yl-1H-pyrazolo[3,4-b]pyridin-4-amine (Compound No. 243), 1-Ethyl-5-(1-oxa-2-azaspiro[4.5]dec-2-en-3-yl)-N-pyridin-2-yl-1H-pyrazolo[3,4-b]pyridin-4-amine (Compound No. 244), 1-Ethyl-5-(1-oxa-2-azaspiro[4.5]dec-2-en-3-yl)-N-pyrimidin-2-yl-1H-pyrazolo[3,4-b]pyridin-4-amine (Compound No. 245), 1-Ethyl-5-(1-oxa-2-azaspiro[4.5]dec-2-en-3-yl)-N-pyrimidin-5-yl-1H-523 pyrazolo[3,4-b]pyridin-4-amine (Compound No. 246), 1-Ethyl-5-(1-oxa-2-azaspiro[4.5]dec-2-en-3-yl)-N-1,2,4-triazin-5-yl-1H-pyrazolo[3,4-b]pyridin-4-amine (Compound No. 247), 1-Ethyl-5-(1-oxa-2-azaspiro[4.5]dec-2-en-3-yl)-N-1,3-thiazol-2-yl-1H-pyrazolo[3,4-b]pyridin-4-amine (Compound No. 248), 1-Ethyl-5-(1-oxa-2-azaspiro[4.5]dec-2-en-3-yl)-N-4H-1,2,4-triazol-4-yl-1H-pyrazolo[3,4-b]pyridin-4-amine (Compound No. 249), 1-Ethyl-5-(1-oxa-2-azaspiro[4.5]dec-2-en-3-yl)-N-2H-tetrazol-5-yl-1H-pyrazolo[3,4-b]pyridin-4-amine (Compound No. 250), 1-Ethyl-5-(1-oxa-2-azaspiro[4.5]dec-2-en-3-yl)-N-1H-tetrazol-5-yl-1H-pyrazolo[3,4-b]pyridin-4-amine (Compound No. 251), 1-Ethyl-5-(1-oxa-2-azaspiro[4.4]non-2-en-3-yl)-N-pyridin-3-yl-1H-pyrazolo[3,4-b]pyridin-4-amine (Compound No. 252), 1-Ethyl-5-(1-oxa-2-azaspiro[4.4]non-2-en-3-yl)-N-pyridin-2-yl-1H-pyrazolo[3,4-b]pyridin-4-amine (Compound No. 253), 1-Ethyl-5-(1-oxa-2-azaspiro[4.4]non-2-en-3-yl)-N-pyrimidin-2-yl-1H-pyrazolo[3,4-b]pyridin-4-amine (Compound No. 254), 1-Ethyl-5-(1-oxa-2-azaspiro[4.4]non-2-en-3-yl)-N-pyrimidin-5-yl-1H-pyrazolo[3,4-b]pyridin-4-amine (Compound No. 255), 1-Ethyl-5-(1-oxa-2-azaspiro[4.4]non-2-en-3-yl)-N-1,2,4-triazin-5-yl-1H-pyrazolo[3,4-b]pyridin-4-amine (Compound No. 256), 1-Ethyl-5-(1-oxa-2-azaspiro[4.4]non-2-en-3-yl)-N-1H-tetrazol-5-yl-1H-pyrazolo[3,4-b]pyridin-4-amine (Compound No. 257), 1-Ethyl-5-(1-oxa-2-azaspiro[4.4]non-2-en-3-yl)-N-2H-tetrazol-5-yl-1H-pyrazolo[3,4-b]pyridin-4-amine (Compound No. 258), 1-Ethyl-5-(1-oxa-2-azaspiro[4.4]non-2-en-3-yl)-N-4H-1,2,4-triazol-4-yl-1H-pyrazolo[3,4-b]pyridin-4-amine (Compound No. 259), 1-Ethyl-5-(1-oxa-2-azaspiro[4.4]non-2-en-3-yl)-N-1,3-thiazol-2-yl-1H-pyrazolo[3,4-b]pyridin-4-amine (Compound No. 260), 1-Ethyl-N-furan-3-yl-5-(1-oxa-2-azaspiro[4.5]dec-2-en-3-yl)-1H-pyrazolo[3,4-b]pyridin-4-amine (Compound No. 261), 1-Ethyl-N-furan-3-yl-5-(1-oxa-2-azaspiro[4.4]non-2-en-3-yl)-1H-pyrazolo[3,4-b]pyridin-4-amine (Compound No. 262), 1-Ethyl-N-furan-3-yl-5-(5-oxa-6-azaspiro[3.4]oct-6-en-7-yl)-1H-pyrazolo[3,4-b]pyridin-4-amine (Compound No. 263), 1-Ethyl-5-(1-oxa-2-azaspiro[4.4]non-2-en-3-yl)-N-pyrazin-2-yl-1H-pyrazolo[3,4-b]pyridin-4-amine (Compound No. 264), 1-Ethyl-5-(1-oxa-2-azaspiro[4.5]dec-2-en-3-yl)-N-pyrazin-2-yl-1H-pyrazolo[3,4-b]pyridin-4-amine (Compound No. 265), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carbonitrile (Compound No. 266), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylic acid (Compound No. 267), Methyl 7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylate (Compound No. 268), Ethyl 7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylate (Compound No. 269), tert-Butyl 7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxylate (Compound No. 270), 7-{4-[(1,1-Dioxidotetrahydro-2H-thiopyran-4-yl)amino]-1-ethyl-1H-pyrazolo[3,4-b]pyridin-5-yl}-N-methyl-5-oxa-6-azaspiro[3.4]oct-6-ene-2-carboxamide (Compound No. 271), 7-{4-[(1,1-Dioxidotetrahydro-2H-thiopyran-4-yl)amino]-1-ethyl-1H-pyrazolo[3,4-b]pyridin-5-yl}-N-ethyl-5-oxa-6-azaspiro[3.4]oct-6-ene-2-carboxamide (Compound No. 272), N-cyclopropyl-7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxamide (Compound No. 273), 7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-ene-2-carboxamide (Compound No. 274), 7-[4-(Cyclohexylamino)-1-ethyl-1H-pyrazolo[3,4-b]pyridin-5-yl]-N-cyclopropyl-5-oxa-6-azaspiro[3.4]oct-6-ene-2-carboxamide (Compound No. 275), N-cyclopropyl-7-[1-ethyl-4-(tetrahydro-2H-pyran-4-ylamino)-1H-pyrazolo[3,4-b]pyridin-5-yl]-5-oxa-6-azaspiro[3.4]oct-6-ene-2-carboxamide (Compound No. 276), 1-Ethyl-5-(8-methoxy-1-oxa-2-azaspiro[4.5]dec-2-en-3-yl)-N-(tetrahydro-2H-pyran-4-yl)-1H-pyrazolo[3,4-b]pyridin-4-amine (Compound No. 277), 5-(8-Ethoxy-1-oxa-2-azaspiro[4.5]dec-2-en-3-yl)-1-ethyl-N-(tetrahydro-2H-pyran-4-yl)-1H-pyrazolo[3,4-b]pyridin-4-amine (Compound No. 278), N-cyclohexyl-5-(8-ethoxy-1-oxa-2-azaspiro[4.5]dec-2-en-3-yl)-1-ethyl-1H-pyrazolo[3,4-b]pyridin-4-amine (Compound No. 279), N-cyclohexyl-1-ethyl-5-(8-methoxy-1-oxa-2-azaspiro[4.5]dec-2-en-3-yl)-1H-pyrazolo[3,4-b]pyridin-4-amine (Compound No. 280), 3-{4-[(1,1-Dioxidotetrahydro-2H-thiopyran-4-yl)amino]-1-ethyl-1H-pyrazolo[3,4-b]pyridin-5-yl}-N-ethyl-1-oxa-2-azaspiro[4.5]dec-2-ene-8-carboxamide (Compound No. 281), N-cyclopropyl-3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxamide (Compound No. 282), 3-[4-(Cyclohexylamino)-1-ethyl-1H-pyrazolo[3,4-b]pyridin-5-yl]-N-cyclopropyl-1-oxa-2-azaspiro[4.5]dec-2-ene-8-carboxamide (Compound No. 283), N-cyclopropyl-3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 284), N-ethyl-3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxamide (Compound No. 285), 3-[4-(Cyclohexylamino)-1-ethyl-1H-pyrazolo[3,4-b]pyridin-5-yl]-N-ethyl-1-oxa-2-azaspiro[4.5]dec-2-ene-8-carboxamide (Compound No. 286), Ethyl 3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylate (Compound No. 287), Methyl 3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylate (Compound No. 288), tert-Butyl 3-{4-[(1,1-dioxidotetrahydro-2H-thiopyran-4-yl)amino]-1-ethyl-1H-pyrazolo[3,4-b]pyridin-5-yl}-1-oxa-2-azaspiro[4.5]dec-2-ene-8-carboxylate (Compound No. 289), N-(1,1-dioxidotetrahydro-2H-thiopyran-4-yl)-1-ethyl-5-(8-methoxy-1-oxa-2-azaspiro[4.5]dec-2-en-3-yl)-1H-pyrazolo[3,4-b]pyridin-4-amine (Compound No. 290), N-(1,1-dioxidotetrahydro-2H-thiopyran-4-yl)-5-(8-ethoxy-1-oxa-2-azaspiro[4.5]dec-2-en-3-yl)-1-ethyl-1H-pyrazolo[3,4-b]pyridin-4-amine (Compound No. 291), 1-Ethyl-5-(1-oxa-2-azaspiro[4.4]non-2-en-3-yl)-N-1,2,4-triazin-3-yl-1H-pyrazolo[3,4-b]pyridin-4-amine (Compound No. 292), 1-Ethyl-5-(5-oxa-6-azaspiro[3.4]oct-6-en-7-yl)-N-1,2,4-triazin-3-yl-1H-pyrazolo[3,4-b]pyridin-4-amine (Compound No. 293), 1-Ethyl-5-(1-oxa-2-azaspiro[4.5]dec-2-en-3-yl)-N-1,2,4-triazin-3-yl-1H-pyrazolo[3,4-b]pyridin-4-amine (Compound No. 294), 1-Ethyl-5-(2-methoxy-5-oxa-6-azaspiro[3.4]oct-6-en-7-yl)-N-(tetrahydro-2H-pyran-4-yl)-1H-pyrazolo[3,4-b]pyridin-4-amine (Compound No. 295), N-cyclohexyl-1-ethyl-5-(2-methoxy-5-oxa-6-azaspiro[3.4]oct-6-en-7-yl)-1H-pyrazolo[3,4-b]pyridin-4-amine (Compound No. 296), N-(1,1-dioxidotetrahydro-2H-thiopyran-4-yl)-1-ethyl-5-(2-methoxy-5-oxa-6-azaspiro[3.4]oct-6-en-7-yl)-1H-pyrazolo[3,4-b]pyridin-4-amine (Compound No. 297), N-(1,1-dioxidotetrahydro-2H-thiopyran-4-yl)-5-(2-ethoxy-5-oxa-6-azaspiro[3.4]oct-6-en-7-yl)-1-ethyl-1H-pyrazolo[3,4-b]pyridin-4-amine (Compound No. 298), N-cyclohexyl-5-(2-ethoxy-5-oxa-6-azaspiro[3.4]oct-6-en-7-yl)-1-ethyl-1H-pyrazolo[3,4-b]pyridin-4-amine (Compound No. 299), 5-(2-Ethoxy-5-oxa-6-azaspiro[3.4]oct-6-en-7-yl)-1-ethyl-N-(tetrahydro-2H-pyran-4-yl)-1H-pyrazolo[3,4-b]pyridin-4-amine (Compound No. 300), {7-[4-(Cyclohexylamino)-1-ethyl-1H-pyrazolo[3,4-b]pyridin-5-yl]-5-oxa-6-azaspiro[3.4]oct-6-en-2-yl}methanol (Compound No. 301), {7-{4-[(1,1-Dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methanol (Compound No. 302), N-(1,1-dioxidotetrahydro-2H-thiopyran-4-yl)-1-ethyl-5-[2-(methoxymethyl)-5-oxa-6-azaspiro[3.4]oct-6-en-7-yl]-1H-pyrazolo[3,4-b]pyridin-4-amine (Compound No. 303), N-(1,1-dioxidotetrahydro-2H-thiopyran-4-yl)-5-[2-(ethoxymethyl)-5-oxa-6-azaspiro[3.4]oct-6-en-7-yl]-1-ethyl-1H-pyrazolo[3,4-b]pyridin-4-amine (Compound No. 304), N-cyclohexyl-5-[2-(ethoxymethyl)-5-oxa-6-azaspiro[3.4]oct-6-en-7-yl]-1-ethyl-1H-pyrazolo [3,4-b]pyridin-4-amine (Compound No. 305), 5-[2-(Ethoxymethyl)-5-oxa-6-azaspiro[3.4]oct-6-en-7-yl]-1-ethyl-N-(tetrahydro-2H -pyran-4-yl)-1H-pyrazolo[3,4-b]pyridin-4-amine (Compound No. 306), 1-Ethyl-5-[2-(methoxymethyl)-5-oxa-6-azaspiro[3.4]oct-6-en-7-yl]-N-(tetrahydro-2H -pyran-4-yl)-1H-pyrazolo[3,4-b]pyridin-4-amine (Compound No. 307), N-cyclohexyl-1-ethyl-5-[2-(methoxymethyl)-5-oxa-6-azaspiro[3.4]oct-6-en-7-yl]-1H-pyrazolo [3,4-b]pyridin-4-amine (Compound No. 308), 5-[2-(Aminomethyl)-5-oxa-6-azaspiro[3.4]oct-6-en-7-yl]-N-cyclohexyl-1-ethyl-1H-pyrazolo [3,4-b]pyridin-4-amine (Compound No. 309), 5-[2-(Aminomethyl)-5-oxa-6-azaspiro[3.4]oct-6-en-7-yl]-1-ethyl-N-(tetrahydro-2H -pyran-4-yl)-1H-pyrazolo[3,4-b]pyridin-4-amine (Compound No. 310), 5-[2-(Aminomethyl)-5-oxa-6-azaspiro[3.4]oct-6-en-7-yl]-N-(1,1-dioxidotetrahydro -2H-thiopyran-4-yl)-1-ethyl-1H-pyrazolo[3,4-b]pyridin-4-amine (Compound No. 311), N-[(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methyl]acetamide (Compound No. 312), N-[(7-{4-[(1,1-dioxidotetrahydro-2H-thiopyran-4-yl)amino]-1-ethyl-1H-pyrazolo[3,4-b]pyridin-5-yl}-5-oxa-6-azaspiro[3.4]oct-6-en-2-yl)methyl]propanamide (Compound No. 313), N-({7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}methyl)propanamide (Compound No. 314), N-({7-[4-(cyclohexylamino)-1-ethyl-1H-pyrazolo[3,4-b]pyridin-5-yl]-5-oxa-6-azaspiro[3.4]oct-6-en-2-yl}methyl)propanamide (Compound No. 315), N-({7-[4-(cyclohexylamino)-1-ethyl-1H-pyrazolo[3,4-b]pyridin-5-yl]-5-oxa-6-azaspiro[3.4]oct-6-en-2-yl}methyl)acetamide (Compound No. 316), N-({7-[1-ethyl-4-(tetrahydro-2H-pyran-4-ylamino)-1H-pyrazolo[3,4-b]pyridin-5-yl]-5-oxa-6-azaspiro[3.4]oct-6-en-2-yl}methyl)acetamide (Compound No. 317), 1-Ethyl-N-(tetrahydro-2H-pyran-4-yl)-5-[2-(1H-tetrazol-5-yl)-5-oxa-6-azaspiro[3.4]oct-6-en-7-yl]-1H-pyrazolo[3,4-b]pyridin-4-amine (Compound No. 318), N-cyclohexyl-1-ethyl-5-[2-(1H-tetrazol-5-yl)-5-oxa-6-azaspiro[3.4]oct-6-en-7-yl]-1H-pyrazolo [3,4-b]pyridin-4-amine (Compound No. 319), N-(1,1-dioxidotetrahydro-2H-thiopyran-4-yl)-1-ethyl-5-[2-(1H-tetrazol-5-yl)-5-oxa-6-azaspiro[3.4]oct-6-en-7-yl]-1H-pyrazolo[3,4-b]pyridin-4-amine (Compound No. 320), 1-Ethyl-N-(tetrahydro-2H-pyran-4-yl)-5-[8-(1H-tetrazol-5-yl)-1-oxa-2-azaspiro[4.5]dec-2-en-3-yl]-1H-pyrazolo[3,4-b]pyridin-4-amine (Compound No. 321), N-cyclohexyl-1-ethyl-5-[8-(1H-tetrazol-5-yl)-1-oxa-2-azaspiro[4.5]dec-2-en-3-yl]-1H-pyrazolo [3,4-b]pyridin-4-amine (Compound No. 322), N-(1,1-dioxidotetrahydro-2H-thiopyran-4-yl)-1-ethyl-5-[8-(1H-tetrazol-5-yl)-1-oxa-2-azaspiro[4.5]dec-2-en-3-yl]-1H-pyrazolo[3,4-b]pyridin-4-amine (Compound No. 323), N-(1,1-dioxidotetrahydro-2H-thiopyran-4-yl)-1-ethyl-5-[8-(2H-tetrazol-5-yl)-1-oxa-2-azaspiro[4.5]dec-2-en-3-yl]-1H-pyrazolo[3,4-b]pyridin-4-amine (Compound No. 324), N-cyclohexyl-1-ethyl-5-[8-(2H-tetrazol-5-yl)-1-oxa-2-azaspiro[4.5]dec-2-en-3-yl]-1H-pyrazolo [3,4-b]pyridin-4-amine (Compound No. 325), 1-Ethyl-N-(tetrahydro-2H-pyran-4-yl)-5-[8-(2H-tetrazol-5-yl)-1-oxa-2-azaspiro[4.5]dec-2-en-3-yl]-1H-pyrazolo[3,4-b]pyridin-4-amine (Compound No. 326), 1-Ethyl-N-(tetrahydro-2H-pyran-4-yl)-5-[2-(2H-tetrazol-5-yl)-5-oxa-6-azaspiro[3.4]oct-6-en-7-yl]-1H-pyrazolo[3,4-b]pyridin-4-amine (Compound No. 327), N-cyclohexyl-1-ethyl-5-[2-(2H-tetrazol-5-yl)-5-oxa-6-azaspiro[3.4]oct-6-en-7-yl]-1H-pyrazolo [3,4-b]pyridin-4-amine (Compound No. 328), N-(1,1-dioxidotetrahydro-2H-thiopyran-4-yl)-1-ethyl-5-[2-(2H-tetrazol-5-yl)-5-oxa-6-azaspiro[3.4]oct-6-en-7-yl]-1H-pyrazolo[3,4-b]pyridin-4-amine (Compound No. 329), Ethyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 330), Ethyl 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 331), Methyl 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 332), Methyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 333), tert-Butyl 3-[1-ethyl-4-(tetrahydro-2H-pyran-4-ylamino)-1H-pyrazolo[3,4-b]pyridin-5-yl]-1-oxa-2-azaspiro[4.5]dec-2-ene-8-carboxylate (Compound No. 334), tert-Butyl 3-[4-(cyclohexylamino)-1-ethyl-1H-pyrazolo[3,4-b]pyridin-5-yl]-1-oxa-2-azaspiro[4.5]dec-2-ene-8-carboxylate (Compound No. 335), N-(1,1-dioxidotetrahydro-2H-thiopyran-4-yl)-1-ethyl-5-(5-oxa-6-azaspiro[3.4]oct-6-en-7-yl)-1H-pyrazolo[3,4-b]pyridin-4-amine (Compound No. 336), N-(1,1-dioxidotetrahydro-2H-thiopyran-4-yl)-1-ethyl-5-(1-oxa-2-azaspiro[4.4]non-2-en-3-yl)-1H-pyrazolo[3,4-b]pyridin-4-amine (Compound No. 337), 3-[4-(Cyclohexylamino)-1-ethyl-1H-pyrazolo[3,4-b]pyridin-5-yl]-1-oxa-2-azaspiro[4.5]dec-2-en-8-amine (Compound No. 338), or its pharmaceutically acceptable salts, pharmaceutically acceptable, stereoisomers, tautomers, or racemates, thereof.

3. A pharmaceutical composition comprising a therapeutically effective amount of a compound as defined in claim 1 along with one or more of pharmaceutically acceptable carriers, excipients or diluents.

4. A pharmaceutical composition comprising a therapeutically effective amount of a compound of claim 1, along with one or more of pharmaceutically acceptable carriers, excipients or diluents and at least one other compound selected fromβ2-agonists, corticosteroids, leukotriene antagonists, 5-lipoxygenase inhibitors, chemokine inhibitors, p38 kinase inhibitors, anticholinergics, antiallergics, PAF (platelet activating factor) antagonists, EGFR (epidermal growth factor receptor) kinase inhibitors, muscarinic receptor antagonists or combination(s) thereof.

5. A compound of claim 1 for use in a method for treating, inhibiting, or suppressing CNS diseases in a mammal.

6. A compound of claim 1 for use in a method for the treatment, inhibition, or suppression of rejection of transplant, rheumatoid arthritis, bronchitis, chronic obstructive pulmonary disease (COPD), asthma, psoriasis, allergic rhinitis, shock, atopic dermatitis, eosinophilic granuloma, allergic conjunctivitis, osteoarthritis, colitis, pancreatitis, and cancer in a mammal.

7. A pharmaceutical composition comprising a therapeutically effective amount of a compound as defined in claim 2 along with one or more of pharmaceutically acceptable carriers, excipients or diluents.

8. A pharmaceutical composition comprising a therapeutically effective amount of a compound of claim 2, along with one or more of pharmaceutically acceptable carriers, excipients or diluents and at least one other compound selected fromβ2-agonists, corticosteroids, leukotriene antagonists, 5-lipoxygenase inhibitors, chemokine inhibitors, p38 kinase inhibitors, anticholinergics, antiallergics, PAF (platelet activating factor) antagonists, EGFR (epidermal growth factor receptor) kinase inhibitors, muscarinic receptor antagonists or combination(s) thereof.

9. A compound of claim 2 for use in a method for treating, inhibiting, or suppressing CNS diseases in a mammal.

10. A pharmaceutical composition of claim 3 for use in a method for treating, inhibiting, or suppressing CNS diseases in a mammal.

11. A pharmaceutical composition of claim 4 for use in a method for treating, inhibiting, or suppressing CNS diseases in a mammal.

12. A compound of claim 2 for use in a method for the treatment, inhibition, or suppression of rejection of transplant, rheumatoid arthritis, bronchitis, chronic obstructive pulmonary disease (COPD), asthma, psoriasis, allergic rhinitis, shock, atopic dermatitis, eosinophilic granuloma, allergic conjunctivitis, osteoarthritis, colitis, pancreatitis, and cancer in a mammal.

13. A pharmaceutical composition of claim 3 for use in a method for the treatment, inhibition, or suppression of rejection of transplant, rheumatoid arthritis, bronchitis, chronic obstructive pulmonary disease (COPD), asthma, psoriasis, allergic rhinitis, shock, atopic dermatitis, eosinophilic granuloma, allergic conjunctivitis, osteoarthritis, colitis, pancreatitis, and cancer in a mammal.

14. A pharmaceutical composition of claim 4 for use in a method for the treatment, inhibition, or suppression of rejection of transplant, rheumatoid arthritis, bronchitis, chronic obstructive pulmonary disease (COPD), asthma, psoriasis, allergic rhinitis, shock, atopic dermatitis, eosinophilic granuloma, allergic conjunctivitis, osteoarthritis, colitis, pancreatitis, and cancer in a mammal.

\* \* \* \* \*

UNITED STATES PATENT AND TRADEMARK OFFICE
CERTIFICATE OF CORRECTION

PATENT NO. : 8,420,666 B2
APPLICATION NO. : 12/531043
DATED : April 16, 2013
INVENTOR(S) : Rudra et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 737 days.

Signed and Sealed this
First Day of September, 2015

Michelle K. Lee
*Director of the United States Patent and Trademark Office*